(12) United States Patent
Anderson et al.

(10) Patent No.: US 10,981,906 B2
(45) Date of Patent: Apr. 20, 2021

(54) SUBSTITUTED PYRROLOPYRIDINE JAK INHIBITORS AND METHODS OF MAKING AND USING THE SAME

(71) Applicant: ACLARIS THERAPEUTICS, INC., Wayne, PA (US)

(72) Inventors: David Randolph Anderson, Salem, CT (US); Susan Landis Hockerman, Kirkwood, MO (US); James Robert Blinn, O'Fallon, MO (US); Eric Jon Jacobsen, Chesterfield, MO (US)

(73) Assignee: ACLARIS THERAPEUTICS, INC., Wayne, PA (US)

( * ) Notice: Subject to any disclaimer, the term of this patent is extended or adjusted under 35 U.S.C. 154(b) by 0 days.

(21) Appl. No.: 16/179,695

(22) Filed: Nov. 2, 2018

(65) Prior Publication Data

US 2019/0135808 A1 May 9, 2019

Related U.S. Application Data

(60) Provisional application No. 62/581,428, filed on Nov. 3, 2017, provisional application No. 62/670,448, filed on May 11, 2018.

(51) Int. Cl.
| | | |
|---|---|---|
| *C07D 471/04* | (2006.01) | |
| *A61K 31/4545* | (2006.01) | |
| *A61K 31/437* | (2006.01) | |
| *A61K 45/06* | (2006.01) | |

(52) U.S. Cl.
CPC .......... *C07D 471/04* (2013.01); *A61K 31/437* (2013.01); *A61K 31/4545* (2013.01); *A61K 45/06* (2013.01)

(58) Field of Classification Search
CPC .................................................. C07D 471/04
See application file for complete search history.

(56) References Cited

U.S. PATENT DOCUMENTS

| 5,760,068 | A | 6/1998 | Talley et al. |
|---|---|---|---|
| 7,799,782 | B2 | 9/2010 | Munson et al. |
| 7,879,844 | B2 | 2/2011 | Inoue et al. |
| 8,163,767 | B2 | 4/2012 | Inoue et al. |
| 8,722,693 | B2 | 5/2014 | Rodgers et al. |
| 8,921,376 | B2 | 12/2014 | Ledeboer et al. |
| 9,556,187 | B2 | 1/2017 | Hayashi et al. |
| 10,800,775 | B2 * | 10/2020 | Anderson ............ C07D 471/04 |
| 2007/0135461 | A1 | 6/2007 | Rodgers et al. |
| 2007/0135466 | A1 | 6/2007 | Ledeboer et al. |
| 2009/0264399 | A1 | 10/2009 | Inoue et al. |
| 2010/0105661 | A1 | 4/2010 | Shirakami et al. |
| 2010/0113416 | A1 | 5/2010 | Friedman et al. |
| 2011/0039822 | A1 | 2/2011 | Inoue et al. |
| 2012/0149681 | A1 | 6/2012 | Rodgers et al. |
| 2014/0221379 | A1 | 8/2014 | Rodgers et al. |
| 2015/0158864 | A1 | 6/2015 | Thorarensen et al. |
| 2015/0329542 | A1 | 11/2015 | Coe et al. |
| 2016/0272648 | A1 | 9/2016 | Rodgers et al. |
| 2017/0349579 | A1 | 12/2017 | Rodgers et al. |
| 2018/0055846 | A1 | 3/2018 | Bates et al. |
| 2019/0135807 | A1 | 5/2019 | Anderson et al. |
| 2019/0135813 | A1 | 5/2019 | Rodgers et al. |

FOREIGN PATENT DOCUMENTS

| WO | 1999065909 | A1 | 12/1999 | |
|---|---|---|---|---|
| WO | 2000000202 | A1 | 1/2000 | |
| WO | 2004099205 | A1 | 11/2004 | |
| WO | WO-2008077057 | A2 * | 6/2008 | ........... C07D 413/14 |
| WO | 2017097224 | A1 | 6/2017 | |
| WO | 2019090143 | A1 | 5/2019 | |
| WO | 2019090158 | A1 | 5/2019 | |
| WO | 2020033955 | A1 | 2/2020 | |
| WO | 2020223728 | A1 | 11/2020 | |

OTHER PUBLICATIONS

Inoue, T., et al. "Discovery of 3,6-dihydroimidazo[4,5-d]pyrrolo[2,3-b]pyridine-2(1H)-one derivatives as novel JAK inhibitors." Bioorganic & Medicinal Chemistry. (2015), vol. 23, pp. 4846-4859. (Year: 2015).*
Banker et al., "Modem Pharmaceutics" 2002, 4th Edition, Drugs and the Pharmaceutical Sciences (cover and TOC).
Bundgaard, "Design of Prodrugs" 1985, Elsevier (cover and TOC).
Eliel et al., "Stereochemistry of Organic Compounds" Sep. 1994, John Wiley & Sons, Inc., New York, NY (cover and TOC).
Brunton et al., "Goodman & Gilman's The Pharmacological Basis of Therapeutics" 2011, 12th Edition, McGraw Hill, New York (cover and TOC).
Higuchi and Stella, "Pro-drugs as Novel Drug Delivery Systems," ACS Symposium Series; American Chemical Society, Washington, DC (1975), 14:1-115.
Roche "Bioreversible Carriers in Drug Design" 1987, University of Nebraska Medical Center, College of Pharmacy, Pergamon Press (cover and TOC).
Stahl et al., "Handbook of Pharmaceutical Salts: Properties, Selection, and Use" 2002, Wiley-VCHA, Zurich, Switzerland (abstract only).
Testa et al. "Hydrolysis in Drug and Prodrug Metabolism: Chemistry, Biochemistry, and Enzymology" 2003, Wiley-VHCA, Zurich, Switzerland (cover and TOC).
International Search Report and Written Opinion for PCT/US2018/059050 dated Feb. 25, 2019.
International Search Report and Written Opinion for PCT/US2018/059071 dated Feb. 25, 2019.

(Continued)

*Primary Examiner* — John S Kenyon
(74) *Attorney, Agent, or Firm* — Troutman Pepper Hamilton Sanders LLP

(57) ABSTRACT

The present invention relates to new pyrrolopyridine compounds and compositions and their application as pharmaceuticals for the treatment of disease. Methods of inhibition of JAK1 and JAK3 kinase activity in a human or animal subject are also provided for the treatment diseases such as pruritus, alopecia, androgenetic alopecia, alopecia areata, vitiligo and psoriasis.

21 Claims, No Drawings

(56) References Cited

OTHER PUBLICATIONS

International Search Report and Written Opinion for PCT/US2019/046182 dated Dec. 17, 2019.
McMahon "VEGF Receptor Signaling in Tumor Angiogenesis" 2000, The Oncologist 5(supp 1):3-10.
Papp et al. "Phase 2 Trial of Selective Tyrosine Kinase 2 Inhibition in Psoriasis" 2018, New England Journal of Medicine 379(14):1313-1321.
Pineda et al. "Translation Research: The Role of VEGF in Tumor Angiogenesis" 2000, The Oncologist 5(supp 1):1-2.
PubChem CID 118115872, pp. 1-9, Feb. 23, 2016.
PubChem CID 59291875, pp. 1-10, Aug. 20, 2012.
Notification, International Search Report and Written Opinion for PCT/US2020/044542 dated Oct. 29, 2020.

\* cited by examiner

SUBSTITUTED PYRROLOPYRIDINE JAK INHIBITORS AND METHODS OF MAKING AND USING THE SAME

CROSS-REFERENCE TO RELATED APPLICATIONS

This application claims the benefit of U.S. Provisional Application No. 62/581,428 filed Nov. 3, 2017 and U.S. Provisional Application No. 62/670,448 filed May 11, 2018. The disclosures of both of these applications are incorporated herein by reference. The disclosure of the application is incorporated herein by reference.

SUMMARY

Embodiments herein are directed to having the structures of Formulas (I)-(IV), or a derivative thereof, where the R groups, ring labels, and n values are defined herein:

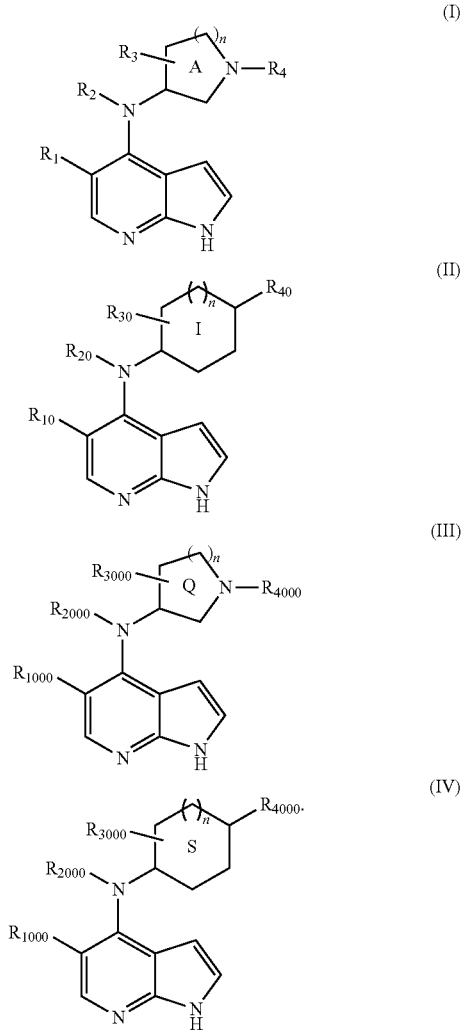

Disclosed herein are new pyrrolopyridine compounds and compositions and their application as pharmaceuticals for the treatment of disease. Methods of inhibition of JAK1 and JAK3 kinase activity in a human or animal subject are also provided for the treatment of JAK1 and/or JAK3-mediated conditions.

The Janus Kinases (JAKs) are a subgroup of non-receptor tyrosine kinases that are essential to transducing signals originating from type I and type II cytokine receptors and whose enzymatic activity is essential for the biological activity of the cytokines. The JAK kinase family consists of four family members: JAK1, JAK2, JAK3 and Tyk2, and these kinases are central to the regulation of cytokine signaling in the immune system, as well as more broadly in other tissues. The kinase activity of JAKs is directed towards the JAKs themselves, the intracellular portion of the cytokine receptor, and several other substrates including the members of the STAT family of transcription factors. The STATs (STAT1 through STAT6) have specific and distinct effects on gene transcription in numerous cell types, including immune cells, and are critical in processes such as cell proliferation and differentiation. Due to the broad role these kinases have in immunity and inflammation, numerous small molecule drugs have been developed to intervene in diseases where JAK kinase signaling contributes to disease. Initially, these drugs were developed for systemic administration for the prevention of organ transplant rejection. Subsequently they have been developed as potential therapies for hematologic malignancies, and autoimmune and inflammatory diseases including rheumatoid arthritis, ulcerative colitis, inflammatory bowel disease, ankylosing spondylitis, psoriasis, atopic dermatitis, alopecia disorders, and vitiligo, to name a few. More recently, due to the hematologic, immunosuppressive and metabolic toxicities associated with systemic inhibition of the JAK kinases, local delivery of these inhibitors as topical agents has been described. These include alopecia areata, atopic dermatitis, vitiligo, psoriasis, inflammatory bowel diseases, and dry eye, among others. This document describes compounds that are expected to have excellent oral and topical bioavailability and would be useful for systemic autoimmune disease, as well as compounds designed to have limited stability and hence limited systemic exposure, therefore, be best suited for local (e.g., topical) drug delivery.

Signal transduction of cytokine receptors activated by cytokines has been shown to occur through JAK kinases associated with receptor cytoplasmic domains. Receptor stimulation results in the activation of the JAKs and subsequent phosphorylation of the cytoplasmic domain of the associated receptor chains. This creates an SH2-binding domain, which serves to recruit the latent cytoplasmic transcription factors known as STATs (Signal Transducer and Activator of Transcription). While bound to the phosphorylated cytokine receptors, the STATs themselves become phosphorylated on tyrosine residues—which leads to SH2-domain mediated homo- and hetero-dimer formation and translocation to the nucleus. Once there, these proteins induce the transcription of genes associated with activation of the original cytokine receptor. This sequence of events (STAT protein phosphorylation in minutes, and STAT-induced gene transcription in hours) are both amenable to characterizing the cellular potency of compounds and informing structure-activity relationships.

DETAILED DESCRIPTION

Before the present compositions and methods are described, it is to be understood that this invention is not limited to the particular processes, formulations, compositions, or methodologies described, as these may vary. It is also to be understood that the terminology used in the description is for the purpose of describing the particular versions or embodiments only and is not intended to limit the scope of embodiments herein which will be limited only by the appended claims. Unless defined otherwise, all technical and scientific terms used herein have the same meanings as commonly understood by one of ordinary skill in the art. Although any methods and materials similar or equivalent to those described herein can be used in the practice or testing of embodiments of embodiments herein, the preferred methods, devices, and materials are now described. All publications mentioned herein are incorporated by reference in their entirety. Nothing herein is to be construed as an admission that embodiments herein are not entitled to antedate such disclosure by virtue of prior invention.

Definitions

It must also be noted that as used herein and in the appended claims, the singular forms "a," "an," and "the" include plural reference unless the context clearly dictates otherwise. Thus, for example, reference to a "JAK inhibitor" is a reference to one or more JAK inhibitors and equivalents thereof known to those skilled in the art, and so forth.

The term "about," as used herein, is intended to qualify the numerical values which it modifies, denoting such a value as variable within a margin of error. When no particular margin of error, such as a standard deviation to a mean value given in a chart or table of data, is recited, the term "about" should be understood to mean plus or minus 10% of the numerical value of the number with which it is being used. Therefore, about 50% means in the range of 45%-55%.

In embodiments or claims where the term comprising is used as the transition phrase, such embodiments can also be envisioned with replacement of the term "comprising" with the terms "consisting of" or "consisting essentially of."

As used herein, the term "consists of" or "consisting of" means that the composition, formulation or the method includes only the elements, steps, or ingredients specifically recited in the particular claimed embodiment or claim.

As used herein, the term "consisting essentially of" or "consists essentially of" means that the composition, formulation or the method includes only the elements, steps or ingredients specifically recited in the particular claimed embodiment or claim and may optionally include additional elements, steps or ingredients that do not materially affect the basic and novel characteristics of the particular embodiment or claim. For example, the only active ingredient(s) in the formulation or method that treats the specified condition (e.g., nutrient depletion) is the specifically recited therapeutic(s) in the particular embodiment or claim.

As used herein, two embodiments are "mutually exclusive" when one is defined to be something which is different from the other. For example, an embodiment wherein two groups combine to form a cycloalkyl is mutually exclusive with an embodiment in which one group is ethyl the other group is hydrogen. Similarly, an embodiment wherein one group is $CH_2$ is mutually exclusive with an embodiment wherein the same group is NH.

As used herein, the term "a derivative thereof" refers to a salt thereof, a pharmaceutically acceptable salt thereof, a free acid form thereof, a free base form thereof, a solvate thereof, a deuterated derivative thereof, a hydrate thereof, an N-oxide thereof, a clathrate thereof, a prodrug thereof, a polymorph thereof, a stereoisomer thereof, a geometric isomer thereof, a tautomer thereof, a mixture of tautomers thereof, an enantiomer thereof, a diastereomer thereof, a racemate thereof, a mixture of stereoisomers thereof, an isotope thereof (e.g., tritium, deuterium), or a combination thereof.

As used herein, the term "pharmaceutically acceptable salt" refers to a salt prepared from a base or acid which is acceptable for administration to a patient. The term "pharmaceutically acceptable salts" embraces salts commonly used to form alkali metal salts and to form addition salts of free acids or free bases. Such salts can be derived from pharmaceutically-acceptable inorganic or organic bases and from pharmaceutically-acceptable inorganic or organic acids.

When ranges of values are disclosed, and the notation "from n1 . . . to n2" or "between n1 . . . and n2" is used, where n1 and n2 are the numbers, then unless otherwise specified, this notation is intended to include the numbers themselves and the range between them. This range may be integral or continuous between and including the end values. By way of example, the range "from 2 to 6 carbons" is intended to include two, three, four, five, and six carbons, since carbons come in integer units. Compare, by way of example, the range "from 1 to 3 µM (micromolar)," which is intended to include 1 µM, 3 µM, and everything in between to any number of significant figures (e.g., 1.255 µM, 2.1 µM, 2.9999 µM, etc.).

The term "acyl," as used herein, alone or in combination, refers to a carbonyl attached to an alkenyl, alkyl, aryl, cycloalkyl, heteroaryl, heterocycle, or any other moiety were the atom attached to the carbonyl is carbon. An "acetyl" group refers to a —C(O)CH$_3$ group. An "alkylcarbonyl" or "alkanoyl" group refers to an alkyl group attached to the parent molecular moiety through a carbonyl group. Examples of such groups include methylcarbonyl and ethylcarbonyl. Examples of acyl groups include formyl, alkanoyl and aroyl.

The term "alkenyl," as used herein, alone or in combination, refers to a straight-chain or branched-chain hydrocarbon radical having one or more double bonds and containing from 2 to 20 carbon atoms. In certain embodiments, said alkenyl will comprise from 2 to 6 carbon atoms. The term "alkenylene" refers to a carbon-carbon double bond system attached at two or more positions such as ethenylene (—CH═CH—). Examples of suitable alkenyl radicals include ethenyl, propenyl, 2-methylpropenyl, 1,4-butadienyl and the like. Unless otherwise specified, the term "alkenyl" may include "alkenylene" groups.

The term "alkoxy," as used herein, alone or in combination, refers to an alkyl ether radical, wherein the term alkyl is as defined below. Examples of suitable alkyl ether radicals include methoxy, ethoxy, n-propoxy, isopropoxy, n-butoxy, iso-butoxy, sec-butoxy, tert-butoxy, and the like.

The term "alkyl," as used herein, alone or in combination, refers to a straight-chain or branched-chain alkyl radical containing from 1 to 20 carbon atoms. In certain embodiments, said alkyl will comprise from 1 to 10 carbon atoms. In further embodiments, said alkyl will comprise from 1 to 8 carbon atoms. Alkyl groups may be optionally substituted as defined herein.

Examples of alkyl radicals include methyl, ethyl, n-propyl, isopropyl, n-butyl, isobutyl, sec-butyl, tert-butyl, pentyl, iso-amyl, hexyl, octyl, noyl and the like. The term "alkylene," as used herein, alone or in combination, refers to a saturated aliphatic group derived from a straight or branched chain saturated hydrocarbon attached at two or more positions, such as methylene (—CH$_2$—). Unless otherwise specified, the term "alkyl" may include "alkylene" groups.

The term "alkylamino," as used herein, alone or in combination, refers to an alkyl group attached to the parent molecular moiety through an amino group. Suitable alkylamino groups may be mono- or dialkylated, forming groups such as, for example, N-methylamino, N-ethylamino, N,N-dimethylamino, N,N-ethylmethylamino and the like.

The term "alkylidene," as used herein, alone or in combination, refers to an alkenyl group in which one carbon atom of the carbon-carbon double bond belongs to the moiety to which the alkenyl group is attached.

The term "alkylthio," as used herein, alone or in combination, refers to an alkyl thioether (R—S—) radical wherein the term alkyl is as defined above and wherein the sulfur may be singly or doubly oxidized. Examples of suitable alkyl thioether radicals include methylthio, ethylthio, n-propylthio, isopropylthio, n-butylthio, iso-butylthio, sec-butylthio, tert-butylthio, methanesulfonyl, ethanesulfinyl, and the like.

The term "alkynyl," as used herein, alone or in combination, refers to a straight-chain or branched chain hydrocarbon radical having one or more triple bonds and containing from 2 to 20 carbon atoms. In certain embodiments, said alkynyl comprises from 2 to 6 carbon atoms. In further embodiments, said alkynyl comprises from 2 to 4 carbon atoms. The term "alkynylene" refers to a carbon-carbon triple bond attached at two positions such as ethynylene (—C≡C—).

Examples of alkynyl radicals include ethynyl, propynyl, hydroxypropynyl, butyn-1-yl, butyn-2-yl, pentyn-1-yl, 3-methylbutyn-1-yl, hexyn-2-yl, and the like. Unless otherwise specified, the term "alkynyl" may include "alkynylene" groups.

The terms "amido" and "carbamoyl," as used herein, alone or in combination, refer to an amino group as described below attached to the parent molecular moiety through a carbonyl group, or vice versa. The term "C-amido" as used herein, alone or in combination, refers to a —C(O)N(RR') group with R and R' as defined herein or as defined by the specifically enumerated "R" groups designated. The term "N-amido" as used herein, alone or in combination, refers to a RC(O)NH(R')— group, with R and R' as defined herein or as defined by the specifically enumerated "R" groups designated. The term "acylamino" as used herein, alone or in combination, embraces an acyl group attached to the parent moiety through an amino group. An example of an "acylamino" group is acetylamino (CH$_3$C(O)NH—).

The term "amino," as used herein, alone or in combination, refers to —NRR', wherein R and R' are independently chosen from hydrogen, alkyl, acyl, heteroalkyl, aryl, cycloalkyl, heteroaryl, and heterocycloalkyl, any of which may themselves be optionally substituted. Additionally, R and R' may combine to form heterocycloalkyl, either of which may be optionally substituted.

The term "aryl," as used herein, alone or in combination, means a carbocyclic aromatic system containing one, two or three rings wherein such polycyclic ring systems are fused together. The term "aryl" embraces aromatic groups such as phenyl, naphthyl, anthracenyl, and phenanthryl.

The term "arylalkenyl" or "aralkenyl," as used herein, alone or in combination, refers to an aryl group attached to the parent molecular moiety through an alkenyl group.

The term "arylalkoxy" or "aralkoxy," as used herein, alone or in combination, refers to an aryl group attached to the parent molecular moiety through an alkoxy group.

The term "arylalkyl" or "aralkyl," as used herein, alone or in combination, refers to an aryl group attached to the parent molecular moiety through an alkyl group.

The term "arylalkynyl" or "aralkynyl," as used herein, alone or in combination, refers to an aryl group attached to the parent molecular moiety through an alkynyl group.

The term "arylalkanoyl" or "aralkanoyl" or "aroyl," as used herein, alone or in combination, refers to an acyl radical derived from an aryl-substituted alkanecarboxylic acid such as benzoyl, napthoyl, phenylacetyl, 3-phenylpropionyl (hydrocinnamoyl), 4-phenylbutyryl, (2-naphthyl)acetyl, 4-chlorohydrocinnamoyl, and the like.

The term aryloxy as used herein, alone or in combination, refers to an aryl group attached to the parent molecular moiety through an oxy.

The terms "benzo" and "benz," as used herein, alone or in combination, refer to the divalent radical C$_6$H$_4$= derived from benzene. Examples include benzothiophene and benzimidazole.

The term "carbamate," as used herein, alone or in combination, refers to an ester of carbamic acid (—NHCOO—) which may be attached to the parent molecular moiety from either the nitrogen or acid end, and which may be optionally substituted as defined herein.

The term "O-carbamyl" as used herein, alone or in combination, refers to a —OC(O)NRR', group—with R and R' as defined herein.

The term "N-carbamyl" as used herein, alone or in combination, refers to a ROC(O)NR'— group, with R and R' as defined herein.

The term "carbonyl," as used herein, when alone includes formyl [—C(O)H] and in combination is a —C(O)— group.

The term "carboxyl" or "carboxy," as used herein, refers to —C(O)OH or the corresponding "carboxylate" anion, such as is in a carboxylic acid salt. An "O-carboxy" group refers to a RC(O)O— group, where R is as defined herein. A "C-carboxy" group refers to a —C(O)OR groups where R is as defined herein.

The term, "compound," as used herein is meant to include all stereoisomers, geometric isomers, and tautomers, of the structures depicted. The term "compound" also includes the incorporation of all isotopes in any enrichment (e.g., tritium, deuterium) at any position in the structures depicted.

The term "cyano," as used herein, alone or in combination, refers to —CN.

The term "cycloalkyl," or, alternatively, "carbocycle," as used herein, alone or in combination, refers to a saturated or partially saturated monocyclic, bicyclic or tricyclic alkyl group wherein each cyclic moiety contains from 3 to 12 carbon atom ring members and which may optionally be a benzo fused ring system which is optionally substituted as defined herein. In certain embodiments, said cycloalkyl will comprise from 5 to 7 carbon atoms. Examples of such cycloalkyl groups include cyclopropyl, cyclobutyl, cyclopentyl, cyclohexyl, cycloheptyl, tetrahydronapthyl, indanyl, octahydronaphthyl, 2,3-dihydro-1H-indenyl, adamantyl and the like. "Bicyclic" and "tricyclic" as used herein are intended to include both fused ring systems, such as decahydronaphthalene, octahydronaphthalene as well as the multicyclic (multicentered) saturated or partially unsaturated type. The latter type of isomer is exemplified in general by, bicyclo[1,1,1]pentane, camphor, adamantane, and bicyclo[3,2,1]octane.

The term "ester," as used herein, alone or in combination, refers to a carboxy group bridging two moieties linked at carbon atoms.

The term "ether," as used herein, alone or in combination, refers to an oxy group bridging two moieties linked at carbon atoms.

The term "halo," or "halogen," as used herein, alone or in combination, refers to fluorine, chlorine, bromine, or iodine.

The term "haloalkoxy," as used herein, alone or in combination, refers to a haloalkyl group attached to the parent molecular moiety through an oxygen atom.

The term "haloalkyl," as used herein, alone or in combination, refers to an alkyl radical having the meaning as defined above wherein one or more hydrogens are replaced with a halogen. Specifically embraced are monohaloalkyl, dihaloalkyl and polyhaloalkyl radicals. A monohaloalkyl radical, for one example, may have an iodo, bromo, chloro or fluoro atom within the radical. Dihalo and polyhaloalkyl radicals may have two or more of the same halo atoms or a combination of different halo radicals. Examples of haloalkyl radicals include fluoromethyl, difluoromethyl, trifluoromethyl, chloromethyl, dichloromethyl, trichloromethyl, pentafluoroethyl, heptafluoropropyl, difluorochloromethyl, dichlorofluoromethyl, difluoroethyl, difluoropropyl, dichloroethyl and dichloropropyl. "Haloalkylene" refers to a haloalkyl group attached at two or more positions. Examples include fluoromethylene (—CFH—), difluoromethylene (—CF$_2$—), chloromethylene (—CHCl—) and the like.

The term "halocycloalkyl" as used herein, alone or in combination, refers to an cycloalkyl radical having the meaning as defined above wherein one or more hydrogens are replaced with a halogen. Specifically embraced are monohalocycloalkyl, dihalocycloalkyl and polyhalochaloalkyl radicals. A monohaloalkyl radical, for one example, may have an iodo, bromo, chloro or fluoro atom within the radical. Dihalo and polyhaloalkyl radicals may have two or more of the same halo atoms or a combination of different halo radicals. Examples of haloalkyl radicals include fluorocyclopropyl, difluorocyclopropyl, fluorocyclobutyl, chlorocyclobutyl, and chlorocyclopentyl.

The term "heteroalkyl," as used herein, alone or in combination, refers to a stable straight or branched chain, or combinations thereof, fully saturated or containing from 1 to 3 degrees of unsaturation, consisting of the stated number of carbon atoms and from one to three heteroatoms chosen from N, O, and S, and wherein the N and S atoms may optionally be oxidized, and the N heteroatom may optionally be quaternized. The heteroatom(s) may be placed at any interior position of the heteroalkyl group. Up to two heteroatoms may be consecutive, such as, for example, —CH$_2$—NH—OCH$_3$.

The term "heteroaryl," as used herein, alone or in combination, refers to a 5 to 15 membered unsaturated heteromonocyclic ring, or a fused monocyclic, bicyclic, or tricyclic ring system in which at least one of the fused rings is aromatic, which contains at least one atom chosen from N, O, and S. In certain embodiments, said heteroaryl will comprise from 1 to 4 heteroatoms as ring members. In further embodiments, said heteroaryl will comprise from 1 to 2 heteroatoms as ring members. In certain embodiments, said heteroaryl will comprise from 5 to 7 atoms. The term also embraces fused polycyclic groups wherein heterocyclic rings are fused with aryl rings, wherein heteroaryl rings are fused with other heteroaryl rings, wherein heteroaryl rings are fused with heterocycloalkyl rings, or wherein heteroaryl rings are fused with cycloalkyl rings. Examples of heteroaryl groups include pyrrolyl, pyrrolinyl, imidazolyl, pyrazolyl, pyridyl, pyrimidinyl, pyrazinyl, pyridazinyl, triazolyl, pyranyl, furyl, thienyl, oxazolyl, isoxazolyl, oxadiazolyl, thiazolyl, thiadiazolyl, isothiazolyl, indolyl, isoindolyl, indolizinyl, benzimidazolyl, quinolyl, isoquinolyl, quinoxalinyl, quinazolinyl, indazolyl, benzotriazolyl, benzodioxolyl, benzopyranyl, benzoxazolyl, benzoxadiazolyl, benzothiazolyl, benzothiadiazolyl, benzofuryl, benzothienyl, chromonyl, coumarinyl, benzopyranyl, tetrahydroquinolinyl, tetrazolopyridazinyl, tetrahydroisoquinolinyl, thienopyridinyl, furopyridinyl, pyrrolopyridinyl and the like. Exemplary tricyclic heterocyclic groups include carbazolyl, benzidolyl, phenanthrolinyl, dibenzofuranyl, acridinyl, phenanthridinyl, xanthenyl and the like.

The terms "heterocycloalkyl" and, interchangeably, "heterocycle," as used herein, alone or in combination, each refer to a saturated, partially unsaturated, or fully unsaturated (but nonaromatic) monocyclic, bicyclic, or tricyclic heterocyclic group containing at least one heteroatom as a ring member, wherein each said heteroatom may be independently chosen from nitrogen, oxygen, and sulfur. In certain embodiments, said hetercycloalkyl will comprise from 1 to 4 heteroatoms as ring members. In further embodiments, said hetercycloalkyl will comprise from 1 to 2 heteroatoms as ring members. In certain embodiments, said hetercycloalkyl will comprise from 3 to 8 ring members in each ring. In further embodiments, said hetercycloalkyl will comprise from 3 to 7 ring members in each ring. In yet further embodiments, said hetercycloalkyl will comprise from 5 to 6 ring members in each ring. "Heterocycloalkyl" and "heterocycle" are intended to include sulfones, sulfoxides, N-oxides of tertiary nitrogen ring members, and carbocyclic fused and benzo fused ring systems; additionally, both terms also include systems where a heterocycle ring is fused to an aryl group, as defined herein, or an additional heterocycle group. Examples of heterocycle groups include aziridinyl, azetidinyl, 1,3-benzodioxolyl, dihydroisoindolyl, dihydroisoquinolinyl, dihydrocinnolinyl, dihydrobenzodioxinyl, dihydro[1,3]oxazolo[4,5-b]pyridinyl, benzothiazolyl, dihydroindolyl, dihy-dropyridinyl, 1,3-dioxanyl, 1,4-dioxanyl, 1,3-dioxolanyl, isoindolinyl, morpholinyl, piperazinyl, pyrrolidinyl, tetrahydropyridinyl, piperidinyl, thiomorpholinyl, and the like. The heterocycle groups may be optionally substituted unless specifically prohibited.

The term "hydrazinyl" as used herein, alone or in combination, refers to two amino groups joined by a single bond, i.e., —N—N—.

The term "hydroxy," as used herein, alone or in combination, refers to —OH.

The term "hydroxyalkyl," as used herein, alone or in combination, refers to a hydroxy group attached to the parent molecular moiety through an alkyl group.

The term "imino," as used herein, alone or in combination, refers to =N—.

The term "iminohydroxy," as used herein, alone or in combination, refers to =N(OH) and =N—O—.

The phrase "in the main chain" refers to the longest contiguous or adjacent chain of carbon atoms starting at the point of attachment of a group to the compounds of any one of the formulas disclosed herein.

The term "isocyanato" refers to a —NCO group.

The term "isothiocyanato" refers to a —NCS group.

The phrase "linear chain of atoms" refers to the longest straight chain of atoms independently selected from carbon, nitrogen, oxygen and sulfur.

The term "lower," as used herein, alone or in a combination, where not otherwise specifically defined, means containing from 1 to and including 6 carbon atoms (i.e., $C_1$-$C_6$ alkyl).

The term "lower aryl," as used herein, alone or in combination, means phenyl or naphthyl, either of which may be optionally substituted as provided.

The term "lower heteroaryl," as used herein, alone or in combination, means either 1) monocyclic heteroaryl comprising five or six ring members, of which between one and four said members may be heteroatoms chosen from N, O, and S, or 2) bicyclic heteroaryl, wherein each of the fused rings comprises five or six ring members, comprising between them one to four heteroatoms chosen from N, O, and S.

The term "lower cycloalkyl," as used herein, alone or in combination, means a monocyclic cycloalkyl having between three and six ring members (i.e., $C_3$-$C_6$ cycloalkyl). Lower cycloalkyls may be unsaturated. Examples of lower cycloalkyl include cyclopropyl, cyclobutyl, cyclopentyl, and cyclohexyl.

The term "lower heterocycloalkyl," as used herein, alone or in combination, means a monocyclic heterocycloalkyl having between three and six ring members, of which between one and four may be heteroatoms chosen from N, O, and S (i.e., $C_3$-$C_6$ heterocycloalkyl). Examples of lower heterocycloalkyls include pyrrolidinyl, piperidinyl, piperazinyl, and morpholinyl. Lower heterocycloalkyls may be unsaturated.

The term "lower amino," as used herein, alone or in combination, refers to —NRR', wherein R and R' are independently chosen from hydrogen and lower alkyl, either of which may be optionally substituted.

The term "mercaptyl" as used herein, alone or in combination, refers to an RS— group, where R is as defined herein.

The term "nitro," as used herein, alone or in combination, refers to —$NO_2$.

As used herein, an "N-oxide" is formed from the tertiary basic amines or imines present in the molecule, using a convenient oxidizing agent.

The terms "oxy" or "oxa," as used herein, alone or in combination, refer to —O—.

The term "oxo," as used herein, alone or in combination, refers to =O.

The term "perhaloalkoxy" refers to an alkoxy group where all of the hydrogen atoms are replaced by halogen atoms.

The term "perhaloalkyl" as used herein, alone or in combination, refers to an alkyl group where all of the hydrogen atoms are replaced by halogen atoms.

The term "substantially free" as used herein, alone or in combination, refers to a compound which is free from all other compounds within the limits of detection as measured by any means including nuclear magnetic resonance (NMR), gas chromatography/mass spectroscopy (GC/MS), or liquid chromatography/mass spectroscopy (LC/MS).

The terms "sulfonate," "sulfonic acid," and "sulfonic," as used herein, alone or in combination, refer the —SO3H group and its anion as the sulfonic acid is used in salt formation.

The term "sulfanyl," as used herein, alone or in combination, refers to —S—.

The term "sulfinyl," as used herein, alone or in combination, refers to —S(O)—.

The term "sulfonyl," as used herein, alone or in combination, refers to —$S(O)_2$—.

The term "N-sulfonamido" refers to a RS($=O)_2$NR'— group with R and R' as defined herein.

The term "S-sulfonamido" refers to a —$S(=O)_2$NRR', group, with R and R' as defined herein.

The terms "thia" and "thio," as used herein, alone or in combination, refer to a —S— group or an ether wherein the oxygen is replaced with sulfur. The oxidized derivatives of the thio group, namely sulfinyl and sulfonyl, are included in the definition of thia and thio.

The term "thiol," as used herein, alone or in combination, refers to an —SH group.

The term "thiocarbonyl," as used herein, when alone includes thioformyl —C(S)H and in combination is a —C(S)— group.

The term "N-thiocarbamyl" refers to an ROC(S)NR'— group, with R and R' as defined herein.

The term "O-thiocarbamyl" refers to a —OC(S)NRR', group with R and R' as defined herein.

The term "thiocyanato" refers to a —CNS group.

The term "trihalomethanesulfonamido" refers to a $X_3$CS$(O)_2$NR— group with X is a halogen and R as defined herein.

The term "trihalomethanesulfonyl" refers to a $X_3$CS$(O)_2$— group where X is a halogen.

The term "trihalomethoxy" refers to a $X_3$CO— group where X is a halogen.

The term "trisubstituted silyl," as used herein, alone or in combination, refers to a silicone group substituted at its three free valences with groups as listed herein under the definition of amino. Examples include trimethysilyl, tert-butyldimethylsilyl, triphenylsilyl and the like.

Any definition herein may be used in combination with any other definition to describe a composite structural group. By convention, the trailing element of any such definition is that which attaches to the parent moiety. For example, the composite group alkylamido would represent an alkyl group attached to the parent molecule through an amido group, and the term alkoxyalkyl would represent an alkoxy group attached to the parent molecule through an alkyl group.

When a group is defined to be "null," what is meant is that said group is absent.

The term "optionally substituted" means the anteceding group may be substituted or unsubstituted. When substituted, the substituents of an "optionally substituted" group may include, without limitation, one or more substituents independently selected from the following groups or a particular designated set of groups, alone or in combination: lower alkyl, lower alkenyl, lower alkynyl, lower alkanoyl, lower heteroalkyl, lower heterocycloalkyl, lower haloalkyl, lower haloalkenyl, lower haloalkynyl, lower perhaloalkyl, lower perhaloalkoxy, lower cycloalkyl, phenyl, aryl, aryloxy, lower alkoxy, lower haloalkoxy, oxo, lower acyloxy, carbonyl, carboxyl, lower alkylcarbonyl, lower carboxyester, lower carboxamido, cyano, hydrogen, halogen, hydroxy, amino, lower alkylamino, arylamino, amido, nitro, thiol, lower alkylthio, lower haloalkylthio, lower perhaloalkylthio, arylthio, sulfonate, sulfonic acid, trisubstituted silyl, N3, SH, $SCH_3$, $C(O)CH_3$, $CO_2CH_3$, $CO_2H$, pyridinyl, thiophene, furanyl, lower carbamate, and lower urea. Where structurally feasible, two substituents may be joined together to form a fused five-, six-, or seven-membered carbocyclic or heterocyclic ring consisting of zero to three heteroatoms, for example forming methylenedioxy or ethylenedioxy. An optionally substituted group may be unsubstituted (e.g., —$CH_2CH_3$), fully substituted (e.g., —$CF_2CF_3$), monosubstituted (e.g., —$CH_2CH_2F$) or substituted at a level anywhere in-between fully substituted and monosubstituted (e.g., —$CH_2CF_3$). Where substituents are recited without qualification as to substitution, both substituted and unsubstituted forms are encompassed. Where a substituent is qualified as "substituted," the substituted form is specifically intended. Additionally, different sets of optional substituents to a particular moiety may be defined as needed; in these cases, the optional substitution will be as defined, often immediately following the phrase, "optionally substituted with."

The term R or the term R', appearing by itself and without a number designation, unless otherwise defined, refers to a moiety chosen from hydrogen, alkyl, cycloalkyl, heteroalkyl, aryl, heteroaryl and heterocycloalkyl, any of which may be optionally substituted. Such R and R' groups should be understood to be optionally substituted as defined herein. Whether an R group has a number designation or not, every R group, including R, R' and Rn where n=(1, 2, 3, . . . n), every substituent, and every term should be understood to be independent of every other in terms of selection from a group. Should any variable, substituent, or term (e.g. aryl, heterocycle, R, etc.) occur more than one time in a formula or generic structure, its definition at each occurrence is independent of the definition at every other occurrence. Those of skill in the art will further recognize that certain groups may be attached to a parent molecule or may occupy a position in a chain of elements from either end as written. For example, an unsymmetrical group such as —C(O)N(R)— may be attached to the parent moiety at either the carbon or the nitrogen.

Stereogenic centers exist in some of the compounds disclosed herein. These centers are designated by the symbols "R" or "S," depending on the configuration of substituents around the stereogenic center. It should be understood that the invention encompasses all stereochemical isomeric forms, including diastereomeric, enantiomeric, atropisomeric, racemic and epimeric forms, as well as d-isomers and l-isomers, and mixtures thereof. Individual stereoisomers of compounds can be prepared synthetically from commercially available starting materials which contain fixed stereogenic centers or by preparation of racemic mixtures of products followed by enantiomeric separation such as conversion to a mixture of diastereomers followed by separation or recrystallization, chromatographic techniques, direct separation of enantiomers on chiral chromatographic columns, or any other appropriate method known in the art. Starting compounds of particular stereochemical configuration are either commercially available or can be made and resolved by techniques known in the art. Additionally, the compounds disclosed herein may exist as geometric isomers. The present invention includes all cis, trans, syn, anti, entgegen (E), and zusammen (Z) isomers as well as the appropriate mixtures thereof. Additionally, compounds may exist as tautomers; all tautomeric isomers are provided by this invention. Additionally, the compounds disclosed herein can exist in unsolvated as well as solvated forms with pharmaceutically acceptable solvents such as water, ethanol, and the like. In general, the solvated forms are considered equivalent to the unsolvated forms.

The term "bond" refers to a covalent linkage between two atoms, or two moieties when the atoms joined by the bond are considered to be part of larger substructure. A bond may be single, double, or triple unless otherwise specified. A dashed line between two atoms in a drawing of a molecule indicates that an additional bond may be present or absent at that position.

The term "disease" as used herein is intended to be generally synonymous, and is used interchangeably with, the terms "disorder," "syndrome," and "condition" (as in medical condition), in that all reflect an abnormal condition of the human or animal body or of one of its parts that impairs normal functioning, is typically manifested by distinguishing signs and symptoms, and causes the human or animal to have a reduced duration or quality of life.

The term "combination therapy" means the administration of two or more therapeutic agents to treat a therapeutic condition or disorder described in the present disclosure. Such administration encompasses co-administration of these therapeutic agents in a substantially simultaneous manner, such as in a single topical composition having a fixed ratio of active ingredients or in multiple, separate topical compositions for each active ingredient. In addition, such administration also encompasses use of each type of therapeutic agent in a sequential manner. In either case, the treatment regimen will provide beneficial effects of the drug combination in treating the conditions or disorders described herein.

"JAK1 and/or JAK3 inhibitor" is used herein to refer to a compound that exhibits an $IC_{50}$ with respect to JAK1 and/or JAK3 activity of no more than about 100 μM and more typically not more than about 50 μM, as measured in the JAK1 and JAK3 enzyme assays described generally herein. In some embodiments, the compounds will exhibit an $IC_{50}$ with respect to JAK1 and/or JAK3 of about 1 μM to about 50 μM. $IC_{50}$ is that concentration of inhibitor which reduces the activity of an enzyme (e.g., JAK1 and/or JAK3) to half-maximal level. Certain compounds disclosed herein have been discovered to exhibit inhibition against JAK1 and/or JAK3. In some embodiments, the compounds will exhibit an $IC_{50}$ with respect to JAK1 and/or JAK3 of no more than about 300 nM. In some embodiments, the compounds will exhibit an $IC_{50}$ with respect to JAK1 and/or JAK3 of no more than about 1 nM. In certain embodiments, compounds will exhibit an $IC_{50}$ with respect to JAK1 and/or JAK3 of no more than about 50 μM; in further embodiments, compounds will exhibit an $IC_{50}$ with respect to JAK1 and/or JAK3 of no more than about 10 μM; in yet further embodiments, compounds will exhibit an $IC_{50}$ with respect to JAK1 and/or JAK3 of not more than about 5 μM; in yet further embodiments, compounds will exhibit an $IC_{50}$ with respect to JAK1 and/or JAK3 of not more than about 1 μM, as measured in the JAK1 and/or JAK3 assay described herein.

The phrase "therapeutically effective" is intended to qualify the amount of active ingredients used in the treatment of a disease or disorder or on the effecting of a clinical endpoint.

As used herein, the term "therapeutic" means an agent utilized to treat, combat, ameliorate, prevent or improve an unwanted condition or disease of a patient. In part, embodiments of the present invention are directed to the treatment of JAK1 and/or JAK3-mediated diseases.

The term "therapeutically acceptable" refers to those compounds, or a derivative thereof, which are suitable for use in contact with the tissues of patients without undue toxicity, irritation, and allergic response, are commensurate with a reasonable benefit/risk ratio, and are effective for their intended use.

As used herein, reference to "treatment" of a patient is intended to include prophylaxis. Treatment may also be preemptive in nature, i.e., it may include prevention of disease. Prevention of a disease may involve complete protection from disease, for example as in the case of prevention of infection with a pathogen, or may involve prevention of disease progression. For example, prevention of a disease may not mean complete foreclosure of any effect related to the diseases at any level, but instead may mean prevention of the symptoms of a disease to a clinically significant or detectable level. Prevention of diseases may also mean prevention of progression of a disease to a later stage of the disease.

"Administering" when used in conjunction with a therapeutic means to administer a therapeutic directly into or onto a target tissue or to administer a therapeutic to a patient whereby the therapeutic positively impacts the tissue to which it is targeted. Thus, as used herein, the term "administering", when used in conjunction with a compound of embodiments herein, can include, but is not limited to, providing the compound into or onto the target tissue; providing the compound systemically to a patient by, e.g., intravenous injection whereby the therapeutic reaches the target tissue; providing the compound in the form of the encoding sequence thereof to the target tissue (e.g., by so-called gene-therapy techniques). "Administering" a composition may be accomplished by injection, topically, orally, or by any of these methods in combination with other known techniques.

The term "patient" is generally synonymous with the term "subject" and includes all mammals including humans. Examples of patients include humans, livestock such as cows, goats, sheep, pigs, and rabbits, and companion animals such as dogs, cats, rabbits, and horses. Preferably, the patient is a human.

The term "prodrug" refers to a compound that is made more active in vivo. Certain compounds disclosed herein may also exist as prodrugs, as described in Hydrolysis in Drug and Prodrug Metabolism: Chemistry, Biochemistry, and Enzymology (Testa, Bernard and Mayer, Joachim M. Wiley-VHCA, Zurich, Switzerland 2003). Prodrugs of the compounds described herein are structurally modified forms of the compound that readily undergo chemical changes under physiological conditions to provide the compound. Additionally, prodrugs can be converted to the compound by chemical or biochemical methods in an ex vivo environment. For example, prodrugs can be slowly converted to a compound when placed in a transdermal patch reservoir with a suitable enzyme or chemical reagent. Prodrugs are often useful because, in some situations, they may be easier to administer than the compound, or parent drug. They may, for instance, be bioavailable by oral administration whereas the parent drug is not. The prodrug may also have improved solubility in pharmaceutical compositions over the parent drug. A wide variety of prodrug derivatives are known in the art, such as those that rely on hydrolytic cleavage or oxidative activation of the prodrug.

The term "therapeutically acceptable salt," as used herein, represents salts or zwitterionic forms of the compounds disclosed herein which are water or oil-soluble or dispersible and therapeutically acceptable as defined herein. The salts can be prepared during the final isolation and purification of the compounds or separately by reacting the appropriate compound in the form of the free base with a suitable acid. Representative acid addition salts include acetate, adipate, alginate, L-ascorbate, aspartate, benzoate, benzenesulfonate (besylate), bisulfate, butyrate, camphorate, camphorsulfonate, citrate, digluconate, formate, fumarate, gentisate, glutarate, glycerophosphate, glycolate, hemisulfate, heptanoate, hexanoate, hippurate, hydrochloride, hydrobromide, hydroiodide, 2-hydroxyethansulfonate (isethionate), lactate, maleate, malonate, DL-mandelate, mesitylenesulfonate, methanesulfonate, naphthylenesulfonate, nicotinate, 2-naphthalenesulfonate, oxalate, pamoate, pectinate, persulfate, 3-phenylproprionate, phosphonate, picrate, pivalate, propionate, pyroglutamate, succinate, sulfonate, tartrate, L-tartrate, trichloroacetate, trifluoroacetate, phosphate, glutamate, bicarbonate, para-toluenesulfonate (p-tosylate), and undecanoate. Also, basic groups in the compounds disclosed herein can be quaternized with methyl, ethyl, propyl, and butyl chlorides, bromides, and iodides; dimethyl, diethyl, dibutyl, and diamyl sulfates; decyl, lauryl, myristyl, and steryl chlorides, bromides, and iodides; and benzyl and phenethyl bromides. Examples of acids which can be employed to form therapeutically acceptable addition salts include inorganic acids such as hydrochloric, hydrobromic, sulfuric, and phosphoric, and organic acids such as oxalic, maleic, succinic, and citric. Salts can also be formed by coordination of the compounds with an alkali metal or alkaline earth ion. Hence, the present invention contemplates sodium, potassium, magnesium, and calcium salts of the compounds disclosed herein, and the like.

Novel compounds and pharmaceutical compositions, certain of which have been found to inhibit JAK1 and/or JAK3 kinase have been discovered, together with methods of synthesizing and using the compounds including, without limitation, methods for the treatment of JAK1 and/or JAK3 mediated diseases in a patient by topically administering the compounds.

Compounds of the present invention may be selective amongst the JAK1 and/or JAK3 isoforms in various ways. For example, compounds described herein may be selective for JAK1 and/or JAK3 over other isoforms, such as JAK2 and Tyk-2, be a pan-inhibitor of all the isoforms, or be selective for only one isoform. In certain embodiments, compounds of the present invention are selective for JAK1 and/or JAK3 over other isoforms. In some embodiments, the compounds disclosed herein are selective for JAK1 and/or JAK3 over JAK2 and Tyk-2. Selectivity may be determined using enzyme assays, cellular assays or both. In some embodiments, the compounds disclosed herein are at least about 10× selective for JAK1 and/or JAK3 receptors over JAK2 receptor. In some embodiments, the compounds disclosed herein are at least about 10× selective for JAK1 and/or JAK3 receptors over Tyk-2 receptor.

Compounds

Embodiments herein are directed to compounds and pharmaceutical compositions, certain of which have been found to inhibit JAK1 and/or JAK3 Kinase, together with methods of synthesizing and using the compounds. Some embodiments include methods for the treatment of diseases in a patient by topically administering the compounds of embodiments herein.

Certain compounds disclosed herein may possess useful JAK1 and/or JAK3 inhibiting activity and may be used in the treatment or prophylaxis of a disease or condition in which JAK1 and/or JAK3 plays an active role. Thus, embodiments are also directed to pharmaceutical compositions comprising one or more compounds disclosed herein together with a pharmaceutically acceptable carrier, as well as methods of making and using the compounds and compositions. Certain embodiments are directed to methods for inhibiting JAK1 and/or JAK3. Other embodiments are directed to methods for treating a JAK1 and/or JAK3-mediated disorder in a patient in need of such treatment, comprising administering to said patient a therapeutically effective amount of a compound or composition according to the present invention. Also provided is the use of certain compounds disclosed herein in the manufacture of a medicament for the treatment of a disease or condition ameliorated by the inhibition of JAK1 and/or JAK3.

Also provided are embodiments wherein any embodiment herein may be combined with any one or more of the other embodiments, unless otherwise stated and provided the combination is not mutually exclusive.

Also provided is a compound chosen from the Examples disclosed herein. The compounds of embodiments herein may also refer to a salt thereof, an ester thereof, a free acid form thereof, a free base form thereof, a solvate thereof, a deuterated derivative thereof, a hydrate thereof, an N-oxide thereof, a clathrate thereof, a prodrug thereof, a polymorph thereof, a stereoisomer thereof, an enantiomer thereof, a diastereomer thereof, a racemate thereof, a mixture of stereoisomers thereof, a tautomer thereof, a mixture of tautomers thereof, or a combination of the foregoing of the compounds of embodiments herein.

Compounds described herein may contain a stereogenic center and may be chiral and thus exist as enantiomers. Where the compounds according to embodiments herein possess two or more stereogenic centers, they may additionally exist as diastereomers. Embodiments herein includes all possible stereoisomers as substantially pure resolved enantiomers, racemic mixtures thereof, as well as mixtures of diastereomers. In some embodiments, the formulas are shown without a definitive stereochemistry at certain positions. Embodiments herein includes all stereoisomers of such formulas and pharmaceutically acceptable salts thereof. Diastereoisomeric pairs of stereoisomers may be separated by, for example, fractional crystallization from a suitable solvent, and pairs of enantiomers thus obtained may be separated into individual stereoisomers by conventional means, for example by the use of an optically active acid or base as a resolving agent or on a chiral HPLC column. Further, any enantiomer or diastereomer of a compound of the general formula may be obtained by stereospecific or stereoselective synthesis using optically pure or enantioenriched starting materials or reagents of known configuration. The scope of embodiments herein as described and claimed encompasses the racemic forms of the compounds as well as the individual enantiomers, diastereomers, and stereoisomer-enriched mixtures.

Conventional techniques for the preparation/isolation of individual enantiomers include stereoselective synthesis from a suitable enantioenriched or optically pure precursors or resolution of the racemate using, for example, chiral high pressure liquid chromatography (HPLC). Alternatively, the racemate (or a racemic precursor) may be reacted with a suitable optically active compound, for example, an alcohol, or, in the case where the compound contains an acidic or basic moiety, an acid or base such as tartaric acid or 1-phenylethylamine. The resulting diastereomeric mixture may be separated by chromatography and/or fractional crystallization and one or both of the diastereoisomers converted to the corresponding pure enantiomer(s) by means well known to one skilled in the art. Chiral compounds of embodiments herein (and chiral precursors thereof) may be obtained in enantiomerically-enriched form using chromatography, typically HPLC, on an asymmetric resin with a mobile phase consisting of a hydrocarbon, typically heptane or hexane, containing from 0 to 50% isopropanol, typically from 2 to 20%, and from 0 to 5% of an alkylamine, typically 0.1% diethylamine. Concentration of the eluate affords the enriched mixture. Stereoisomer conglomerates may be separated by conventional techniques known to those skilled in the art. See, e.g., "Stereochemistry of Organic Compounds" by Ernest L. Eliel (Wiley, New York, 1994).

Atropisomers are stereoisomers resulting from hindered rotation about single bonds where the steric strain barrier to rotation is high enough to allow for the isolation of the conformers. Oki (Oki, M; Topics in Stereochemistry 1983, 1) defined atropisomers as conformers that interconvert with a half-life of more than 1000 seconds at a given temperature. The scope of embodiments herein as described and claimed encompasses the racemic forms of the compounds as well as the individual atropisomers (an atropisomer "substantially free" of its corresponding atropisomer) and stereoisomer-enriched mixtures, i.e., mixtures of atropisomers.

Separation of atropisomers is possibly by chiral resolution methods such as selective crystallization. In an atropo-enantioselective or atroposelective synthesis one atropisomer is formed at the expense of the other. Atroposelective synthesis may be carried out by use of chiral auxiliaries like a Corey-Bakshi-Shibata (CBS) catalyst (asymmetric catalyst derived from proline) in the total synthesis of knipholone or by approaches based on thermodynamic equilibration when an isomerization reaction favors one atropisomer over the other.

Suitable pharmaceutically acceptable acid addition salts of the compounds of embodiments herein may be prepared from an inorganic acid or an organic acid. All of these salts may be prepared by conventional means from the corresponding compound of embodiments herein by treating, for example, the compound with the appropriate acid or base.

Pharmaceutically acceptable acids include both inorganic acids, for example hydrochloric, hydrobromic, hydroiodic, nitric, carbonic, sulfuric, phosphoric and diphosphoric acid; and organic acids, for example formic, acetic, trifluoroacetic, propionic, succinic, glycolic, embonic (pamoic), methanesulfonic, ethanesulfonic, 2-hydroxyethanesulfonic, pantothenic, benzenesulfonic, toluenesulfonic, sulfanilic, mesylic, cyclohexylaminosulfonic, stearic, algenic, β-hydroxybutyric, malonic, galactic, galacturonic, citric, fumaric, gluconic, glutamic, lactic, maleic, malic, mandelic, mucic, ascorbic, oxalic, pantothenic, succinic, tartaric, benzoic, acetic, xinafoic (1-hydroxy-2-naphthoic acid), napadisilic (1,5-naphthalenedisulfonic acid) and the like.

Salts derived from pharmaceutically-acceptable inorganic bases include aluminum, ammonium, calcium, copper, ferric, ferrous, lithium, magnesium, manganic, manganous, potassium, sodium, zinc and the like. Salts derived from pharmaceutically-acceptable organic bases include salts of primary, secondary and tertiary amines, including alkyl amines, arylalkyl amines, heterocyclyl amines, cyclic amines, naturally-occurring amines and the like, such as arginine, betaine, caffeine, choline, chloroprocaine, diethanolamine, N-methylglucamine, N,N'-dibenzylethylenediamine, diethylamine, 2-diethylaminoethanol, 2-dimethylaminoethanol, ethanolamine, ethylenediamine, N-ethylmorpholine, N-ethylpiperidine, glucamine, glucosamine, histidine, hydrabamine, isopropylamine, lysine, methylglucamine, morpholine, piperazine, piperidine, polyamine resins, procaine, purines, theobromine, triethylamine, trimethylamine, tripropylamine, tromethamine and the like.

Other preferred salts according to embodiments herein are quaternary ammonium compounds wherein an equivalent of an anion (X—) is associated with the positive charge of the N atom. X— may be an anion of various mineral acids such as, for example, chloride, bromide, iodide, sulphate, nitrate, phosphate, or an anion of an organic acid such as, for example, acetate, maleate, fumarate, citrate, oxalate, succinate, tartrate, malate, mandelate, trifluoroacetate, methanesulphonate and p-toluenesulphonate. X— is preferably an anion selected from chloride, bromide, iodide, sulphate, nitrate, acetate, maleate, oxalate, succinate or trifluoroacetate. More preferably X— is chloride, bromide, trifluoroacetate or methanesulphonate.

As used herein, an N-oxide is formed from the tertiary basic amines or imines present in the molecule, using a convenient oxidizing agent.

The compounds of embodiments herein may exist in both unsolvated and solvated forms. The term solvate is used herein to describe a molecular complex comprising a compound of embodiments herein and an amount of one or more pharmaceutically acceptable solvent molecules. The term hydrate is employed when said solvent is water. Examples of solvate forms include, but are not limited to, compounds of embodiments herein in association with water, acetone, dichloromethane, 2-propanol, ethanol, methanol, dimethylsulfoxide (DMSO), ethyl acetate, acetic acid, ethanolamine, or mixtures thereof. It is specifically contemplated that in embodiments herein one solvent molecule can be associated with one molecule of the compounds of embodiments herein, such as a hydrate.

Furthermore, it is specifically contemplated that in embodiments herein, more than one solvent molecule may be associated with one molecule of the compounds of embodiments herein, such as a dihydrate. Additionally, it is specifically contemplated that in embodiments herein less than one solvent molecule may be associated with one molecule of the compounds of embodiments herein, such as a hemihydrate. Furthermore, solvates of embodiments herein are contemplated as solvates of compounds of embodiments herein that retain the biological effectiveness of the non-solvate form of the compounds.

Embodiments herein also include isotopically-labeled compounds of embodiments herein, wherein one or more atoms is replaced by an atom having the same atomic number, but an atomic mass or mass number different from the atomic mass or mass number usually found in nature. Examples of isotopes suitable for inclusion in the compounds of embodiments herein include isotopes of hydrogen, such as $^2H$ and $^3H$, carbon, such as $^{11}C$, $^{13}C$ and $^{14}C$, chlorine, such as $^{31}Cl$, fluorine, such as $^{18}F$, iodine, such as $^{123}I$ and $^{125}I$, nitrogen, such as $^{13}N$ and $^{15}N$, oxygen, such as $^{15}O$, $^{17}O$ and $^{18}O$, phosphorus, such as $^{32}P$, and sulfur, such as $^{35}S$. Certain isotopically-labeled compounds of embodiments herein, for example, those incorporating a radioactive isotope, are useful in drug and/or substrate tissue distribution studies. The radioactive isotopes tritium, $^3H$, and carbon-14, $^{14}C$, are particularly useful for this purpose in view of their ease of incorporation and ready means of detection. Substitution with heavier isotopes such as deuterium, 2H, may afford certain therapeutic advantages resulting from greater metabolic stability, for example, increased in vivo half-life or reduced dosage requirements, and hence may be preferred in some circumstances. Substitution with positron emitting isotopes, such as $^{11}C$, $^{18}F$, $^{15}O$ and $^{13}N$, can be useful in Positron Emission Topography (PET) studies for examining substrate receptor occupancy.

Isotopically-labeled compounds of embodiments herein can generally be prepared by conventional techniques known to those skilled in the art or by processes analogous to those described herein, using an appropriate isotopically-labeled reagent in place of the non-labeled reagent otherwise employed.

Preferred isotopically-labeled compounds include deuterated derivatives of the compounds of embodiments herein. As used herein, the term deuterated derivative embraces compounds of embodiments herein where in a particular position at least one hydrogen atom is replaced by deuterium. Deuterium (D or $^2H$) is a stable isotope of hydrogen which is present at a natural abundance of 0.015 molar %.

Hydrogen deuterium exchange (deuterium incorporation) is a chemical reaction in which a covalently bonded hydrogen atom is replaced by a deuterium atom. Said exchange (incorporation) reaction can be total or partial.

Typically, a deuterated derivative of a compound of embodiments herein has an isotopic enrichment factor (ratio between the isotopic abundance and the natural abundance of that isotope, i.e. the percentage of incorporation of deuterium at a given position in a molecule in the place of hydrogen) for each deuterium present at a site designated as a potential site of deuteration on the compound of at least 3500 (52.5% deuterium incorporation).

In some embodiments, the isotopic enrichment factor is at least 5000 (75% deuterium). In some embodiments, the isotopic enrichment factor is at least 6333.3 (95% deuterium incorporation). In some embodiments, the isotopic enrichment factor is at least 6633.3 (99.5% deuterium incorporation). It is understood that the isotopic enrichment factor of each deuterium present at a site designated as a site of deuteration is independent from the other deuteration sites.

The isotopic enrichment factor can be determined using conventional analytical methods known to one of ordinary skilled in the art, including mass spectrometry (MS) and nuclear magnetic resonance (NMR).

Prodrugs of the compounds described herein are also within the scope of embodiments herein. Thus, certain derivatives of the compounds of embodiments herein, which derivatives may have little or no pharmacological activity themselves, when administered into or onto the body may be converted into compounds of embodiments herein having the desired activity, for example, by hydrolytic cleavage. Such derivatives are referred to as 'prodrugs'. Further information on the use of prodrugs may be found in Pro-drugs as Novel Delivery Systems, Vol. 14, ACS Symposium Series (T. Higuchi and W. Stella) and Bioreversible Carriers in Drug Design, Pergamon Press, 1987 (ed. E. B. Roche, American Pharmaceutical Association).

Prodrugs in accordance with embodiments herein can, for example, be produced by replacing appropriate functionalities present in the compounds of embodiments herein with certain moieties known to those skilled in the art as 'promoieties' as described, for example, in Design of Prodrugs by H. Bundgaard (Elsevier, 1985).

In the case of compounds of embodiments herein that are solids, it is understood by those skilled in the art that the inventive compounds and salts may exist in different crystalline or polymorphic forms, or in an amorphous form, all of which are intended to be within the scope of embodiments herein.

The compounds disclosed herein can exist as and therefore include all stereoisomers, conformational isomers and mixtures thereof in all proportions as well as isotopic forms such as deuterated compounds.

The compounds disclosed herein can exist as therapeutically acceptable salts. The present invention includes compounds listed above in the form of salts, including acid addition salts. Suitable salts include those formed with both organic and inorganic acids. Such acid addition salts will normally be pharmaceutically acceptable. However, salts of non-pharmaceutically acceptable salts may be of utility in the preparation and purification of the compound in question. Basic addition salts may also be formed and be pharmaceutically acceptable. For a more complete discussion of the preparation and selection of salts, refer to Pharmaceutical Salts: Properties, Selection, and Use (Stahl, P. Heinrich. Wiley-VCHA, Zurich, Switzerland, 2002).

Basic addition salts can be prepared during the final isolation and purification of the compounds by reacting a carboxy group with a suitable base such as the hydroxide, carbonate, or bicarbonate of a metal cation or with ammonia or an organic primary, secondary, or tertiary amine. The cations of therapeutically acceptable salts include lithium, sodium, potassium, calcium, magnesium, and aluminum, as well as nontoxic quaternary amine cations such as ammonium, tetramethylammonium, tetraethylammonium, methylamine, dimethylamine, trimethylamine, triethylamine, diethylamine, ethylamine, tributylamine, pyridine, N,N-dimethylaniline, N-methylpiperidine, N-methylmorpholine, dicyclohexylamine, procaine, dibenzylamine, N,N-dibenzylphenethylamine, 1-ephenamine, and N,N'-dibenzylethylenediamine. Other representative organic amines useful for the formation of base addition salts include ethylenediamine, ethanolamine, diethanolamine, piperidine, and piperazine.

In certain embodiments, compounds have structural Formula (I):

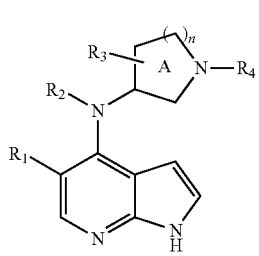

(I)

wherein:
  $R_1$ is selected from $-CO_2R_5$, $-C_1-C_5$alkyl-$CO_2R_5$, $-C_3-C_6$-cycloalkyl-$CO_2R_5$, $-NHCO_2R_5$, $-N(C_1-C_5$ alkyl)-$CO_2R_5$, $-O-CO_2R_5$, or $-C_1-C_5$alkyl-$O-CO_2R_5$;
  $R_2$ is selected from H, $-C_1-C_4$alkyl, $-C_3-C_6$cycloalkyl, or $-C_1-C_2$alkyl-$C_3-C_6$cycloalkyl, wherein the alkyl or cycloalkyl groups are optionally substituted with one or more groups selected from halogen, $-OH$, or $-O-C_1-C_5$alkyl;
  n is 0, 1 or 2;
  Ring A is substituted at one or more carbons with one, two, or three $R_3$ substituents wherein each $R_3$ group is independently selected from H, halogen, $-C_1-C_4$alkyl, $-C_3-C_6$cycloalkyl, $-OH$, or $-O-C_1-C_5$alkyl wherein each alkyl or cycloalkyl group is optionally substituted with one or more groups selected from: halogen, $-OH$, $-C_1-C_5$alkylalkoxy, or $-O-C_1-C_5$alkyl;
  Two $R_3$ groups on the same or different carbon atoms of the ring A may be optionally joined to form a spirocyclic or bicyclic ring system with ring A;
  $R_4$ is selected from $-C(O)-R_6$, $-CH_2R_6$, $-C(O)-CH=CH_2$, $-C(O)-C(CH_2OCH_3)=CH_2$, $-C(O)-CH=CHCH_3$, $-C(O)-CH=CHCH_2NR_7R_8$, $-C(O)-C_1-C_5$alkyl, or $-C(O)-C_3-C_6$cycloalkyl, wherein the alkyl or cycloalkyl groups may be optionally substituted with one or more groups selected from $-OH$, halogen, alkyne, or $-CN$;
  $R_5$ is selected from $-C_1-C_5$alkyl, or $-C_3-C_5$cycloalkyl wherein the alkyl or cycloalkyl groups may be optionally substituted by one or more groups selected from halogen, $-OH$, or $-O-C_1-C_5$alkyl;
  $R_6$ is selected from $-C_1-C_5$alkyl, $-C_3-C_6$cycloalkyl, $-C_1-C_5$alkyl-$C_3-C_6$cycloalkyl, $-NR_7R_8$, $-O$-aryl, $-O$-heteroaryl, aryl, or heteroaryl wherein the alkyl, cycloalkyl, aryl or heteroaryl groups can be optionally substituted by one or more groups selected from halogen, $-CN$, alkyne, $-OH$, trifluoromethyl, $-O-C_1-C_5$alkyl, or $-O-C_3-C_6$cycloalkyl;
  $R_7$ and $R_8$ are independently selected from H, $-C_1-C_5$ alkyl, $-C_1-C_5$ alkoxy, or $-C_3-C_5$ cycloalkyl wherein the alkyl groups may be optionally substituted by one or more groups selected from halogen, $-OH$, or $-CN$;
  $R_7$ and $R_8$ may be optionally joined to form a ring to form a heterocycle such as piperidine, pyrrolidine, or with another heteroatom to form a ring such as morpholine.

In certain embodiments, compounds have structural Formula (Ia):

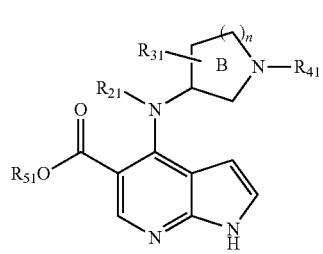

(Ia)

wherein:
  $R_{21}$ is selected from H, $-C_1-C_4$alkyl, $-C_3-C_6$cycloalkyl, or $-C_1-C_2$alkyl-$C_3-C_6$cycloalkyl, wherein the alkyl or cycloalkyl groups are optionally substituted with one or more groups selected from halogen, $-OH$, or $-O-C_1-C_5$alkyl;
  n is 0, 1 or 2;
  Ring B is substituted at one or more carbons with one, two, or three $R_{31}$ substituents wherein each $R_{31}$ group is independently selected from H, halogen, $-C_1-C_4$alkyl, $-C_3-C_6$cycloalkyl, $-OH$, or $-O-C_1-C_5$alkyl wherein each alkyl or cycloalkyl group is optionally substituted with one or more groups selected from: halogen, $-OH$, $-C_1-C_5$alkylalkoxy, or $-O-C_1-C_5$alkyl;
  Two $R_{31}$ groups on the same or different carbon atoms of the ring B may be optionally joined to form a spirocyclic or bicyclic ring system with ring B;
  $R_{41}$ is selected from $-C(O)-R_{61}$, $-CH_2R_{61}$, $-C(O)-CH=CH_2$, $-C(O)-C(CH_2OCH_3)=CH_2$, $-C(O)-CH=CHCH_3$, $-C(O)-CH=CHCH_2NR_{71}R_{81}$, $-C(O)-C_1-C_5$alkyl, or $-C(O)-C_3-C_6$cycloalkyl, wherein the alkyl or cycloalkyl groups may be optionally substituted with one or more groups selected from $-OH$, halogen, alkyne, or $-CN$;
  $R_{51}$ is selected from $-C_1-C_5$alkyl, or $-C_3-C_5$cycloalkyl wherein the alkyl or cycloalkyl groups may be optionally substituted by one or more groups selected from halogen, $-OH$, or $-O-C_1-C_5$alkyl;
  $R_{61}$ is selected from $-C_1-C_5$alkyl, $-C_3-C_6$cycloalkyl, $-C_1-C_5$alkyl-$C_3-C_6$cycloalkyl, $-NR_{71}R_{81}$, $-O$-aryl, $-O$-heteroaryl, aryl, or heteroaryl wherein the alkyl, cycloalkyl, aryl or heteroaryl groups can be optionally substituted by one or more groups selected from halogen, —CN, alkyne, —OH, trifluoromethyl, —O—$C_1$-$C_5$alkyl, or —O—$C_3$-$C_6$cycloalkyl;

$R_{71}$ and $R_{81}$ are independently selected from H, —$C_1$-$C_5$ alkyl, —$C_1$-$C_5$ alkoxy, or —$C_3$-$C_5$ cycloalkyl wherein the alkyl groups may be optionally substituted by one or more groups selected from halogen, —OH, or —CN;

$R_{71}$ and $R_{18}$ may be optionally joined to form a ring to form a heterocycle such as piperidine, pyrrolidine, or with another heteroatom to form a ring such as morpholine.

In certain embodiments, compounds have structural Formula (Ib):

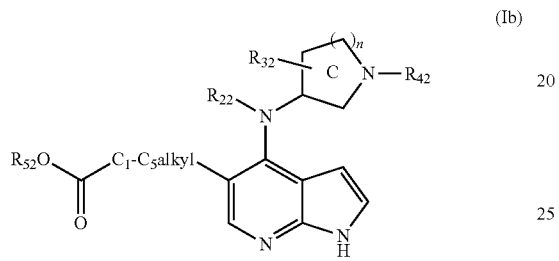

(Ib)

wherein:

$R_{22}$ is selected from H, —$C_1$-$C_4$alkyl, —$C_3$-$C_6$cycloalkyl, or —$C_1$-$C_2$alkyl-$C_3$-$C_6$cycloalkyl, wherein the alkyl or cycloalkyl groups are optionally substituted with one or more groups selected from halogen, —OH, or —O—$C_1$-$C_5$alkyl;

n is 0, 1 or 2;

Ring C is substituted at one or more carbons with one, two, or three $R_{32}$ substituents wherein each $R_{32}$ group is independently selected from H, halogen, —$C_1$-$C_4$alkyl, —$C_3$-$C_6$cycloalkyl, —OH, or —O—$C_1$-$C_5$alkyl wherein each alkyl or cycloalkyl group is optionally substituted with one or more groups selected from: halogen, —OH, —$C_1$-$C_5$alkylalkoxy, or —O—$C_1$-$C_5$alkyl;

Two $R_{32}$ groups on the same or different carbon atoms of the ring C may be optionally joined to form a spirocyclic or bicyclic ring system with ring C;

$R_{42}$ is selected from —C(O)—$R_{62}$, —$CH_2R_{62}$, —C(O)—CH=$CH_2$, —C(O)—C($CH_2OCH_3$)=$CH_2$, —C(O)—CH=$CHCH_3$, —C(O)—CH=$CHCH_2NR_{72}R_{82}$, —C(O)—$C_1$-$C_5$alkyl, or —C(O)—$C_3$-$C_6$cycloalkyl, wherein the alkyl or cycloalkyl groups may be optionally substituted with one or more groups selected from —OH, halogen, alkyne, or —CN;

$R_{52}$ is selected from —$C_1$-$C_5$alkyl, or —$C_3$-$C_5$cycloalkyl wherein the alkyl or cycloalkyl groups may be optionally substituted by one or more groups selected from halogen, —OH, or —O—$C_1$-$C_5$alkyl;

$R_{62}$ is selected from —$C_1$-$C_5$alkyl, —$C_3$-$C_6$cycloalkyl, —$C_1$-$C_5$alkyl-$C_3$-$C_6$cycloalkyl, —$NR_{73}R_{83}$, —O-aryl, —O-heteroaryl, aryl, or heteroaryl wherein the alkyl, cycloalkyl, aryl or heteroaryl groups can be optionally substituted by one or more groups selected from halogen, —CN, alkyne, —OH, trifluoromethyl, —O—$C_1$-$C_5$alkyl, or —O—$C_3$-$C_6$cycloalkyl;

$R_{72}$ and $R_{82}$ are independently selected from H, —$C_1$-$C_5$ alkyl, —$C_1$-$C_5$ alkoxy, or —$C_3$-$C_5$ cycloalkyl wherein the alkyl groups may be optionally substituted by one or more groups selected from halogen, —OH, or —CN;

$R_{72}$ and $R_{82}$ may be optionally joined to form a ring to form a heterocycle such as piperidine, pyrrolidine, or with another heteroatom to form a ring such as morpholine.

In certain embodiments, compounds have structural Formula (Ic):

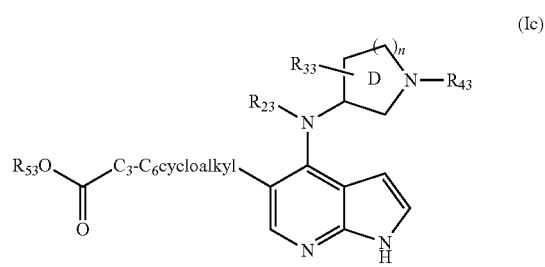

(Ic)

wherein:

$R_{23}$ is selected from H, —$C_1$-$C_4$alkyl, —$C_3$-$C_6$cycloalkyl, or —$C_1$-$C_2$alkyl-$C_3$-$C_6$cycloalkyl, wherein the alkyl or cycloalkyl groups are optionally substituted with one or more groups selected from halogen, —OH, or —O—$C_1$-$C_5$alkyl;

n is 0, 1 or 2;

Ring D is substituted at one or more carbons with one, two, or three $R_{33}$ substituents wherein each $R_{33}$ group is independently selected from H, halogen, —$C_1$-$C_4$alkyl, —$C_3$-$C_6$cycloalkyl, —OH, or —O—$C_1$-$C_5$alkyl wherein each alkyl or cycloalkyl group is optionally substituted with one or more groups selected from: halogen, —OH, —$C_1$-$C_5$alkylalkoxy, or —O—$C_1$-$C_5$ alkyl;

Two $R_{33}$ groups on the same or different carbon atoms of the ring D may be optionally joined to form a spirocyclic or bicyclic ring system with ring D;

$R_{43}$ is selected from —C(O)—$R_{63}$, —$CH_2R_{63}$, —C(O)—CH=$CH_2$, —C(O)—C($CH_2OCH_3$)=$CH_2$, —C(O)—CH=$CHCH_3$, —C(O)—CH=$CHCH_2NR_{73}R_{83}$, —C(O)—$C_1$-$C_5$alkyl, or —C(O)—$C_3$-$C_6$cycloalkyl, wherein the alkyl or cycloalkyl groups may be optionally substituted with one or more groups selected from —OH, halogen, alkyne, or —CN;

$R_{53}$ is selected from —$C_1$-$C_5$alkyl, or —$C_3$-$C_5$cycloalkyl wherein the alkyl or cycloalkyl groups may be optionally substituted by one or more groups selected from halogen, —OH, or —O—$C_1$-$C_5$alkyl;

$R_{63}$ is selected from —$C_1$-$C_5$alkyl, —$C_3$-$C_6$cycloalkyl, —$C_1$-$C_5$alkyl-$C_3$-$C_6$cycloalkyl, —$NR_{73}R_{83}$, —O-aryl, —O-heteroaryl, aryl, or heteroaryl wherein the alkyl, cycloalkyl, aryl or heteroaryl groups can be optionally substituted by one or more groups selected from halogen, —CN, alkyne, —OH, trifluoromethyl, —O—$C_1$-$C_5$alkyl, or —O—$C_3$-$C_6$cycloalkyl;

$R_{73}$ and $R_{83}$ are independently selected from H, —$C_1$-$C_5$ alkyl, —$C_1$-$C_5$ alkoxy, or —$C_3$-$C_5$ cycloalkyl wherein the alkyl groups may be optionally substituted by one or more groups selected from halogen, —OH, or —CN;

$R_{73}$ and $R_{83}$ may be optionally joined to form a ring to form a heterocycle such as piperidine, pyrrolidine, or with another heteroatom to form a ring such as morpholine.

In certain embodiments, compounds have structural Formula (Id):

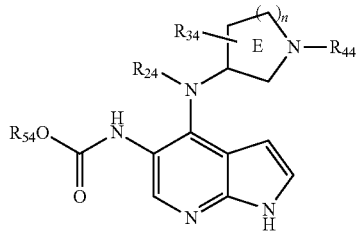

(Id)

wherein:

R$_{24}$ is selected from H, —C$_1$-C$_4$alkyl, —C$_3$-C$_6$cycloalkyl, or —C$_1$-C$_2$alkyl-C$_3$-C$_6$cycloalkyl, wherein the alkyl or cycloalkyl groups are optionally substituted with one or more groups selected from halogen, —OH, or —O—C$_1$-C$_5$alkyl;

n is 0, 1 or 2;

Ring E is substituted at one or more carbons with one, two, or three R$_{34}$ substituents wherein each R$_{34}$ group is independently selected from H, halogen, —C$_1$-C$_4$alkyl, —C$_3$-C$_6$cycloalkyl, —OH, or —O—C$_1$-C$_5$alkyl wherein each alkyl or cycloalkyl group is optionally substituted with one or more groups selected from: halogen, —OH, —C$_1$-C$_5$alkylalkoxy, or —O—C$_1$-C$_5$alkyl;

Two R$_{34}$ groups on the same or different carbon atoms of the ring E may be optionally joined to form a spirocyclic or bicyclic ring system with ring E;

R$_{44}$ is selected from —C(O)—R$_{64}$, —CH$_2$R$_{64}$, —C(O)—CH=CH$_2$, —C(O)—C(CH$_2$OCH$_3$)=CH$_2$, —C(O)—CH=CHCH$_3$, —C(O)—CH=CHCH$_2$NR$_{74}$R$_{84}$, —C(O)—C$_1$-C$_5$alkyl, or —C(O)—C$_3$-C$_6$cycloalkyl, wherein the alkyl or cycloalkyl groups may be optionally substituted with one or more groups selected from —OH, halogen, alkyne, or —CN;

R$_{54}$ is selected from —C$_1$-C$_5$alkyl, or —C$_3$-C$_5$cycloalkyl wherein the alkyl or cycloalkyl groups may be optionally substituted by one or more groups selected from halogen, —OH, or —O—C$_1$-C$_5$alkyl;

R$_{64}$ is selected from —C$_1$-C$_5$alkyl, —C$_3$-C$_6$cycloalkyl, —C$_1$-C$_5$alkyl-C$_3$-C$_6$cycloalkyl, —NR$_{74}$R$_{84}$, —O-aryl, —O-heteroaryl, aryl, or heteroaryl wherein the alkyl, cycloalkyl, aryl or heteroaryl groups can be optionally substituted by one or more groups selected from halogen, —CN, alkyne, —OH, trifluoromethyl, —O—C$_1$-C$_5$alkyl, or —O—C$_3$-C$_6$cycloalkyl;

R$_{74}$ and R$_{84}$ are independently selected from H, —C$_1$-C$_5$ alkyl, —C$_1$-C$_5$ alkoxy, or —C$_3$-C$_5$ cycloalkyl wherein the alkyl groups may be optionally substituted by one or more groups selected from halogen, —OH, or —CN;

R$_{74}$ and R$_{84}$ may be optionally joined to form a ring to form a heterocycle such as piperidine, pyrrolidine, or with another heteroatom to form a ring such as morpholine.

In certain embodiments, compounds have structural Formula (Ie):

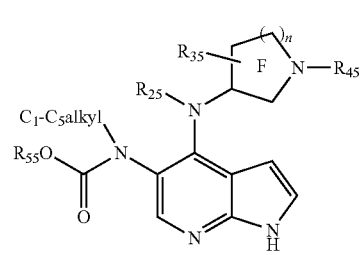

(Ie)

wherein:

R$_{25}$ is selected from H, —C$_1$-C$_4$alkyl, —C$_3$-C$_6$cycloalkyl, or —C$_1$-C$_2$alkyl-C$_3$-C$_6$cycloalkyl, wherein the alkyl or cycloalkyl groups are optionally substituted with one or more groups selected from halogen, —OH, or —O—C$_1$-C$_5$alkyl;

n is 0, 1 or 2;

Ring F is substituted at one or more carbons with one, two, or three R$_{35}$ substituents wherein each R$_{35}$ group is independently selected from H, halogen, —C$_1$-C$_4$alkyl, —C$_3$-C$_6$cycloalkyl, —OH, or —O—C$_1$-C$_5$alkyl wherein each alkyl or cycloalkyl group is optionally substituted with one or more groups selected from: halogen, —OH, —C$_1$-C$_5$alkylalkoxy, or —O—C$_1$-C$_5$alkyl;

Two R$_{35}$ groups on the same or different carbon atoms of the ring F may be optionally joined to form a spirocyclic or bicyclic ring system with ring F;

R$_{45}$ is selected from —C(O)—R$_{65}$, —CH$_2$R$_{65}$, —C(O)—CH=CH$_2$, —C(O)—C(CH$_2$OCH$_3$)=CH$_2$, —C(O)—CH=CHCH$_3$, —C(O)—CH=CHCH$_2$NR$_{75}$R$_{85}$, —C(O)—C$_1$-C$_5$alkyl, or —C(O)—C$_3$-C$_6$cycloalkyl, wherein the alkyl or cycloalkyl groups may be optionally substituted with one or more groups selected from —OH, halogen, alkyne, or —CN;

R$_{55}$ is selected from —C$_1$-C$_5$alkyl, or —C$_3$-C$_5$cycloalkyl wherein the alkyl or cycloalkyl groups may be optionally substituted by one or more groups selected from halogen, —OH, or —O—C$_1$-C$_5$alkyl;

R$_{65}$ is selected from —C$_1$-C$_5$alkyl, —C$_3$-C$_6$cycloalkyl, —C$_1$-C$_5$alkyl-C$_3$-C$_6$cycloalkyl, —NR$_{75}$R$_{85}$, —O-aryl, —O-heteroaryl, aryl, or heteroaryl wherein the alkyl, cycloalkyl, aryl or heteroaryl groups can be optionally substituted by one or more groups selected from halogen, —CN, alkyne, —OH, trifluoromethyl, —O—C$_1$-C$_5$alkyl, or —O—C$_3$-C$_6$cycloalkyl;

R$_{75}$ and R$_{85}$ are independently selected from H, —C$_1$-C$_5$ alkyl, —C$_1$-C$_5$ alkoxy, or —C$_3$-C$_5$ cycloalkyl wherein the alkyl groups may be optionally substituted by one or more groups selected from halogen, —OH, or —CN;

R$_{75}$ and R$_{85}$ may be optionally joined to form a ring to form a heterocycle such as piperidine, pyrrolidine, or with another heteroatom to form a ring such as morpholine.

In certain embodiments, compounds have structural Formula (If):

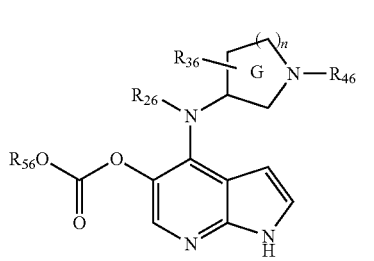 (If)

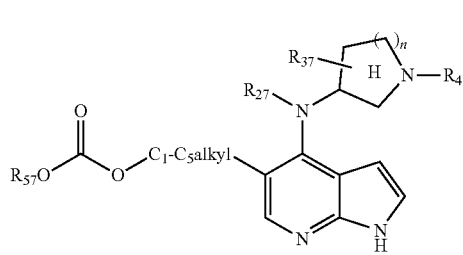 (Ig)

wherein:

R$_{26}$ is selected from H, —C$_1$-C$_4$alkyl, —C$_3$-C$_6$cycloalkyl, or —C$_1$-C$_2$alkyl-C$_3$-C$_6$cycloalkyl, wherein the alkyl or cycloalkyl groups are optionally substituted with one or more groups selected from halogen, —OH, or —O—C$_1$-C$_5$alkyl;

n is 0, 1 or 2;

Ring G is substituted at one or more carbons with one, two, or three R$_{36}$ substituents wherein each R$_{36}$ group is independently selected from H, halogen, —C$_1$-C$_4$alkyl, —C$_3$-C$_6$cycloalkyl, —OH, or —O—C$_1$-C$_5$alkyl wherein each alkyl or cycloalkyl group is optionally substituted with one or more groups selected from: halogen, —OH, —C$_1$-C$_5$alkylalkoxy, or —O—C$_1$-C$_5$alkyl;

Two R$_{36}$ groups on the same or different carbon atoms of the ring G may be optionally joined to form a spirocyclic or bicyclic ring system with ring G;

R$_{46}$ is selected from —C(O)—R$_{66}$, —CH$_2$R$_{66}$, —C(O)—CH=CH$_2$, —C(O)—C(CH$_2$OCH$_3$)=CH$_2$, —C(O)—CH=CHCH$_3$, —C(O)—CH=CHCH$_2$NR$_{76}$R$_{86}$, —C(O)—C$_1$-C$_5$alkyl, or —C(O)—C$_3$-C$_6$cycloalkyl, wherein the alkyl or cycloalkyl groups may be optionally substituted with one or more groups selected from —OH, halogen, alkyne, or —CN;

R$_{56}$ is selected from —C$_1$-C$_5$alkyl, or —C$_3$-C$_5$cycloalkyl wherein the alkyl or cycloalkyl groups may be optionally substituted by one or more groups selected from halogen, —OH, or —O—C$_1$-C$_5$alkyl;

R$_{66}$ is selected from —C$_1$-C$_5$alkyl, —C$_3$-C$_6$cycloalkyl, —C$_1$-C$_5$alkyl-C$_3$-C$_6$cycloalkyl, —NR$_{76}$R$_{86}$, —O-aryl, —O-heteroaryl, aryl, or heteroaryl wherein the alkyl, cycloalkyl, aryl or heteroaryl groups can be optionally substituted by one or more groups selected from halogen, —CN, alkyne, —OH, trifluoromethyl, —O—C$_1$-C$_5$alkyl, or —O—C$_3$-C$_6$cycloalkyl;

R$_{76}$ and R$_{86}$ are independently selected from H, —C$_1$-C$_5$ alkyl, —C$_1$-C$_5$ alkoxy, or —C$_3$-C$_5$ cycloalkyl wherein the alkyl groups may be optionally substituted by one or more groups selected from halogen, —OH, or —CN;

R$_{76}$ and R$_{86}$ may be optionally joined to form a ring to form a heterocycle such as piperidine, pyrrolidine, or with another heteroatom to form a ring such as morpholine.

In certain embodiments, compounds have structural Formula (Ig):

wherein:

R$_{27}$ is selected from H, —C$_1$-C$_4$alkyl, —C$_3$-C$_6$cycloalkyl, or —C$_1$-C$_2$alkyl-C$_3$-C$_6$cycloalkyl, wherein the alkyl or cycloalkyl groups are optionally substituted with one or more groups selected from halogen, —OH, or —O—C$_1$-C$_5$alkyl;

n is 0, 1 or 2;

Ring H is substituted at one or more carbons with one, two, or three R$_{37}$ substituents wherein each R$_{37}$ group is independently selected from H, halogen, —C$_1$-C$_4$alkyl, —C$_3$-C$_6$cycloalkyl, —OH, or —O—C$_1$-C$_5$alkyl wherein each alkyl or cycloalkyl group is optionally substituted with one or more groups selected from: halogen, —OH, —C$_1$-C$_5$alkylalkoxy, or —O—C$_1$-C$_5$alkyl;

Two R$_{37}$ groups on the same or different carbon atoms of the ring H may be optionally joined to form a spirocyclic or bicyclic ring system with ring H;

R$_{47}$ is selected from —C(O)—R$_{67}$, —CH$_2$R$_{67}$, —C(O)—CH=CH$_2$, —C(O)—C(CH$_2$OCH$_3$)=CH$_2$, —C(O)—CH=CHCH$_3$, —C(O)—CH=CHCH$_2$NR$_{77}$R$_{87}$, —C(O)—C$_1$-C$_5$alkyl, or —C(O)—C$_3$-C$_6$cycloalkyl, wherein the alkyl or cycloalkyl groups may be optionally substituted with one or more groups selected from —OH, halogen, alkyne, or —CN;

R$_{57}$ is selected from —C$_1$-C$_5$alkyl, or —C$_3$-C$_5$cycloalkyl wherein the alkyl or cycloalkyl groups may be optionally substituted by one or more groups selected from halogen, —OH, or —O—C$_1$-C$_5$alkyl;

R$_{67}$ is selected from —C$_1$-C$_5$alkyl, —C$_3$-C$_6$cycloalkyl, —C$_1$-C$_5$alkyl-C$_3$-C$_6$cycloalkyl, —NR$_{77}$R$_{87}$, —O-aryl, —O-heteroaryl, aryl, or heteroaryl wherein the alkyl, cycloalkyl, aryl or heteroaryl groups can be optionally substituted by one or more groups selected from halogen, —CN, alkyne, —OH, trifluoromethyl, —O—C$_1$-C$_5$alkyl, or —O—C$_3$-C$_6$cycloalkyl;

R$_{77}$ and R$_{87}$ are independently selected from H, —C$_1$-C$_5$ alkyl, —C$_1$-C$_5$ alkoxy, or —C$_3$-C$_5$ cycloalkyl wherein the alkyl groups may be optionally substituted by one or more groups selected from halogen, —OH, or —CN;

R$_{77}$ and R$_{87}$ may be optionally joined to form a ring to form a heterocycle such as piperidine, pyrrolidine, or with another heteroatom to form a ring such as morpholine.

In certain embodiments, compounds have structural Formula (II):

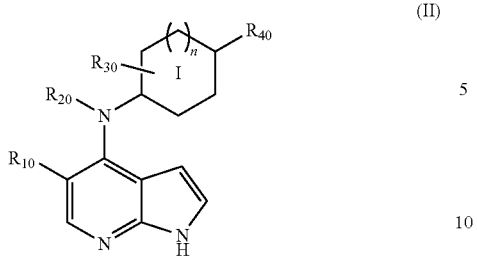
(II)

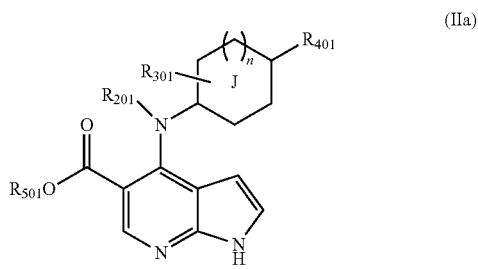
(IIa)

wherein:

$R_{10}$ is selected from $-CO_2R_{50}$, $-C_1-C_5$-alkyl-$CO_2R_{50}$, $-C_3-C_6$-cycloalkyl-$CO_2R_{50}$, $-NHCO_2R_{50}$, $-N(C_1-C_5$ alkyl)-$CO_2R_{50}$, $-O-CO_2R_{50}$, or $-C_1-C_5$alkyl-$O-CO_2R_{50}$;

$R_{20}$ is selected from H, $-C_1-C_4$alkyl, $-C_3-C_6$cycloalkyl, or $-C_1-C_2$alkyl-$C_3-C_6$cycloalkyl wherein the alkyl or cycloalkyl groups are optionally substituted with one or more groups selected from halogen, $-OH$, or $-O-C_1-C_5$alkyl;

n is 0 or 1;

Ring I is substituted at one or more carbons with one, two, or three $R_{30}$ substituents wherein each $R_{30}$ group is independently selected from H, halogen, $-C_1-C_4$alkyl, $-C_3-C_6$cycloalkyl, $-OH$, $-O-C_1-C_5$alkyl, $-NR_{70}C(O)-CH=CH_2$, $-NR_{70}C(O)-C(CH_2OCH_3)=CH_2$, $-NR_{70}C(O)-CH=CHCH_3$, or $-NR_{70}C(O)-CH=CHCH_2NR_{80}R_{90}$ wherein each alkyl or cycloalkyl group is optionally substituted with one or more groups selected from: halogen, $-OH$, $-C_1-C_5$alkylalkoxy, or $-O-C_1-C_5$alkyl;

Two $R_{30}$ groups on the same carbon atom or two or three $R_{30}$ groups on different carbon atoms of ring I may be optionally joined to form a spirocyclic, bicyclic, or tricyclic ring system with ring I such as adamantyl;

$R_{40}$ is selected from H, $-OH$, $-C(O)-R_{60}$, $-OR_{60}$, $-O-C(O)-R_{60}$, $-NR_{70}-C(O)-R_{60}$, $-C_1-C_4$alkyl-$C(O)-R_{60}$, $-SO_2-R_{601}$, $-SO_2-NR_{80}R_{90}$, $-C_1-C_4$alkyl-$SO_2-R_{60}$, or $-C_1-C_4$alkyl-$SO_2NR_{80}R_{90}$;

$R_{50}$ is selected from $-C_1-C_5$alkyl, or $-C_3-C_5$cycloalkyl wherein the alkyl or cycloalkyl groups may be optionally substituted by one or more groups selected from halogen, $-OH$, or $-O-C_1-C_5$alkyl;

$R_{60}$ is selected from $-C_1-C_5$alkyl, $-C_3-C_6$cycloalkyl or $-C_1-C_5$alkyl-$C_3-C_5$cycloalkyl wherein the alkyl or cycloalkyl groups can be optionally substituted by one or more groups selected from halogen, $-CN$, alkyne, $-OH$, or $-O-C_1-C_5$alkyl;

$R_{70}$ is selected from H, $-C_1-C_5$alkyl or $-C_3-C_5$cycloalkyl;

$R_{80}$ and $R_{90}$ are independently selected from H, $-C_1-C_5$alkyl, $-C_1-C_5$alkoxy, or $-C_3-C_6$cycloalkyl wherein the alkyl groups may be optionally substituted by one or more groups selected from halogen, $-OH$, or $-CN$; and $R_{80}$ and $R_{90}$ may be optionally joined to form a ring to form a heterocycle such as piperidine, pyrrolidine, or with another heteroatom to form a ring such as morpholine.

In certain embodiments, compounds have structural Formula (IIa):

wherein:

$R_{201}$ is selected from H, $-C_1-C_4$alkyl, $-C_3-C_6$cycloalkyl, or $-C_1-C_2$alkyl-$C_3-C_6$cycloalkyl wherein the alkyl or cycloalkyl groups are optionally substituted with one or more groups selected from halogen, $-OH$, or $-O-C_1-C_5$alkyl;

n is 0 or 1;

Ring J is substituted at one or more carbons with one, two, or three $R_{301}$ substituents wherein each $R_{301}$ group is independently selected from H, halogen, $-C_1-C_4$alkyl, $-C_3-C_6$cycloalkyl, $-OH$, $-O-C_1-C_5$alkyl, $-NR_{701}C(O)-CH=CH_2$, $-NR_{701}C(O)-C(CH_2OCH_3)=CH_2$, $-NR_{701}C(O)-CH=CHCH_3$, or $-NR_{701}C(O)-CH=CHCH_2NR_{801}R_{901}$ wherein each alkyl or cycloalkyl group is optionally substituted with one or more groups selected from: halogen, $-OH$, $-C_1-C_5$alkylalkoxy, or $-O-C_1-C_5$alkyl;

Two $R_{301}$ groups on the same carbon atom or two or three $R_{301}$ groups on different carbon atoms of ring J may be optionally joined to form a spirocyclic, bicyclic, or tricyclic ring system with ring J such as adamantyl;

$R_{401}$ is selected from H, $-OH$, $-C(O)-R_{601}$, $-OR_{601}$, $-O-C(O)-R_{601}$, $-NR_{701}-C(O)-R_{601}$, $-C_1-C_4$alkyl-$C(O)-R_{601}$, $-SO_2-R_{601}$, $-SO_2-NR_{801}R_{901}$, $-C_1-C_4$alkyl-$SO_2-R_{601}$, or $-C_1-C_4$alkyl-$SO_2NR_{801}R_{901}$;

$R_{501}$ is selected from $-C_1-C_5$alkyl, or $-C_3-C_5$cycloalkyl wherein the alkyl or cycloalkyl groups may be optionally substituted by one or more groups selected from halogen, $-OH$, or $-O-C_1-C_5$alkyl;

$R_{601}$ is selected from $-C_1-C_5$alkyl, $-C_3-C_6$cycloalkyl or $-C_1-C_5$alkyl-$C_3-C_5$cycloalkyl wherein the alkyl or cycloalkyl groups can be optionally substituted by one or more groups selected from halogen, $-CN$, alkyne, $-OH$, or $-O-C_1-C_5$alkyl;

$R_{701}$ is selected from H, $-C_1-C_5$alkyl or $-C_3-C_5$cycloalkyl;

$R_{801}$ and $R_{901}$ are independently selected from H, $-C_1-C_5$alkyl, $-C_1-C_5$alkoxy, or $-C_3-C_6$cycloalkyl wherein the alkyl groups may be optionally substituted by one or more groups selected from halogen, $-OH$, or $-CN$; or $R_{801}$ and $R_{901}$ may be optionally joined to form a ring to form a heterocycle such as piperidine, pyrrolidine, or with another heteroatom to form a ring such as morpholine.

In certain embodiments, compounds have structural Formula (IIb):

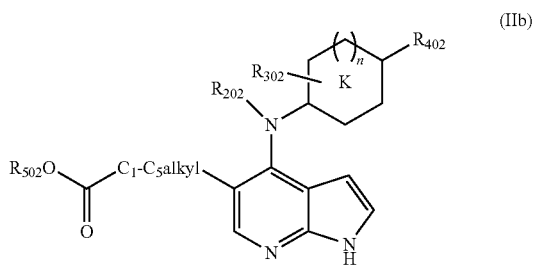
(IIb)

(IIc)

wherein:

R$_{202}$ is selected from H, —C$_1$-C$_4$alkyl, —C$_3$-C$_6$cycloalkyl, or —C$_1$-C$_2$alkyl-C$_3$-C$_6$cycloalkyl wherein the alkyl or cycloalkyl groups are optionally substituted with one or more groups selected from halogen, —OH, or —O—C$_1$-C$_5$alkyl;

n is 0 or 1;

Ring K is substituted at one or more carbons with one, two, or three R$_{302}$ substituents wherein each R$_{302}$ group is independently selected from H, halogen, —C$_1$-C$_4$alkyl, —C$_3$-C$_6$cycloalkyl, —OH, —O—C$_1$-C$_5$alkyl, —NR$_{702}$C(O)—CH=CH$_2$, —NR$_{702}$C(O)—C(CH$_2$OCH$_3$)=CH$_2$, —NR$_{702}$C(O)—CH=CHCH$_3$, or —NR$_{702}$C(O)—CH=CHCH$_2$NR$_{802}$R$_{902}$ wherein each alkyl or cycloalkyl group is optionally substituted with one or more groups selected from: halogen, —OH, —C$_1$-C$_5$alkylalkoxy, or —O—C$_1$-C$_5$alkyl;

Two R$_{302}$ groups on the same carbon atom or two or three R$_{302}$ groups on different carbon atoms of ring K may be optionally joined to form a spirocyclic, bicyclic, or tricyclic ring system with ring K such as adamantyl;

R$_{402}$ is selected from H, —OH, —C(O)—R$_{602}$, —OR$_{602}$, —O—C(O)—R$_{602}$, —NR$_{702}$—C(O)—R$_{602}$, —C$_1$-C$_4$alkyl-C(O)—R$_{602}$, —SO$_2$—R$_{602}$, —SO$_2$—NR$_{802}$R$_{902}$, —C$_1$-C$_4$alkyl-SO$_2$—R$_{602}$, or —C$_1$-C$_4$alkyl-SO$_2$NR$_{802}$R$_{902}$;

R$_{502}$ is selected from —C$_1$-C$_5$alkyl, or —C$_3$-C$_5$cycloalkyl wherein the alkyl or cycloalkyl groups may be optionally substituted by one or more groups selected from halogen, —OH, or —O—C$_1$-C$_5$alkyl;

R$_{602}$ is selected from —C$_1$-C$_5$alkyl, —C$_3$-C$_6$cycloalkyl or —C$_1$-C$_5$alkyl-C$_3$-C$_5$cycloalkyl wherein the alkyl or cycloalkyl groups can be optionally substituted by one or more groups selected from halogen, —CN, alkyne, —OH, or —O—C$_1$-C$_5$alkyl;

R$_{702}$ is selected from H, —C$_1$-C$_5$alkyl or —C$_3$-C$_5$cycloalkyl;

R$_{802}$ and R$_{902}$ are independently selected from H, —C$_1$-C$_5$alkyl, —C$_1$-C$_5$alkoxy, —C$_3$-C$_6$cycloalkyl wherein the alkyl groups may be optionally substituted by one or more groups selected from halogen, —OH, or —CN; and R$_{802}$ and R$_{902}$ may be optionally joined to form a ring to form a heterocycle such as piperidine, pyrrolidine, or with another heteroatom to form a ring such as morpholine.

In certain embodiments, compounds have structural Formula (IIc):

wherein:

R$_{203}$ is selected from H, —C$_1$-C$_4$alkyl, —C$_3$-C$_6$cycloalkyl, or —C$_1$-C$_2$alkyl-C$_3$-C$_6$cycloalkyl wherein the alkyl or cycloalkyl groups are optionally substituted with one or more groups selected from halogen, —OH, or —O—C$_1$-C$_5$alkyl;

n is 0 or 1;

Ring L is substituted at one or more carbons with one, two, or three R$_{303}$ substituents wherein each R$_{303}$ group is independently selected from H, halogen, —C$_1$-C$_4$alkyl, —C$_3$-C$_6$cycloalkyl, —OH, —O—C$_1$-C$_5$alkyl, —NR$_{703}$C(O)—CH=CH$_2$, —NR$_{703}$C(O)—C(CH$_2$OCH$_3$)=CH$_2$, —NR$_{703}$C(O)—CH=CHCH$_3$, or —NR$_{703}$C(O)—CH=CHCH$_2$NR$_{803}$R$_{903}$ wherein each alkyl or cycloalkyl group is optionally substituted with one or more groups selected from: halogen, —OH, —C$_1$-C$_5$alkylalkoxy, or —O—C$_1$-C$_5$alkyl;

Two R$_{303}$ groups on the same carbon atom or two or three R$_{303}$ groups on different carbon atoms of ring L may be optionally joined to form a spirocyclic, bicyclic, or tricyclic ring system with ring L such as adamantyl;

R$_{403}$ is selected from H, —OH, —C(O)—R$_{603}$, —OR$_{603}$, —O—C(O)—R$_{603}$, —NR$_{703}$—C(O)—R$_{603}$, —C$_1$-C$_4$alkyl-C(O)—R$_{603}$, —SO$_2$—R$_{603}$, —SO$_2$—NR$_{803}$R$_{903}$, —C$_1$-C$_4$alkyl-SO$_2$—R$_{603}$, or —C$_1$-C$_4$alkyl-SO$_2$NR$_{803}$R$_{903}$;

R$_{503}$ is selected from —C$_1$-C$_5$alkyl, or —C$_3$-C$_5$cycloalkyl wherein the alkyl or cycloalkyl groups may be optionally substituted by one or more groups selected from halogen, —OH, or —O—C$_1$-C$_5$alkyl;

R$_{603}$ is selected from —C$_1$-C$_5$alkyl, —C$_3$-C$_6$cycloalkyl or —C$_1$-C$_5$alkyl-C$_3$-C$_5$cycloalkyl wherein the alkyl or cycloalkyl groups can be optionally substituted by one or more groups selected from halogen, —CN, alkyne, —OH, or —O—C$_1$-C$_5$alkyl;

R$_{703}$ is selected from H, —C$_1$-C$_5$alkyl or —C$_3$-C$_5$cycloalkyl;

R$_{803}$ and R$_{903}$ are independently selected from H, —C$_1$-C$_5$alkyl, —C$_1$-C$_5$alkoxy, —C$_3$-C$_6$cycloalkyl wherein the alkyl groups may be optionally substituted by one or more groups selected from halogen, —OH, or —CN; and R$_{803}$ and R$_{903}$ may be optionally joined to form a ring to form a heterocycle such as piperidine, pyrrolidine, or with another heteroatom to form a ring such as morpholine.

In certain embodiments, compounds have structural Formula (IId):

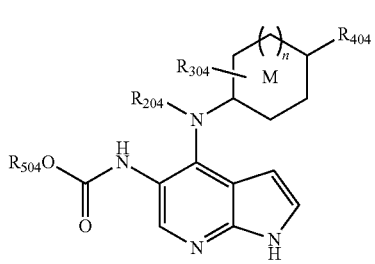

(IId)

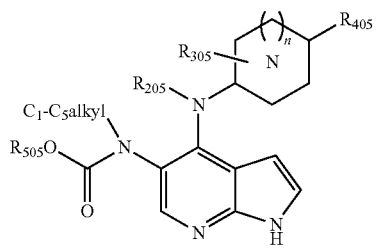

(IIe)

wherein:

$R_{204}$ is selected from H, —$C_1$-$C_4$alkyl, —$C_3$-$C_6$cycloalkyl, or —$C_1$-$C_2$alkyl-$C_3$-$C_6$cycloalkyl wherein the alkyl or cycloalkyl groups are optionally substituted with one or more groups selected from halogen, —OH, or —O—$C_1$-$C_5$alkyl;

n is 0 or 1;

Ring M is substituted at one or more carbons with one, two, or three $R_{304}$ substituents wherein each $R_{304}$ group is independently selected from H, halogen, —$C_1$-$C_4$alkyl, —$C_3$-$C_6$cycloalkyl, —OH, —O—$C_1$-$C_5$alkyl, —$NR_{704}C(O)$—CH=$CH_2$, —$NR_{704}C(O)$—C($CH_2OCH_3$)=$CH_2$, —$NR_{704}C(O)$—CH=CHCH$_3$, or —$NR_{704}C(O)$—CH=CHCH$_2NR_{804}R_{904}$ wherein each alkyl or cycloalkyl group is optionally substituted with one or more groups selected from: halogen, —OH, —$C_1$-$C_5$alkylalkoxy, or —O—$C_1$-$C_5$alkyl;

Two $R_{304}$ groups on the same carbon atom or two or three $R_{304}$ groups on different carbon atoms of ring M may be optionally joined to form a spirocyclic, bicyclic, or tricyclic ring system with ring M such as adamantyl;

$R_{404}$ is selected from H, —OH, —C(O)—$R_{604}$, —$OR_{604}$, —O—C(O)—$R_{604}$, —$NR_{704}$—C(O)—$R_{604}$, —$C_1$-$C_4$alkyl-C(O)—$R_{604}$, —$SO_2$—$R_{604}$, —$SO_2$—$NR_{804}R_{904}$, —$C_1$-$C_4$alkyl-$SO_2$—$R_{604}$, or —$C_1$-$C_4$alkyl-$SO_2NR_{804}R_{904}$;

$R_{504}$ is selected from —$C_1$-$C_5$alkyl, or —$C_3$-$C_5$cycloalkyl wherein the alkyl or cycloalkyl groups may be optionally substituted by one or more groups selected from halogen, —OH, or —O—$C_1$-$C_5$alkyl;

$R_{604}$ is selected from —$C_1$-$C_5$alkyl, —$C_3$-$C_6$cycloalkyl or —$C_1$-$C_5$alkyl-$C_3$-$C_5$cycloalkyl where the alkyl or cycloalkyl groups can be optionally substituted by one or more groups selected from halogen, —CN, alkyne, —OH, or —O—$C_1$-$C_5$alkyl;

$R_{704}$ is selected from H, —$C_1$-$C_5$alkyl or —$C_3$-$C_5$cycloalkyl;

$R_{804}$ and $R_{904}$ are independently selected from H, —$C_1$-$C_5$alkyl, or —$C_1$-$C_5$alkoxy, —$C_3$-$C_6$cycloalkyl wherein the alkyl groups may be optionally substituted by one or more groups selected from halogen, —OH, or —CN; and $R_{804}$ and $R_{904}$ may be optionally joined to form a ring to form a heterocycle such as piperidine, pyrrolidine, or with another heteroatom to form a ring such as morpholine.

In certain embodiments, compounds have structural Formula (IIe):

wherein:

$R_{205}$ is selected from H, —$C_1$-$C_4$alkyl, —$C_3$-$C_6$cycloalkyl, —$C_1$-$C_2$alkyl-$C_3$-$C_6$cycloalkyl wherein the alkyl or cycloalkyl groups are optionally substituted with one or more groups selected from halogen, —OH, or —O—$C_1$-$C_5$alkyl;

n is 0 or 1;

Ring N is substituted at one or more carbons with one, two, or three $R_{305}$ substituents wherein each $R_{305}$ group is independently selected from H, halogen, —$C_1$-$C_4$alkyl, —$C_3$-$C_6$cycloalkyl, —OH, —O—$C_1$-$C_5$alkyl, —$NR_{705}C(O)$—CH=$CH_2$, —$NR_{705}C(O)$—C($CH_2OCH_3$)$CH_2$, —$NR_{705}C(O)$—CH=CHCH$_3$, or —$NR_{705}C(O)$—CH=CHCH$_2NR_{805}R_{905}$ wherein each alkyl or cycloalkyl group is optionally substituted with one or more groups selected from: halogen, —OH, —$C_1$-$C_5$alkylalkoxy, or —O—$C_1$-$C_5$alkyl;

Two $R_{305}$ groups on the same carbon atom or two or three $R_{305}$ groups on different carbon atoms of ring N may be optionally joined to form a spirocyclic, bicyclic, or tricyclic ring system with ring N such as adamantyl;

$R_{405}$ is selected from H, —OH, —C(O)—$R_{605}$, —$OR_{605}$, —O—C(O)—$R_{605}$, —$NR_{705}$—C(O)—$R_{605}$, —$C_1$-$C_4$alkyl-C(O)—$R_{605}$, —$SO_2$—$R_{605}$, —$SO_2$—$NR_{805}R_{905}$, —$C_1$-$C_4$alkyl-$SO_2$—$R_{605}$, or —$C_1$-$C_4$alkyl-$SO_2NR_{805}R_{905}$;

$R_{505}$ is selected from —$C_1$-$C_5$alkyl, or —$C_3$-$C_5$cycloalkyl wherein the alkyl or cycloalkyl groups may be optionally substituted by one or more groups selected from halogen, —OH, or —O—$C_1$-$C_5$alkyl;

$R_{605}$ is selected from —$C_1$-$C_5$alkyl, —$C_3$-$C_6$cycloalkyl or —$C_1$-$C_5$alkyl-$C_3$-$C_5$cycloalkyl wherein the alkyl or cycloalkyl groups can be optionally substituted by one or more groups selected from halogen, —CN, alkyne, —OH, or —O—$C_1$-$C_5$alkyl;

$R_{705}$ is selected from H, —$C_1$-$C_5$alkyl or —$C_3$-$C_5$cycloalkyl;

$R_{805}$ and $R_{905}$ are independently selected from H, —$C_1$-$C_5$alkyl, —$C_1$-$C_5$alkoxy, —$C_3$-$C_6$cycloalkyl wherein the alkyl groups may be optionally substituted by one or more groups selected from halogen, —OH, or —CN; and $R_{805}$ and $R_{905}$ may be optionally joined to form a ring to form a heterocycle such as piperidine, pyrrolidine, or with another heteroatom to form a ring such as morpholine.

In certain embodiments, compounds have structural Formula (IIf):

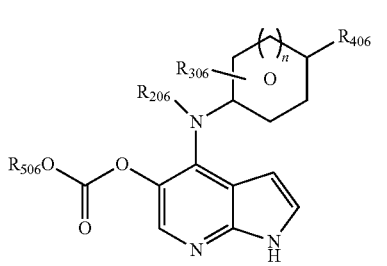 (IIf)

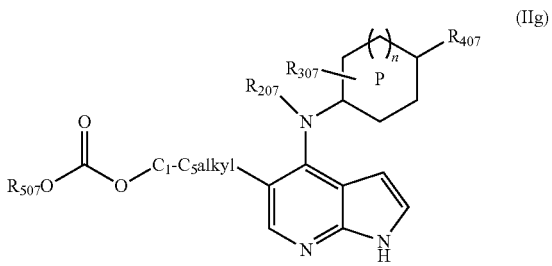 (IIg)

wherein:

$R_{206}$ is selected from H, —$C_1$-$C_4$alkyl, —$C_3$-$C_6$cycloalkyl, or —$C_1$-$C_2$alkyl-$C_3$-$C_6$cycloalkyl wherein the alkyl or cycloalkyl groups are optionally substituted with one or more groups selected from halogen, —OH, or —O—$C_1$-$C_5$alkyl;

n is 0 or 1;

Ring O is substituted at one or more carbons with one, two, or three $R_{306}$ substituents wherein each $R_{306}$ group is independently selected from H, halogen, —$C_1$-$C_4$alkyl, —$C_3$-$C_6$cycloalkyl, —OH, —O—$C_1$-$C_5$alkyl, —$NR_{706}$C(O)—CH=$CH_2$, —$NR_{706}$C(O)—C($CH_2OCH_3$)=$CH_2$, —$NR_{706}$C(O)—CH=$CHCH_3$, or —$NR_{706}$C(O)—CH=$CHCH_2NR_{806}R_{906}$ wherein each alkyl or cycloalkyl group is optionally substituted with one or more groups selected from: halogen, —OH, —$C_1$-$C_5$alkylalkoxy, or —O—$C_1$-$C_5$alkyl;

Two $R_{306}$ groups on the same carbon atom or two or three $R_{306}$ groups on different carbon atoms of ring O may be optionally joined to form a spirocyclic, bicyclic, or tricyclic ring system with ring O such as adamantyl;

$R_{406}$ is selected from H, —OH, —C(O)—$R_{606}$, —$OR_{60}$, —O—C(O)—$R_{606}$, —$NR_{706}$—C(O)—$R_{606}$, —$C_1$-$C_4$alkyl-C(O)—$R_{606}$, —$SO_2$—$R_{606}$, —$SO_2$—$NR_{806}R_{906}$, —$C_1$-$C_4$alkyl-$SO_2$—$R_{606}$, or —$C_1$-$C_4$alkyl-$SO_2NR_{806}R_{906}$;

$R_{506}$ is selected from —$C_1$-$C_5$alkyl, or —$C_3$-$C_5$cycloalkyl wherein the alkyl or cycloalkyl groups may be optionally substituted by one or more groups selected from halogen, —OH, or —O—$C_1$-$C_5$alkyl;

$R_{606}$ is selected from —$C_1$-$C_5$alkyl, —$C_3$-$C_6$cycloalkyl or —$C_1$-$C_5$alkyl-$C_3$-$C_5$cycloalkyl wherein the alkyl or cycloalkyl groups can be optionally substituted by one or more groups selected from halogen, —CN, alkyne, —OH, or —O—$C_1$-$C_5$alkyl;

$R_{706}$ is selected from H, —$C_1$-$C_5$alkyl or —$C_3$-$C_5$cycloalkyl;

$R_{806}$ and $R_{906}$ are independently selected from H, —$C_1$-$C_5$alkyl, —$C_1$-$C_5$alkoxy, —$C_3$-$C_6$cycloalkyl wherein the alkyl groups may be optionally substituted by one or more groups selected from halogen, —OH, or —CN; and $R_{806}$ and $R_{906}$ may be optionally joined to form a ring to form a heterocycle such as piperidine, pyrrolidine, or with another heteroatom to form a ring such as morpholine.

In certain embodiments, compounds have structural Formula (IIg):

wherein:

$R_{207}$ is selected from H, —$C_1$-$C_4$alkyl, —$C_3$-$C_6$cycloalkyl, or —$C_1$-$C_2$alkyl-$C_3$-$C_6$cycloalkyl wherein the alkyl or cycloalkyl groups are optionally substituted with one or more groups selected from halogen, —OH, or —O—$C_1$-$C_5$alkyl;

n is 0 or 1;

Ring P is substituted at one or more carbons with one, two, or three $R_{307}$ substituents wherein each $R_{307}$ group is independently selected from H, halogen, —$C_1$-$C_5$alkyl, —$C_3$-$C_6$cycloalkyl, —OH, —O—$C_1$-$C_5$alkyl, —$NR_{707}$C(O)—CH=$CH_2$, —$NR_{707}$C(O)—C($CH_2OCH_3$)=$CH_2$, —$NR_{707}$C(O)—CH=$CHCH_3$, or —$NR_{707}$C(O)—CH=$CHCH_2NR_{807}R_{907}$ wherein each alkyl or cycloalkyl group is optionally substituted with one or more groups selected from: halogen, —OH, —$C_1$-$C_5$alkylalkoxy, or —O—$C_1$-$C_5$alkyl;

Two $R_{307}$ groups on the same carbon atom or two or three $R_{307}$ groups on different carbon atoms of ring P may be optionally joined to form a spirocyclic, bicyclic, or tricyclic ring system with ring P such as adamantyl;

$R_{407}$ is selected from H, —OH, —C(O)—$R_{607}$, —$OR_{607}$, —O—C(O)—$R_{607}$, —$NR_{707}$—C(O)—$R_{607}$, —$C_1$-$C_4$alkyl-C(O)—$R_{607}$, —$SO_2$—$R_{607}$, —$SO_2$—$NR_{807}R_{907}$, —$C_1$-$C_4$alkyl-$SO_2$—$R_{607}$, or —$C_1$-$C_4$alkyl-$SO_2NR_{807}R_{907}$;

$R_{507}$ is selected from —$C_1$-$C_5$alkyl, or —$C_3$-$C_5$cycloalkyl wherein the alkyl or cycloalkyl groups may be optionally substituted by one or more groups selected from halogen, —OH, or —O—$C_1$-$C_5$alkyl;

$R_{607}$ is selected from —$C_1$-$C_5$alkyl, —$C_3$-$C_6$cycloalkyl or —$C_1$-$C_5$alkyl-$C_3$-$C_5$cycloalkyl wherein the alkyl or cycloalkyl groups can be optionally substituted by one or more groups selected from halogen, —CN, alkyne, —OH, or —O—$C_1$-$C_5$alkyl;

$R_{707}$ is selected from H, —$C_1$-$C_5$alkyl or —$C_3$-$C_5$cycloalkyl;

$R_{807}$ and $R_{907}$ are independently selected from H, —$C_1$-$C_5$alkyl, —$C_1$-$C_5$alkoxy, —$C_3$-$C_6$cycloalkyl wherein the alkyl groups may be optionally substituted by one or more groups selected from halogen, —OH, or —CN; and $R_{807}$ and $R_{907}$ may be optionally joined to form a ring to form a heterocycle such as piperidine, pyrrolidine, or with another heteroatom to form a ring such as morpholine.

In certain embodiments, compounds have structural Formula (III):

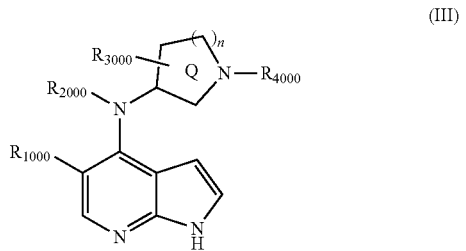

(III)

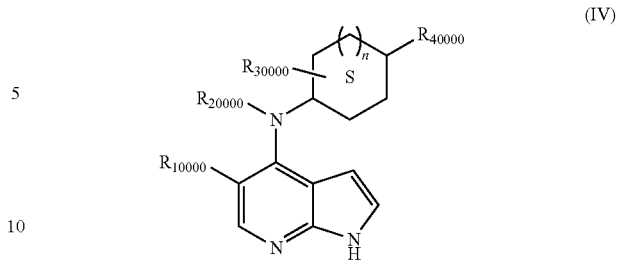

(IV)

wherein:
$R_{1000}$ is selected from —$CO_2R_{5000}$, —$C_1$-$C_5$alkyl-$CO_2R_{5000}$, —$C_3$-$C_6$-cycloalkyl-$CO_2R_{5000}$, —$NHCO_2R_{5000}$, —$N(C_1$-$C_5$ alkyl)-$CO_2R_{5000}$, —O—$CO_2R_{5000}$, or —$C_1$-$C_5$alkyl-O—$CO_2R_{5000}$;

$R_{2000}$ is selected from H, —$C_1$-$C_4$alkyl, —$C_3$-$C_6$cycloalkyl, or —$C_1$-$C_2$alkyl-$C_3$-$C_6$cycloalkyl, wherein the alkyl or cycloalkyl groups are optionally substituted with one or more groups selected from halogen, —OH, or —O—$C_1$-$C_5$alkyl;

n is 0, 1 or 2;

Ring Q is substituted at one or more carbons with one, two, or three $R_3$ substituents wherein each $R_{3000}$ group is independently selected from H, halogen, —$C_1$-$C_4$alkyl, —$C_3$-$C_6$cycloalkyl, —OH, or —O—$C_1$-$C_5$alkyl wherein each alkyl or cycloalkyl group is optionally substituted with one or more groups selected from: halogen, —OH, —$C_1$-$C_5$alkylalkoxy, or —O—$C_1$-$C_5$alkyl;

Two $R_{3000}$ groups on the same or different carbon atoms of the ring Q may be optionally joined to form a spirocyclic or bicyclic ring system with ring Q;

$R_{4000}$ is selected from —C(O)—$R_{6000}$, —$CH_2R_{6000}$, —C(O)—CH=$CH_2$, —C(O)—C($CH_2OCH_3$)=$CH_2$, —C(O)—CH=$CHCH_3$, —C(O)—CH=$CHCH_2NR_7R_8$, —C(O)—$C_1$-$C_5$alkyl, or —C(O)—$C_3$-$C_6$cycloalkyl, wherein the alkyl or cycloalkyl groups may be optionally substituted with one or more groups selected from —OH, halogen, alkyne, or —CN;

$R_{5000}$ is selected from H, —$C_1$-$C_5$alkyl, and —$C_3$-$C_6$cycloalkyl wherein the alkyl or cycloalkyl groups may be optionally substituted by one or more groups selected from halogen, —OH, —$C_3$-$C_6$cycloalkyl, or —O—$C_1$-$C_5$alkyl;

$R_{6000}$ is selected from —$C_1$-$C_5$alkyl, —$C_3$-$C_6$cycloalkyl, —$C_1$-$C_5$alkyl-$C_3$-$C_6$cycloalkyl, —$NR_{7000}R_{8000}$, —O-aryl, —O-heteroaryl, aryl, or heteroaryl wherein the alkyl, cycloalkyl, aryl or heteroaryl groups can be optionally substituted by one or more groups selected from halogen, —CN, alkyne, —OH, trifluoromethyl, —O—$C_1$-$C_5$alkyl, or —O—$C_3$-$C_6$cycloalkyl;

$R_{7000}$ and $R_{8000}$ are independently selected from H, —$C_1$-$C_5$ alkyl, —$C_1$-$C_5$ alkoxy, or —$C_3$-$C_5$ cycloalkyl wherein the alkyl groups may be optionally substituted by one or more groups selected from halogen, —OH, or —CN;

$R_{7000}$ and $R_{8000}$ may be optionally joined to form a ring to form a heterocycle such as piperidine, pyrrolidine, or with another heteroatom to form a ring such as morpholine.

In certain embodiments of the present invention, compounds have structural Formula (IV):

wherein:
$R_{10000}$ is selected from —$CO_2R_{50000}$, —$C_1$-$C_5$-alkyl-$CO_2R_{50000}$, —$C_3$-$C_6$-cycloalkyl-$CO_2R_{50000}$, —$NHCO_2R_{50000}$, —$N(C_1$-$C_5$ alkyl)-$CO_2R_{50000}$, —O—$CO_2R_{50000}$, or —$C_1$-$C_5$alkyl-O—$CO_2R_{50000}$;

$R_{20000}$ is selected from H, —$C_1$-$C_4$alkyl, —$C_3$-$C_6$cycloalkyl, or —$C_1$-$C_2$alkyl-$C_3$-$C_6$cycloalkyl wherein the alkyl or cycloalkyl groups are optionally substituted with one or more groups selected from halogen, —OH, or —O—$C_1$-$C_5$alkyl;

n is 0 or 1;

Ring S is substituted at one or more carbons with one, two, or three $R_{30}$ substituents wherein each $R_{30000}$ group is independently selected from H, halogen, —$C_1$-$C_4$alkyl, —$C_3$-$C_6$cycloalkyl, —OH, —O—$C_1$-$C_5$alkyl, —$NR_{70000}C(O)$—CH=$CH_2$, —$NR_{70000}C(O)$—C($CH_2OCH_3$)=$CH_2$, —$NR_{70000}C(O)$—CH=$CHCH_3$, or —$NR_{70000}C(O)$—CH=$CHCH_2NR_{80000}R_{90000}$ wherein each alkyl or cycloalkyl group is optionally substituted with one or more groups selected from: halogen, —CN, —OH, —$C_1$-$C_5$alkylalkoxy, or —O—$C_1$-$C_5$alkyl;

Two $R_{30000}$ groups on the same carbon atom or two or three $R_{30}$ groups on different carbon atoms of ring S may be optionally joined to form a spirocyclic, bicyclic, or tricyclic ring system with ring S such as adamantyl;

$R_{40000}$ is selected from H, —OH, —C(O)—$R_{60000}$, —$OR_{60000}$, —O—C(O)—$R_{60000}$, —$NR_{70000}$—C(O)—$R_{60000}$, —$C_1$-$C_4$alkyl-C(O)—$R_{60000}$, —$SO_2$—$R_{60000}$, —$SO_2$—$NR_{80000}R_{90000}$, —$C_1$-$C_4$alkyl-$SO_2$—$R_{60000}$, or —$C_1$-$C_4$alkyl-$SO_2NR_{80000}R_{90000}$;

$R_{50000}$ is selected from H, —$C_1$-$C_5$alkyl, and —$C_3$-$C_6$cycloalkyl wherein the alkyl or cycloalkyl groups may be optionally substituted by one or more groups selected from halogen, —OH, —$C_3$-$C_6$cycloalkyl, or —O—$C_1$-$C_5$alkyl;

$R_{60000}$ is selected from —$C_1$-$C_5$alkyl, —$C_3$-$C_6$cycloalkyl or —$C_1$-$C_5$alkyl-$C_3$-$C_6$cycloalkyl wherein the alkyl or cycloalkyl groups can be optionally substituted by one or more groups selected from halogen, —CN, alkyne, —OH, or —O—$C_1$-$C_5$alkyl;

$R_{70000}$ is selected from H, —$C_1$-$C_5$alkyl or —$C_3$-$C_6$cycloalkyl;

$R_{80000}$ and $R_{90000}$ are independently selected from H, —$C_1$-$C_5$alkyl, —$C_1$-$C_5$alkoxy, or —$C_3$-$C_6$cycloalkyl wherein the alkyl groups may be optionally substituted by one or more groups selected from halogen, —OH, or —CN; and $R_{80000}$ and $R_{90000}$ may be optionally joined to form a ring to form a heterocycle such as piperidine, pyrrolidine, or with another heteroatom to form a ring such as morpholine.

In certain embodiments, compounds of structural Formula (II), Formula (IIa) or Formula (IV) are not the following:

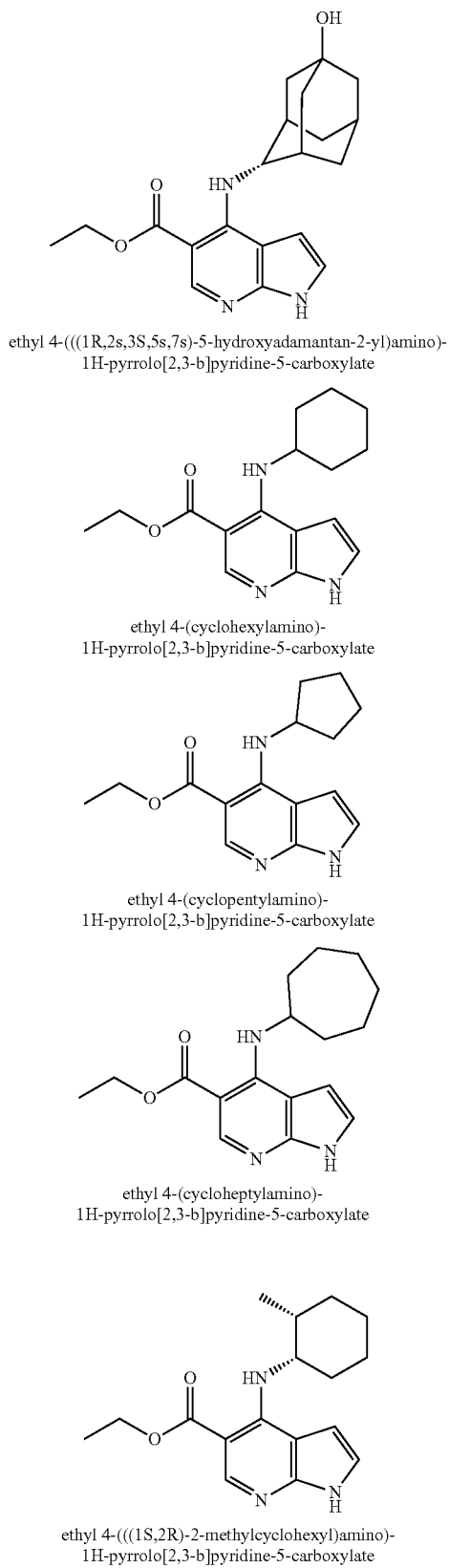

ethyl 4-(((1R,2s,3S,5s,7s)-5-hydroxyadamantan-2-yl)amino)-1H-pyrrolo[2,3-b]pyridine-5-carboxylate ethyl 4-(cyclohexylamino)-1H-pyrrolo[2,3-b]pyridine-5-carboxylate ethyl 4-(cyclopentylamino)-1H-pyrrolo[2,3-b]pyridine-5-carboxylate ethyl 4-(cycloheptylamino)-1H-pyrrolo[2,3-b]pyridine-5-carboxylate ethyl 4-(((1S,2R)-2-methylcyclohexyl)amino)-1H-pyrrolo[2,3-b]pyridine-5-carboxylate

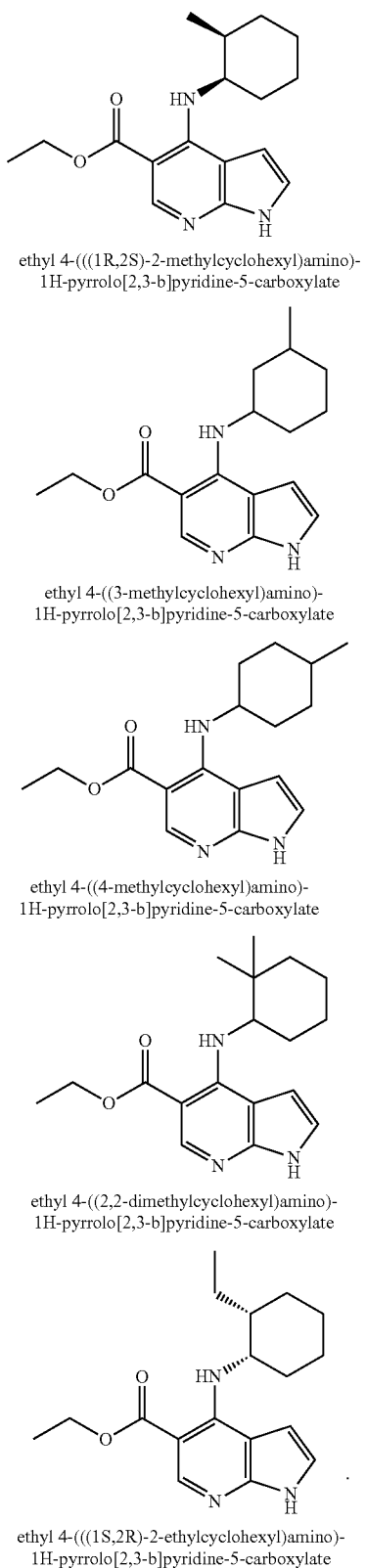

ethyl 4-(((1R,2S)-2-methylcyclohexyl)amino)-1H-pyrrolo[2,3-b]pyridine-5-carboxylate ethyl 4-((3-methylcyclohexyl)amino)-1H-pyrrolo[2,3-b]pyridine-5-carboxylate ethyl 4-((4-methylcyclohexyl)amino)-1H-pyrrolo[2,3-b]pyridine-5-carboxylate ethyl 4-((2,2-dimethylcyclohexyl)amino)-1H-pyrrolo[2,3-b]pyridine-5-carboxylate ethyl 4-(((1S,2R)-2-ethylcyclohexyl)amino)-1H-pyrrolo[2,3-b]pyridine-5-carboxylate The invention is further illustrated by the following examples of compounds of Formula (I)

| Example # | Structure | Name |
|---|---|---|
| 1 | 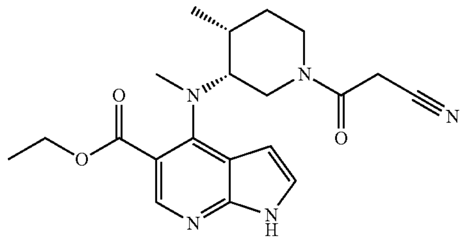 [SMILES: CCOC(=O)c1cnc2[nH]ccc2c1N(C)[C@H]1CN(C(=O)CC#N)CC[C@H]1C] | ethyl 4-(((3R,4R)-1-(2-cyanoacetyl)-4-methylpiperidin-3-yl)(methyl)amino)-1H-pyrrolo[2,3-b]pyridine-5-carboxylate |
| 2 | 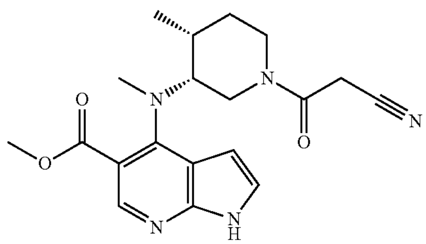 [SMILES: COC(=O)c1cnc2[nH]ccc2c1N(C)[C@H]1CN(C(=O)CC#N)CC[C@H]1C] | methyl 4-(((3R,4R)-1-(2-cyanoacetyl)-4-methylpiperidin-3-yl)(methyl)amino)-1H-pyrrollo[2,3-b]pyridine-5-carboxylate |
| 3 | 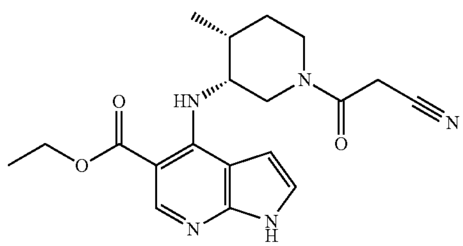 [SMILES: CCOC(=O)c1cnc2[nH]ccc2c1N[C@H]1CN(C(=O)CC#N)CC[C@H]1C] | ethyl 4-(((3R,4R)-1-(2-cyanoacetyl)-4-methylpiperidin-3-yl)amino)-1H-pyrrolo[2,3-b]pyridine-5-carboxylate |
| 4 | 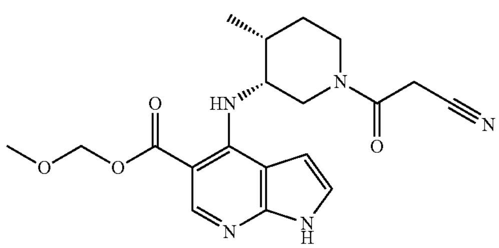 [SMILES: COCOC(=O)c1cnc2[nH]ccc2c1N[C@H]1CN(C(=O)CC#N)CC[C@H]1C] | methoxymethyl 4-(((3R,4R)-1-(2-cyanoacetyl)-4-methylpiperidin-3-yl)amino)-1H-pyrrolo[2,3-b]pyridine-5-carboxylate |
| 5 | 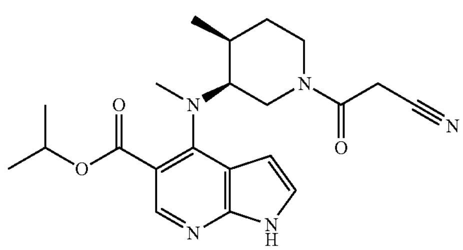 [SMILES: CC(C)OC(=O)c1cnc2[nH]ccc2c1N(C)[C@@H]1CN(C(=O)CC#N)CC[C@@H]1C] | isopropyl 4-(((3S,4S)-1-(2-cyanoacetyl)-4-methylpiperidin-3-yl)(methyl)amino)-1H-pyrrolo[2,3-b]pyridine-5-carboxylate |
| 6 | 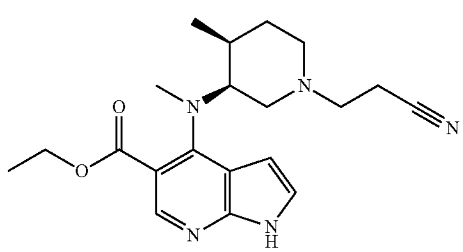 [SMILES: CCOC(=O)c1cnc2[nH]ccc2c1N(C)[C@@H]1CN(CCC#N)CC[C@@H]1C] | ethyl 4-(((3S,4S)-1-(2-cyanoethyl)-4-methylpiperidin-3-yl)methyl)amino)-1H-pyrrolo[2,3-b]pyridine-5-carboxylate |

| Example # | Structure | Name |
|---|---|---|
| 7 | 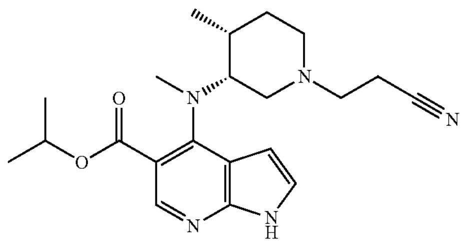 [SMILES: CC(C)OC(=O)c1cnc2[nH]ccc2c1N(C)[C@H]1CN(CCC#N)CC[C@H]1C] | isopropyl 4-(((3R,4R)-1-(2-cyanoethyl)-4-methylpiperidin-3-yl)(methyl)amino)-1H-pyrrolo[2,3-b]pyridine-5-carboxylate |
| 8 | 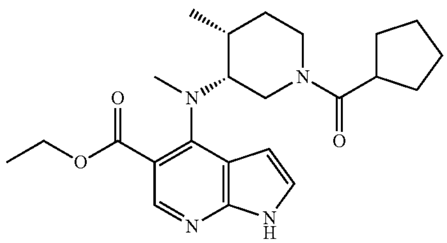 [SMILES: CCOC(=O)c1cnc2[nH]ccc2c1N(C)[C@H]1CN(C(=O)C2CCCC2)CC[C@H]1C] | ethyl 4-(((3R,4R)-1-(cyclopentanecarbonyl)-4-methylpiperidin-3-yl)(methyl)amino)-1H-pyrrolo[2,3-b]pyridine-5-carboxylate |
| 9 | 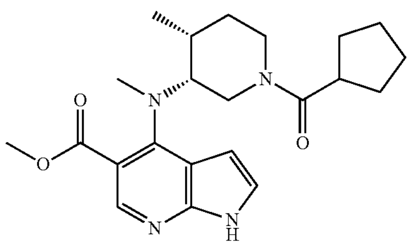 [SMILES: COC(=O)c1cnc2[nH]ccc2c1N(C)[C@H]1CN(C(=O)C2CCCC2)CC[C@H]1C] | methyl 4-(((3R,4R)-1-(cyclopentanecarbonyl)-4-methylpiperidin-3-yl)(methyl)amino)-1H-pyrrolo[2,3-b]pyridine-5-carboxylate |
| 10 | 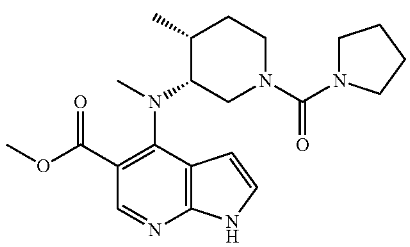 [SMILES: COC(=O)c1cnc2[nH]ccc2c1N(C)[C@H]1CN(C(=O)N2CCCC2)CC[C@H]1C] | methyl 4-(methyl((3R,4R)-4-methyl-1-(pyrrolidine-1-carbonyl)piperidin-3-yl)amino)-1H-pyrrolo[2,3-b]pyridine-5-carboxylate |
| 11 | 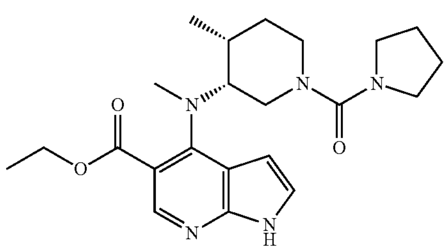 [SMILES: CCOC(=O)c1cnc2[nH]ccc2c1N(C)[C@H]1CN(C(=O)N2CCCC2)CC[C@H]1C] | ethyl 4-(methyl((3R,4R)-4-methyl-1-(pyrrolidine-1-carbonyl)piperidin-3-yl)amino)-1H-pyrrolo[2,3-b]pyridine-5-carboxylate |
| 12 | 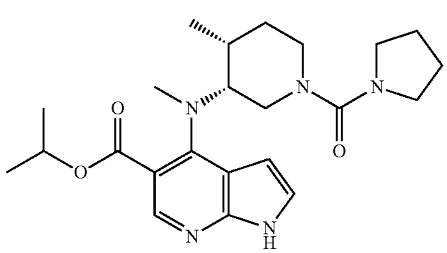 [SMILES: CC(C)OC(=O)c1cnc2[nH]ccc2c1N(C)[C@H]1CN(C(=O)N2CCCC2)CC[C@H]1C] | isopropyl 4-(methyl((3R,4R)-4-methyl-1-(pyrrolidine-1-carbonyl)piperidin-3-yl)amino)-1H-pyrrolo[2,3-b]pyridine-5-carboxylate |

| Example # | Structure | Name |
|---|---|---|
| 13 | 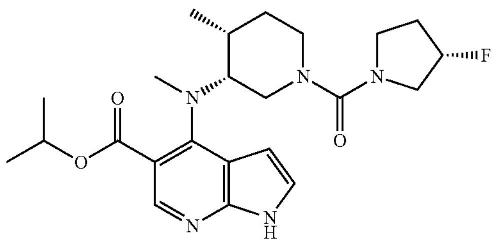 [SMILES: CC(C)OC(=O)c1cnc2[nH]ccc2c1N(C)[C@H]1CN(C(=O)N2CC[C@H](F)C2)CC[C@H]1C] | isopropyl 4-(((3R,4R)-1-((S)-3-fluoropyrrolidine-1-carbonyl)-4-methylpiperidin-3-yl)(methyl)amino)-1H-pyrrolo[2,3-b]pyridine-5-carboxylate |
| 14 | 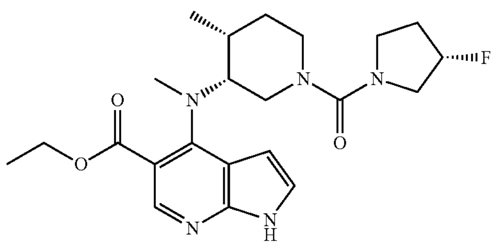 [SMILES: CCOC(=O)c1cnc2[nH]ccc2c1N(C)[C@H]1CN(C(=O)N2CC[C@H](F)C2)CC[C@H]1C] | ethyl 4-(((3R,4R)-1-((S)-3-fluoropyrrolidine-1-carbonyl)-4-methylpiperidin-3-yl)(methyl)amino)-1H-pyrrolo[2,3-b]pyridine-5-carboxylate |
| 15 | 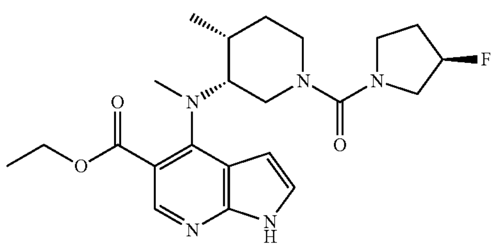 [SMILES: CCOC(=O)c1cnc2[nH]ccc2c1N(C)[C@H]1CN(C(=O)N2CC[C@@H](F)C2)CC[C@H]1C] | ethyl 4-(((3R,4R)-1-((R)-3-fluoropyrrolidine-1-carbonyl)-4-methylpiperidin-3-yl)(methyl)amino)-1H-pyrrolo[2,3-b]pyridine-5-carboxylate |
| 16 | 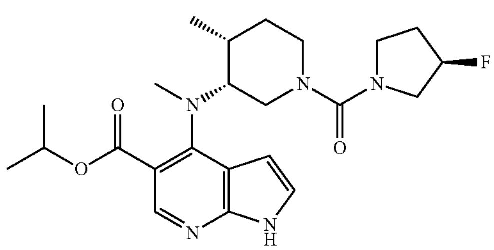 [SMILES: CC(C)OC(=O)c1cnc2[nH]ccc2c1N(C)[C@H]1CN(C(=O)N2CC[C@@H](F)C2)CC[C@H]1C] | isopropyl 4-(((3R,4R)-1-((R)-3-fluoropyrrolidine-1-carbonyl)-4-methylpiperidin-3-yl)(methyl)amino)-1H-pyrrolo[2,3-b]pyridine-5-carboxylate |
| 17 | 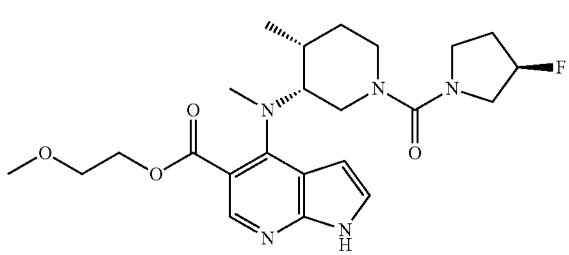 [SMILES: COCCOC(=O)c1cnc2[nH]ccc2c1N(C)[C@H]1CN(C(=O)N2CC[C@@H](F)C2)CC[C@H]1C] | 2-methoxyethyl 4-(((3R,4R)-1-((R)-3-fluoropyrrolidine-1-carbonyl)-4-methylpiperidin-3-yl)methyl)amino)-1H-pyrrolo[2,3-b]pyridine-5-carboxylate |
| 18 | 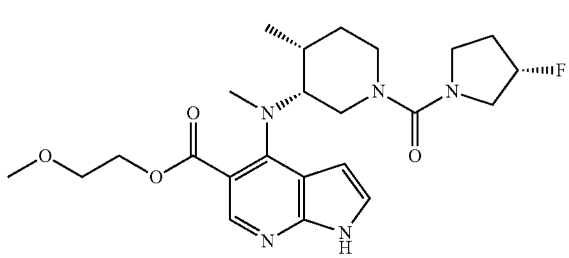 [SMILES: COCCOC(=O)c1cnc2[nH]ccc2c1N(C)[C@H]1CN(C(=O)N2CC[C@H](F)C2)CC[C@H]1C] | 2-methoxyethyl 4-(((3R,4R)-1-((S)-3-fluoropyrrolidine-1-carbonyl)-4-methylpiperidin-3-yl)(methyl)amino)-1H-pyrrolo[2,3-b]pyridine-5-carboxylate |

| Example # | Structure | Name |
|---|---|---|
| 19 | 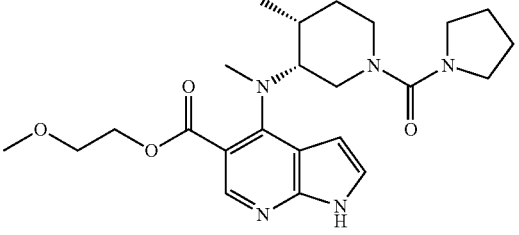 [SMILES: COCCOC(=O)c1cnc2[nH]ccc2c1N(C)[C@H]1CN(C(=O)N2CCCC2)CC[C@H]1C] | 2-methoxyethyl 4-(methyl((3R,4R)-4-methyl-1-(pyrrolidine-1-carbonyl)piperidin-3-yl)amino)-1H-pyrrolo[2,3-b]pyridine-5-carboxylate |
| 20 | 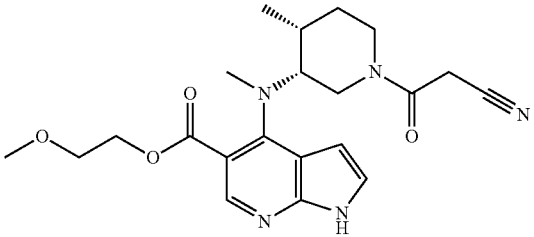 [SMILES: COCCOC(=O)c1cnc2[nH]ccc2c1N(C)[C@H]1CN(C(=O)CC#N)CC[C@H]1C] | 2-methoxyethyl 4-(((3R,4R)-1-(2-cyanoacetyl)-4-methylpiperidin-3-yl)(methyl)amino)-1H-pyrrolo[2,3-b]pyridine-5-carboxylate |
| 21 | 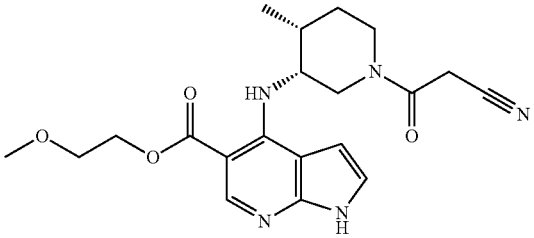 [SMILES: COCCOC(=O)c1cnc2[nH]ccc2c1N[C@H]1CN(C(=O)CC#N)CC[C@H]1C] | 2-methoxyethyl 4-(((3R,4R)-1-(2-cyanoacetyl)-4-methylpiperidin-3-yl)amino)-1H-pyrrolo[2,3-b]pyridine-5-carboxylate |
| 22 | 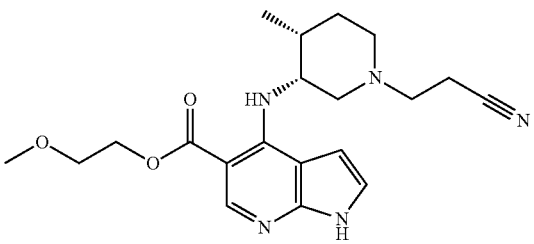 [SMILES: COCCOC(=O)c1cnc2[nH]ccc2c1N[C@H]1CN(CCC#N)CC[C@H]1C] | 2-methoxyethyl 4-(((3R,4R)-1-(2-cyanoethyl)-4-methylpiperidin-3-yl)amino)-1H-pyrrolo[2,3-b]pyridine-5-carboxylate |
| 23 | 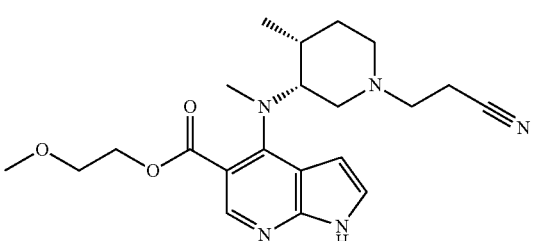 | 2-methoxyethyl 4-(((3R,4R)-1-(2-cyanoethyl)-4-methylpiperridin-3-yl)(methyl)amino)-1H-pyrrolo[2,3-b]pyridine-5-carboxylate |
| 24 | 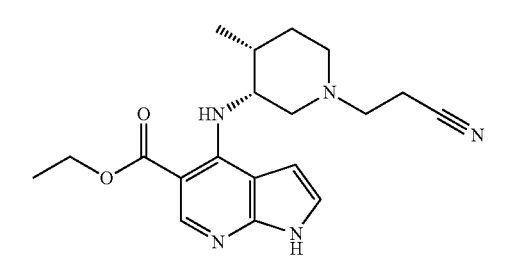 [SMILES: CCOC(=O)c1cnc2[nH]ccc2c1N[C@H]1CN(CCC#N)CC[C@H]1C] | ethyl 4-(((3R,4R)-1-(2-caynoethyl)-4-methylpiperidin-3-yl)amino)-1H-pyrrolo[2,3-b[pyridine-5-carboxylate |

| Example # | Structure | Name |
|---|---|---|
| 25 | 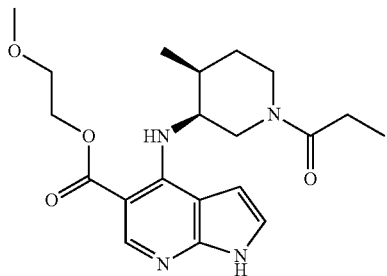 [SMILES: CCC(=O)N1CC[C@H](C)[C@H](Nc2c(C(=O)OCCOC)cnc3[nH]ccc23)C1] | 2-methoxyethyl 4-(((3S,4S)-4-methyl-1-propionylpiperidin-3-yl)amino)-1H-pyrrolo[2,3-b]pyridine-5-carboxylate |
| 26 | 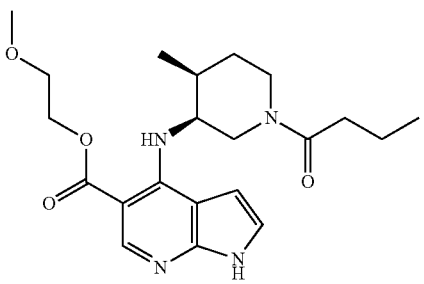 [SMILES: CCCC(=O)N1CC[C@H](C)[C@H](Nc2c(C(=O)OCCOC)cnc3[nH]ccc23)C1] | 2-methoxyethyl 4-(((3S,4S)-1-butyryl-4-methylpiperidin-3-yl)amino)-1H-pyrrolo[2,3-b]pyridine-5-carboxylate |
| 27 | 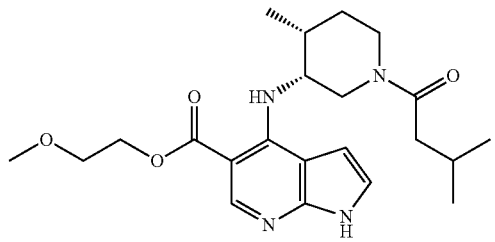 [SMILES: COCCOC(=O)c1cnc2[nH]ccc2c1N[C@H]1CN(C(=O)CC(C)C)CC[C@H]1C] | 2-methoxyethyl 4-(((3R,4R)-4-methyl-1-(3-methylbutanoyl)piperidin-3-yl)amino)-1H-pyrrolo[2,3-b]pyridine-5-carboxylate |
| 28 | 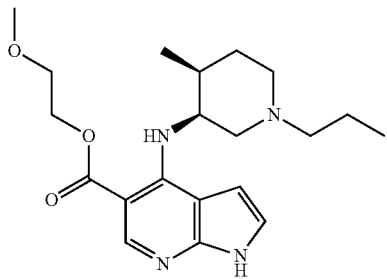 [SMILES: CCCN1CC[C@H](C)[C@H](Nc2c(C(=O)OCCOC)cnc3[nH]ccc23)C1] | 2-methoxyethyl 4-(((3S,4S)-4-methyl-1-propylpiperidin-3-yl)amino)-1H-pyrrolo[2,3-b]pyridine-5-carboxylate |
| 29 | 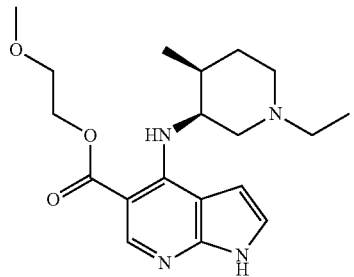 [SMILES: CCN1CC[C@H](C)[C@H](Nc2c(C(=O)OCCOC)cnc3[nH]ccc23)C1] | 2-methoxyethyl 4-(((3S,4S)-1-ethyl-4-methylpiperidin-3-yl)amino)-1H-pyrrolo[2,3-b]pyridine-5-carboxylate |

-continued

| Example # | Structure | Name |
|---|---|---|
| 30 | 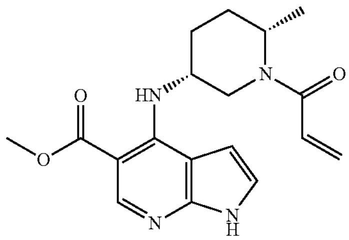 [SMILES: C=CC(=O)N1C[C@H](Nc2c(C(=O)OC)cnc3[nH]ccc23)CC[C@@H]1C] | methyl 4-(((3R,6S)-1-acryloyl-6-methylpiperidin-3-yl)amino)-1H-pyrrolo[2,3-b]pyridine-5-carboxylate |
| 31 | 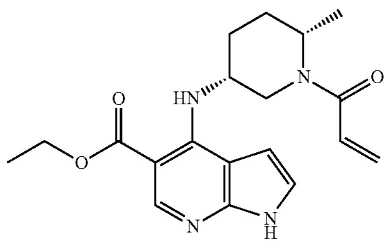 [SMILES: C=CC(=O)N1C[C@H](Nc2c(C(=O)OCC)cnc3[nH]ccc23)CC[C@@H]1C] | ethyl 4-(((3R,6S)-1-acryloyl-6-methylpiperidin-3-yl)amino)-1H-pyrrolo[2,3-b]pyridine-5-carboxylate |
| 32 | 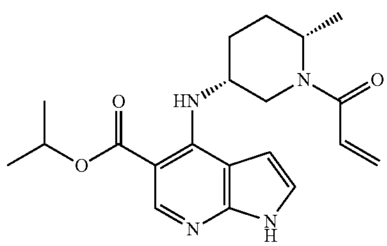 [SMILES: C=CC(=O)N1C[C@H](Nc2c(C(=O)OC(C)C)cnc3[nH]ccc23)CC[C@@H]1C] | isopropyl 4-(((3R,6S)-1-acryloyl-6-methylpiperidin-3-yl)amino)-1H-pyrrolo[2,3-b]pyridine-5-carboxylate |
| 33 | 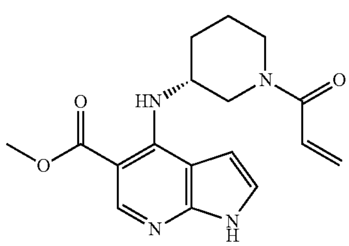 [SMILES: C=CC(=O)N1CCC[C@@H](Nc2c(C(=O)OC)cnc3[nH]ccc23)C1] | methyl (R)-4-((1-acryloylpiperidin-3-yl)amino)-1H-pyrrolo[2,3-b]pyridine-5-carboxylate |
| 34 | 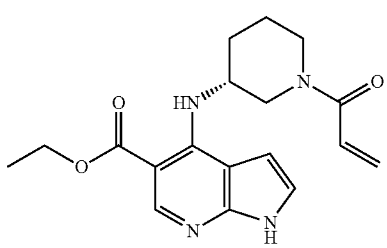 [SMILES: C=CC(=O)N1CCC[C@@H](Nc2c(C(=O)OCC)cnc3[nH]ccc23)C1] | ethyl (R)-4-((1-acryloylpiperidin-3-yl)amino)-1H-pyrrolo[2,3-b]pyridine-5-carboxylate |
| 35 | 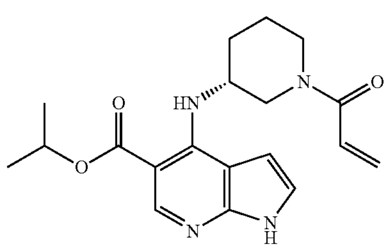 [SMILES: C=CC(=O)N1CCC[C@@H](Nc2c(C(=O)OC(C)C)cnc3[nH]ccc23)C1] | isopropyl (R)-4-((1-acryloylpiperidin-3-yl)amino)-1H-pyrrolo[2,3-b]pyridine-5-carboxylate |

-continued

| Example # | Structure | Name |
|---|---|---|
| 36 | 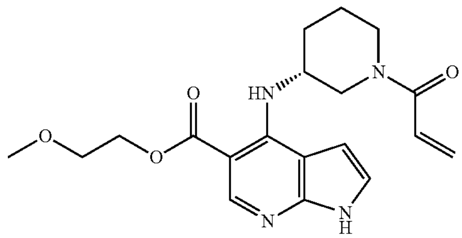 [SMILES: C=CC(=O)N1CCC[C@@H](Nc2c(C(=O)OCCOC)cnc3[nH]ccc23)C1] | 2-methoxyethyl (R)-4-((1-acryloylpiperidin-3-yl)amino)-1H-pyrrolo[2,3-b]pyridine-5-carboxylate |
| 37 | 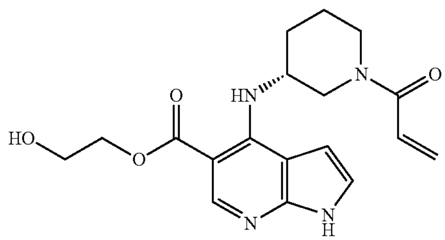 [SMILES: C=CC(=O)N1CCC[C@@H](Nc2c(C(=O)OCCO)cnc3[nH]ccc23)C1] | 2-hydroxyethyl (R)-4-((1-acryloylpiperidin-3-yl)amino)-1H-pyrrolo[2,3-b]pyridine-5-carboxylate |
| 38 | 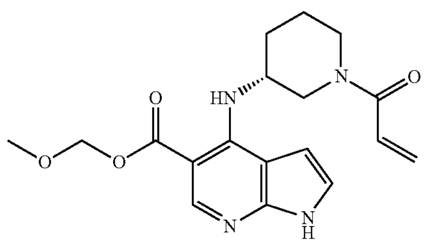 [SMILES: C=CC(=O)N1CCC[C@@H](Nc2c(C(=O)OCOC)cnc3[nH]ccc23)C1] | methoxymethyl (R)-4-((1-acryloylpiperidin-3-yl)amino)-1H-pyrrolo[2,3-b]pyridine-5-carboxylate |
| 39 | 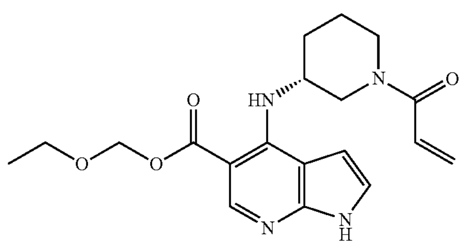 [SMILES: C=CC(=O)N1CCC[C@@H](Nc2c(C(=O)OCOCC)cnc3[nH]ccc23)C1] | ethoxymethyl (R)-4-((1-acryloylpiperidin-3-yl)amino)-1H-pyrrolo[2,3-b]pyridine-5-carboxylate |
| 40 | 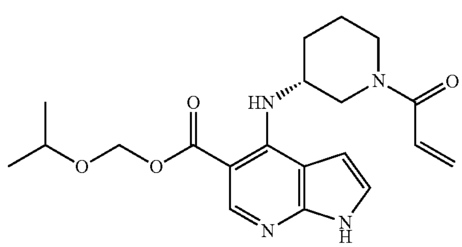 [SMILES: C=CC(=O)N1CCC[C@@H](Nc2c(C(=O)OCOC(C)C)cnc3[nH]ccc23)C1] | isopropoxymethyl (R)-4-((1-acryloylpiperidin-3-yl)amino)-1H-pyrrolo[2,3-b]pyridine-5-carboxylate |
| 41 | 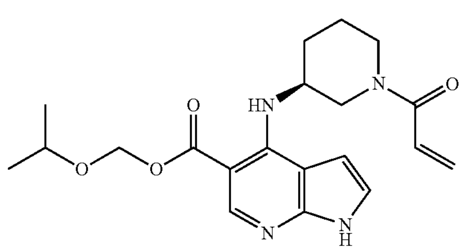 [SMILES: C=CC(=O)N1CCC[C@H](Nc2c(C(=O)OCOC(C)C)cnc3[nH]ccc23)C1] | isopropoxymethyl (S)-4-((1-acryloylpiperidin-3-yl)amino)-1H-pyrrolo[2,3-b]pyridine-5-carboxylate |

-continued

| Example # | Structure | Name |
|---|---|---|
| 42 | 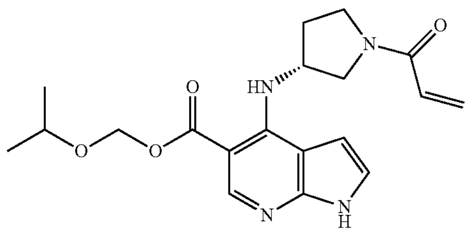 [SMILES: C=CC(=O)N1CC[C@@H](Nc2c(C(=O)OCOC(C)C)cnc3[nH]ccc23)C1] | isopropoxymethyl (R)-4-((1-acryloylpyrrolidin-3-yl)amino)-1H-pyrrolo[2,3-b]pyridine-5-carboxylate |
| 43 | 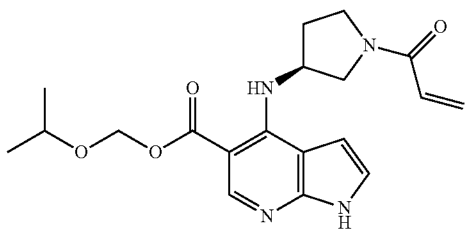 [SMILES: C=CC(=O)N1CC[C@H](Nc2c(C(=O)OCOC(C)C)cnc3[nH]ccc23)C1] | isopropoxymethyl (S)-4-((1-acryloylpyrrolidin-3-yl)amino)-1H-pyrrolo[2,3-b]pyridine-5-carboxylate |
| 44 | 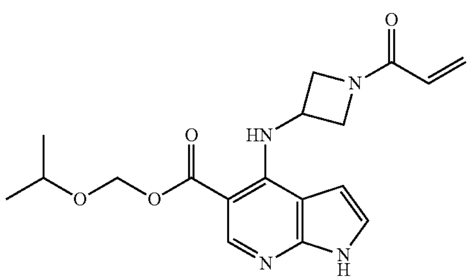 [SMILES: C=CC(=O)N1CC(Nc2c(C(=O)OCOC(C)C)cnc3[nH]ccc23)C1] | isopropoxymethyl 4-((1-acryloylazetidin-3-yl)amino)-1H-pyrrolo[2,3-b]pyridine-5-carboxylate |
| 45 | 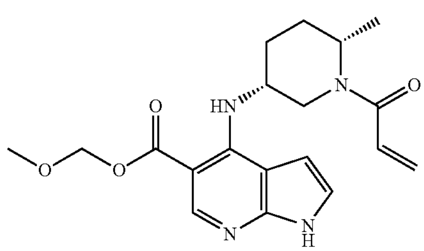 [SMILES: C=CC(=O)N1C[C@H](Nc2c(C(=O)OCOC)cnc3[nH]ccc23)CC[C@@H]1C] | methoxymethyl 4-(((3R,6S)-1-acryloyl-6-methylpiperidin-3-yl)amino)-1H-pyrrolo[2,3-b]pyridine-5-carboxylate |
| 46 | 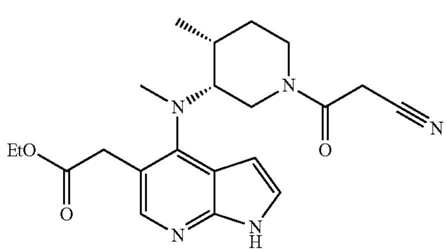 [SMILES: CCOC(=O)Cc1cnc2[nH]ccc2c1N(C)[C@H]1CN(C(=O)CC#N)CC[C@H]1C] | ethyl 2-(4-(((3R,4R)-1-(2-cyanoacetyl)-4-methylpiperidin-3-yl)(methyl)amino)-1H-pyrrolo[2,3-b]pyridin-5-yl)acetate |
| 47 | 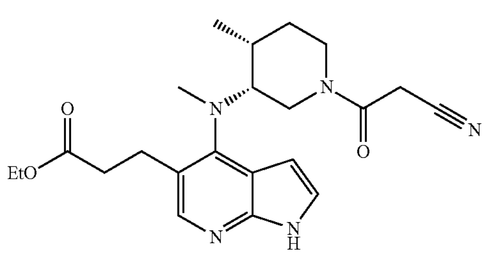 [SMILES: CCOC(=O)CCc1cnc2[nH]ccc2c1N(C)[C@H]1CN(C(=O)CC#N)CC[C@H]1C] | ethyl 3-(4-(((3R,4R)-1-(2-cyanoacetyl)-4-methylpiperidin-3-yl)(methyl)amino)-1H-pyrrolo[2,3-b]pyridin-5-yl)propanoate |

| Example # | Structure | Name |
|---|---|---|
| 48 | 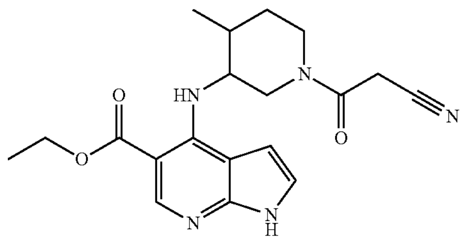 [SMILES: CCOC(=O)c1cnc2[nH]ccc2c1NC1CN(C(=O)CC#N)CCC1C] | ethyl 4-((1-(2-cyanoacetyl)-4-methylpiperidin-3-yl)amino)-1H-pyrrolo[2,3-b]pyridine-5-carboxylate |
| 49 | 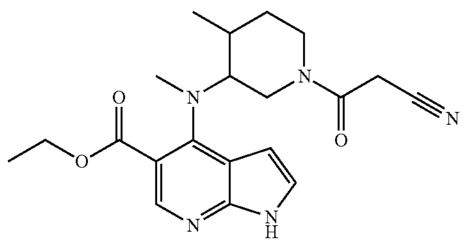 [SMILES: CCOC(=O)c1cnc2[nH]ccc2c1N(C)C1CN(C(=O)CC#N)CCC1C] | ethyl 4-((1-(2-cyanoacetyl)-4-methylpiperidin-3-yl)(methyl)amino)-1H-pyrrolo[2,3-b]pyridine-5-carboxylate |
| 50 | 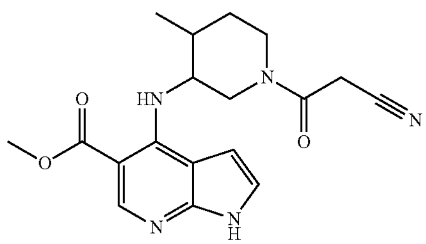 [SMILES: COC(=O)c1cnc2[nH]ccc2c1NC1CN(C(=O)CC#N)CCC1C] | methyl 4-((1-(2-cyanoacetyl)-4-methylpiperidin-3-yl)amino)-1H-pyrrolo[2,3-b]pyridine-5-carboxylate |
| 51 | 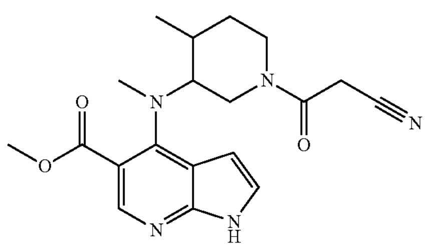 [SMILES: COC(=O)c1cnc2[nH]ccc2c1N(C)C1CN(C(=O)CC#N)CCC1C] | methyl 4-((1-(2-cyanoacetyl)-4-methylpiperidin-3-yl)(methyl)amino)-1H-pyrrolo[2,3-b]pyridine-5-carboxylate |
| 52 | 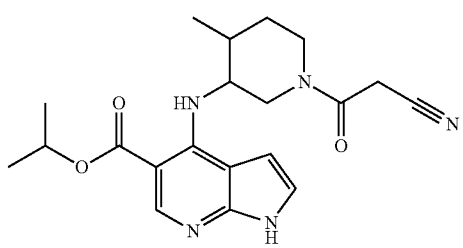 [SMILES: CC(C)OC(=O)c1cnc2[nH]ccc2c1NC1CN(C(=O)CC#N)CCC1C] | isopropyl 4-((1-(2-cyanoacetyl)-4-methylpiperidin-3-yl)amino)-1H-pyrrolo[2,3-b]pyridine-5-carboxylate |
| 53 | 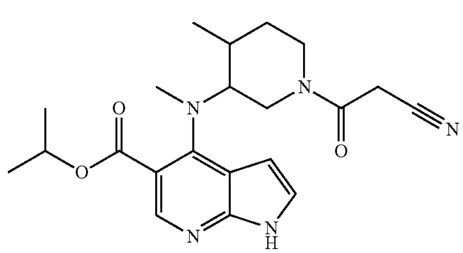 [SMILES: CC(C)OC(=O)c1cnc2[nH]ccc2c1N(C)C1CN(C(=O)CC#N)CCC1C] | isopropyl 4-((1-(2-cyanoacetyl)-4-methylpiperidin-3-yl)(methyl)amino)-1H-pyrrolo[2,3-b]pyridine-5-carboxylate |

| Example # | Structure | Name |
|---|---|---|
| 54 | 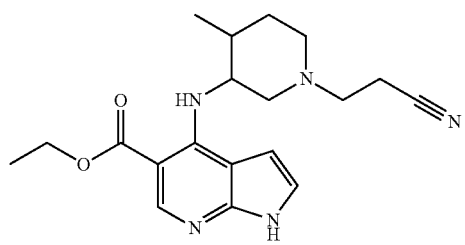 [SMILES: CCOC(=O)c1cnc2[nH]ccc2c1NC1CN(CCC#N)CCC1C] | ethyl 4-((1-(2-cyanoethyl)-4-methylpiperidin-3-yl)amino)-1H-pyrrolo[2,3-b]pyridine-5-carboxylate |
| 55 | 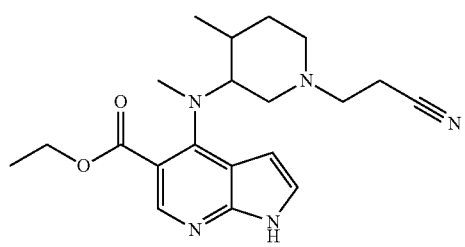 [SMILES: CCOC(=O)c1cnc2[nH]ccc2c1N(C)C1CN(CCC#N)CCC1C] | ethyl 4-((1-(2-cyanoethyl)-4-methylpiperidin-3-yl)(methyl)amino)-1H-pyrrolo[2,3-b]pyridine-5-carboxylate |
| 56 | 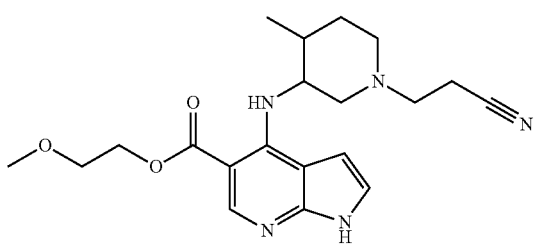 [SMILES: COCCOC(=O)c1cnc2[nH]ccc2c1NC1CN(CCC#N)CCC1C] | 2-methoxyethyl 4-((1-(2-cyanoethyl)-4-methylpiperidin-3-yl)amino)-1H-pyrrolo[2,3-b]pyridine-5-carboxylate |
| 57 | 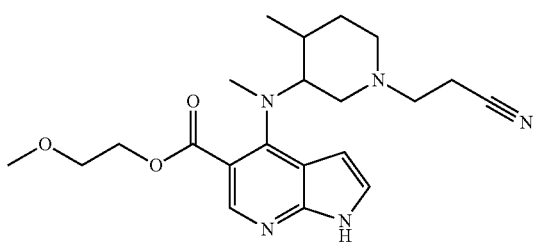 [SMILES: COCCOC(=O)c1cnc2[nH]ccc2c1N(C)C1CN(CCC#N)CCC1C] | 2-methoxyethyl 4-((1-(2-cyanoethyl)-4-methylpiperidin-3-yl)amino)-1H-pyrrolo[2,3-b]pyridine-5-carboxylate |
| 58 | 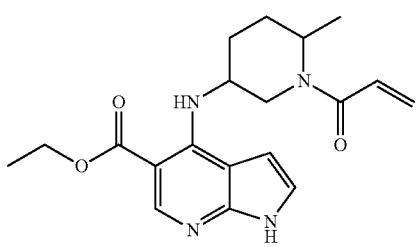 [SMILES: C=CC(=O)N1CC(Nc2c(C(=O)OCC)cnc3[nH]ccc23)CCC1C] | ethyl 4-((1-acryloyl-6-methylpiperidin-3-yl)amino)-1H-pyrrolo[2,3-b]pyridine-5-carboxylate |
| 59 | 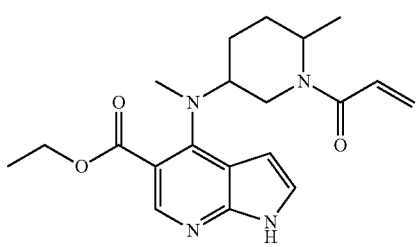 [SMILES: C=CC(=O)N1CC(N(C)c2c(C(=O)OCC)cnc3[nH]ccc23)CCC1C] | ethyl 4-((1-acryloyl-6-methylpiperidin-3-yl)(methyl)amino)-1H-pyrrolo[2,3-b]pyridine-5-carboxylate |

| Example # | Structure | Name |
|---|---|---|
| 60 | 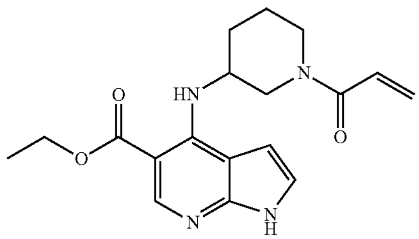 [SMILES: C=CC(=O)N1CCCC(Nc2c(C(=O)OCC)cnc3[nH]ccc23)C1] | ethyl 4-((1-acryloylpiperidin-3-yl)amino)-1H-pyrrolo[2,3-b]pyridine-5-carboxylate |
| 61 | 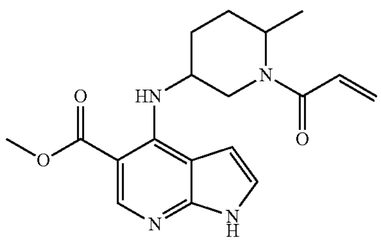 [SMILES: C=CC(=O)N1CC(Nc2c(C(=O)OC)cnc3[nH]ccc23)CCC1C] | methyl 4-((1-acryloyl-6-methylpiperidin-3-yl)amino)-1H-pyrrolo[2,3-b]pyridine-5-carboxylate |
| 62 | 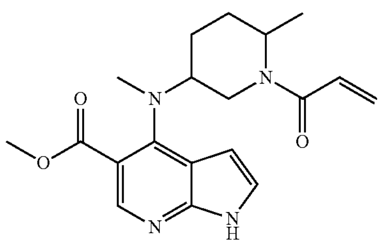 [SMILES: C=CC(=O)N1CC(N(C)c2c(C(=O)OC)cnc3[nH]ccc23)CCC1C] | methyl 4-((1-acryloyl-6-methylpiperidin-3-yl(methyl)amino)-1H-pyrrolo[2,3-b]pyridine-5-carboxylate |
| 63 | 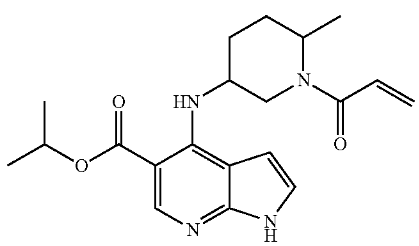 [SMILES: C=CC(=O)N1CC(Nc2c(C(=O)OC(C)C)cnc3[nH]ccc23)CCC1C] | isopropyl 4-((1-acryloyl-6-methylpiperidin-3-yl)amino)-1H-pyrrolo[2,3-b]pyridine-5-carboxylate |
| 64 | 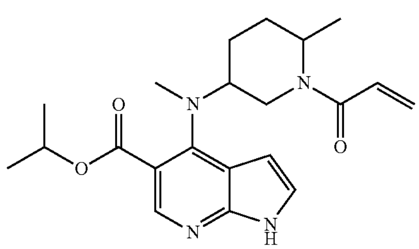 [SMILES: C=CC(=O)N1CC(N(C)c2c(C(=O)OC(C)C)cnc3[nH]ccc23)CCC1C] | isopropyl 4-((1-acryloyl-6-methylpiperidin-3-yl)(methyl)amino)-1H-pyrrolo[2,3-b]pyridine-5-carboxylate |
| 65 | 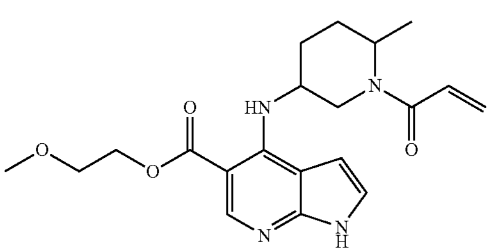 [SMILES: C=CC(=O)N1CC(Nc2c(C(=O)OCCOC)cnc3[nH]ccc23)CCC1C] | 2-methoxyethyl 4-((1-acryloyl-6-methylpiperidin-3-yl)amino)-1H-pyrrolo[2,3-b]pyridine-5-carboxylate |

| Example # | Structure | Name |
|---|---|---|
| 66 | 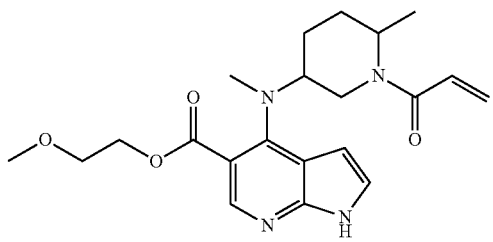 [SMILES: C=CC(=O)N1CC(N(C)c2c(C(=O)OCCOC)cnc3[nH]ccc23)CCC1C] | 2-methoxyethyl 4-((1-acryloyl-6-methylpiperidin-3-yl)(methyl)amino)-1H-pyrrolo[2,3-b]pyridine-5-carboxylate |
| 117 | 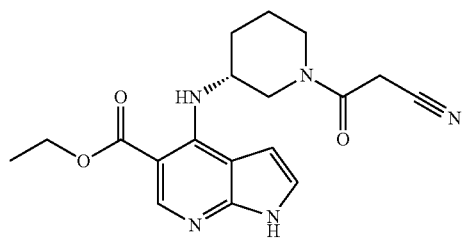 [SMILES: CCOC(=O)c1cnc2[nH]ccc2c1N[C@@H]1CCCN(C(=O)CC#N)C1] | ethyl (R)-4-((1-(2-cyanoacetyl)piperidin-3-yl)amino)-1H-pyrrolo[2,3-b]pyridine-5-carboxylate |
| 118 | 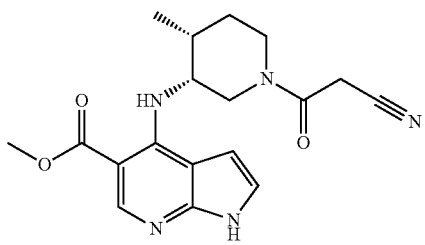 [SMILES: COC(=O)c1cnc2[nH]ccc2c1N[C@H]1CN(C(=O)CC#N)CC[C@H]1C] | methyl 4-(((3R,4R)-1-(2-cyanoacetyl)-4-methylpiperidin-3-yl)amino)-1H-pyrrolo[2,3-b]pyridine-5-carboxylate |
| 119 | 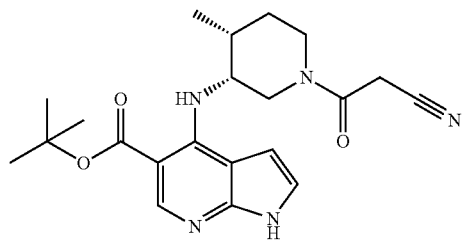 [SMILES: C[C@@H]1CCN(C(=O)CC#N)C[C@@H]1Nc1c(C(=O)OC(C)(C)C)cnc2[nH]ccc12] | tert-butyl 4-(((3R,4R)-1-(2-cyanoacetyl)-4-methylpiperidin-3-yl)amino)-1H-pyrrolo[2,3-b]pyridine-5-carboxylate |
| 123 | 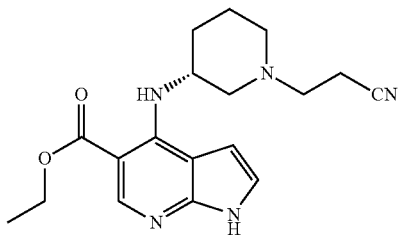 [SMILES: CCOC(=O)c1cnc2[nH]ccc2c1N[C@@H]1CCCN(CCC#N)C1] | ethyl (R)-4-((1-(2-cyanoethyl)piperidin-3-yl)amino)-1H-pyrrolo[2,3-b]pyridine-5-carboxylate |
| 124 | 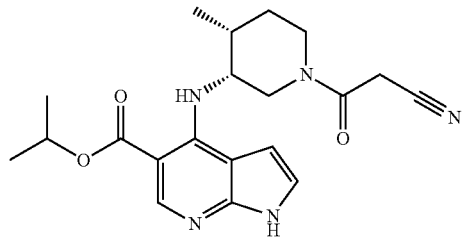 [SMILES: CC(C)OC(=O)c1cnc2[nH]ccc2c1N[C@H]1CN(C(=O)CC#N)CC[C@H]1C] | isopropyl 4-(((3R,4R)-1-(2-(cyanoacetyl)-4-methylpiperidin-3-yl)amino)-1H-pyrrolo[2,3-b]pyridine-5-carboxylate |

| Example # | Structure | Name |
|---|---|---|
| 125 | 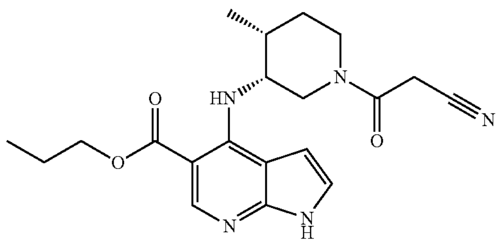 [SMILES: CCCOC(=O)c1cnc2[nH]ccc2c1N[C@H]1CN(C(=O)CC#N)CC[C@H]1C] | propyl 4-(((3R,4R)-1-(2-cyanoacetyl)-4-methylpiperidin-3-yl)amino)-1H-pyrrolo[2,3-b]pyridine-5-carboxylate |
| 126 | 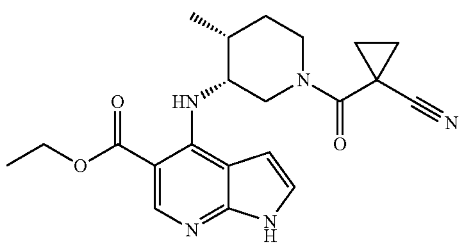 [SMILES: CCOC(=O)c1cnc2[nH]ccc2c1N[C@H]1CN(C(=O)C2(C#N)CC2)CC[C@H]1C] | ethyl 4-(((3R,4R)-1-(1-cyanocyclopropane-1-carbonyl)-4-methylpiperidin-3-yl)amino)-1H-pyrrolo[2,3-b]pyridine-5-carboxylate |
| 127 | 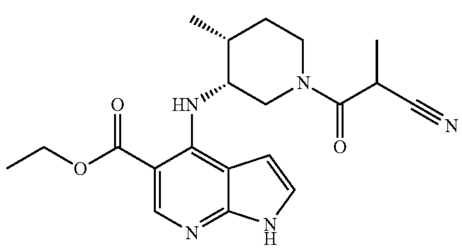 [SMILES: CCOC(=O)c1cnc2[nH]ccc2c1N[C@H]1CN(C(=O)C(C)C#N)CC[C@H]1C] | ethyl 4-(((3R,4R)-1-(2-cyanopropanoyl)-4-methylpiperidin-3-yl)amino)-1H-pyrrolo[2,3-b]pyridine-5-carboxylate |
| 128 | 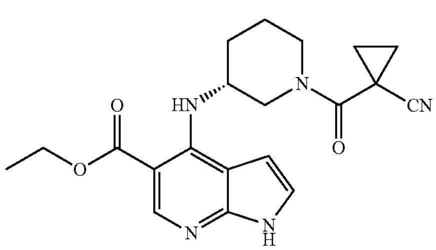 [SMILES: CCOC(=O)c1cnc2[nH]ccc2c1N[C@@H]1CCCN(C(=O)C2(C#N)CC2)C1] | ethyl (R)-4-((1-(1-cyanocyclopropane-1-carbonyl)piperidin-3-yl)amino)-1H-pyrrolo[2,3-b]pyridine-5-carboxylate |
| 129 | 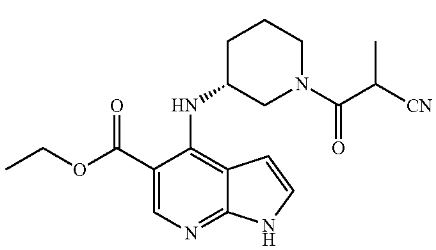 [SMILES: CCOC(=O)c1cnc2[nH]ccc2c1N[C@@H]1CCCN(C(=O)C(C)C#N)C1] | ethyl 4-(((3R)-1-(2-cyanopropanoyl)piperidin-3-yl)amino)-1H-pyrrolo[2,3-b]pyridine-5-carboxylate |
| 130 | 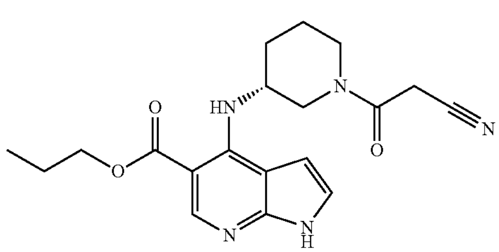 [SMILES: CCCOC(=O)c1cnc2[nH]ccc2c1N[C@@H]1CCCN(C(=O)CC#N)C1] | propyl (R)-4-((1-(2-cyanoacetyl)piperidin-3-yl)amino)-1H-pyrrolo[2,3-b]pyridine-5-carboxylate |

| Example # | Structure | Name |
|---|---|---|
| 131 | 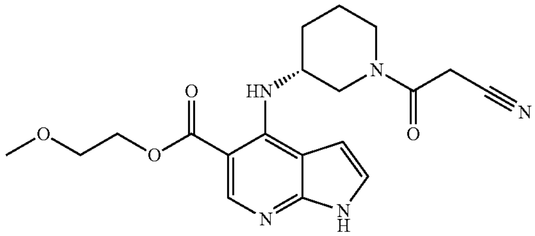 [SMILES: COCCOC(=O)c1cnc2[nH]ccc2c1N[C@@H]1CCCN(C(=O)CC#N)C1] | 2-methoxyethyl (R)-4-((1-(2-cyanoacetyl)piperidin-3-yl)amino)-1H-pyrrolo[2,3-b]pyridine-5-carboxylate |
| 143 | 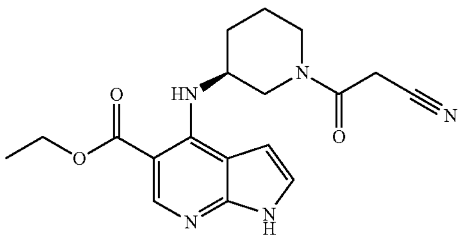 [SMILES: CCOC(=O)c1cnc2[nH]ccc2c1N[C@H]1CCCN(C(=O)CC#N)C1] | ethyl (S)-4-((1-(2-cyanoacetyl)piperidin-3-yl)amino)-1H-pyrrolo[2,3-b]pyridine-5-carboxylate |
| 144 | 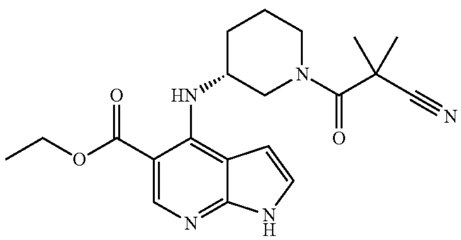 [SMILES: CCOC(=O)c1cnc2[nH]ccc2c1N[C@@H]1CCCN(C(=O)C(C)(C)C#N)C1] | ethyl (R)-4-((1-(2-cyano-2-methylpropanoyl)piperidin-3-yl)amino)-1H-pyrrolo[2,3-b]pyridine-5-carboxylate |
| 146 | 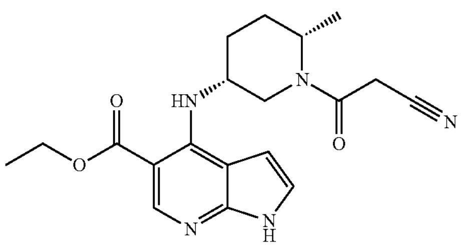 [SMILES: CCOC(=O)c1cnc2[nH]ccc2c1N[C@@H]1CC[C@H](C)N(C(=O)CC#N)C1] | ethyl 4-(((3R,6S)-1-(2-cyanoacetyl)-6-methylpiperidin-3-yl)amino)-1H-pyrrolo[2,3-b]pyridine-5-carboxylate |
| 156 | 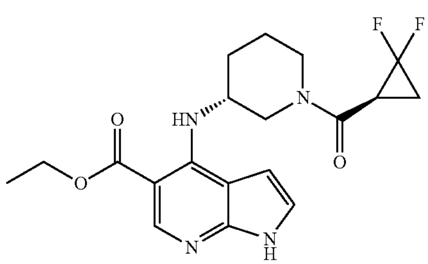 [SMILES: CCOC(=O)c1cnc2[nH]ccc2c1N[C@@H]1CCCN(C(=O)[C@@H]2CC2(F)F)C1] | ethyl 4-(((R)-1-((S)-2,2-difluorocyclopropane-1-carbonyl)piperidin-3-yl)amino)-1H-pyrrolo[2,3-b]pyridine-5-carboxylate |
| 157 | 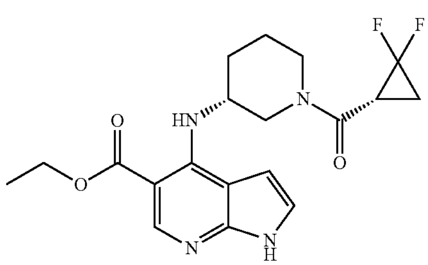 [SMILES: CCOC(=O)c1cnc2[nH]ccc2c1N[C@@H]1CCCN(C(=O)[C@H]2CC2(F)F)C1] | ethyl-4-(((R)-1-((R)-2,2-difluorocyclopropane-1-carbonyl)piperidin-3-yl)amino)-1H-pyrrolo[2,3-b]pyridine-5-carboxylate |

-continued

| Example # | Structure | Name |
|---|---|---|
| 158 | 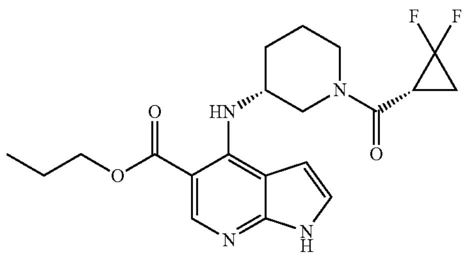 [SMILES: CCCOC(=O)c1cnc2[nH]ccc2c1N[C@@H]1CCCN(C(=O)[C@H]2CC2(F)F)C1] | propyl 4-(((R)-1-((R)-2,2-difluorocyclopropane-1-carbonyl)piperidin-3-yl)amino)-1H-pyrrolo[2,3-b]pyridine-5-carboxylate |
| 159 | 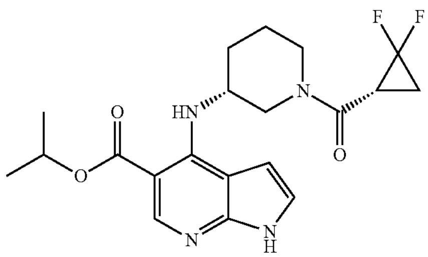 [SMILES: CC(C)OC(=O)c1cnc2[nH]ccc2c1N[C@@H]1CCCN(C(=O)[C@H]2CC2(F)F)C1] | isopropyl 4-(((R)-1-((R)-2,2-difluorocyclopropane-1-carbonyl)piperidin-3-yl)amino)-1H-pyrrolo[2,3-b]pyridine-5-carboxylate |
| 160 | 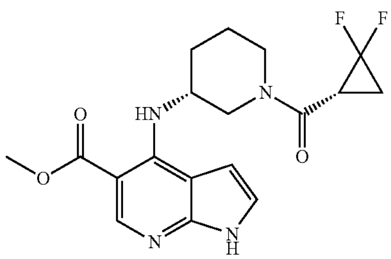 [SMILES: COC(=O)c1cnc2[nH]ccc2c1N[C@@H]1CCCN(C(=O)[C@H]2CC2(F)F)C1] | methyl 4-(((R)-1-((R)-2,2-difluorocyclopropane-1-carbonyl)piperidin-3-yl)amino)-1H-pyrrolo[2,3-b]pyridine-5-carboxylate |
| 170 | 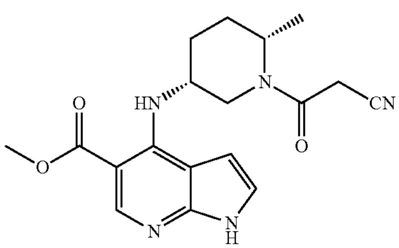 [SMILES: COC(=O)c1cnc2[nH]ccc2c1N[C@@H]1CC[C@H](C)N(C(=O)CC#N)C1] | methyl 4-(((3R,6S)-1-(2-cyanoacetyl)-6-methylpiperidin-3-yl)amino)-1H-pyrrolo[2,3-b]pyridine-5-carboxylate |
| 171 | 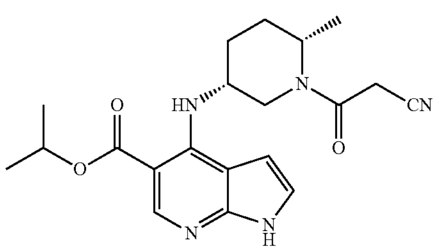 [SMILES: CC(C)OC(=O)c1cnc2[nH]ccc2c1N[C@@H]1CC[C@H](C)N(C(=O)CC#N)C1] | isopropyl 4-(((3R,6S)-1-(2-cyanoacetyl)-6-methylpiperidin-3-yl)amino)-1H-pyrrolo[2,3-b]pyridine-5-carboxylate |
| 172 | 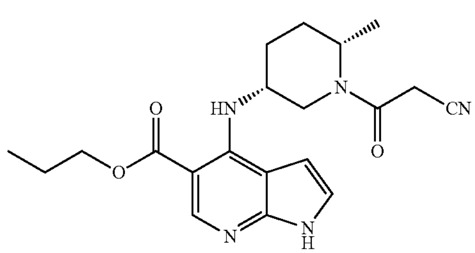 [SMILES: CCCOC(=O)c1cnc2[nH]ccc2c1N[C@@H]1CC[C@H](C)N(C(=O)CC#N)C1] | propyl 4-(((3R,6S)-1-(2-cyanoacetyl)-6-methylpiperidin-3-yl)amino)-1H-pyrrolo[2,3-b]pyridine-5-carboxylate |

-continued

| Example # | Structure | Name |
|---|---|---|
| 173 | 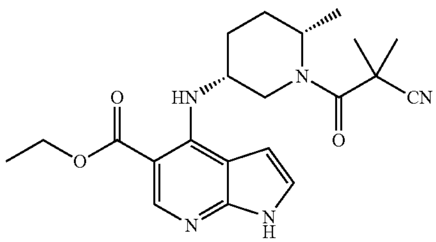 [SMILES: CCOC(=O)c1cnc2[nH]ccc2c1N[C@@H]1CC[C@H](C)N(C(=O)C(C)(C)C#N)C1] | ethyl 4-(((3R,6S)-1-(2-cyano-2-methylpropanoyl)-6-methylpiperidin-3-yl)amino)-1H-pyrrolo[2,3-b]pyridine-5-carboxylate |
| 174 | 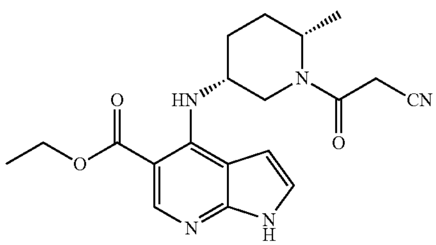 [SMILES: CCOC(=O)c1cnc2[nH]ccc2c1N[C@@H]1CC[C@H](C)N(C(=O)CC#N)C1] | ethyl 4-(((3R,6S)-1-(2-cyanoethyl)-6-methylpiperidin-3-yl)amino)-1H-pyrrolo[2,3-b]pyridine-5-carboxylate |
| 175 | 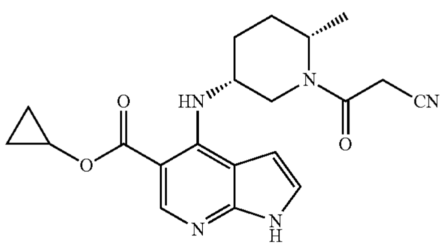 [SMILES: C[C@H]1CC[C@@H](Nc2c(C(=O)OC3CC3)cnc3[nH]ccc23)CN1C(=O)CC#N] | cyclopropyl 4-(((3R,6S)-1-(2-cyanoacetyl)-6-methylpiperidin-3-yl)amino)-1H-pyrrolo[2,3-b]pyridine-5-carboxylate |
| 176 | 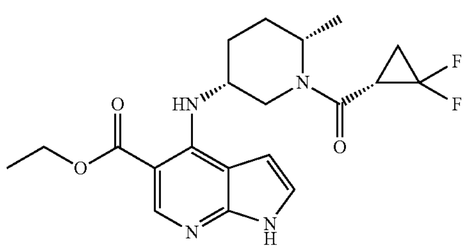 [SMILES: CCOC(=O)c1cnc2[nH]ccc2c1N[C@@H]1CC[C@H](C)N(C(=O)[C@@H]2CC2(F)F)C1] | ethyl 4-(((3R,6S)-1-((S)-2,2-difluorocyclopropane-1-carbonyl)-6-methylpiperidin-3-yl)amino)-1H-pyrrolo[2,3-b]pyridine-5-carboxylate |
| 177 | 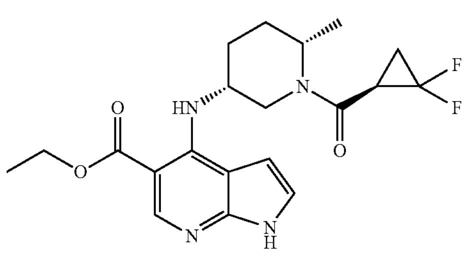 [SMILES: CCOC(=O)c1cnc2[nH]ccc2c1N[C@@H]1CC[C@H](C)N(C(=O)[C@H]2CC2(F)F)C1] | ethyl 4-(((3R,6S)-1-((R)-2,2-difluorocyclopropane-1-carbonyl)-6-methylpiperidin-3-yl)amino)-1H-pyrrolo[2,3-b]pyridine-5-carboxylate |
| 178 | 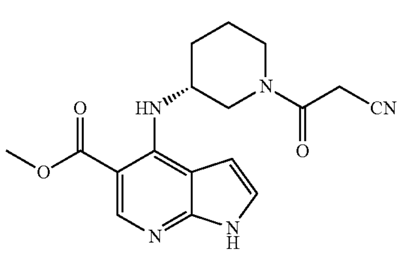 [SMILES: COC(=O)c1cnc2[nH]ccc2c1N[C@@H]1CCCN(C(=O)CC#N)C1] | methyl (R)-4-((1-(2-cyanoacetyl)piperidin-3-yl)amino)-1H-pyrrolo[2,3-b]pyridine-5-carboxylate |

-continued

| Example # | Structure | Name |
|---|---|---|
| 179 | 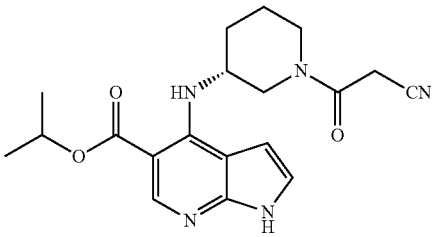 [SMILES: CC(C)OC(=O)c1cnc2[nH]ccc2c1N[C@@H]1CCCN(C(=O)CC#N)C1] | isopropyl (R)-4-((1-(2-cyanoacetyl)piperidin-3-yl)amino)-1H-pyrrolo[2,3-b]pyridine-5-carboxylate |
| 180 | 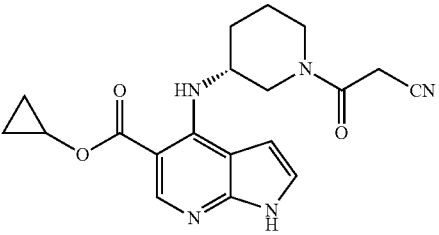 [SMILES: N#CCC(=O)N1CCC[C@@H](Nc2c(C(=O)OC3CC3)cnc3[nH]ccc23)C1] | cyclopropyl (R)-4-((1-(2-cyanoacetyl)piperidin-3-yl)amino)-1H-pyrrolo[2,3-b]pyridine-5-carboxylate |
| 181 | 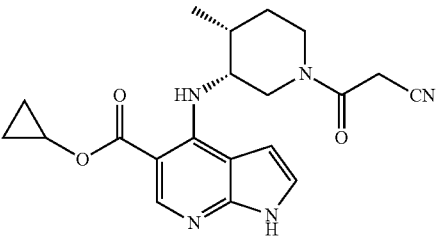 [SMILES: C[C@@H]1CCN(C(=O)CC#N)C[C@@H]1Nc1c(C(=O)OC2CC2)cnc2[nH]ccc12] | cyclopropyl 4-(((3R,4R)-1-(2-cyanoacetyl)-4-methylpiperidin-3-yl)amino)-1H-pyrrolo[2,3-b]pyridine-5-carboxylate |
| 182 | 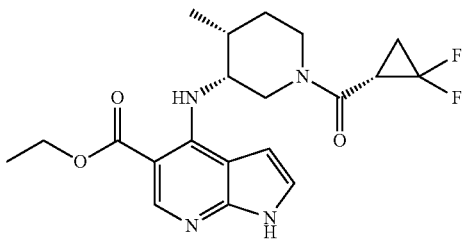 [SMILES: CCOC(=O)c1cnc2[nH]ccc2c1N[C@H]1CN(C(=O)[C@@H]2CC2(F)F)CC[C@H]1C] | ethyl 4-(((3R,4R)-1-((S)-2,2-difluorocyclopropane-1-carbonyl)-4-methylpiperidin-3-yl)amino)-1H-pyrrolo[2,3-b]pyridine-5-carboxylate |
| 183 | 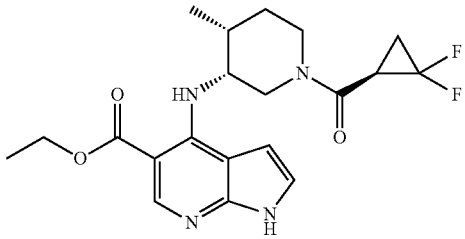 [SMILES: CCOC(=O)c1cnc2[nH]ccc2c1N[C@H]1CN(C(=O)[C@H]2CC2(F)F)CC[C@H]1C] | ethyl 4-(((3R,4R)-1-((R)-2,2-difluorocyclopropane-1-carbonyl)-4-methylpiperidin-3-yl)amino)-1H-pyrrolo[2,3-b]pyridine-5-carboxylate |
| 197 | 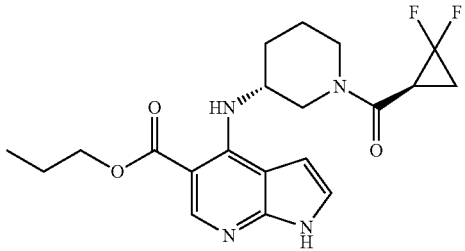 [SMILES: CCCOC(=O)c1cnc2[nH]ccc2c1N[C@@H]1CCCN(C(=O)[C@@H]2CC2(F)F)C1] | propyl 4-(((R)-1-((S)-2,2-difluorocyclopropane-1-carbonyl)piperidin-3-yl)amino)-1H-pyrrolo[2,3-b]pyridine-5-carboxylate |

| Example # | Structure | Name |
|---|---|---|
| 198 | 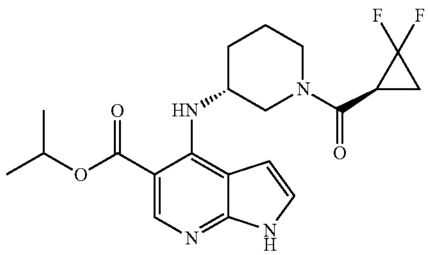 [SMILES: CC(C)OC(=O)c1cnc2[nH]ccc2c1N[C@@H]1CCCN(C(=O)[C@@H]2CC2(F)F)C1] | ispropyl 4-(((R)-1-((S)-2,2-difluorocyclopropane-1-carbonyl)piperidin-3-yl)amino)-1H-pyrrolo[2,3-b]pyridine-5-carboxylate |
| 199 | 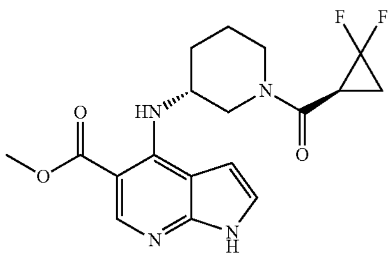 [SMILES: COC(=O)c1cnc2[nH]ccc2c1N[C@@H]1CCCN(C(=O)[C@@H]2CC2(F)F)C1] | methyl 4-(((R)-1-((S)-2,2-difluorocyclopropane-1-carbonyl)piperidin-3-yl)amino)-1H-pyrrolo[2,3-b]pyridine-5-carboxylate |

The invention is further illustrated by the following examples of compounds of Formula (II)

| Example # | Structure | Name |
|---|---|---|
| 67 | 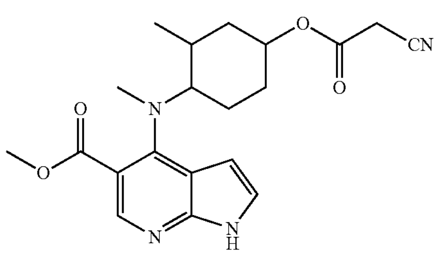 [SMILES: COC(=O)c1cnc2[nH]ccc2c1N(C)C1CCC(OC(=O)CC#N)CC1C] | methyl 4-((4-(2-cyanoacetoxy)-2-methylcyclohexyl)(methyl)amino)-1H-pyrrolo[2,3-b]pyridine-5-carboxylate |
| 68 | 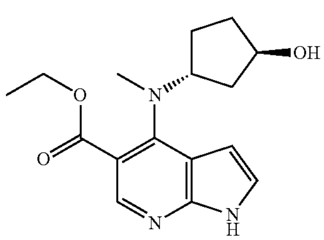 [SMILES: CCOC(=O)c1cnc2[nH]ccc2c1N(C)[C@@H]1CC[C@@H](O)C1] | ethyl 4-(((1R,3R)-3-hydroxycyclopentyl)(methyl)amino)-1H-pyrrolo[2,3-b]pyridine-5-carboxylate |
| 69 | 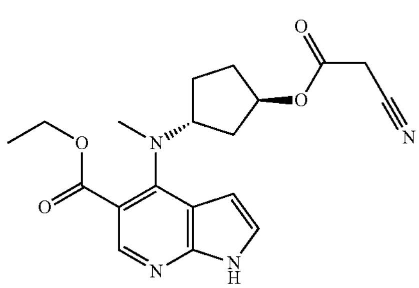 [SMILES: CCOC(=O)c1cnc2[nH]ccc2c1N(C)[C@@H]1CC[C@@H](OC(=O)CC#N)C1] | ethyl 4-(((1R,3R)-3-(2-cyanoacetoxy)cyclopentyl)(methyl)amino)-1H-pyrrolo[2,3-b]pyridine-5-carboxylate |

-continued

| Example # | Structure | Name |
|---|---|---|
| 70 | 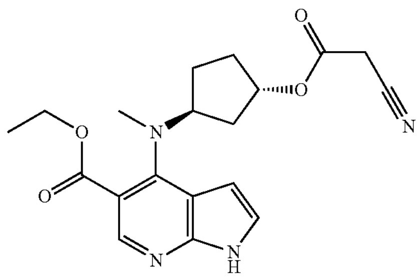 [SMILES: CCOC(=O)c1cnc2[nH]ccc2c1N(C)[C@H]1CC[C@H](OC(=O)CC#N)C1] | ethyl 4-(((1S,3S)-3-(2-cyanoacetoxy)cyclopentyl)(methyl)amino)-1H-pyrrolo[2,3-b]pyridine-5-carboxylate |
| 71 | 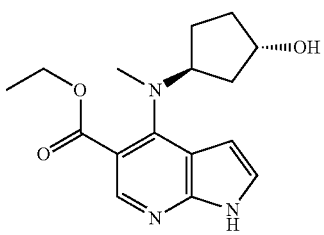 [SMILES: CCOC(=O)c1cnc2[nH]ccc2c1N(C)[C@H]1CC[C@H](O)C1] | ethyl 4-(((1S,3S)-3-hydroxycyclopentyl)(methyl)amino)-1H-pyrrolo[2,3-b]pyridine-5-carboxylate |
| 72 | 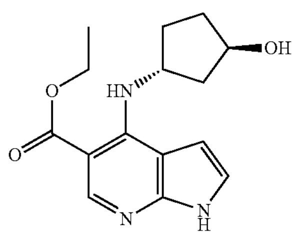 [SMILES: CCOC(=O)c1cnc2[nH]ccc2c1N[C@@H]1CC[C@@H](O)C1] | ethyl 4-(((1R,3R)-3-hydroxycyclopentyl)amino)-1H-pyrrolo[2,3-b]pyridine-5-carboxylate |
| 73 | 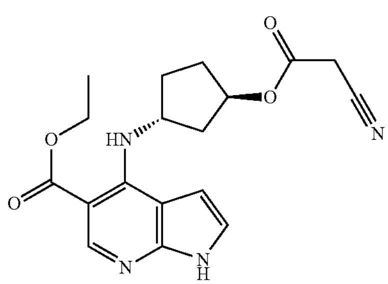 [SMILES: CCOC(=O)c1cnc2[nH]ccc2c1N[C@@H]1CC[C@@H](OC(=O)CC#N)C1] | ethyl 4-(((1R,3R)-3-(2-cyanoacetoxy)cyclopentyl)amino)-1H-pyrrolo[2,3-b]pyridine-5-carboxylate |
| 74 | 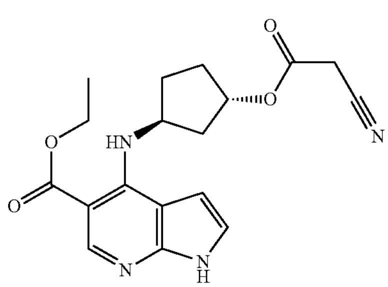 [SMILES: CCOC(=O)c1cnc2[nH]ccc2c1N[C@H]1CC[C@H](OC(=O)CC#N)C1] | ethyl 4-(((1S,3S)-3-(2-cyanoacetoxy)cyclopentyl)amino)-1H-pyrrolo[2,3-b]pyridine-5-carboxylate |
| 75 | 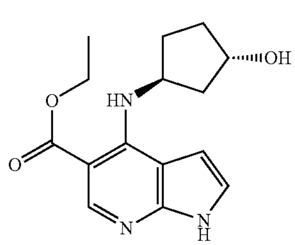 [SMILES: CCOC(=O)c1cnc2[nH]ccc2c1N[C@H]1CC[C@H](O)C1] | ethyl 4-(((1S,3S)-3-hydroxycyclopentyl)amino)-1H-pyrrolo[2,3-b]pyridine-5-carboxylate |

| Example # | Structure | Name |
|---|---|---|
| 76 | 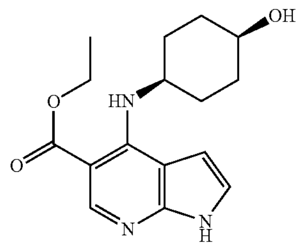 [SMILES: CCOC(=O)c1cnc2[nH]ccc2c1N[C@H]1CC[C@@H](O)CC1] | ethyl 4-(((1S,4S)-4-hydroxycyclohexyl)amino)-1H-pyrrolo[2,3-b]pyridine-5-carboxylate |
| 77 | 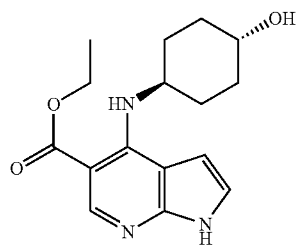 [SMILES: CCOC(=O)c1cnc2[nH]ccc2c1N[C@H]1CC[C@H](O)CC1] | ethyl 4-(((1R,4R)-4-hydroxycyclohexyl)amino)-1H-pyrrolo[2,3-b]pyridine-5-carboxylate |
| 78 | 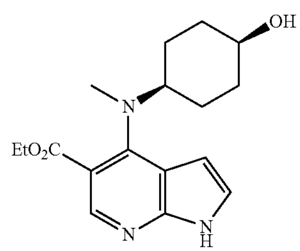 [SMILES: CCOC(=O)c1cnc2[nH]ccc2c1N(C)[C@H]1CC[C@@H](O)CC1] | ethyl 4-(((1S,4S)-4-hydroxycyclohexyl)(methyl)amino)-1H-pyrrolo[2,3-b]pyridine-5-carboxylate |
| 79 | 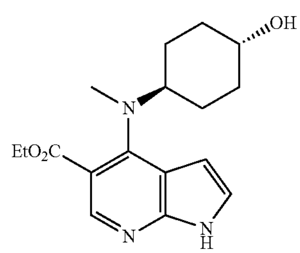 [SMILES: CCOC(=O)c1cnc2[nH]ccc2c1N(C)[C@H]1CC[C@H](O)CC1] | ethyl 4-(((1R,4R)-4-hydroxycyclohexyl)(methyl)amino)-1H-pyrrolo[2,3-b]pyridine-5-carboxylate |
| 80 | 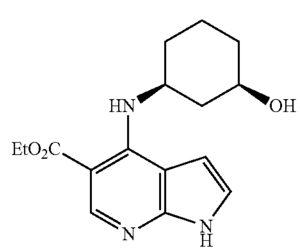 [SMILES: CCOC(=O)c1cnc2[nH]ccc2c1N[C@H]1CCC[C@@H](O)C1] | ethyl 4-(((1S,3R)-3-hydroxycyclohexyl)amino)-1H-pyrrolo[2,3-b]pyridine-5-carboxylate |
| 81 | 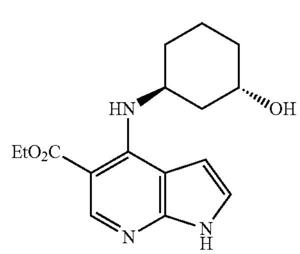 [SMILES: CCOC(=O)c1cnc2[nH]ccc2c1N[C@H]1CCC[C@H](O)C1] | ethyl 4-(((1S,3S)-3-hydroxycyclohexyl)amino)-1H-pyrrolo[2,3-b]pyridine-5-carboxylate |

-continued

| Example # | Structure | Name |
|---|---|---|
| 82 | 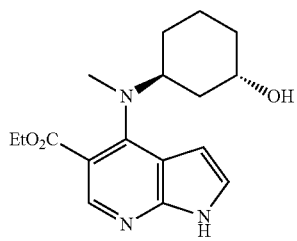 [SMILES: CCOC(=O)c1cnc2[nH]ccc2c1N(C)[C@H]1CCC[C@H](O)C1] | ethyl 4-(((1S,3S)-3-hydroxycyclohexyl)(methyl)amino)-1H-pyrrolo[2,3-b]pyridine-5-carboxylate |
| 83 | 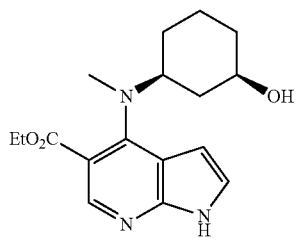 [SMILES: CCOC(=O)c1cnc2[nH]ccc2c1N(C)[C@H]1CCC[C@@H](O)C1] | ethyl 4-(((1S,3R)-3-hydroxycyclohexyl)(methyl)amino)-1H-pyrrolo[2,3-b]pyridine-5-carboxylate |
| 84 | 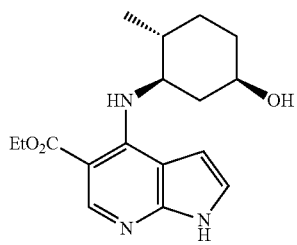 [SMILES: CCOC(=O)c1cnc2[nH]ccc2c1N[C@@H]1C[C@H](O)CC[C@H]1C] | ethyl 4-(((1R,2R,5R)-5-hydroxy-2-methylcyclohexyl)amino)-1H-pyrrolo[2,3-b]pyridine-5-carbonyl |
| 85 | 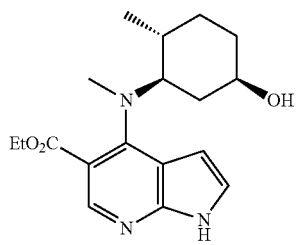 [SMILES: CCOC(=O)c1cnc2[nH]ccc2c1N(C)[C@@H]1C[C@H](O)CC[C@H]1C] | ethyl 4-(((1R,2R,54R)-5-hydroxy-2-methylcyclohexyl)(methyl)amino)-1H-pyrrolo[2,3-b]pyridine-5-carboxylate |
| 86 | 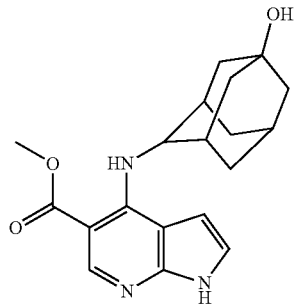 [SMILES: COC(=O)c1cnc2[nH]ccc2c1NC1C2CC3CC1CC(O)(C3)C2] | methyl 4-(((1R,3S,5s,7s)-5-hydroxyadamantan-2-yl)amino)-1H-pyrrolo[2,3-b]pyridine-5-carboxylate |

| Example # | Structure | Name |
|---|---|---|
| 87 | 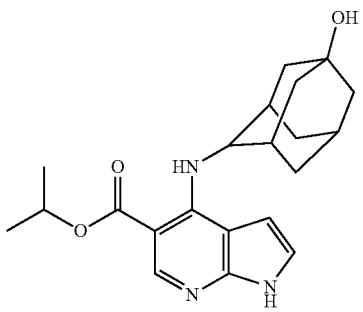 [SMILES: CC(C)OC(=O)c1cnc2[nH]ccc2c1NC1C2CC3CC1CC(O)(C3)C2] | isopropyl 4-(((1R,3S,5s,7s)-5-hydroxyadamantan-2-yl)amino)-1H-pyrrolo[2,3-b]pyridine-5-carboxylate |
| 88 | 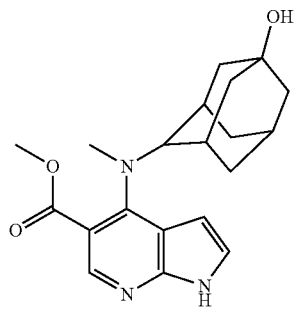 [SMILES: COC(=O)c1cnc2[nH]ccc2c1N(C)C1C2CC3CC1CC(O)(C3)C2] | methyl 4-(((1R,3S,5s,7s)-5-hydroxyadamantan-2-yl)(methyl)amino)-1H-pyrrolo[2,3-b]pyridine-5-carboxylate |
| 89 | 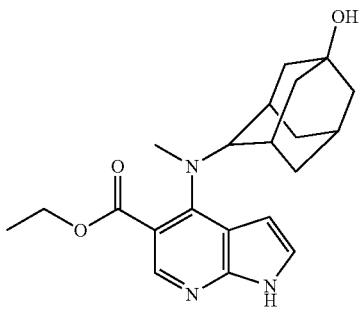 [SMILES: CCOC(=O)c1cnc2[nH]ccc2c1N(C)C1C2CC3CC1CC(O)(C3)C2] | ethyl 4-(((1R,3S,5S,7S)-5-hydroxyadamantan-2-yl)(methyl)amino)-1H-pyrrolo[2,3-b]pyridine-5-carboxylate |
| 90 | 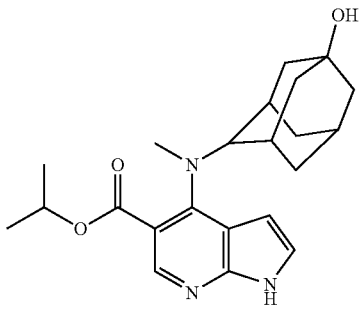 [SMILES: CC(C)OC(=O)c1cnc2[nH]ccc2c1N(C)C1C2CC3CC1CC(O)(C3)C2] | isopropyl 4-(((1R,3S,5S,7S)-5-hydroxyadamantan-2-yl)(methyl)amino)-1H-pyrrolo[2,3-b]pyridine-5-carboxylate |

| Example # | Structure | Name |
|---|---|---|
| 91 | 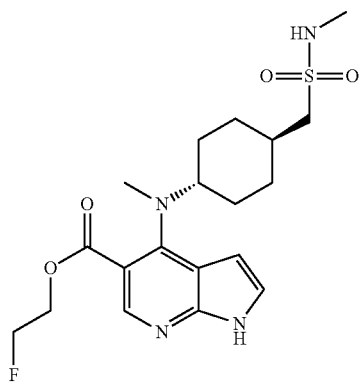 [SMILES: CNS(=O)(=O)C[C@H]1CC[C@H](N(C)c2c(C(=O)OCCF)cnc3[nH]ccc23)CC1] | 2-fluoroethyl 4-(methyl)(1R,4R)-4-((N-methylsulfamoyl)methyl)cyclohexyl)amino)-1H-pyrrolo[2,3-b]pyridine-5-carboxylate |
| 92 | 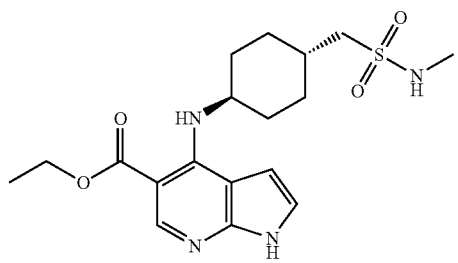 [SMILES: CCOC(=O)c1cnc2[nH]ccc2c1N[C@H]1CC[C@H](CS(=O)(=O)NC)CC1] | ethyl 4-(((1R,4R)-4-((N-methylsulfamoyl)methyl)cyclohexyl)amino)-1H-pyrrolo[2,3-b]pyridine-5-carboxylate |
| 93 | 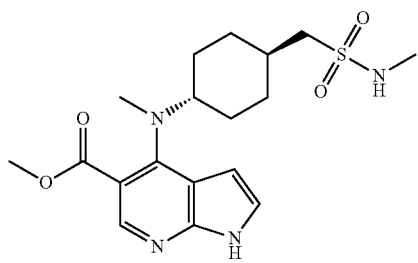 | methyl 4-(methyl)((1R,4R)-4-((N-methylsulfamoyl)methyl)cyclohexyl)amino)-1H-pyrrolo[2,3-b]pyridine-5-carboxylate |
| 94 | 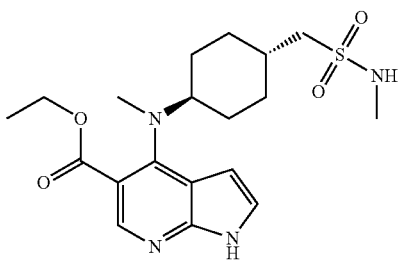 [SMILES: CCOC(=O)c1cnc2[nH]ccc2c1N(C)[C@H]1CC[C@H](CS(=O)(=O)NC)CC1] | ethyl 4-(methyl((1R,4R)-4-((N-methylsulfamoyl)methyl)cyclohexyl)amino)-1H-pyrrolo[2,3-b]pyridine-5-carboxylate |
| 95 | 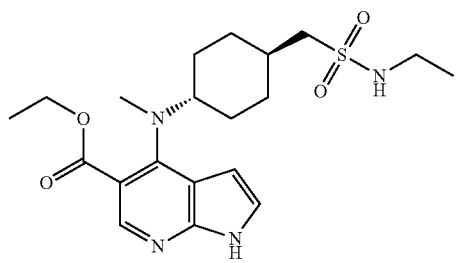 [SMILES: CCNS(=O)(=O)C[C@H]1CC[C@H](N(C)c2c(C(=O)OCC)cnc3[nH]ccc23)CC1] | ethyl 4-(((1R,4R)-4-((N-ethylsulfamoyl)methyl)cyclohexyl)(methyl)amino)-1H-pyrrolo[2,3-b]pyridine-5-carboxylate |

| Example # | Structure | Name |
|---|---|---|
| 96 | 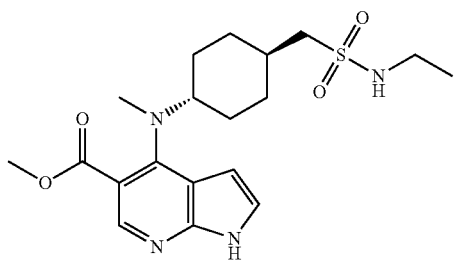 [SMILES: CCNS(=O)(=O)C[C@H]1CC[C@H](N(C)c2c(C(=O)OC)cnc3[nH]ccc23)CC1] | methyl 4-(((1R,4R)-4-((N-ethylsulfamoyl)methyl)cyclohexyl)(methyl)amino)-1H-pyrrolo[2,3-b]pyridine-5-carboxylate |
| 97 | 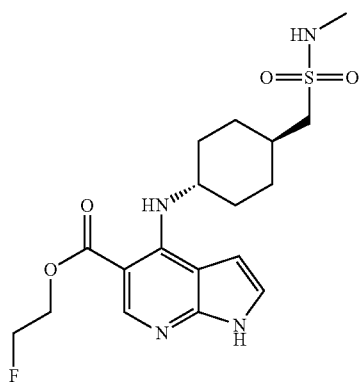 [SMILES: CNS(=O)(=O)C[C@H]1CC[C@H](Nc2c(C(=O)OCCF)cnc3[nH]ccc23)CC1] | 2-Fluoroethyl 4-(((1R,4R)-4-((N-methylsulfamoyl)methyl)cyclohexyl)amino)-1H-pyrrolo[2,3-b]pyridine-5-carboxylate |
| 98 | 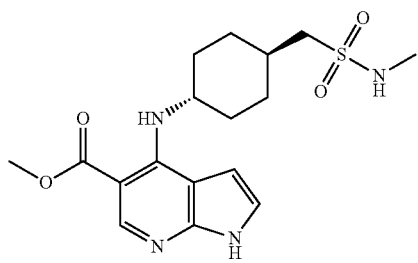 | methyl 4-(((1R,4R)-4-((N-methylsulfamoyl)methyl)cyclohexyl)amino)-1H-pyrrolo[2,3-b]pyridine-5-carboxylate |
| 99 | 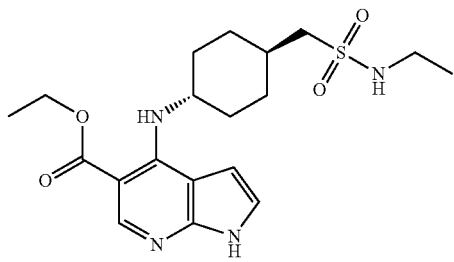 [SMILES: CCNS(=O)(=O)C[C@H]1CC[C@H](Nc2c(C(=O)OCC)cnc3[nH]ccc23)CC1] | ethyl 4-(((1R,4R)-4-((N-ethylsulfamoyl)methyl)cyclohexyl)amino)-1H-pyrrolo[2,3-b]pyridine-5-carboxylate |
| 100 | 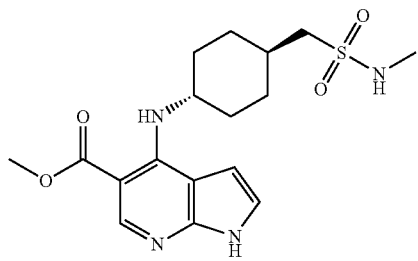 | methyl 4-(((1R,4R)-4-((N-ethylsulfamoyl)methyl)cyclohexyl)amino)-1H-pyrrolo[2,3-b]pyridine-5-carboxylate |

-continued

| Example # | Structure | Name |
|---|---|---|
| 101 | 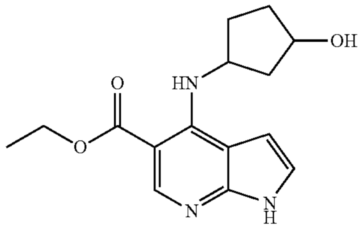 [SMILES: CCOC(=O)c1cnc2[nH]ccc2c1NC1CCC(O)C1] | ethyl 4-((3-hydroxycyclopentyl)amino)-1H-pyrrolo[2,3-b]pyridine-5-carboxylate |
| 102 | 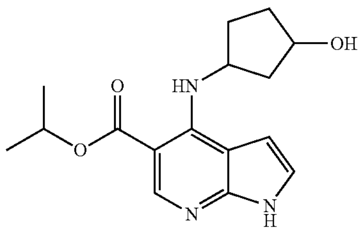 [SMILES: CC(C)OC(=O)c1cnc2[nH]ccc2c1NC1CCC(O)C1] | isopropyl 4-((3-hydroxycyclopentyl)amino)-1H-pyrrolo[2,3-b]pyridine-5-carboxylate |
| 103 | 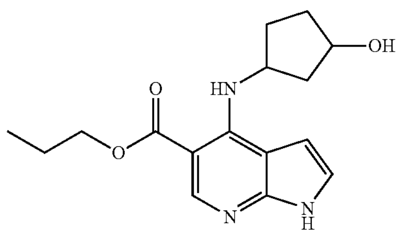 [SMILES: CCCOC(=O)c1cnc2[nH]ccc2c1NC1CCC(O)C1] | propyl 4-((3-hydroxycyclopentyl)amino)-1H-pyrrolo[2,3-b]pyridine-5-carboxylate |
| 104 | 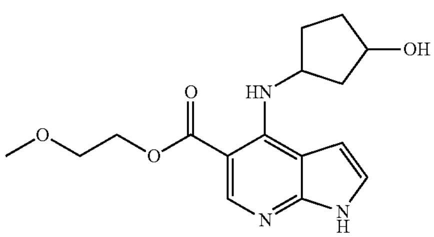 [SMILES: COCCOC(=O)c1cnc2[nH]ccc2c1NC1CCC(O)C1] | 2-methoxyethyl 4-((3-hydroxycyclopentyl)amino)-1H-pyrrolo[2,3-b]pyridine-5-carboxylate |
| 105 | 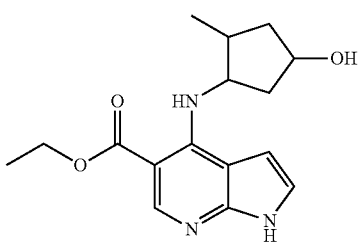 [SMILES: CCOC(=O)c1cnc2[nH]ccc2c1NC1CC(O)CC1C] | ethyl 4-((4-hydroxy-2-methylcyclopentyl)amino)-1H-pyrrolo[2,3-b]pyridine-5-carboxylate |
| 106 | 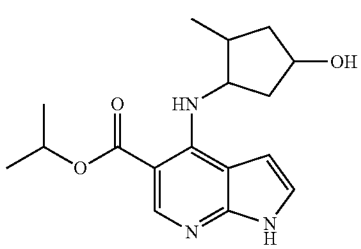 [SMILES: CC(C)OC(=O)c1cnc2[nH]ccc2c1NC1CC(O)CC1C] | isopropyl 4-((4-hydroxy-2-methylcyclopentyl)amino)-1H-pyrrolo[2,3-b]pyridine-5-carboxylate |

| Example # | Structure | Name |
|---|---|---|
| 107 | 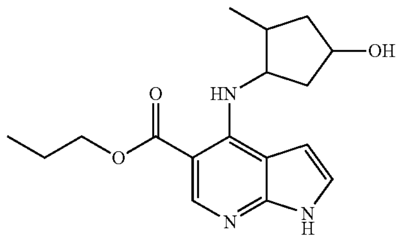 [SMILES: CCCOC(=O)c1cnc2[nH]ccc2c1NC1CC(O)CC1C] | propyl 4-((4-hydroxy-2-methylcyclopentyl)amino)-1H-pyrrolo[2,3-b]pyridine-5-carboxylate |
| 108 | 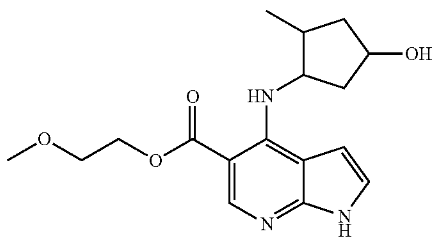 [SMILES: COCCOC(=O)c1cnc2[nH]ccc2c1NC1CC(O)CC1C] | 2-methoxyethyl 4-((4-hydroxy-2-methylcyclopentyl)amino)-1H-pyrrolo[2,3-b]pyridine-5-carboxylate |
| 109 | 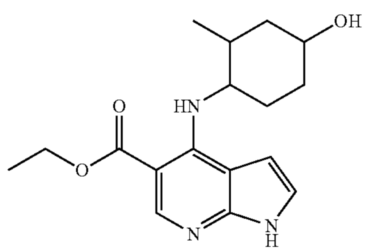 [SMILES: CCOC(=O)c1cnc2[nH]ccc2c1NC1CCC(O)CC1C] | ethyl 4-((4-hydroxy-2-methylcyclohexyl)amino)-1H-pyrrolo[2,3-b]pyridine-5-carboxylate |
| 110 | 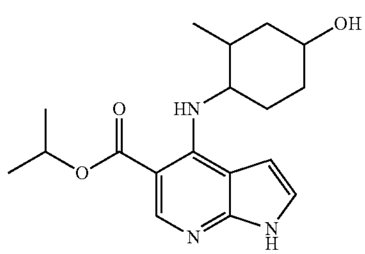 [SMILES: CC(C)OC(=O)c1cnc2[nH]ccc2c1NC1CCC(O)CC1C] | isopropyl 4-((4-hydroxy-2-methylcyclohexyl)amino)-1H-pyrrolo[2,3-b]pyridine-5-carboxylate |
| 111 | 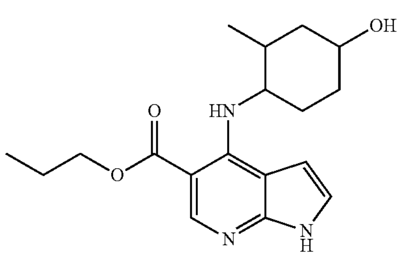 [SMILES: CCCOC(=O)c1cnc2[nH]ccc2c1NC1CCC(O)CC1C] | propyl 4-((4-hydroxy-2-methylcyclohexyl)amino)-1H-pyrrolo[2,3-b]pyridine-5-carboxylate |
| 112 | 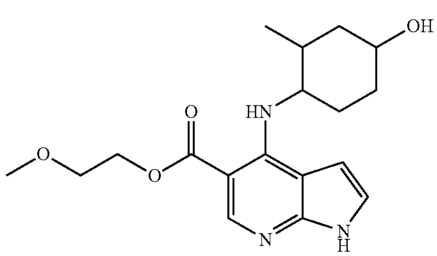 [SMILES: COCCOC(=O)c1cnc2[nH]ccc2c1NC1CCC(O)CC1C] | 2-methoxyethyl 4-((4-hydroxy-2-methylcyclohexyl)amino)-1H-pyrrolo[2,3-b]pyridine-5-carboxylate |

-continued

| Example # | Structure | Name |
|---|---|---|
| 113 | 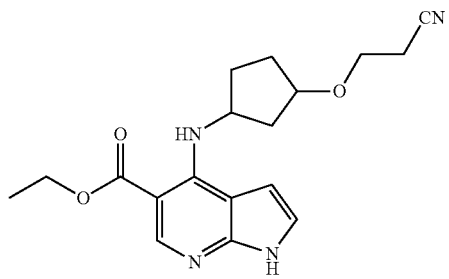 [SMILES: CCOC(=O)c1cnc2[nH]ccc2c1NC1CCC(OCCC#N)C1] | ethyl 4-((3-(2-cyanoethoxy)cyclopentyl)amino)-1H-pyrrolo[2,3-b]pyridine-5-carboxylate |
| 114 | 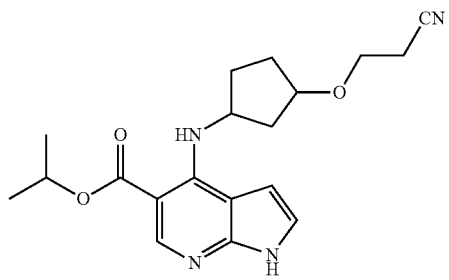 [SMILES: CC(C)OC(=O)c1cnc2[nH]ccc2c1NC1CCC(OCCC#N)C1] | isopropyl 4-((3-(2-cyanoethoxy)cyclopentyl)amino)-1H-pyrrolo[2,3-b]pyridine-5-carboxylate |
| 115 | 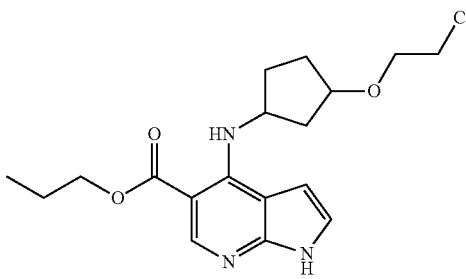 | propyl 4-((3-(2-cyanoethoxy)cyclopentyl)amino)-1H-pyrrolo[2,3-b]pyridine-5-carboxylate |
| 116 | 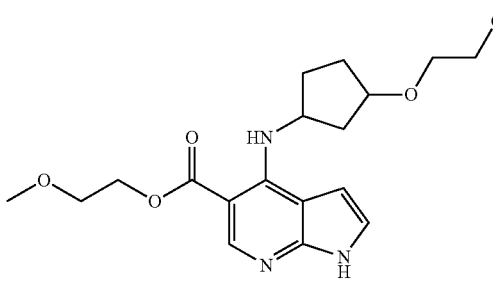 | 2-methoxyethyl 4-((3-(2-cyanoethoxy)cyclopentyl)amino)-1H-pyrrolo[2,3-b]pyridine-5-carboxylate |
| 141 | 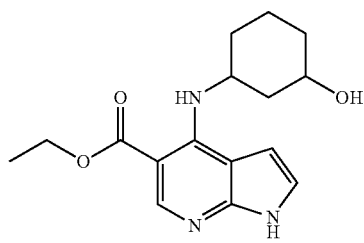 [SMILES: CCOC(=O)c1cnc2[nH]ccc2c1NC1CCCC(O)C1] | ethyl 4-((3-hydroxycyclohexyl)amino)-1H-pyrrolo[2,3-b]pyridine-5-carboxylate |

-continued

| Example # | Structure | Name |
|---|---|---|
| 142 | 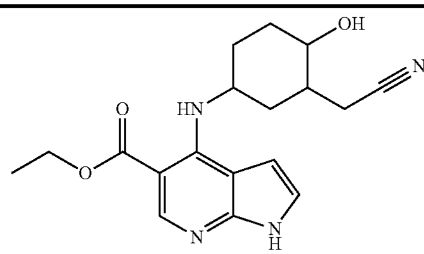 | ethyl 4-((3-(cyanomethyl)-4-hydroxycyclohexyl)amino)-1H-pyrrolo[2,3-b]pyridine-5-carboxylate |
| 162 | 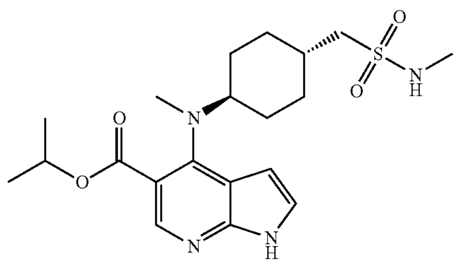 [SMILES: CNS(=O)(=O)C[C@H]1CC[C@H](N(C)c2c(C(=O)OC(C)C)cnc3[nH]ccc23)CC1] | isopropyl 4-(methyl((1R,4R)-4-((N-methylsulfamoyl)methyl)cyclohexyl)amino)-1H-pyrrolo[2,3-b]pyridine-5-carboxylate |
| 163 | 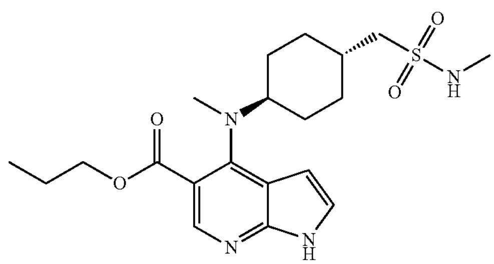 [SMILES: CCCOC(=O)c1cnc2[nH]ccc2c1N(C)[C@H]1CC[C@H](CS(=O)(=O)NC)CC1] | propyl 4-(methyl((1R,4R)-4-((N-methylsulfamoyl)methyl)cyclohexyl)amino)-1H-pyrrolo[2,3-b]pyridine-5-carboxylate |
| 164 | 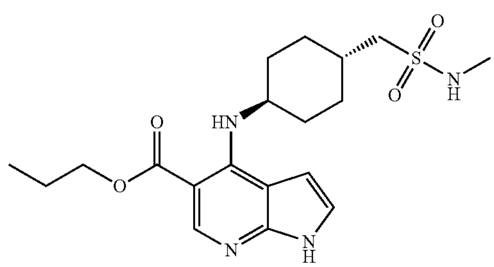 [SMILES: CCCOC(=O)c1cnc2[nH]ccc2c1N[C@H]1CC[C@H](CS(=O)(=O)NC)CC1] | propyl 4-(((1R,4R)-4-((N-methylsulfamoyl)methyl)cyclohexyl)amino)-1H-pyrrolo[2,3-b]pyridine-5-carboxylate |
| 165 | 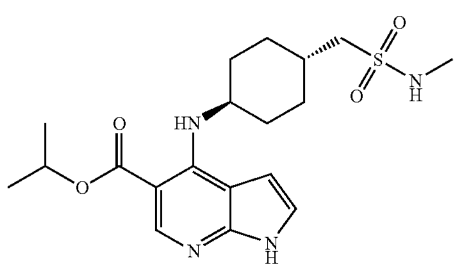 [SMILES: CNS(=O)(=O)C[C@H]1CC[C@H](Nc2c(C(=O)OC(C)C)cnc3[nH]ccc23)CC1] | isopropyl 4-(((1R,4R)-4-((N-methylsulfamoyl)methyl)cyclohexyl)amino)-1H-pyrrolo[2,3-b]pyridine-5-carboxylate |
| 166 | 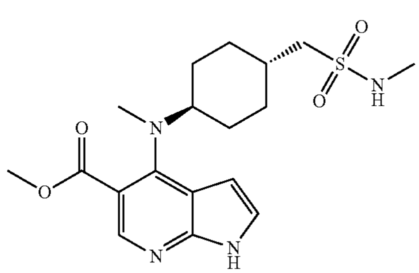 | methyl 4-(methyl((1R,4R)-4-((N-methylsulfamoyl)methyl)cyclohexyl)amino)-1H-pyrrolo[2,3-b]pyridine-5-carboxylate |

| Example # | Structure | Name |
|---|---|---|
| 167 | 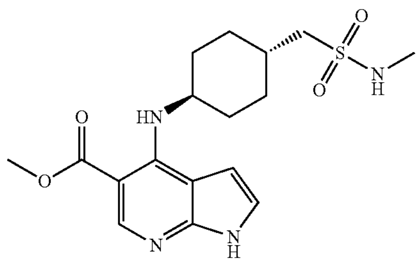 | methyl 4-(((1R,4R)-4-((N-methylsulfamoyl)methyl)cyclohexyl)amino)-1H-pyrrolo[2,3-b]pyridine-5-carboxylate |
| 184 | 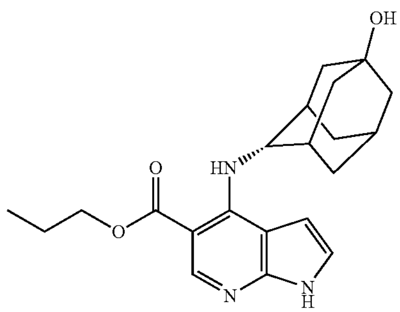 | propyl 4-(((1R,2s,3S,5r,7s)-5-hydroxyadamantan-2-yl)amino)-1H-pyrrolo[2,3-b]pyridin-5-carboxylate |
| 185 | 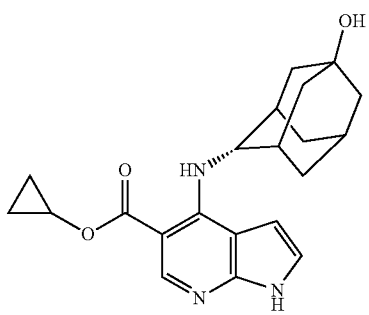 | cyclopropyl 4-(((1R,2s,3S,5r,7s)-5-hydroxyadamantan-2-yl)amino)-1H-pyrrolo[2,3-b]pyridine-5-carboxylate |
| 195 | 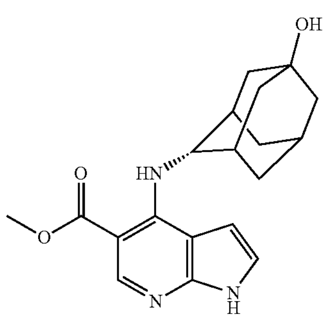 | methyl 4-(((1R,2s,3S,5r,7s)-5-hydroxyadamantan-2-yl)amino)-1H-pyrrolo[2,3-b]pyridine-5-carboxylate |
| 196 | 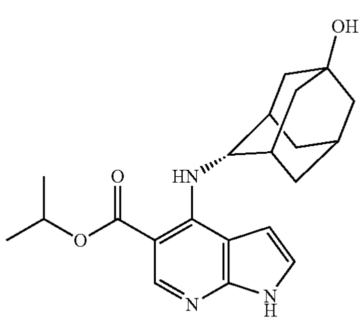 | isopropyl 4-(((1R,2s,3S,5r,7s)-5-hydroxyadamantan-2-yl)amino)-1H-pyrrolo[2,3-b]pyridine-5-carboxylate |

The invention is further illustrated by the following examples of compounds of Formula (III)

The invention is further illustrated by the following examples of compounds of Formula (IV)

| Example # | Structure | Name |
|---|---|---|
| 120 | 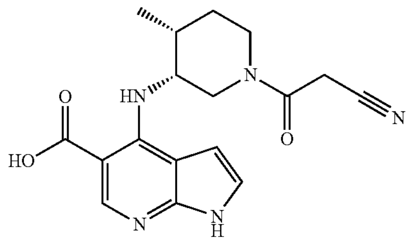 [SMILES: C[C@@H]1CCN(C(=O)CC#N)C[C@@H]1Nc1c(C(=O)O)cnc2[nH]ccc12] | 4-(((3R,4R)-1-(2-cyanoacetyl)-4-methylpiperidin-3-yl)amino)-1H-pyrrolo[2,3-b]pyridine-5-carboxylic acid |
| 121 | 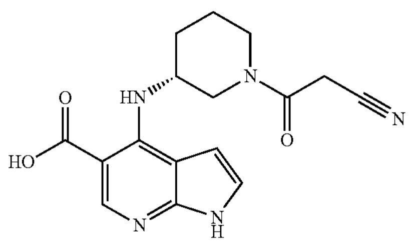 [SMILES: N#CCC(=O)N1CCC[C@@H](Nc2c(C(=O)O)cnc3[nH]ccc23)C1] | (R)-4-((1-(2-cyanoacetyl)piperidin-3-yl)amino)-1H-pyrrolo[2,3-b]pyridine-5-carboxylic acid |
| 145 | 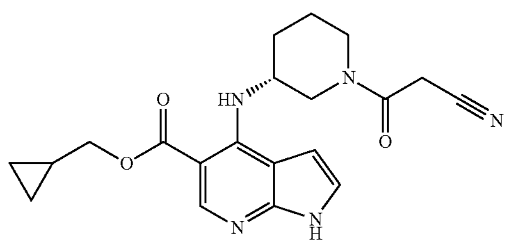 [SMILES: N#CCC(=O)N1CCC[C@@H](Nc2c(C(=O)OCC3CC3)cnc3[nH]ccc23)C1] | cyclopropylmethyl (R)-4-((1-(2-cyanoacetyl)piperidin-3-yl0amino)-1H-pyrrolo[2,3-b]pyridine-5-carboxylate |
| 161 | 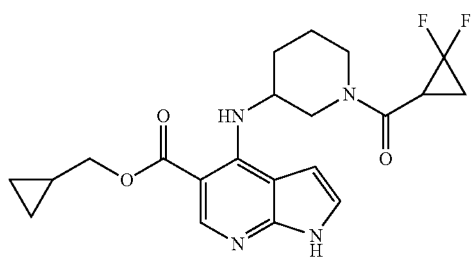 [SMILES: O=C(OCC1CC1)c1cnc2[nH]ccc2c1NC1CCCN(C(=O)C2CC2(F)F)C1] | cyclopropylmethyl 4-((1-(2,2-difluorocyclopropane-1-carbonyl)piperidin-3-yl)amino)-1H-pyrrolo[2,3-b]pyridine-5-carboxylate |
| 186 | 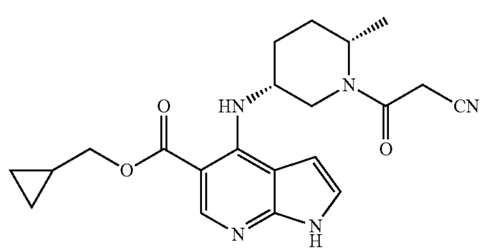 [SMILES: C[C@H]1CC[C@@H](Nc2c(C(=O)OCC3CC3)cnc3[nH]ccc23)CN1C(=O)CC#N] | cyclopropylmethyl 4-(((3R,6S)-1-(2-cyanoacetyl)-6-methylpiperidin-3-yl)amino)-1H-pyrrolo[2,3-b]pyridine-5-carboxylate |
| 187 | 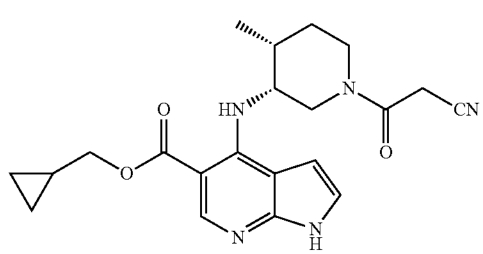 [SMILES: C[C@@H]1CCN(C(=O)CC#N)C[C@@H]1Nc1c(C(=O)OCC2CC2)cnc2[nH]ccc12] | cyclopropylmethyl 4-(((3R,4R)-1-(2-cyanoacetyl)-4-methylpiperidin-3-yl)amino)-1H-pyrrolo[2,3-b]pyridine-5-carboxylate |

| Example # | Structure | Name |
|---|---|---|
| 132 | 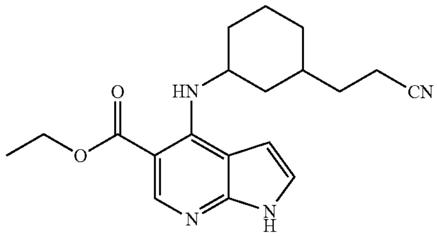 [SMILES: CCOC(=O)c1cnc2[nH]ccc2c1NC1CCCC(CCC#N)C1] | ethyl 4-((3-(2-cyanoethyl)cyclohexyl)amino)-1H-pyrrolo[2,3-b]pyridine-5-carboxylate |
| 133 | 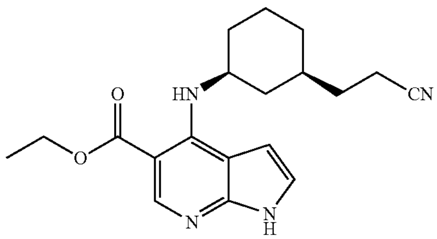 [SMILES: CCOC(=O)c1cnc2[nH]ccc2c1N[C@H]1CCC[C@@H](CCC#N)C1] | (rac)-(cis)-Ethyl 4-((3-(2-cyanoethyl)cyclohexyl)amino)-1H-pyrrolo[2,3-b]pyridine-5-carboxylate |
| 134 | 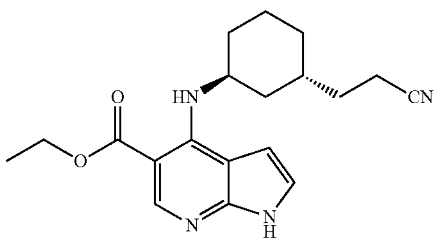 [SMILES: CCOC(=O)c1cnc2[nH]ccc2c1N[C@H]1CCC[C@H](CCC#N)C1] | (rac)-(trans)-Ethyl 4-((3-(2-cyanoethyl)cyclohexyl)amino)-1H-pyrrolo[2,3-b]pyridine-5-carboxylate |
| 135 | Cis isomer, single enantiomer | (cis) Ethyl 4-((3-(2-cyanoethyl)cyclohexyl)amino)-1H-pyrrolo[2,3-b]pyridine-5-carboxylate, enantiomer 1 |
| 136 | Cis isomer, single enantiomer | (cis) Ethyl 4-((3-(2-cyanoethyl)cyclohexyl)amino)-1H-pyrrolo[2,3-b]pyridine-5-carboxylate, enantiomer 2 |
| 137 | Trans isomer, single enantiomer | (trans) Ethyl 4-((3-(2-cyanoethyl)cyclohexyl)amino)-1H-pyrrolo[2,3-b]pyridine-5-carboxylate enantiomer 1 |

-continued

| Example # | Structure | Name |
|---|---|---|
| 138 | Trans isomer, single enantiomer | (trans)-Ethyl 4-((3-(2-cyanoethyl)cyclohexyl)amino)-1H-pyrrolo[2,3-b]pyridine-5-carboxylate, enantiomer 2 |
| 139 | 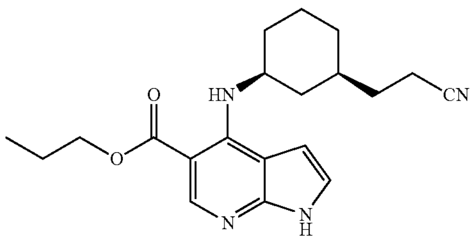 [SMILES: CCCOC(=O)c1cnc2[nH]ccc2c1N[C@H]1CCC[C@@H](CCC#N)C1] | (rac) (cis) Propyl 4-((3-(2-cyanoethyl)cyclohexyl)amino)-1H-pyrrolo[2,3-b]pyridine-5-carboxylate |
| 140 | 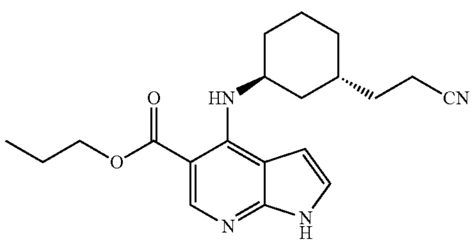 [SMILES: CCCOC(=O)c1cnc2[nH]ccc2c1N[C@H]1CCC[C@H](CCC#N)C1] | (rac)-(trans)-Propyl 4-((3-(2-cyanoethyl)cyclohexyl)amino)-1H-pyrrolo[2,3-b]pyridine-5-carboxylate |
| 147 | 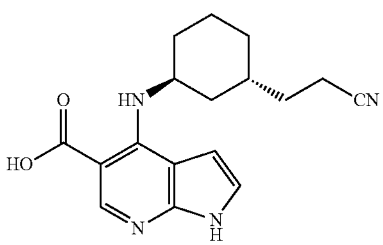 [SMILES: N#CCC[C@H]1CCC[C@H](Nc2c(C(=O)O)cnc3[nH]ccc23)C1] | 4-(((1S,3R)-3-(2-cyanoethyl)cyclohexyl)amino)-1H-pyrrolo[2,3-b]pyridine-5-carboxylic acid |
| 148 | 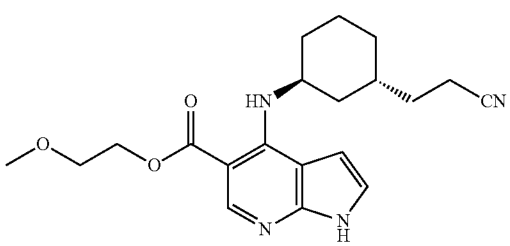 [SMILES: COCCOC(=O)c1cnc2[nH]ccc2c1N[C@H]1CCC[C@H](CCC#N)C1] | racemic, trans -2-methoxyethyl 4-((3-(2-cyanoethy)cyclohexyl)amino)-1H-pyrrolo[2,3-b]pyridine-5-carboxylate |
| 149 | Cis-enantiomer 1 | cis-2-methoxyethyl 4-((3-(2-cyanoethyl)cyclohexyl)amino)-1H-pyrrolo[2,3-b]pyridine-5-carboxylate, enantiomer 1 |

| Example # | Structure | Name |
|---|---|---|
| 150 | 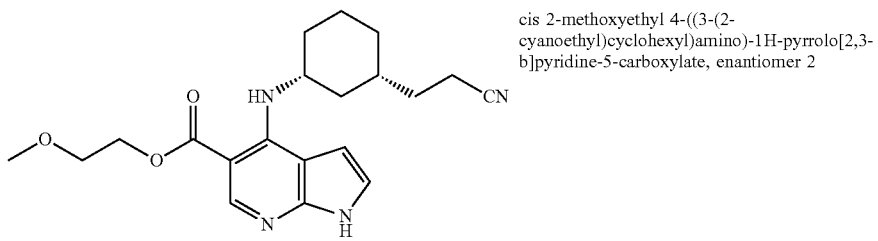<br>Cis-enantiomer 2 | cis 2-methoxyethyl 4-((3-(2-cyanoethyl)cyclohexyl)amino)-1H-pyrrolo[2,3-b]pyridine-5-carboxylate, enantiomer 2 |
| 151 | 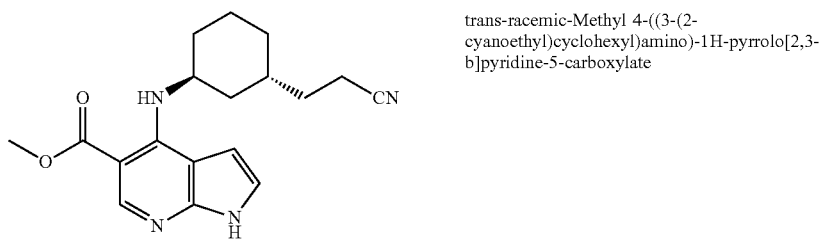<br>Trans | trans-racemic-Methyl 4-((3-(2-cyanoethyl)cyclohexyl)amino)-1H-pyrrolo[2,3-b]pyridine-5-carboxylate |
| 152 | 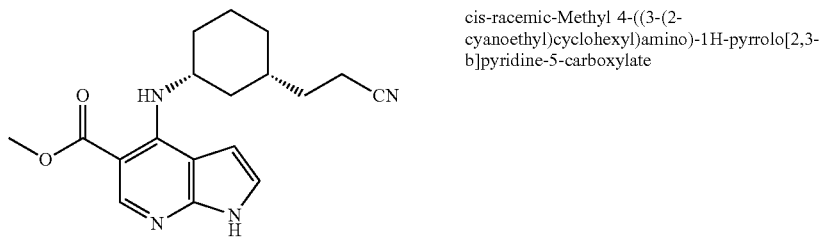<br>Cis | cis-racemic-Methyl 4-((3-(2-cyanoethyl)cyclohexyl)amino)-1H-pyrrolo[2,3-b]pyridine-5-carboxylate |
| 153 | 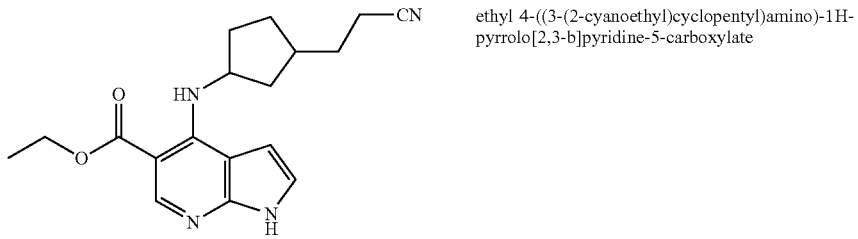 | ethyl 4-((3-(2-cyanoethyl)cyclopentyl)amino)-1H-pyrrolo[2,3-b]pyridine-5-carboxylate |
| 168 | 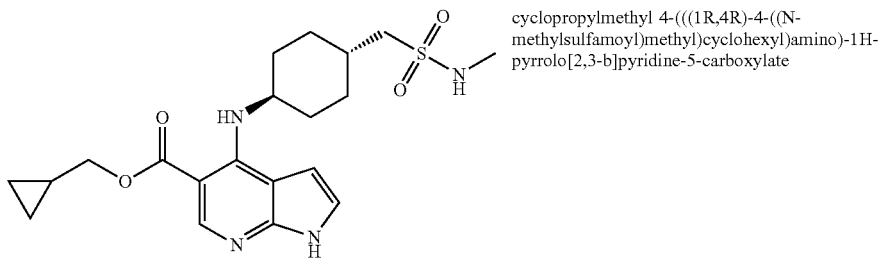 | cyclopropylmethyl 4-(((1R,4R)-4-((N-methylsulfamoyl)methyl)cyclohexyl)amino)-1H-pyrrolo[2,3-b]pyridine-5-carboxylate |

| Example # | Structure | Name |
|---|---|---|
| 169 | 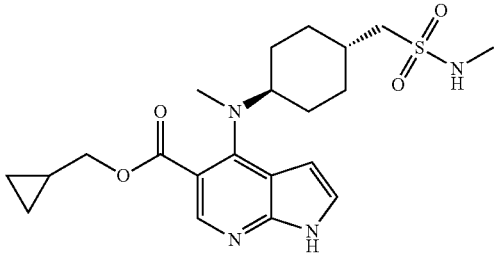 [SMILES: CNS(=O)(=O)C[C@H]1CC[C@H](N(C)c2c(C(=O)OCC3CC3)cnc3[nH]ccc23)CC1] | cyclopropylmethyl 4-(methyl((1R,4R)-4-((N-methylsulfamoyl)methyl)cyclohexyl)amino)-1H-pyrrolo[2,3-b]pyridine-5-carboxylate |
| 188 | 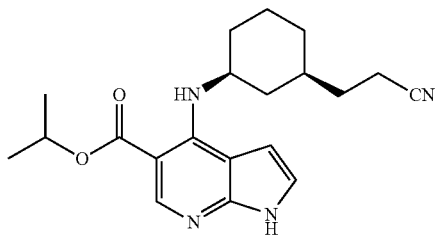 [SMILES: CC(C)OC(=O)c1cnc2[nH]ccc2c1N[C@H]1CCC[C@@H](CCC#N)C1] | isopropyl 4-(((1S,3S)-3-(2-cyanoethyl)cyclohexyl)amino)-1H-pyrrolo[2,3-b]pyridine-5-carboxylate |
| 189 | 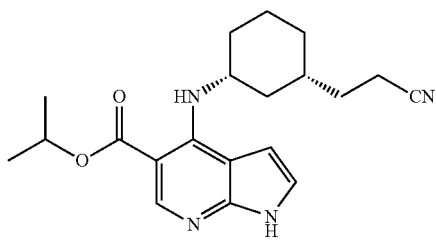 [SMILES: CC(C)OC(=O)c1cnc2[nH]ccc2c1N[C@@H]1CCC[C@H](CCC#N)C1] | isopropyl 4-(((1R,3R)-3-(2-cyanoethyl)cyclohexyl)amino)-1H-pyrrolo[2,3-b]pyridine-5-carboxylate |
| 190 | 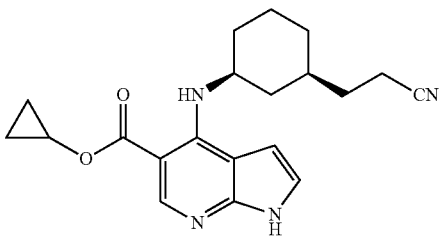 [SMILES: N#CCC[C@@H]1CCC[C@H](Nc2c(C(=O)OC3CC3)cnc3[nH]ccc23)C1] | cyclopropyl 4-(((1S,3S)-3-(2-cyanoethyl)cyclohexyl)amino)-1H-pyrrolo[2,3-b]pyridine-5-carboxylate |
| 191 | 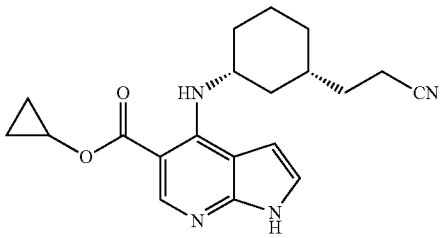 [SMILES: N#CCC[C@H]1CCC[C@@H](Nc2c(C(=O)OC3CC3)cnc3[nH]ccc23)C1] | cyclopropyl 4-(((1R,3R)-3-(2-cyanoethyl)cyclohexyl)amino)-1H-pyrrolo[2,3-b]pyridine-5-carboxylate |
| 192 | 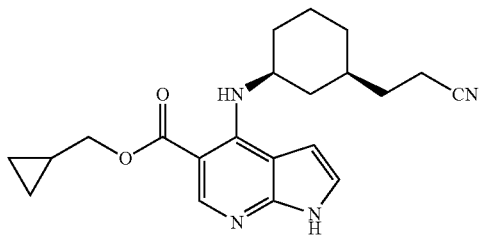 [SMILES: N#CCC[C@@H]1CCC[C@H](Nc2c(C(=O)OCC3CC3)cnc3[nH]ccc23)C1] | cyclopropylmethyl 4-(((1S,3S)-3-(2-cyanoethyl)cyclohexyl)amino)-1H-pyrrolo[2,3-b]pyridine-5-carboxylate |

| Example # | Structure | Name |
|---|---|---|
| 193 | 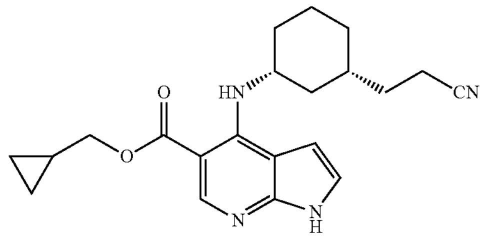 [SMILES: N#CCC[C@H]1CCC[C@@H](Nc2c(C(=O)OCC3CC3)cnc3[nH]ccc23)C1] | cyclopropylmethyl 4-(((1R,3R)-3-(2-cyanoethyl)cyclohexyl)amino)-1H-pyrrolo[2,3-b]pyridine-5-carboxylate |
| 194 | 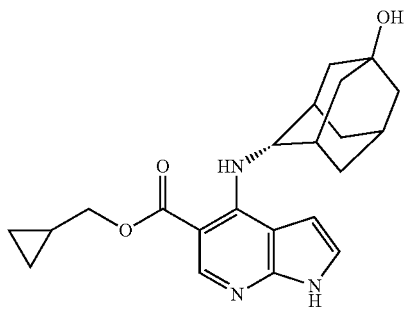 | cyclopropylmethyl 4-(((1R,2s,3S,5r,7s)-5-hydroxyadamantan-2-yl)amino)-1H-pyrrolo[2,3-b]pyridine-5-carboxylate |

Pharmaceutical Compositions

Some embodiments herein are directed to a pharmaceutical composition comprising a compound of embodiments herein and a pharmaceutically acceptable carrier or diluent.

Also provided is a pharmaceutical composition comprising a compound as disclosed herein, together with a pharmaceutically acceptable carrier.

While it may be possible for the compounds described herein to be administered as the raw chemical, it is also possible to present them as a pharmaceutical formulation. Accordingly, provided herein are pharmaceutical formulations which comprise one or more of certain compounds disclosed herein, or a derivative thereof, together with one or more pharmaceutically acceptable carriers thereof and optionally one or more other therapeutic ingredients. The carrier(s) must be "acceptable" in the sense of being compatible with the other ingredients of the formulation and not deleterious to the recipient thereof. Proper formulation is dependent upon the route of administration chosen. Any of the well-known techniques, carriers, and excipients may be used as suitable and as understood in the art. The pharmaceutical compositions disclosed herein may be manufactured in any manner known in the art, e.g., by means of conventional mixing, dissolving, granulating, dragee-making, levigating, emulsifying, encapsulating, entrapping or compression processes.

In some embodiments, the pharmaceutical compositions for use in accordance with embodiments herein can be formulated in conventional manner using one or more physiologically acceptable carriers or excipients.

The formulations include those suitable for oral, parenteral (including subcutaneous, intradermal, intramuscular, intravenous, intraarticular, and intramedullary), intraperitoneal, intrathecal, intradural, transmucosal, transdermal, rectal, intranasal, topical (including, for example, dermal, buccal, sublingual and intraocular), intravitreal, or intravaginal administration although the most suitable route may depend upon for example the condition and disorder of the recipient. The formulation could include those suitable for administration by depot injections or by implants. The formulation could include those suitable for administration by inhalation, such as, for example, a gas, vapor, or powder. The formulation could include those suitable for administration, e.g., as an aerosol via a nebulizer, humidifier, inhaler and vaporizer or the like. The formulations may conveniently be presented in unit dosage form and may be prepared by any of the methods well known in the art of pharmacy. Typically, these methods include the step of bringing into association a compound disclosed herein or a derivative thereof ("active ingredient") with the carrier which constitutes one or more accessory ingredients. In general, the formulations are prepared by uniformly and intimately bringing into association the active ingredient with liquid carriers or finely divided solid carriers or both and then, if necessary, shaping the product into the desired formulation.

Formulations of the compounds disclosed herein suitable for oral administration may be presented as discrete units such as capsules, cachets or tablets each containing a predetermined amount of the active ingredient; as a powder or granules; as a solution or a suspension in an aqueous liquid or a non-aqueous liquid; or as an oil-in-water liquid emulsion or a water-in-oil liquid emulsion. The active ingredient may also be presented as a bolus, electuary or paste.

Pharmaceutical preparations which can be used orally include tablets, push-fit capsules made of gelatin, as well as soft, sealed capsules made of gelatin and a plasticizer, such as glycerol or sorbitol. Tablets may be made by compression or molding, optionally with one or more accessory ingredients. Compressed tablets may be prepared by compressing in a suitable machine the active ingredient in a free-flowing form such as a powder or granules, optionally mixed with binders, inert diluents, or lubricating, surface active or dispersing agents. Molded tablets may be made by molding in a suitable machine a mixture of the powdered compound moistened with an inert liquid diluent. The tablets may optionally be coated or scored and may be formulated so as to provide slow or controlled release of the active ingredient therein. All formulations for oral administration should be in dosages suitable for such administration. The push-fit capsules can contain the active ingredients in admixture with filler such as lactose, binders such as starches, and/or lubricants such as talc or magnesium stearate and, optionally, stabilizers. In soft capsules, the active compounds may be dissolved or suspended in suitable liquids, such as fatty oils, liquid paraffin, or liquid polyethylene glycols. In addition, stabilizers may be added. Dragee cores are provided with suitable coatings. For this purpose, concentrated sugar solutions may be used, which may optionally contain gum arabic, talc, polyvinyl pyrrolidone, carbopol gel, polyethylene glycol, and/or titanium dioxide, lacquer solutions, and suitable organic solvents or solvent mixtures. Dyestuffs or pigments may be added to the tablets or dragee coatings for identification or to characterize different combinations of active compound doses.

The compounds may be formulated for parenteral administration by injection, e.g., by bolus injection or continuous infusion. Formulations for injection may be presented in unit dosage form, e.g., in ampoules or in multi-dose containers, with an added preservative. The compositions may take such forms as suspensions, solutions or emulsions in oily or aqueous vehicles, and may contain formulatory agents such as suspending, stabilizing and/or dispersing agents. The formulations may be presented in unit-dose or multi-dose containers, for example sealed ampoules and vials, and may be stored in powder form or in a freeze-dried (lyophilized) condition requiring only the addition of the sterile liquid carrier, for example, saline or sterile pyrogen-free water, immediately prior to use. Extemporaneous injection solutions and suspensions may be prepared from sterile powders, granules and tablets of the kind previously described.

Formulations for parenteral administration include aqueous and non-aqueous (oily) sterile injection solutions of the active compounds which may contain antioxidants, buffers, bacteriostats and solutes which render the formulation isotonic with the blood of the intended recipient; and aqueous and non-aqueous sterile suspensions which may include suspending agents and thickening agents. Suitable lipophilic solvents or vehicles include fatty oils such as sesame oil, or synthetic fatty acid esters, such as ethyl oleate or triglycerides, or liposomes. Aqueous injection suspensions may contain substances which increase the viscosity of the suspension, such as sodium carboxymethyl cellulose, sorbitol, or dextran. Optionally, the suspension may also contain suitable stabilizers or agents which increase the solubility of the compounds to allow for the preparation of highly concentrated solutions.

In addition to the formulations described previously, the compounds may also be formulated as a depot preparation. Such long acting formulations may be administered by implantation (for example subcutaneously or intramuscularly) or by intramuscular injection. Thus, for example, the compounds may be formulated with suitable polymeric or hydrophobic materials (for example as an emulsion in an acceptable oil) or ion exchange resins, or as sparingly soluble derivatives, for example, as a sparingly soluble salt.

For buccal or sublingual administration, the compositions may take the form of tablets, lozenges, pastilles, or gels formulated in conventional manner. Such compositions may comprise the active ingredient in a flavored basis such as sucrose and acacia or tragacanth.

The compounds may also be formulated in rectal compositions such as suppositories or retention enemas, e.g., containing conventional suppository bases such as cocoa butter, polyethylene glycol, or other glycerides.

Certain compounds disclosed herein may be administered topically, that is by non-systemic administration. This includes the application of a compound disclosed herein externally to the epidermis or the buccal cavity and the instillation of such a compound into the ear, eye and nose. In contrast, systemic administration refers to oral, intravenous, intraperitoneal and intramuscular administration.

In some embodiments, the compounds disclosed herein may be administered ophthalmically. In some embodiments, the compounds disclosed herein may be administered as an ophthalmic composition. The compounds of embodiments herein may be administered as, for example, liquid preparations, including eye lotions, spray, or eye drops for topical administration. In some embodiments, the compounds disclosed herein may be administered as semi-solid preparations, for example, applied to the eyelid, such as cream, lotion, gel, ointment, or paste. In some embodiments, the compounds disclosed herein may be administered as solid dosage forms, for example, applied to the eye surface to produce modified release, such as a powder. In some embodiments, the compounds of embodiments herein are administered through devices for surgical implantation, parenteral products, (e.g., intracorneal or intravitreous products), liquids for irrigation, or the like. In some embodiments, the composition comprising the compounds disclosed herein are sterile and free from particulate matters. In some embodiments, the compounds disclosed herein may be administered by intraocular injection, intraorbital injection, or an intravitreal injection. In some embodiments, the intraocular injection may be to the anterior chamber of the eye, posterior chamber of the eye, or a combination thereof. For example, the compounds disclosed herein may be administered to the posterior intraorbital region of the eye.

In some embodiments, formulations suitable for topical administration include liquid or semi-liquid preparations suitable for penetration through the skin to the site of inflammation such as a solution, powder, fluid emulsion, fluid suspension, semi-solid, ointment, paste, cream, gel, jelly, foam, liniment, lotion, and drops suitable for administration to the eye, ear or nose. The active ingredient for topical administration may comprise, for example, from 0.001% to 10% w/w (by weight) of the formulation. In certain embodiments, the active ingredient may comprise as much as 10% w/w. In other embodiments, it may comprise less than 5% w/w. In certain embodiments, the active ingredient may comprise from 2% w/w to 5% w/w. In other embodiments, it may comprise from 0.1% to 1% w/w of the formulation.

Gels for topical or transdermal administration may comprise, generally, a mixture of volatile solvents, nonvolatile solvents, and water. In certain embodiments, the volatile solvent component of the buffered solvent system may include lower ($C_1$-$C_6$) alkyl alcohols, lower alkyl glycols and lower glycol polymers. In further embodiments, the volatile solvent is ethanol. The volatile solvent component is thought to act as a penetration enhancer, while also producing a cooling effect on the skin as it evaporates. The nonvolatile solvent portion of the buffered solvent system is selected from lower alkylene glycols and lower glycol polymers. In certain embodiments, propylene glycol is used. The nonvolatile solvent slows the evaporation of the volatile solvent and reduces the vapor pressure of the buffered solvent system. The amount of this nonvolatile solvent component, as with the volatile solvent, is determined by the pharmaceutical compound or drug being used. When too little of the nonvolatile solvent is in the system, the pharmaceutical compound may crystallize due to evaporation of volatile solvent, while an excess may result in a lack of bioavailability due to poor release of drug from solvent mixture. The buffer component of the buffered solvent system may be selected from any buffer commonly used in the art; in certain embodiments, water is used. A common ratio of ingredients is about 20% of the nonvolatile solvent, about 40% of the volatile solvent, and about 40% water. There are several optional ingredients which can be added to the topical composition. These include, but are not limited to, chelators and gelling agents. Appropriate gelling agents can include, but are not limited to, semisynthetic cellulose derivatives (such as hydroxypropylmethylcellulose) and synthetic polymers, and cosmetic agents.

Lotions include those suitable for application to the skin or eye. An eye lotion may comprise a sterile aqueous solution optionally containing a bactericide and may be prepared by methods similar to those for the preparation of drops. Lotions or liniments for application to the skin may also include an agent to hasten drying and to cool the skin, such as an alcohol or acetone, and/or a moisturizer such as glycerol or an oil such as castor oil or *arachis* oil.

Creams, ointments or pastes are semi-solid formulations of the active ingredient for external application. They may be made by mixing the active ingredient in finely-divided or powdered form, alone or in solution or suspension in an aqueous or non-aqueous fluid, with the aid of suitable machinery, with a greasy or non-greasy base. The base may comprise hydrocarbons such as hard, soft or liquid paraffin, glycerol, beeswax, a metallic soap; a mucilage; an oil of natural origin such as almond, corn, *arachis*, castor or olive oil; wool fat or its derivatives or a fatty acid such as steric or oleic acid together with an alcohol such as propylene glycol or a macrogel. The formulation may incorporate any suitable surface active agent such as an anionic, cationic or non-ionic surfactant such as a sorbitan ester or a polyoxyethylene derivative thereof. Suspending agents such as natural gums, cellulose derivatives or inorganic materials such as silicaceous silicas, and other ingredients such as lanolin, may also be included.

Drops may comprise sterile aqueous or oily solutions or suspensions and may be prepared by dissolving the active ingredient in a suitable aqueous solution of a bactericidal and/or fungicidal agent and/or any other suitable preservative, and, in certain embodiments, including a surface active agent. The resulting solution may then be clarified by filtration, transferred to a suitable container which is then sealed and sterilized by autoclaving or maintaining at 98-100° C. for half an hour. Alternatively, the solution may be sterilized by fungicidal agents suitable for inclusion in the drops are phenylmercuric nitrate or acetate (0.002%), benzalkonium chloride (0.01%) and chlorhexidine acetate (0.01%). Suitable solvents for the preparation of an oily solution include glycerol, diluted alcohol and propylene glycol.

Formulations for topical administration in the mouth, for example buccally or sublingually, include lozenges comprising the active ingredient in a flavored basis such as sucrose and acacia or tragacanth, and pastilles comprising the active ingredient in a basis such as gelatin and glycerin or sucrose and acacia.

For administration by inhalation, compounds may be conveniently delivered from an insufflator, nebulizer pressurized packs or other convenient means of delivering an aerosol spray. Pressurized packs may comprise a suitable propellant such as dichlorodifluoromethane, trichlorofluoromethane, dichlorotetrafluoroethane, carbon dioxide or other suitable gas. In the case of a pressurized aerosol, the dosage unit may be determined by providing a valve to deliver a metered amount. Alternatively, for administration by inhalation or insufflation, the compounds according to the invention may take the form of a dry powder composition, for example a powder mix of the compound and a suitable powder base such as lactose or starch. The powder composition may be presented in unit dosage form, in for example, capsules, cartridges, gelatin or blister packs from which the powder may be administered with the aid of an inhalator or insufflator.

Preferred unit dosage formulations are those containing an effective dose, as herein below recited, or an appropriate fraction thereof, of the active ingredient.

It should be understood that in addition to the ingredients particularly mentioned above, the formulations described above may include other agents conventional in the art having regard to the type of formulation in question, for example those suitable for oral administration may include flavoring agents.

Compounds may be administered at a dose of from 0.1 to 500 mg/kg per day. The dose range for adult humans is generally from 5 mg to 2 g/day. Tablets or other forms of presentation provided in discrete units may conveniently contain an amount of one or more compounds which is effective at such dosage or as a multiple of the same, for instance, units containing 5 mg to 500 mg, usually around 10 mg to 200 mg.

The amount of active ingredient that may be combined with the carrier materials to produce a single dosage form will vary depending upon the host treated and the particular mode of administration.

When employed as pharmaceuticals, the compounds can be administered in the form of pharmaceutical compositions. These compositions can be prepared in a manner well known in the pharmaceutical arts, and can be administered by a variety of routes, depending upon whether local or systemic treatment is desired and upon the area to be treated. Administration of the disclosed compounds or compositions may be oral, parenteral (including subcutaneous, intradermal, intramuscular, intravenous, intraarticular, and intramedullary), pulmonary (e.g., by inhalation or insufflation of powders or aerosols, including by nebulizer; intratracheal or intranasal), intraperitoneal, transmucosal, transdermal, rectal, topical (including dermal, buccal, sublingual and intraocular), or intravaginal administration. Parenteral administration includes intravenous, intraarterial, subcutaneous, intraperitoneal, intramuscular or injection or infusion; or intracranial, e.g., intrathecal or intraventricular, administration. Parenteral administration can be in the form of a single bolus dose, or may be, for example, by a continuous perfusion pump. Pharmaceutical compositions for topical administration may include foams, transdermal patches, ointments, lotions, creams, gels, solutions, fluid emulsions, fluid suspensions, semi-solids, pastes, drops, suppositories, sprays, liquids and powders. Conventional pharmaceutical carriers, aqueous, powder or oily bases, thickeners and the like may be necessary or desirable. Coated condoms, gloves and the like may also be useful. In some embodiments, the compounds can be contained in such formulations with pharmaceutically acceptable diluents, fillers, disintegrants, binders, lubricants, surfactants, hydrophobic vehicles, water soluble vehicles, emulsifiers, buffers, humectants, moisturizers, solubilizers, preservatives and the like. The artisan can refer to various pharmacologic references for guidance. For example, Modern Pharmaceutics, 5th Edition, Banker & Rhodes, CRC Press (2009); and Goodman & Gilman's The Pharmaceutical Basis of Therapeutics, 13th Edition, McGraw Hill, New York (2018) can be consulted.

In some embodiments, a method of treating a JAK1 and/or JAK3 mediated disease administering a pharmaceutical composition of embodiments disclosed herein. In some embodiments, the compound is in a therapeutically effective amount. In some embodiments, the therapeutically effective amount is an amount disclosed herein.

Some embodiments disclosed herein also include pharmaceutical compositions which contain, as the active ingredient, one or more of the compounds disclosed herein in combination with one or more pharmaceutically acceptable carriers (excipients).

In some embodiments, a method of making a pharmaceutical composition comprises mixing the active ingredient with an excipient, diluting the active ingredient using an excipient, or enclosing the active ingredient within a carrier in the form of, for example, a capsule, sachet, paper, or other container. When the excipient serves as a diluent, it can be a solid, semi-solid, or liquid material, which acts as a vehicle, carrier or medium for the active ingredient. Thus, the compositions can be in the form of tablets, pills, powders, lozenges, sachets, cachets, elixirs, suspensions, emulsions, solutions, syrups, aerosols (as a solid or in a liquid medium), ointments containing, for example, up to 10% by weight of the active compound, soft and hard gelatin capsules, suppositories, sterile injectable solutions, and sterile packaged powders.

Some examples of suitable excipients include lactose, dextrose, sucrose, sorbitol, mannitol, starches, gum acacia, calcium phosphate, alginates, tragacanth, gelatin, calcium silicate, microcrystalline cellulose, polyvinylpyrrolidone, cellulose, water, syrup, and methyl cellulose, including eutectic solvents, eutectic-based ionic liquids, or ionic liquids. The formulations can additionally include: lubricating agents such as talc, magnesium stearate, and mineral oil; wetting agents; emulsifying and suspending agents; preserving agents such as methyl- and propylhydroxy-benzoates; sweetening agents; and flavoring agents. The compositions can be formulated so as to provide quick, sustained or delayed release of the active ingredient after administration to the patient by employing procedures known in the art.

The compositions can be formulated in a unit dosage form. The term "unit dosage forms" refers to physically discrete units suitable as unitary dosages for human subjects and other mammals, each unit containing a predetermined quantity of active material calculated to produce the desired therapeutic effect, in association with a suitable pharmaceutical excipient.

The active compound can be effective over a wide dosage range and can be generally administered in a therapeutically effective amount. It will be understood, however, that the amount of the compound actually administered will usually be determined by a physician, according to the relevant circumstances, including the condition to be treated, the chosen route of administration, the actual compound administered, the age, weight, and response of the individual patient, the severity of the patient's symptoms, and the like.

In some embodiments, the pharmaceutical composition may comprise about 0.01% to about 50% of one or more compounds disclosed herein. In some embodiments, the one or more compounds is in an amount of about 0.01% to about 50%, about 0.01% to about 45%, about 0.01% to about 40%, about 0.01% to about 30%, about 0.01% to about 20%, about 0.01% to about 10%, about 0.01% to about 5%, about 0.05% to about 50%, about 0.05% to about 45%, about 0.05% to about 40%, about 0.05% to about 30%, about 0.05% to about 20%, about 0.05% to about 10%, about 0.1% to about 50%, about 0.1% to about 45%, about 0.1% to about 40%, about 0.1% to about 30%, about 0.1% to about 20%, about 0.1% to about 100%, about 0.1% to about 5%, about 0.5% to about 50%, about 0.5% to about 45%, about 0.5% to about 40%, about 0.5% to about 30%, about 0.5% to about 20%, about 0.5% to about 100%, about 0.5% to about 5%, about 1% to about 50%, about 1% to about 45%, about 1% to about 40%, about 1% to about 35%, about 1% to about 30%, about 1% to about 25%, about 1% to about 20%0, about 1% to about 15%, about 1% to about 10%, about 1% to about 5%, about 5% to about 45%, about 5% to about 40%, about 5% to about 35%, about 5% to about 30%, about 5% to about 25%, about 5% to about 20%, about 5% to about 15%, about 5% to about 10%, about 10% to about 45%, about 10% to about 40%, about 10% to about 35%, about 10% to about 30%, about 10% to about 25%, about 10% to about 20%, about 10% to about 15%, or a value within one of these ranges. Specific examples may include about 0.01%, about 0.05%, about 0.1%, about 0.25%, about 0.5%, about 0.75%, about 1%, about 5%, about 10%, about 15%, about 20%, about 25%, about 30%, about 35%, about 40%, about 45%, about 50%, about 60%, about 70%, about 80%, about 90%, or a range between any two of these values. The foregoing all representing weight percentages of the composition. In some embodiments, the composition is suitable for topical administration. In some embodiments, the composition is suitable for oral, parenteral (including subcutaneous, intradermal, intramuscular, intravenous, intraarticular, and intramedullary), intraperitoneal, intrathecal, intradural, transmucosal, transdermal, rectal, intranasal, topical (including, for example, dermal, buccal sublingual and intraocular), intravitreal or intravaginal administration.

In some embodiments, the compound is in a therapeutically effective amount. In some embodiments, the therapeutically effective amount may be about 1 mg to about 1000 mg, about 1 mg to about 900 mg, about 1 mg to about 800 mg, about 1 mg to about 700 mg, about 1 mg to about 600 mg, about 1 mg to about 500 mg, about 1 mg to about 400 mg, about 1 mg to about 300 mg, about 1 mg to about 200 mg, about 1 mg to about 100 mg, about 10 mg to about 1000 mg, about 50 mg to about 1000 mg, about 100 mg to about 1000 mg, about 200 mg to about 1000 mg, about 300 mg to about 1000 mg, about 400 mg to about 1000 mg, about 500 mg to about 1000 mg, about 10 mg to about 500 mg, about 50 mg to about 500 mg, about 100 mg to about 500 mg, about 10 mg to about 300 mg, about 50 mg to about 300 mg, from about 100 mg to about 300 mg, about 10 mg to about 150 mg, about 50 mg to about 150 mg, about 60 mg to about 120 mg, about 50 mg to about 120 mg or a range between any two of these values. Specific examples include, for example, about 1000 mg, about 900 mg, about 800 mg, about 700 mg, about 750 mg, about 600 mg, about 500 mg, about 400 mg, about 450 mg, about 300 mg, about 250 mg, about 200 mg, about 175 mg, about 150 mg, about 125 mg, about 120 mg, about 110 mg, about 100 mg, about 90 mg, about 80 mg, about 70 mg, about 60 mg, about 50 mg, about 30 mg, about 20 mg, or any value between the ranges disclosed above.

In some embodiments, the therapeutically effective amount can vary according to, for example, the particular use for which the treatment is made, the manner of administration of the compound, the health and condition of the patient, and the judgment of the prescribing physician. The proportion or concentration of a compound in a pharmaceutical composition can vary depending upon a number of factors including dosage, chemical characteristics (e.g., hydrophobicity), and the route of administration. For example, the compounds can be provided in an aqueous physiological buffer solution containing about 0.1 to about 10% w/v of the compound for parenteral administration. Some typical dose ranges for the compounds are from about 1 µg/kg to about 1 g/kg of body weight per day. In some embodiments, the dose range is from about 0.01 mg/kg to about 100 mg/kg of body weight per day. The dosage is likely to depend on such variables as the type and extent of progression of the disease or disorder, the overall health status of the particular patient, the relative biological efficacy of the compound selected, formulation of the excipient, and its route of administration. Effective doses can be extrapolated from dose-response curves derived from in vitro or animal model test systems.

The amount of compound or composition administered to a patient will vary depending upon what is being administered, the purpose of the administration, such as prophylaxis or therapy, the state of the patient, the manner of administration, and the like. In therapeutic applications, compositions can be administered to a patient already suffering from a disease in an amount sufficient to cure or at least partially arrest the symptoms of the disease and its complications.

For preparing solid compositions such as tablets, the principal active ingredient can be mixed with a pharmaceutical excipient to form a solid pre-formulation composition containing a homogeneous mixture of a compound of the present invention. When referring to these pre-formulation compositions as homogeneous, the active ingredient is typically dispersed evenly throughout the composition so that the composition can be readily subdivided into equally therapeutically effective unit dosage forms such as tablets, pills and capsules. This solid pre-formulation is then subdivided into unit dosage forms of the type described above containing from, for example, about 0.1 to about 1000 mg of the active ingredient.

The tablets or pills of the present invention can be coated or otherwise compounded to provide a dosage form affording the advantage of prolonged action. For example, the tablet or pill can comprise an inner dosage and an outer dosage component, the latter being in the form of an envelope over the former. The two components can be separated by an enteric layer which serves to resist disintegration in the stomach and permit the inner component to pass intact into the duodenum or to be delayed in release. A variety of materials can be used for such enteric layers or coatings, such materials including a number of polymeric acids and mixtures of polymeric acids with such materials as shellac, cetyl alcohol, and cellulose acetate.

The liquid forms in which the compounds and compositions of the present invention can be incorporated for administration orally or by injection include aqueous solutions, suitably flavored syrups, aqueous or oil suspensions, and flavored emulsions with edible oils such as cottonseed oil, sesame oil, coconut oil, or peanut oil, as well as elixirs and similar pharmaceutical vehicles.

Compositions for inhalation or insufflation include solutions and suspensions in pharmaceutically acceptable, aqueous or organic solvents, or mixtures thereof, and powders. The liquid or solid compositions may contain suitable pharmaceutically acceptable excipients as described supra. In some embodiments, the compositions are administered by the oral or nasal respiratory route for local or systemic effect. Compositions in can be nebulized by use of inert gases. Nebulized solutions may be breathed directly from the nebulizing device or the nebulizing device can be attached to a face masks tent, or intermittent positive pressure breathing machine. Solution, suspension, or powder compositions can be administered orally or nasally from devices which deliver the formulation in an appropriate manner.

In some embodiments, the compositions administered to a patient can be in the form of pharmaceutical compositions described above. In some embodiments, these compositions can be sterilized by conventional sterilization techniques, or may be sterile filtered. Aqueous solutions can be packaged for use as is, or lyophilized, the lyophilized preparation being combined with a sterile aqueous carrier prior to administration. In some embodiments, the pH of the compound preparations is about 3 to about 11, about 5 to about 9, about 5.5 to about 6.5, or about 5.5 to about 7.5. It will be understood that use of certain of the foregoing excipients, carriers, or stabilizers will result in the formation of pharmaceutical salts.

Methods of Use

The present invention relates to a method of modulation of a JAK1 and/or JAK3-mediated function in a subject comprising the administration of a therapeutically effective amount of a compound as disclosed herein.

The present invention also relates to a method of inhibiting at least one JAK1 and/or JAK3 function comprising the step of contacting JAK1 and/or JAK3 with a compound as described herein. The cell phenotype, cell proliferation, activity of JAK1 and/or JAK3, change in biochemical output produced by active JAK1 and/or JAK3, expression of JAK1 and/or JAK3, or binding of JAK1 and/or JAK3 with a natural binding partner may be monitored. Such methods may be modes of treatment of disease, biological assays, cellular assays, biochemical assays, or the like.

Also provided herein is a method of treating a JAK1 and/or JAK3-mediated disease comprising administering to a patient in need thereof a therapeutically effective amount of a compound as disclosed herein, a derivative thereof, or a combination thereof. In certain embodiments, the therapeutically effective amount of a compound as disclosed herein, a derivative thereof, or a combination thereof, may be in the form of a pharmaceutical composition. In embodiments, the pharmaceutical composition may include a pharmaceutically acceptable excipient.

In embodiments, diseases or disorders associated with a JAK1 kinase and/or a JAK3 kinase that are treated by compounds of the present invention include autoimmune disorders, chronic inflammatory disorders, acute inflammatory disorders, auto-inflammatory disorders, fibrotic disorders, metabolic disorders, neoplasias, or cardiovascular or cerebrovascular disorders. Thus, in some embodiments, the present invention provides a method for treating a JAK1 and/or JAK3 mediated disease or disorder in a patient in need thereof, wherein said method comprises administering to said patient a therapeutically effective amount of a provided compound, or composition thereof. Such JAK1 and/or JAK3-mediated diseases or disorders include, but are not limited to, those described herein.

In some embodiments, said JAK1 and/or JAK3-mediated disease or disorder is chosen from a skin disorder, pruritus, a hair loss disorder, a cancer, a neoplasm, Alzheimer's disease, an inflammatory condition, connective tissue diseases and an autoimmune condition.

In certain embodiments, said JAK1 and/or JAK3-mediated disease or disorder is a neoplasm, a malignancy, a myeloproliferative disorder, a hematopoietic neoplasm, a myeloid neoplasm, a lymphoid neoplasm, including myelofibrosis, primary myelofibrosis, polycythemia vera, essential thrombocythemia, acute and chronic leukemias, lymphomas, cutaneous lymphomas including mycosis fungoides, other myeloid malignancies, and myelodysplastic syndrome.

In certain embodiments, said JAK1 and/or JAK3-mediated disease is selected from the group consisting of an autoimmune disorders or responses, broad activation of the immune responses, bacterial infection, viral infection, inflammation, a chronic and/or acute inflammatory disorder or condition, and/or auto-inflammatory disorder, fibrotic disorders, metabolic disorders, a neoplasm, or cardiovascular or cerebrovascular disorders, a skin disorder, pruritus, a hair loss disorder, a cancer or malignancy, autoimmune connective tissue diseases and an autoimmune condition; Still's disease, adult-onset Still's disease, Th17-associated inflammation, polychondritis (e.g. relapsing polychondritis); myositis, polymyositis, autoimmune myositis, dermatomyositis, juvenile dermatomyositis; myasthenia gravis; Arthritis (e.g. rheumatoid arthritis, juvenile rheumatoid arthritis, systemic-onset juvenile rheumatoid arthritis, osteoarthritis, infectious arthritis, inflammatory arthritis, inflammatory bowel disease-associated arthritis, idiopathic arthritis, juvenile idiopathic arthritis, systemic juvenile idiopathic arthritis, psoriatic arthritis), spondylitis/spondyloarthritis/spondyloarthropathy (ankylosing spondylitis), gout, scleroderma (systemic scleroderma, juvenile scleroderma), Reiter's syndrome/reactive arthritis, lyme disease, lupus/systemic lupus erythematosus (SLE) (lupus erythematosus, pediatric systemic lupus erythematosus, cutaneous lupus (subacute cutaneous lupus, chronic cutaneous lupus/discoid lupus, chilblain lupus erythematosus), polymyalgia rheumatica, enthesitis, mixed connective tissue disease, enthesopathy; carditis, myocarditis, angiogenesis disorders, myelodysplastic syndrome, atherosclerosis, restenosis (restenosis of an atherosclerotic coronary artery), acute coronary syndrome, myocardial infarction, cardiac-allograft vasculopathy, transplant arteriopathy; vasculitis (large vessel vasculitis, small vessel vasculitis, giant-cell arteritis, polyarteritis nodosa, vasculitis syndromes including: Takayasu's arteritis, Wegener's granulomatosis, Behcet's Disease), stimulator of interferon genes (STING) associated vasculopathy with onset in infancy (SAVI); gastrointestinal disorders, enterocolitis, colitis, inflammatory bowel disease (ulcerative colitis, Crohn's disease), irritable bowel syndrome, enteritis syndrome/spastic colon, celiac disease; acute and chronic pancreatitis; primary biliary cirrhosis, primary sclerosing cholangitis, jaundice, cirrhosis (for example, primary biliary cirrhosis or cirrhosis due to fatty liver disease (for example, alcoholic and nonalcoholic steatosis); esophagitis, gastritis, gastric and duodenal ulcers, peritonitis; Nephropathies: immunologically mediated glomerulonephropathy, autoimmune nephropathy, membranous glomerulopathy, chronic progressive nephropathies, diabetic kidney disease/diabetic nephropathy, renal fibrosis, renal ischemic/reperfusion injury, HIV associated nephropathy, ureteral obstructive nephropathy, glomerulosclerosis, proteinuria, nephrotic syndrome, polycystic kidney disease, autosomal dominant polycystic kidney disease, a nephropathy is an immunologically mediated nephropathy, autoimmune nephropathy, chronic progressive nephropathies, diabetic nephropathy, renal fibrosis, ischemic/reperfusion injury associated, HIV associated nephropathy, ureteral obstructive nephropathy, glomerulonephritis, chronic kidney disease (for example, diabetic nephropathy), hypertension induced nephropathy, glomerulosclerosis, proteinuria, nephrotic syndrome, polycystic kidney disease, autosomal dominant polycystic kidney disease, diabetic kidney disease, lupus nephritis; interstitial cystitis; periodontitis, gingivitis; pulmonary inflammation, sinusitis, pneumonia, bronchitis, asthma, bronchial asthma, Churg-Strauss syndrome, bronchiolitis, bronchiolitis obliterans, chronic obstructive pulmonary disease (COPD), interstitial lung disease (pulmonary fibrosis, idiopathic pulmonary fibrosis), acute lung injury, pulmonary fibrosis (for example, idiopathic pulmonary fibrosis or cystic fibrosis), chronic obstructive pulmonary disease, adult respiratory distress syndrome, acute lung injury, drug-induced lung injury; Meniere's disease; ocular disorders including, (e.g.), ocular inflammation, uveitis, dry eye/keratoconjunctivitis sicca, scleritis, episcleritis, keratitis/keratopathy, choroiditis, retinal vasculitis, optic neuritis, retinopathy (diabetic retinopathy, immune mediated retinopathy, macular degeneration, wet macular degeneration, dry (age related) macular degeneration); Mastocytosis, iron deficiency anemia, uremia, hypereosinophilic syndrome (HES), systemic mast cell disease (SMCD), myelodysplastic syndrome, idiopathic thrombocytic pupura; bone resorption diseases; Neurodegenerative disorders, neurological/neuromuscular disorders (e.g.), multiple sclerosis, Parkinson's disease, Huntington's disease, amyotrophic lateral sclerosis (ALS) (familial ALS, sporadic ALS), Alzheimer's disease, myasthenia gravis, Lambert-Eaton myasthenic syndrome (LEMS), Guillain-Barret syndrome, meningitis, encephalitis, traumatic brain injury; nervous system damage, delusional parasitosis, dysregulation of neuronal processes and sensory perception, stroke/neuronal ischemia, spinal cord injury, peripheral neuropathy, tactile hallucinations, spinal cord injury, psychiatric disease; pain (acute pain, chronic pain, neuropathic pain, or fibromyalgia) paresthetica, nerve irritation, peripheral neuropathy; pruritus/itch (atopic pruritus, xerotic pruritus, pruritus associated with psoriasis/psoriatic itch/psoriasis-associated itch), acute pruritus, chronic pruritus, idiopathic pruritus, chronic idiopathic itch, biliary itch, hepatobiliary-associated itch, renal associated itch/renal itch, uremic itch, cholestasis, intrahepatic cholestasis of pregnancy, lichen simplex chronicus associated pruritus, lymphoma-associated itch, leukemia-associated itch, prurigo nodularis, atopic dermatitis-associated itch, atopic itch/atopic puritis, bullous itch, brachioradial pruritus) neurogenic itch, neuropathic itch, notalgia paresthetica, pruritic popular eruption of HIV, psychogenic itch, swimmer's itch, pruritus or uremic itch, urticarial itch; dermatologic disorders (e.g.), dermatologic drug reactions/drug eruptions, xerosis/dryskin, skin rash, skin sensitization, skin irritation, sunburn, shaving, body louse, head lice/pediculosis, pubic lice, cutaneous larva migrans, scabies, parasitic infection, insect infestation, urticarial/hives, popular uritcariaurticaria, insect bites, insect stings, dandruff, foreign objects or devices on skin, fungal infection, herpes, varicella/chicken pox, eosinophilic folliculitis, dermatosis of pregnancy/pruritic urticarial papules and plaques of pregnancy (PUPP), inflammatory dermatoses, neutrophilic dermatoses, histiocytoid neutrophilic dermatosis, bowel-bypass syndrome dermatosis, psoriasis/psoriasis vulgaris, lichen planus, lichen sclerosus, acne (acne vulgaris, comedonal acne, inflammatory acne, nodulo-cystic acne, scarring acne, acne keloidalis nuchae), atopies (allergic contact sensitization, allergic dermatitis) dermatitis (atopic dermatitis/eczema, contact dermatitis, photodermatitis, seborrheic dermatitis, stasis dermatitis, acute febrile neutrophilic dermatosis (Sweet's syndrome), chronic atypical neutrophilic dermatosis with lipodystrophy and elevated temperature syndrome (CANDLE Syndrome), hidradenitis suppurativa, hives, pyoderma gangrenosum, alopecia (eyebrow alopecia, intranasal hair alopecia, scarring alopecia (central centrifugal cicatricial alopecia), nonscarring alopecia (alopecia areata (AA) (patchy AA, alopecia totalis (AT), alopecia universalis (AU), ophiasis pattern alopecia areata, sisaihpo pattern alopecia areata)), androgenetic/androgenic alopecia (AGA)/male and female pattern AGA), telogen effluvium, tinea capitis, hypotrichosis (hereditary hypotrichosis simplex), lichen planopilaris (frontal fibrosing alopecia), punctate palmoplantar keratoderma, erythema elevatinum diutinum (EED), neutrophilic eccrine hidradenitis, palisading neutrophilic granulomatous dermatitis, neutrophilic urticarial dermatosis, vitiligo including segmental vitiligo (unisegmental vitiligo, bisegmental vitiligo, multisegmental vitiligo) non-segmental vitiligo (acral, facial, or acrofacial vitiligo, centrofacial vitiligo, mucosal vitiligo, confetti vitiligo, trichrome vitiligo, marginal inflammatory vitiligo, quadrichrome vitiligo, blue vitiligo, Koebner phenomenon, vulgaris vitiligo, generalized vitiligo, universal vitiligo), mixed vitiligo/nonsegmental associated with segmental vitiligo, focal vitiligo, solitary mucosal vitiligo or vitiligo with or without leukotricia (involvement of body hair); bullous diseases, immunobullous diseases (bullous pemphigoid, cicatricial pemphigoid, pemphigus vulgaris, linear IgA disease), gestational pemphigoid, xeroderma pigmentosum; disorders of fibrosis and scarring: fibroids, hepatic fibrosis, pulmonary fibrosis, idiopathic pulmonary fibrosis, low grade scarring such as, scleroderma, increased fibrosis, keloids, post-surgical scars; wound healing, surgical scarring, radiation induced fibrosis (for example, head and neck, gastrointestinal or pulmonary), CNS scarring, alimentary track or gastrointestinal fibrosis, renal fibrosis, hepatic or biliary fibrosis, liver fibrosis (for example, non-alcoholic steatohepatitis, hepatitis C, or hepatocellular carcinoma), cardiac fibrosis (for example, endomyocardial fibrosis or atrial fibrosis), ophthalmic scarring, fibrosclerosis, scar growth, wound or scab healing, keloid, mediastinal fibrosis, myelofibrosis, retroperitoneal fibrosis/Ormond's disease, progressive massive fibrosis, nephrogenic systemic fibrosis; Sjorgren's syndrome, sarcoidosis, familial Mediterranean fever, Cryopyrin associated periodic syndrome (Muckle-Wells syndrome, familial cold auto-inflammatory syndrome/familial cold uticaria/TNF receptor associated periodic syndrome, neonatal-onset multisystem inflammatory disease), hyperoxia induced inflammations, reperfusion injury, post-surgical trauma, tissue injury, elevated temperature syndrome; diabetes (Type I diabetes, Type II diabetes)/ diabetes mellitus, Hashimoto's thyroiditis, Graves' disease, Addison's disease, Castleman's disease, hyperparathyroidism, menopause, obesity, steroid-resistance, glucose intolerance, metabolic syndrome, thyroid illness, hypophysitis; systemic immune senescence; autoimmune atrophic gastritis, autoimmune atrophic gastritis of pernicious anemia, autoimmune encephalomyelitis, autoimmune orchitis, Goodpasture's disease, Sjogren's syndrome, autoimmune thrombocytopenia, sympathetic ophthalmia; secondary hematologic manifestations of autoimmune diseases (for example, anemias), autoimmune hemolytic syndromes (autoimmune hemolytic anemia), autoimmune and inflammatory hepatitis, autoimmune ovarian failure, autoimmune thrombocytopenia, silicone implant associated autoimmune disease, drug-induced autoimmunity, HIV-related autoimmune syndromes, metal-induced autoimmunity, autoimmune deafness, autoimmune thyroid disorders; allergy and allergic reactions including hypersensitivity reactions such as Type I hypersensitivity reactions, (e.g. including anaphylaxis), Type II hypersensitivity reactions (e.g. Goodpasture's Disease, autoimmune hemolytic anemia), Type III hypersensitivity reaction diseases (e.g. the Arthus reaction, serum sickness), and Type IV hypersensitivity reactions (e.g. contact dermatitis, allograft rejection); acute and chronic infection, sepsis syndromes (sepsis, septic shock, endotoxic shock, exotoxin-induced toxic shock, gram negative sepsis, gram positive sepsis, fungal sepsis, toxic shock syndrome); acute and chronic infection, sepsis syndromes (sepsis, septic shock, endotoxic shock, exotoxin-induced toxic shock, gram negative sepsis, gram positive sepsis, fungal sepsis, toxic shock syndrome); a rejection: graft vs. host reaction/graft vs. host disease, allograft rejections (for example, acute allograft rejection or chronic allograft rejection), early transplantation rejection; Malignancy, cancer, lymphoma, leukemia, multiple myeloma, a solid tumor, teratoma, metastatic and bone disorders, internal cancers, cancer of the: bone, mouth/pharynx, esophagus, larynx, stomach, intestine, colon, rectum, lung (for example, non-small cell lung cancer or small cell lung cancer), liver (hepatic), pancreas, nerve, brain (for example, glioma, glioblastoma multiforme, astrocytoma, neuroblastoma, and schwannomas), head and neck, throat, ovary, uterus, prostate, testis, bladder, kidney (renal), breast, gall bladder, cervix, thyroid, prostate, eye (ocular malignancies), and skin (melanoma, keratocanthoma); as well as fibrotic cancers, fibroma, fibroadenomas, fibrosarcomas, a myeloproliferative disorder, neoplasm (hematopoietic neoplasm, a myeloid neoplasm, a lymphoid neoplasm (myelofibrosis, primary myelofibrosis, polycythemia vera, essential thrombocythemia)), leukemias (acute lymphocytic leukemia, acute and chronic myelogenous leukemia, chronic lymphocytic leukemia, acute lymphoblastic leukemia, chronic myelomonocytic leukemia (CMML), or promyelocytic leukemia), multiple myeloma and other myeloid malignancies (myeloid metaplasia with myelofibrosis (MMM), primary myelofibrosis (PMF), idiopathic myelofibrosis (IMF)), lymphomas (Hodgkin's disease, cutaneous lymphomas (cutaneous T-cell lymphoma, mycosis fungoides), lymphomas (for example, B-cell lymphoma, T-cell lymphoma, mantle cell lymphoma, hairy cell lymphoma, Burkitt's lymphoma, mast cell tumors, Hodgkin's disease or non-Hodgkin's disease); Kaposi's sarcoma, rhabdomyosarcoma, seminoma, teratocarcinoma, osteosarcoma, thyroid follicular cancer; increased accumulation of exogenous opioids or synthetic opioids, notalgia paraesthetica, obsessive-compulsive disorders, nostalgia associated with obsessive-compulsive disorders, and a combination thereof.

In some embodiments, additional exemplary disorders include, but are not limited to: complications from organ transplants (including xenotransplantation) such as graft vs. host reaction (for example, graft vs. host disease), allograft rejections (for example, acute allograft rejection or chronic allograft rejection), early transplantation, diabetes, a myeloproliferative disorder, a rejection (for example, acute allograft rejection); bone resorption diseases, asthma (e.g., bronchial asthma), atopy, autoimmune thyroid disorders, chronic atypical neutrophilic dermatosis with lipodystrophy and elevated temperature syndrome (CANDLE Syndrome), SAVI (stimulator of interferon genes (STING) associated vasculopathy with onset in infancy), ulcerative colitis, inflammatory bowel disease, Crohn's disease, celiac disease, ulcerative colitis, Behcet's disease, myasthenia gravis, nephropathies, and myocarditis, secondary hematologic manifestations of autoimmune diseases (for example, anemias), autoimmune hemolytic syndromes, autoimmune and inflammatory hepatitis, autoimmune ovarian failure, autoimmune orchitis, autoimmune thrombocytopenia, silicone implant associated autoimmune disease, drug-induced autoimmunity, HIV-related autoimmune syndromes; acute and chronic infection, sepsis syndromes (e.g.) sepsis, septic shock, endotoxic shock, exotoxin-induced toxic shock, gram negative sepsis, gram positive sepsis, fungal sepsis, toxic shock syndrome; hyperoxia induced inflammations, reperfusion injury, post-surgical trauma, tissue injury, pain (e.g.) acute pain, chronic pain, neuropathic pain, or fibromyalgia.

In an embodiment, said vitiligo is segmental vitiligo including unisegmental, bisegmental or multisegmental vitiligo, non-segmental vitiligo including acral, facial, or acrofacial vitiligo, centrofacial vitiligo, mucosal vitiligo, confetti vitiligo, trichrome vitiligo, marginal inflammatory vitiligo, quadrichrome vitiligo, blue vitiligo, Koebner phenomenon, vulgaris vitiligo, generalized vitiligo, universal vitiligo, mixed vitiligo (nonsegmental associated with segmental vitiligo), focal vitiligo, solitary mucosal vitiligo or vitiligo with or without leukotricia (involvement of body hair) or any type of vitiligo set forth in Table 1 below:

TABLE 1

Classification of vitiligo.

| NOMENCLATURE | SUBSET | NOTES |
| --- | --- | --- |
| Non-segmental vitiligo | Acrofacial | Usually limited to face, head, hands, and feet |
|  | Generalized | Symmetrical macules, mainly hands, fingers, face, and trauma-exposed areas |
|  | Mucosal (at least two sites involved) | Involvement of the oral and/or genital mucosae with other sites of skin involvement |
|  | Universal | Depigmentation affects 80%-90% of body surface. |
| Segmental vitiligo | Unisegmental | One or more depigmented macules distributed on one side of the body |
|  | Bisegmental | Two segmental lesions distributed either unilaterally or bilaterally |
|  | Plurisegmental | Multiple segmental lesions distributed either unilaterally or bi-laterally |
| Mixed vitiligo | Occurrence of SV and NSV | SV followed by NSV with a delay of at least 6 months. At least 20% of a dermatomal segment affected by SV. |
| Unclassified vitiligo | Focal vitiligo | Isolated macules that do not have a segmental distribution. No evolution into NSV after at least 2 years |
|  | Mucosal vitiligo (only one site involved) | Exclusive involvement of the oral or genital mucosae |

In an embodiment, said skin disorder is atopic dermatitis, psoriasis, psoriasis vulgaris, skin sensitization, skin irritation, skin rash, contact dermatitis, allergic contact sensitization, allergic dermatitis, inflammatory dermatoses, or neutrophilic dermatoses.

"Pruritus", as used herein, is interchangeable with "itch." In some embodiments, pruritus includes chronic idiopathic pruritus, as well as pruritic components of other pruritic disorders. In some embodiments, pruritus may be a symptom of a disease or condition selected from the group consisting of: allergic reaction, arthropod bites, athlete's foot, atopic dermatitis (AD), atopic itch, atopic dermatitis-associated itch, autoimmune responses, autoimmune connective tissue disease, bacterial infection, biliary itch, broad activation of the immune responses, body louse, bullous diseases, brachioradial pruritus, brain tumors, chronic idiopathic pruritus, contact dermatitis, cholestasis, cutaneous larva migrans, cutaneous T-cell lymphoma, nervous system damage, dandruff, delusional parasitosis, dermatomyositis, dermatosis of pregnancy, diabetes mellitus, drug eruptions, dysregulation of neuronal processes and sensory perception, eczema, eosinophilic folliculitis, foreign objects or devices on skin, fungal infection, gestational pemphigoid, head lice, herpes, hidradenitis suppurativa, hives, Hodgkin's disease, hyperparathyroidism, idiopathic chronic itch, inflammation, insect infestation, insect bites, insect stings, intrahepatic cholestasis of pregnancy, iron deficiency anemia, increased accumulation of exogenous opioids or synthetic opioids, internal cancer, jaundice, lichen planus, lichen sclerosus, lupus erythematosus, lymphoma, lymphoma-associated itch, leukemia-associated itch, malignancy, mastocytosis, menopause, multiple sclerosis, neoplasm, nerve irritation, neurogenic itch, neuropathic itch, notalgia paresthetica, notalgia obsessive-compulsive disorders, paresthetica, parasitic infection, popular urticaria, pediculosis, peripheral neuropathy, photodermatitis, polycythemia vera, psychiatric disease, psychogenic itch, pruritic popular eruption of HIV, pruritic urticarial papules and plaques of pregnancy (PUPPP), psoriasis, psoriasis-associated itch, psoriatic itch, pubic lice, punctate palmoplantar keratoderma, renal itch, rheumatoid arthritis, scabies, scar growth, shaving, seborrheic dermatitis, stasis dermatitis, sunburn, swimmer's itch, systemic immune senescence, tactile hallucinations, Th17-associated inflammation, thyroid illness, uremia, pruritus or uremic itch, urticaria, urticarial itch, varicella, viral infection, wound or scab healing, and xerosis.

In an embodiment, the hair loss disorder is selected from alopecia, alopecia areata, patchy alopecia areata, alopecia totalis, alopecia universalis, ophiasis pattern alopecia areata, sisaihpo pattern alopecia areata, androgenetic alopecia (male and female pattern hair loss), telogen effluvium, tinea capitis, hypotrichosis, hereditary hypotrichosis simplex, scarring alopecia, lichen planopilaris, central centrifugal cicatricial alopecia, or frontal fibrosing alopecia.

In an embodiment, the connective tissue disease is selected from SLE (systemic lupus erythematosus), cutaneous lupus (e.g. SCLE, discoid lupus), chilblain lupus erythematosus, myositis, polymyositis, dermatomyositis, scleroderma, Sjogren's syndrome, polychondritis (relapsing polychondritis), vasculitis, or large vessel vasculitis.

In an embodiment, the nephropathy is selected from an immunologically mediated nephropathy, autoimmune nephropathy, chronic progressive nephropathies, diabetic nephropathy, renal fibrosis, ischemic/reperfusion injury associated, HIV associated nephropathy, ureteral obstructive nephropathy, glomerulosclerosis, proteinuria, nephrotic syndrome, polycystic kidney disease, autosomal dominant polycystic kidney disease or diabetic kidney disease.

In an embodiment, said cancer is a solid tumor.

In an embodiment, said cancer is prostate cancer, renal cancer, hepatic cancer, breast cancer, lung cancer, thyroid cancer, Kaposi's sarcoma, Castleman's disease or pancreatic cancer.

In an embodiment, said cancer is lymphoma, leukemia, or multiple myeloma.

In an embodiment, said myeloproliferative disorder (MPD) is polycythemia vera (PV), essential thrombocythemia (ET), myeloid metaplasia with myelofibrosis (MMM), primary myelofibrosis (PMF), chronic myelogenous leukemia (CML), chronic myelomonocytic leukemia (CMML), hypereosinophilic syndrome (HES), idiopathic myelofibrosis (IMF), or systemic mast cell disease (SMCD).

In an embodiment, said myeloproliferative disorder is myelofibrosis.

In an embodiment, said myeloproliferative disorder is primary myelofibrosis (PMF).

In an embodiment, said bone resorption disease is osteoporosis, osteoarthritis, bone resorption associated with hormonal imbalance, bone resorption associated with hormonal therapy, bone resorption associated with autoimmune disease, or bone resorption associated with cancer.

In some embodiments, the JAK1 and/or JAK-3-mediated disease or disorder is a fibrotic disorder. Exemplary fibrotic disorders include systemic sclerosis/scleroderma, lupus nephritis, connective tissue disease, wound healing, surgical scarring, spinal cord injury, CNS scarring, acute lung injury, pulmonary fibrosis (for example, idiopathic pulmonary fibrosis or cystic fibrosis), chronic obstructive pulmonary disease, adult respiratory distress syndrome, acute lung injury, drug-induced lung injury, glomerulonephritis, chronic kidney disease (for example, diabetic nephropathy), hypertension induced nephropathy, alimentary track or gastrointestinal fibrosis, renal fibrosis, hepatic or biliary fibrosis, liver fibrosis (for example, nonalcoholic steatohepatitis, hepatitis C, or hepatocellular carcinoma), cirrhosis (for example, primary biliary cirrhosis or cirrhosis due to fatty liver disease (for example, alcoholic and nonalcoholic steatosis), radiation induced fibrosis (for example, head and neck, gastrointestinal or pulmonary), primary sclerosing cholangitis, restenosis, cardiac fibrosis (for example, endomyocardial fibrosis or atrial fibrosis), ophthalmic scarring, fibrosclerosis, fibrotic cancers, fibroids, fibroma, fibroadenomas, fibrosarcomas, transplant arteriopathy, keloid, mediastinal fibrosis, myelofibrosis, retroperitoneal fibrosis, progressive massive fibrosis, and nephrogenic systemic fibrosis.

In some embodiments, the JAK1 and/or JAK-3-mediated disease or disorder is a metabolic disorder. Exemplary metabolic disorders include obesity, steroid-resistance, glucose intolerance, and metabolic syndrome. In some embodiments, the JAK1 and/or JAK-3-mediated disease or disorder is a neoplasia. Exemplary neoplasias include cancers. In some embodiments, exemplary neoplasias include angiogenesis disorders, multiple myeloma, leukemias (for example, acute lymphocytic leukemia, acute and chronic myelogenous leukemia, chronic lymphocytic leukemia, acute lymphoblastic leukemia, or promyelocytic leukemia), lymphomas (for example, B-cell lymphoma, T-cell lymphoma, mantle cell lymphoma, hairy cell lymphoma, Burkitt's lymphoma, mast cell tumors, Hodgkin's disease or non-Hodgkin's disease), myelodysplastic syndrome, fibrosarcoma, rhabdomyosarcoma; astrocytoma, neuroblastoma, glioma and schwannomas; melanoma, seminoma, teratocarcinoma, osteosarcoma, xeroderma pigmentosum, keratoacanthoma, thyroid follicular cancer, Kaposi's sarcoma, melanoma, teratoma, rhabdomyosarcoma, metastatic and bone disorders, as well as cancer of the bone, mouth/pharynx, esophagus, larynx, stomach, intestine, colon, rectum, lung (for example, non-small cell lung cancer or small cell lung cancer), liver, pancreas, nerve, brain (for example, glioma or glioblastoma multiforme), head and neck, throat, ovary, uterus, prostate, testis, bladder, kidney, breast, gall bladder, cervix, thyroid, prostate, and skin.

In some embodiments, the JAK1 and/or JAK-3-mediated disorder is a cardiovascular or cerebrovascular disorder. Exemplary cardiovascular disorders include atherosclerosis, restenosis of an atherosclerotic coronary artery, acute coronary syndrome, myocardial infarction, cardiac-allograft vasculopathy and stroke. Exemplary cerebrovascular diseases include central nervous system disorders with an inflammatory or apoptotic component, Alzheimer's disease, Parkinson's disease, Huntington's disease, amyotrophic lateral sclerosis, spinal cord injury, neuronal ischemia and peripheral neuropathy.

Also provided herein is a compound as disclosed herein for use as a medicament.

Also provided herein is a compound as disclosed herein for use as a medicament for the treatment of a JAK1 and/or JAK3-mediated disease.

Also provided is the use of a compound as disclosed herein as a medicament.

Also provided is the use of a compound as disclosed herein as a medicament for the treatment of a JAK1 and/or JAK3-mediated disease.

Also provided is a compound as disclosed herein for use in the manufacture of a medicament for the treatment of a JAK1 and/or JAK3-mediated disease.

Also provided is the use of a compound as disclosed herein for the treatment of a JAK1 and/or JAK3-mediated disease.

Also provided herein is a method of inhibition of JAK1 and/or JAK3 comprising administering a compound as disclosed herein, or a derivative thereof.

Also provided herein is a method for achieving an effect in a patient comprising the administration of a therapeutically effective amount of a compound as disclosed herein, or a salt thereof, to a patient, wherein the effect is chosen from cognition enhancement.

In certain embodiments, the JAK1 and/or JAK3-mediated disease is chosen from pruritus, alopecia, alopecia areata, vitiligo, male pattern androgenetic alopecia, female pattern androgenetic alopecia, atopic dermatitis, rheumatoid arthritis, psoriatic arthritis, and psoriasis.

The compounds can be administered in various modes, e.g. oral, parenteral (including subcutaneous, intradermal, intramuscular, intravenous, intraarticular, and intramedullary), intraperitoneal, intrathecal, intradural, transmucosal, transdermal, rectal, intranasal, topical (including, for example, dermal, buccal, sublingual and intraocular), intravitreal, or intravaginal administration. The specific dose level for any particular patient will depend upon a variety of factors including the activity of the specific compound employed, the age, body weight, general health, sex, diet, time of administration, route of administration, rate of excretion, drug combination, the precise disorder being treated, and the severity of the indication or condition being treated. Also, the route of administration may vary depending on the condition and its severity.

Thus, in another aspect, certain embodiments provide methods for treating JAK1 and/or JAK3-mediated disorders in a human or animal subject in need of such treatment comprising administering to said subject an amount of a compound disclosed herein effective to reduce or prevent said disorder in the subject, in combination with at least one additional agent for the treatment of said disorder that is known in the art. In a related aspect, certain embodiments provide therapeutic compositions comprising at least one compound disclosed herein in combination with one or more additional agents for the treatment of JAK1 and/or JAK3-mediated disorders.

In certain embodiments, a topically or orally administered JAK1 and/or JAK3 inhibitor/antagonist described herein can be used for the treatment of alopecia areata (e.g. patchy alopecia areata, alopecia totalis, alopecia universalis) alone or in combination with topical or intralesional corticosteroids, topical minoxidil, oral finasteride, oral dutasteride, contact sensitization therapy such as with squaric acid dibutyl ester, dinitrochlorobenzene, diphencyprone, topical or oral methoxalen and ultraviolet a (PUVA), topical anthralin, hair transplantation procedures, or other therapies known to have beneficial effects in the condition.

In certain embodiments, a topically or orally administered JAK1 and/or JAK3 inhibitor/antagonist disclosed herein can be used for the treatment of male or female-pattern baldness (androgenetic alopecia) alone or in combination with topical minoxidil, oral finasteride (in male), oral dutasteride (in male), topical antiandrogens, hair transplantation procedures, or other therapies known to have beneficial effects in the condition.

In certain embodiments, the compounds may be used for the treatment of vitiligo (e.g. localized vitiligo, focal vitiligo, generalized vitiligo, segmental vitiligo, acral vitiligo, facial vitiligo, acrofacial vitiligo, mucosal vitiligo, confetti vitiligo, trichrome vitiligo, marginal inflammatory vitiligo, quadrichrome vitiligo, blue vitiligo, Koebner phenomenon, vulgaris vitiligo, mixed acrofacial and vulgaris vitiligo, or universal vitiligo) alone or in combination with topical corticosteroids, topical tacrolimus, topical pimecrolimus, phototherapy such as ultraviolet light therapy with UVB, narrow-band UVB, oral or topical psoralen plus ultraviolet A (PUVA), calcipotriene or other topical vitamin D analogs, excimer laser phototherapy, systemic immunosuppressive agents, surgical treatments such as skin minigrafting, transplantation of autologous epidermal suspension, camouflage such as with make-up or dihydroxyacetone and such, or other therapies known to have beneficial effects in the condition.

Specific JAK1 and/or JAK3-mediated diseases to be treated by the compounds, compositions, and methods disclosed herein include a skin disorder, pruritus, cancer, Alzheimer's disease, an inflammatory condition, and an autoimmune condition.

In an embodiment, said skin disorder is pruritus, atopic dermatitis, psoriasis, acne vulgaris, comedonal acne, inflammatory acne, nodulo-cystic acne, scarring acne, hidradenitis suppurativa, pyoderma gangrenosum, skin sensitization, skin irritation, skin rash, contact dermatitis or allergic contact sensitization.

In an embodiment, said bone resorption disease is osteoporosis, osteoarthritis, bone resorption associated with hormonal imbalance, bone resorption associated with hormonal therapy, bone resorption associated with autoimmune disease, or bone resorption associated with cancer.

Besides being useful for human treatment, certain compounds and formulations disclosed herein may also be useful for veterinary treatment of companion animals, exotic animals and farm animals, including mammals, rodents, and the like. More preferred animals include horses, dogs, and cats.

Combination Therapy

The compounds and pharmaceutical compositions of the present disclosure may be used to prevent or treat a JAK-mediated disorder by the sequential or co-administration of another pharmaceutical agent.

In certain instances, it may be appropriate to administer at least one of the compounds described herein, or a derivative thereof, in combination with another pharmaceutical agent. By way of example only, if one of the side effects experienced by a patient upon receiving one of the compounds herein is hypertension, then it may be appropriate to administer an anti-hypertensive agent in combination with the initial pharmaceutical agent. Or, by way of example only, the therapeutic effectiveness of one of the compounds described herein may be enhanced by administration of an adjuvant (i.e., by itself the adjuvant may only have minimal therapeutic benefit, but in combination with another pharmaceutical agent, the overall therapeutic benefit to the patient is enhanced). Or, by way of example only, the benefit of experienced by a patient may be increased by administering one of the compounds described herein with another pharmaceutical agent (which also includes a therapeutic regimen) that also has therapeutic benefit. By way of example only, in a treatment for diabetes involving administration of one of the compounds described herein, increased therapeutic benefit may result by also providing the patient with another pharmaceutical agent for diabetes. In any case, regardless of the disease, disorder or condition being treated, the overall benefit experienced by the patient may simply be additive of the two pharmaceutical agents or the patient may experience a synergistic benefit.

Specific, non-limiting examples of possible combination therapies include use of compounds of embodiments herein with: chemotherapeutic or anti-proliferative agent, an anti-inflammatory agent, an immunomodulatory or immunosuppressive agent, a neurotrophic factor, an agent for treating cardiovascular disease, an agent for treating diabetes, or an agent for treating immunodeficiency disorders.

Specific, non-limiting examples of possible combination therapies for inflammation include use of certain compounds of the disclosure with: (1) corticosteroids, including but not limited to cortisone, dexamethasone, and methylprednisolone; (2) nonsteroidal anti-inflammatory drugs (NSAIDs), including but not limited to ibuprofen, naproxen, acetaminophen, aspirin, fenoprofen (NALFON™), flurbiprofen (ANSAID™), ketoprofen, oxaprozin (DAYPRO™), diclofenac sodium (VOLTAREN™), diclofenac potassium (CATAFLAM™), etodolac (LODINE™), indomethacin (INDOCIN™), ketorolac (TORADOL™), sulindac (CLINORIL™), tolmetin (TOLECTIN™), meclofenamate (MECLOMEN™), mefenamic acid (PONSTEL™), nabumetone (RELAFEN™) and piroxicam (FELDENE™); (3) immunosuppressants, including but not limited to methotrexate (RHEUMATREX™), leflunomide (ARAVA™), azathioprine (IMURAN™), cyclosporine (NEORAL™, SANDIMMUNE™), tacrolimus and cyclophosphamide (CYTOXAN™); (4) CD20 blockers, including but not limited to rituximab (RITUXAN™); (5) Tumor Necrosis Factor (TNF) blockers, including but not limited to etanercept (ENBREL™), infliximab (REMICADE™) and adalimumab (HUMIRA™); (6) interleukin-1 receptor antagonists, including but not limited to anakinra (KINERET™); (7) interleukin-6 inhibitors, including but not limited to tocilizumab (ACTEMRA™); (8) interleukin-17 inhibitors, including but not limited to AIN457; (9) Janus kinase inhibitors, including but not limited to tasocitinib; and (10) syk inhibitors, including but not limited to fostamatinib.

Specific, non-limiting examples of possible combination therapies for the treatment of cancer include use of certain compounds of the disclosure with: (1) alkylating agents, including but not limited to cisplatin (PLATIN™), carboplatin (PARAPLATIN™), oxaliplatin (ELOXATIN™), streptozocin (ZANOSAR™), busulfan (MYLERAN™) and cyclophosphamide (ENDOXAN™); (2) anti-metabolites, including but not limited to mercaptopurine (PURINETHOL™), thioguanine, pentostatin (NIPENT™), cytosine arabinoside (ARA-C™), gemcitabine (GEMZAR™), fluorouracil (CARAC™), leucovorin (FUSILEV™) and methotrexate (RHEUMATREX™); (3) plant alkaloids and terpenoids, including but not limited to vincristine (ONCOVIN™), vinblastine and paclitaxel (TAXOL™); (4) topoisomerase inhibitors, including but not limited to irinotecan (CAMPTOSAR™), topotecan (HYCAMTIN™) and etoposide (EPOSIN™); (5) cytotoxic antibiotics, including but not limited to actinomycin D (COSMEGEN™), doxorubicin (ADRIAMYCIN™), bleomycin (BLENOXANE™) and mitomycin (MITOSOL™); (6) angiogenesis inhibitors, including but not limited to sunitinib (SUTENT™) and bevacizumab (AVASTIN™); (7) tyrosine kinase inhibitors, including but not limited to imatinib (GLEEVEC™), erlotinib (TARCEVA™), lapatininb (TYKERB™) and axitinib (INLYTA™); and (8) immune checkpoint inhibitors, including but not limited to atezolizumab (TECENTRIQ™), avelumab (BAVENCIO™), durvalumab (IMFINZI™), ipilimumab (YERVOY™), pembrolizumab (KEYTRUDA™), nivolumab (OPDIVO™), and tremelimumab.

In some embodiments, the compounds disclosed in embodiments herein can also be co-administered (concurrently or sequentially) with a variety of other pharmaceutical agents or treatments, for example, pharmaceutical agents or treatments that are administered systemically, such as orally or parenterally. Examples of such systemic treatments include topical or systemic corticosteroids (such as prednisone), antibiotics (such as erythromycin, tetracycline, and dicloxacillin), antifungal agents (such as ketoconazole and fluconazole sold under the tradename Diflucan™), antiviral agents (such as valacyclovir sold under the tradename Valtrex™, acyclovir, and famciclovir sold under the tradename Famvir™), corticosteroids, immunosuppressants (such as cyclophosphamide sold under the tradename Cytoxan™, azathioprine, methotrexate, mycophenolate), biologics (such as rituximab sold under the tradename Rituxan™, etanercept sold under the tradename Enbrel™, adalimumab sold under the tradename Humira™, infliximab sold under the tradename Remicade™, ustenkinumab sold under the tradename Stelara™, and alefacept sold under the tradename Amevive™), and/or thyroid hormone replacement.

In some embodiments, other therapies that can be used in combination with the compounds disclosed herein include, for example, mercaptopurine, topical or systemic corticosteroids such as prednisone, methylprednisolone and prednisolone, alkylating agents such as cyclophosphamide, calcineurin inhibitors such as cyclosporine, sirolimus and tacrolimus, inhibitors of inosine monophosphate dehydrogenase (IMPDH) such as mycophenolate, mycophenolate mofetil, azathioprine, various antibodies, for example, anti-lymphocyte globulin (ALG), antithymocyte globulin (ATG), monoclonal anti-T-cell antibodies (OKT3), and irradiation. These various agents can be used in accordance with their standard or common dosages, as specified in the prescribing information accompanying commercially available forms of the drugs (see also, the prescribing information in the 2006 Edition of The Physician's Desk Reference). In some embodiments, standard dosages of these agents may be reduced when used in combination with the compounds of embodiments herein. Without limiting the scope of this disclosure, it is believed the such combination may result in synergistic results with better efficacy, less toxicity, longer duration of action, or quicker response to therapy. In some embodiments, the combination therapies in embodiments herein may be administered in sub-therapeutic amounts of either the compounds of embodiments herein or the additional pharmaceutical agents, or both. Azathioprine is currently available from Salix Pharmaceuticals, Inc. under the brand name Azasan™; mercaptopurine is currently available from Gate Pharmaceuticals, Inc. under the brand name Purinethol™; prednisone and prednisolone are currently available from Roxane Laboratories, Inc.; methyl prednisolone is currently available from Pfizer; sirolimus (rapamycin) is currently available from Wyeth-Ayerst under the brand name Rapamune™; tacrolimus is currently available from Fujisawa under the brand name Prograf™; cyclosporine is current available from Novartis under the brand name Sandimmune™ and Abbott under the brand name Gengraf™; IMPDH inhibitors such as mycophenolate mofetil and mycophenolic acid are currently available from Roche under the brand name Cellcept™ and Novartis under the brand name Myfortic™; azathioprine is currently available from Glaxo Smith Kline under the brand name Imuran™; and antibodies are currently available from Ortho Biotech under the brand name Orthoclone™, Novartis under the brand name Simulect™ (basiliximab) and Roche under the brand name Zenapax™ (daclizumab).

In some embodiments, the compounds of embodiments herein are administered in conjunction, concomitantly or adjunctively, with the pharmaceutical agents or therapies above and/or with a pharmaceutical agent or therapy for another disease. For example, the compounds of embodiments herein may be combined with thyroid hormone replacement therapy or with anti-inflammatory or immunomodulatory therapies.

In some embodiments, the combination therapies in embodiments herein may be administered in sub-therapeutic amounts of either the compounds of embodiments herein or the additional pharmaceutical agents, or both.

In any case, the multiple pharmaceutical agents (at least one of which is a compound disclosed herein) may be administered in any order or even simultaneously. If simultaneously, the multiple pharmaceutical agents may be provided in a single, unified form, or in multiple forms (by way of example only, either as a single pill or as two separate pills). One of the pharmaceutical agents may be given in multiple doses, or both may be given as multiple doses. If not simultaneous, the timing between the multiple doses may be any duration of time ranging from a few minutes to eight weeks or at any interval appropriate to maintain the desired therapeutic efficacy. In some embodiments, the timing between the multiple doses may be a minute, an hour, six hours, a day, two days, three days, four days, five days, six days, a week, two weeks, three weeks, four weeks, five weeks, six weeks, seven weeks or eight weeks.

One or more additional pharmaceutical agents such as, for example, anti-inflammatory agents, steroids, immunosuppressants, as well as one or more other ITK kinase inhibitors and/or other kinase inhibitors, such as JAK3 kinase, JAK1 kinase, JAK1/2 kinase, or JAK2 kinase inhibitors, such as, for example, those described in WO 99/65909, WO 00/00202, and/or WO/2004/099205, or other agents can be used in combination with the compounds of the present invention for treatment of JAK1 and/or JAK3-associated diseases, disorders or conditions.

In certain embodiments, the additional pharmaceutical agent is selected from taxanes, inhibitors of bcr-abl, inhibitors of EGFR, DNA damaging agents, antimetabolites, paclitaxel, imatinib, dasatinib, nilotinib, erlotinib, gefitinib, cisplatin, oxaliplatin, carboplatin, anthracyclines, AraC, 5-FU, camptothecin, doxorubicin, idarubicin, paclitaxel, docetaxel, vincristine, a MEK inhibitor, U0126, a KSP inhibitor, vorinostat, pembrolizumab, nivolumab, atezolizumab, avelumab, tremelimumab, and durvalumab.

In some embodiments, said composition further comprises an additional pharmaceutical agent selected from a chemotherapeutic or anti-proliferative agent, antiviral, antibiotic, antihistamine, an emollient, systemic phototherapy, psoralen photochemotherapy, laser therapy, hormone replacement therapy, an anti-inflammatory agent, an immunomodulatory or immunosuppressive agent, a neurotrophic factor, an agent for treating cardiovascular disease, an agent for treating diabetes, and an agent for treating immunodeficiency disorders.

In some embodiments, one or more compounds of the embodiments herein can be used in combination with one or more other therapeutics used in the treatment of JAK-mediated disorders, and may improve the treatment response as compared to the response to the other therapeutics alone, without exacerbation of its toxic effects. In some embodiments, compounds of embodiments herein can be used in combination with one or more other ITK inhibitors, and/or JAK1 and/or JAK3 inhibitors and/or JAK2 inhibitors and/or TYK2 inhibitors for the treatment of JAK-mediated disorders. Additive or synergistic effects are desirable outcomes of such combinations. The additional agents can be combined with the present compounds in a single or continuous dosage form, or the agents can be administered simultaneously or sequentially as separate dosage forms. In some embodiments, one or more additional agents can be administered to a patient in combination with at least one JAK1 and/or JAK3 inhibitor/antagonist described herein where the additional agents are administered intermittently as opposed to continuously.

General Synthetic Methods for Preparing Compounds

Compounds of the present invention can be prepared using methods illustrated in general synthetic schemes and experimental procedures detailed below. General synthetic schemes and experimental procedures are presented for purposes of illustration and are not intended to be limiting. Starting materials used to prepare compounds of the present invention are commercially available or can be prepared using routine methods known in the art. Representative procedures for the preparation of compounds of the invention are outlined in Schemes 1-5 below. Additional schemes used for analogs are provided in the examples. Solvents and reagents, whose synthetic preparations are not described below, can be purchased at Sigma-Aldrich or Fisher Scientific. Additional schemes for the synthesis of specific analogs are also provided in the example section.

Scheme 1 depicts the general synthesis of compounds of Formula (I) where $R_1$, $R_2$, $R_3$, and $R_4$ are defined as above, n is 0, 1 or 2, and X is a halogen. $PG_1$ is an indole protecting group such as benzenesulfonyl, toluenesulfonyl, mesitylenesulfonyl, t-butylcarbamate (Boc), allyl, benzyl, triisopropylsilyl (TIPS), 2-(trimethylsilyl)ethoxymethyl (SEM), or p-methoxybenzyl. $PG_2$ is a secondary amine protecting group such as 1-butylcarbamate (Boc), benzyl carbamate (Cbz), benzyl (Bn), p-methoxybenzyl (PMB), or N-acetyl (Ac). Compound CI is formed by coupling DI with EI. Removing the amine protecting group $PG_2$ yields compound BI. Coupling of BI with a compound of formula $HOR_4$ or halo-$R_4$ yields compound AI. Finally, removal of indole protecting group $PG_1$ yields a compound of Formula (I).

Alternatively, one could remove both protecting groups of CI and couple the intermediate with a compound of formula $HOR_4$ to yield compound I.

Scheme 1. General Synthesis of Pyrrolopyridine Analogs of Formula (I).

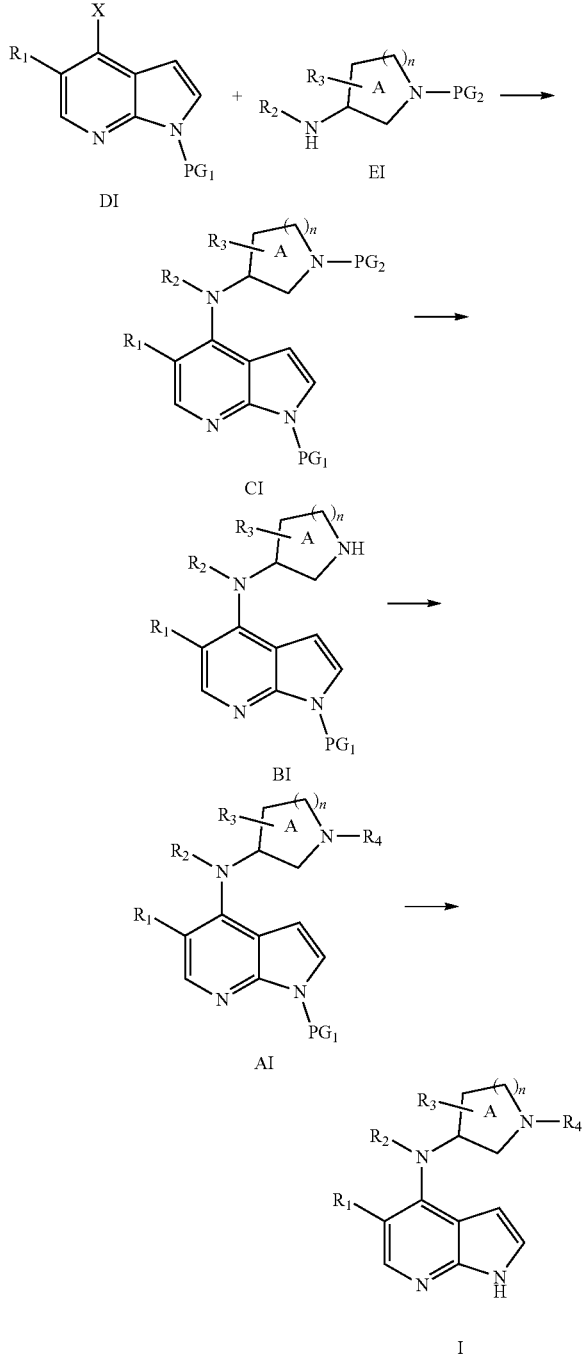

Scheme 2 illustrates a general synthesis for compounds of Formula I in cases when $R_1$ is a —$CO_2R_5$ group. Commercially available ethyl 4-chloro-1H-pyrrolo[2,3-b]pyridine-5-carboxylate (CAS #885500-55-0) can be protected using SEM-Cl under standard reaction conditions using a base such as sodium hydride in a solvent such as DMF or THF followed by the addition of SEM-Cl. The synthesis of diamine 3 (CAS #1251908-18-5) has been described previously (Shirakami et al., WO 2010119875) and may be converted to intermediate 3a by the reduction of the Boc protecting group with lithium aluminum hydride in a solvent such as THF. Alternatively, diamine 3 (CAS #1251908-18-5) may be deprotected using TFA in methylene chloride to give 3b. The secondary or primary amines 3a or 3b may be used to replace the chloride of 2 via nucleophilic aromatic substitution by heating in a solvent such as NMP. The resulting benzyl protected amine 4a or 4b can be deprotected with palladium on carbon in a solvent such as methanol. Once deprotected, amine 5a or 5b may be coupled with a variety of carboxylic acids under standard amide coupling procedures; reaction with acid 6 using tripropylphosphonic anhydride with triethylamine in dichloromethane is shown by way of example. Final deprotection using tetra-butylammonium fluoride in THF can produce the final compound 8a, ethyl 4-(((3R,4R)-1-(2-cyanoacetyl)-4-methylpiperidin-3-yl)(methyl)amino)-1H-pyrrolo[2,3-b]pyridine-5-carboxylate or 8b, ethyl 4-(((3R,4R)-1-(2-cyanoacetyl)-4-methylpiperidin-3-yl)amino)-1H-pyrrolo[2,3-b]pyridine-5-carboxylate. Other amines may be utilized in addition to 3a and 3b. For instance, (R)-1-benzylpiperidin-3-amine may be used and the corresponding analogs lacking a methyl group on the piperidine may be synthesized.

Scheme 2. Synthesis of 5-Ester Pyrrolopyridines.

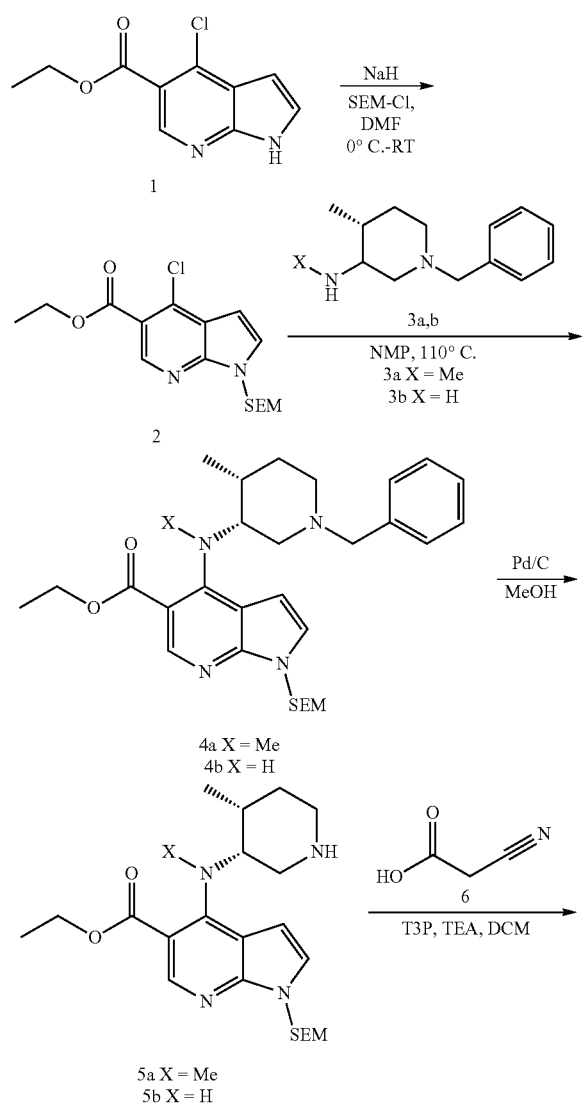

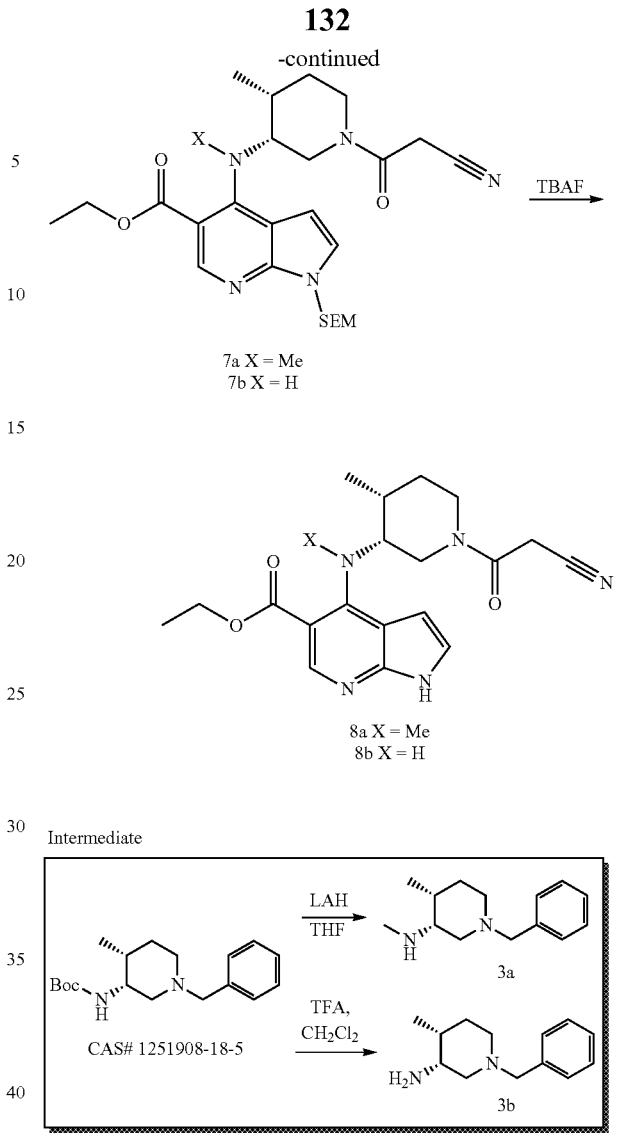

Analogs that have linkers between the carbonyl group of the ester and the pyrrolopyridine core may be accessed by methods described in Scheme 3. Commercially available 4-chloro-1-[tris(1-methylethyl)silyl]-1H-pyrrolo[2,3-b]pyridine (9) may be selectively lithiated at the 5 position using s-BuLi (Heinrich et al., J. Med. Chem. 2013) and reacted with $I_2$ to produce 4-chloro-5-iodo-1-triisopropylsilanyl-1H-pyrrolo[2,3-b]pyridine (10). Alternatively, the lithiated intermediate may be reacted directly with an electrophile such as ethyl 2-bromoacetate to produce intermediate 12. Other electrophiles such as allyl bromide could be used with the ester formed in subsequent steps by known methods. Compound 10 may be transformed in a variety of ways by palladium catalyzed cross coupling to produce analogs of interest. Illustrated here is reaction with ethyl acrylate (Heck reaction) followed by reduction of the double bond to produce intermediate 11. Intermediates 11 and 12 may be transformed into JAK inhibitors by the methods described in Scheme 2 using a protected diamine such as (3R,4R)-1-benzyl-N,4-dimethylpiperidin-3-amine or (3R,4R)-1-benzyl-4-methylpiperidin-3-amine.

Scheme 3. Preparation of 5-Alkyl-ester Pyrrolopyridines.

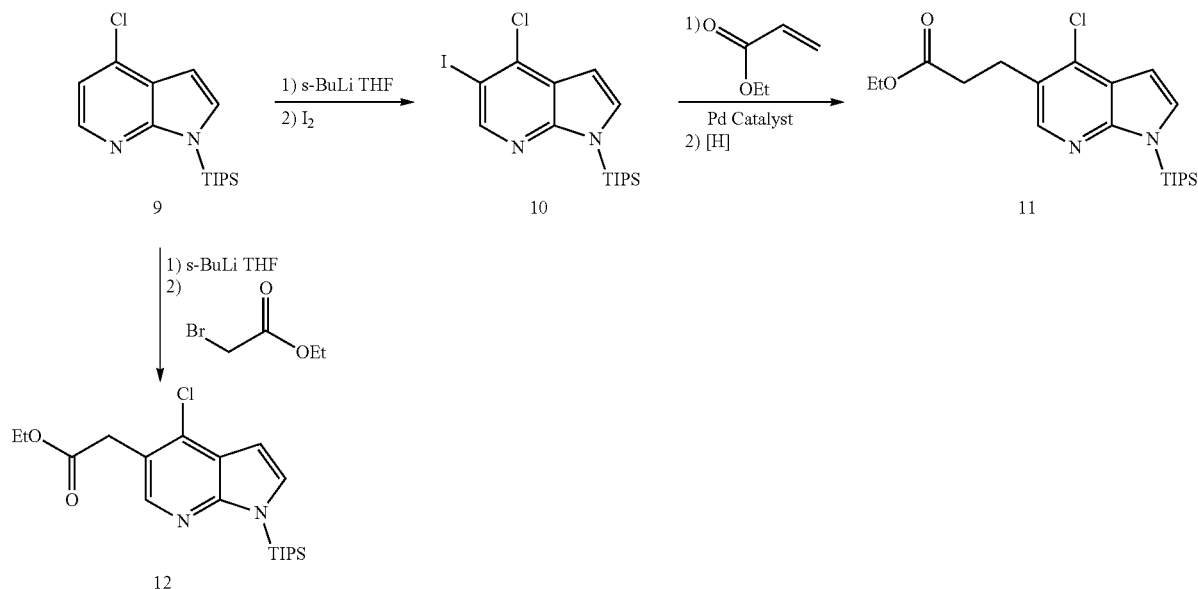

Scheme 4 depicts the general synthesis of compounds of Formula (II). $R_{10}$, $R_{20}$, $R_{30}$, and $R_{40}$ are defined as above, n is 0 or 1, and X is a halogen. $PG_{10}$ is an indole protecting group such as benzenesulfonyl, toluenesulfonyl, mesitylenesulfonyl, t-butylcarbamate (Boc), allyl, benzyl, triisopropylsilyl (TIPS), 2-(trimethylsilyl)ethoxymethyl (SEM), or p-methoxybenzyl. Compound FII is formed by reductive amination of GII with a compound of formula $NH_2R_{20}$. Compound DII is formed by the coupling of FII with a compound of formula EII. Compound CII is formed by removing the ketal group from a compound of DII. Compound BII is formed by the reduction of a ketone from a compound of Formula CII using sodium borohydride. Compound AII is formed by the coupling of a compound of Formula BII with a compound of formula $HOR_{40}$ under standard acylation or alkylation conditions. Finally, removal of indole protecting group $PG_{10}$ yields a compound of Formula (II). In some cases BII is deprotected to provide II where $R_{40}$ is OH.

Scheme 4. General Synthesis of Formula (II).

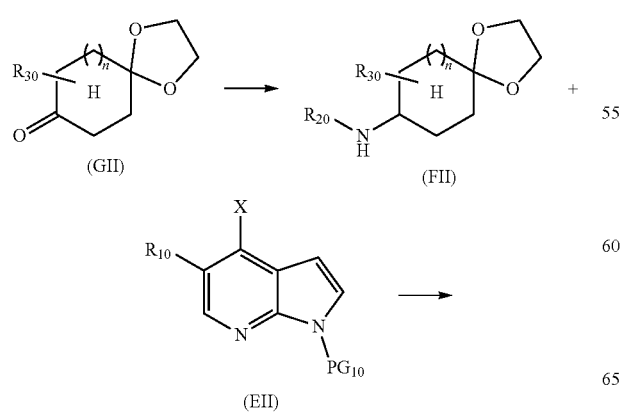

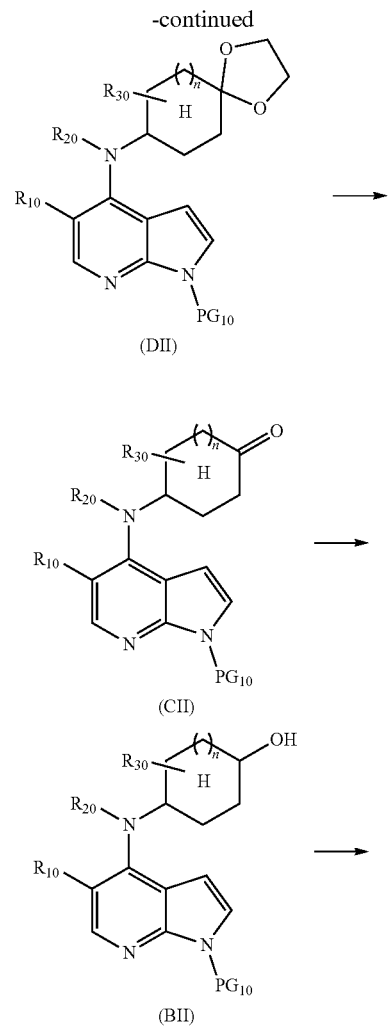

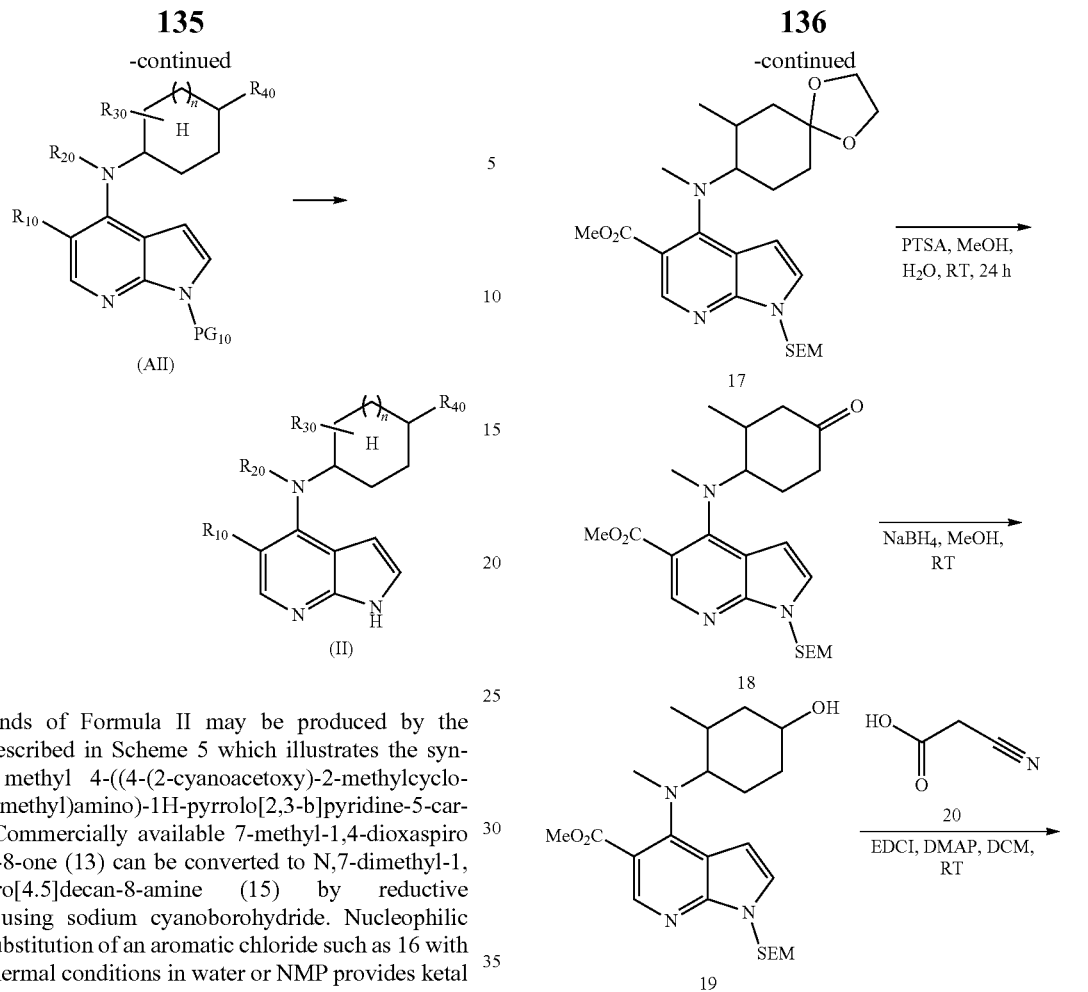

Compounds of Formula II may be produced by the methods described in Scheme 5 which illustrates the synthesis of methyl 4-((4-(2-cyanoacetoxy)-2-methylcyclohexyl) (methyl)amino)-1H-pyrrolo[2,3-b]pyridine-5-carboxylate. Commercially available 7-methyl-1,4-dioxaspiro[4.5]decan-8-one (13) can be converted to N,7-dimethyl-1,4-dioxaspiro[4.5]decan-8-amine (15) by reductive amination using sodium cyanoborohydride. Nucleophilic aromatic substitution of an aromatic chloride such as 16 with 15 under thermal conditions in water or NMP provides ketal protected intermediate 17. Deprotection followed by reduction can produce alcohol 19. Ester formation and deprotection results in the final analog 22.

Scheme 5. Synthesis of 5-Ester Pyrrolopyridines.

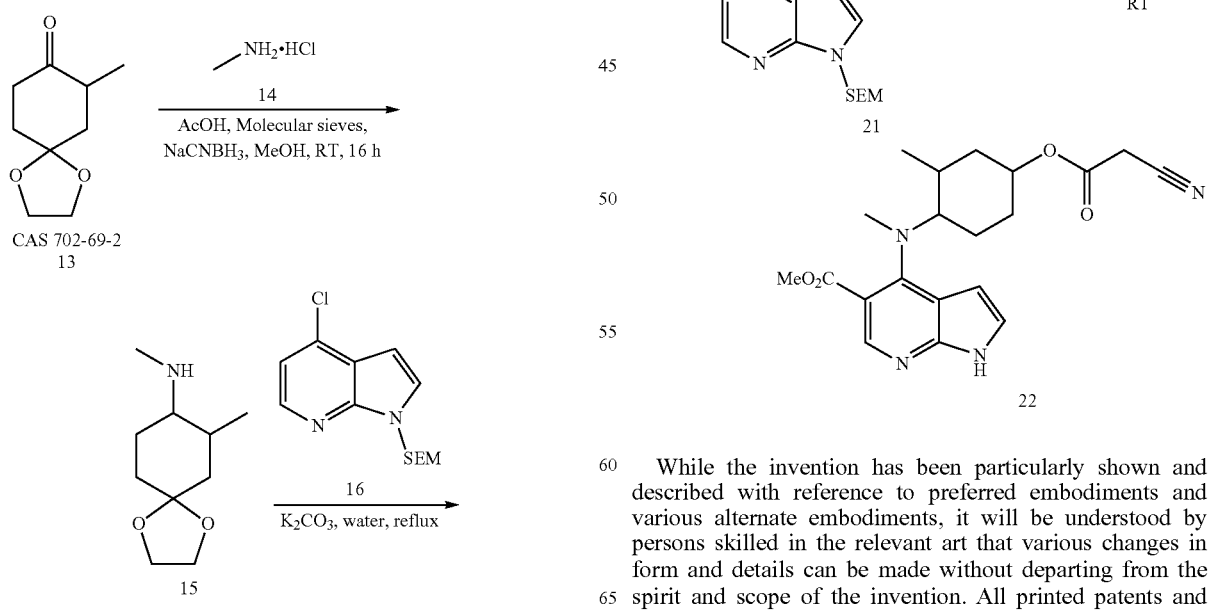

While the invention has been particularly shown and described with reference to preferred embodiments and various alternate embodiments, it will be understood by persons skilled in the relevant art that various changes in form and details can be made without departing from the spirit and scope of the invention. All printed patents and publications referred to in this application are hereby incorporated herein in their entirety by this reference.

Exemplary synthetic methods for certain compounds detailed in the example section are further illustrated by the following:

Synthesis of Example 1: Preparation of ethyl 4-(((3R,4R)-1-(2-cyanoacetyl)-4-methylpiperidin-3-yl)(methyl)amino)-1H-pyrrolo[2,3-b]pyridine-5-carboxylate

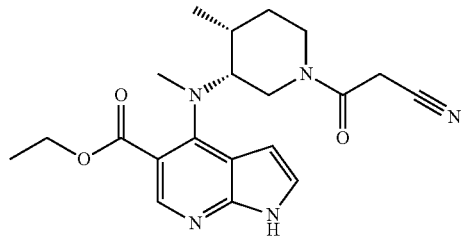 [SMILES: CCOC(=O)c1cnc2[nH]ccc2c1N(C)[C@H]1CN(C(=O)CC#N)CC[C@H]1C]

Scheme 6. Preparation of ethyl 4-(((3R,4R)-1-(2-cyanoacetyl)-4-methylpiperidin-3-yl)(methyl)amino)-1H-pyrrolo[2,3-b]pyridine-5-carboxylate

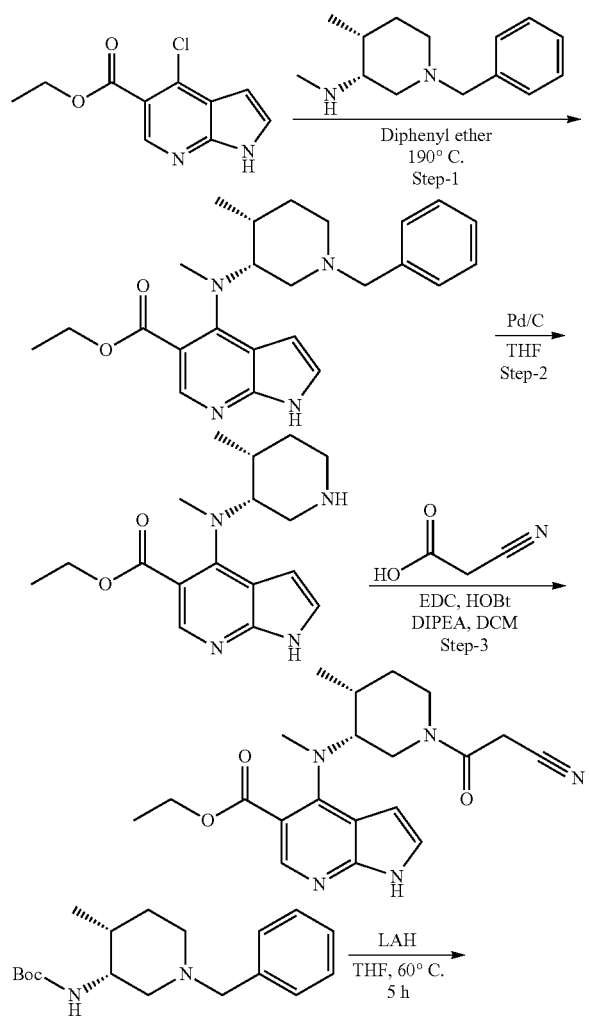

Preparation of (3R,4R)-1-benzyl-N,4-dimethylpiperidin-3-amine

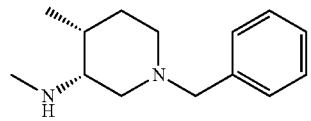 [SMILES: CN[C@H]1CN(Cc2ccccc2)CC[C@H]1C]

To a solution of tert-butyl ((3R,4R)-1-benzyl-4-methylpiperidin-3-yl)carbamate (1 g, 3.28 mmol) in tetrahydrofuran (20 mL), was added lithium aluminium hydride (4.9 mL, 4.9 mmol, 1M in THF) and mixture was heated to 60° C. for 5 hours. After cooling to ambient temperature, the reaction mixture was quenched with water and extracted with ethyl acetate. The organic layer was washed with water, brine and dried over anhydrous sodium sulfate. The solution was filtered and concentrated in vacuo to provide (3R,4R)-1-benzyl-N,4-dimethylpiperidin-3-amine (0.6 g, crude): MS (ES) m/z 219 (M+H).

Step 1: Preparation of ethyl 4-(((3R,4R)-1-benzyl-4-methylpiperidin-3-yl)(methyl)amino)-1H-pyrrolo[2,3-b]pyridine-5-carboxylate

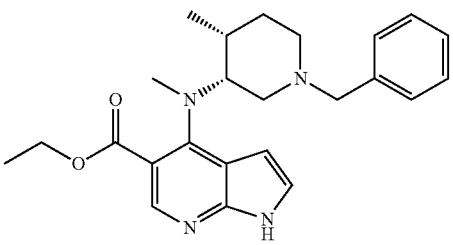 [SMILES: CCOC(=O)c1cnc2[nH]ccc2c1N(C)[C@H]1CN(Cc2ccccc2)CC[C@H]1C]

To a solution of ethyl 4-chloro-1H-pyrrolo[2,3-b]pyridine-5-carboxylate (0.17 g, 0.75 mmol) in diphenyl ether (0.1 mL), was added (3R,4R)-1-benzyl-N,4-dimethylpiperidin-3-amine (0.18 g, 0.83 mmol). The mixture was subjected to microwave irradiation at 190° C. for 0.5 hours. After cooling to ambient temperature, the reaction mixture was quenched with water and extracted with ethyl acetate. The organic layer was washed with water, brine and dried over anhydrous sodium sulfate. The solution was filtered and concentrated in vacuo. The crude material was purified using flash chromatography (50% ethyl acetate/hexane) to provide ethyl 4-(((3R,4R)-1-benzyl-4-methylpiperidin-3-yl)(methyl)amino)-1H-pyrrolo[2,3-b]pyridine-5-carboxylate as a thick liquid (0.035 g, 12% yield): MS (ES) m/z 407.2 (M+H).

Step 2: Preparation of ethyl 4-(methyl((3R,4R)-4-methylpiperidin-3-yl)amino)-1H-pyrrolo[2,3-b]pyridine-5-carboxylate

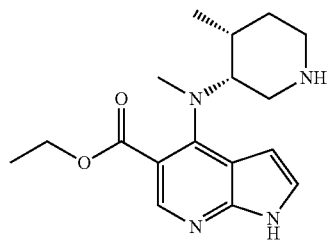 [SMILES: CCOC(=O)c1cnc2[nH]ccc2c1N(C)[C@H]1CNCC[C@H]1C]

To a solution of ethyl 4-(((3R,4R)-1-benzyl-4-methylpiperidin-3-yl)methyl)amino)-1H-pyrrolo[2,3-b]pyridine-5-carboxylate (0.09 g, 0.2 mmol) in tetrahydrofuran (1 mL) was added palladium on carbon (0.25 g, 50% wet w/w) and the mixture stirred under a hydrogen atmosphere at room temperature for 30 hours. The reaction was partitioned between 50% methanol/ethyl acetate and filtered through celite. The filtrate was concentrated in vacuo to provide 4-(methyl((3R,4R)-4-methylpiperidin-3-yl)amino)-1H-pyrrolo[2,3-b]pyridine-5-carboxylate (crude 0.07 g, 100% yield): MS (ES) m/z 317.2 (M+H).

Step 3: Preparation of ethyl 4-(((3R,4R)-1-(2-cyanoacetyl)-4-methylpiperidin-3-yl)(methyl)amino)-1H-pyrrolo[2,3-b] pyridine-5-carboxylate

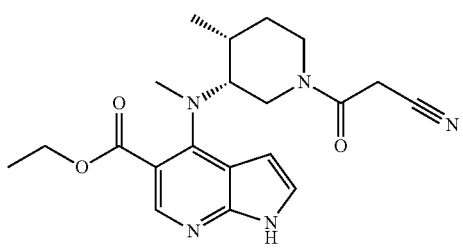 [SMILES: CCOC(=O)c1cnc2[nH]ccc2c1N(C)[C@H]1CN(C(=O)CC#N)CC[C@H]1C]

To a solution of ethyl 4-(methyl((3R,4R)-4-methylpiperidin-3-yl)amino)-1H-pyrrolo[2,3-b]pyridine-5-carboxylate (0.07 g, 0.22 mmol) in dichloromethane (2 mL) was added N-(3-dimethylaminopropyl)-N'-ethylcarbodiimide HCl (0.068 g, 0.4 mmol), 1-hydroxybenzotriazole (0.05 g, 0.44 mmol), N,N-diisopropylethylamine (0.05 g, 0.4 mmol) and cyanoacetic acid (0.028 g, 0.33 mmol) and the mixture was stirred at ambient temperature for 12 hours. The reaction was quenched with water and extracted with dichloromethane. The organic layer was washed with water, brine and dried over anhydrous sodium sulfate. The solution was filtered and concentrated in vacuo. The crude material was purified using flash chromatography (6% methanol/dichloromethane) to provide ethyl 4-(((3R,4R)-1-(2-cyanoacetyl)-4-methylpiperidin-3-yl)(methyl)amino)-1H-pyrrolo[2,3-b] pyridine-5-carboxylate (0.013 g, 5% yield): $^1$H NMR (400 MHz, DMSO-$d_6$, at 90° C.) δ 11.58 (s, 1H), 8.32 (s, 1H), 7.33 (s, 1H), 6.54 (br s, 1H) 4.28-4.29 (m, 2H) 3.81-3.94 (m, 4H), 3.37-3.49 (m, 3H), 2.94 (s, 3H), 2.16 (m, 1H), 1.61 (m, 2H), 1.30-1.33 (t, J=12 Hz, 3H), 0.94-0.96 (m, 3H); MS (ES) m/z 384.2 (M+H).

Synthesis of Example 3: Preparation of ethyl 4-(((3R,4R)-1-(2-cyanoacetyl)-4-methylpiperidin-3-yl)amino)-1H-pyrrolo[2,3-b]pyridine-5-carboxylate Scheme 7. Preparation of ethyl 4-(((3R,4R)-1-(2-cyanoacetyl)-4-methylpiperidin-3-yl)amino)-1H-pyrrolo[2,3-b]pyridine-5-carboxylate.

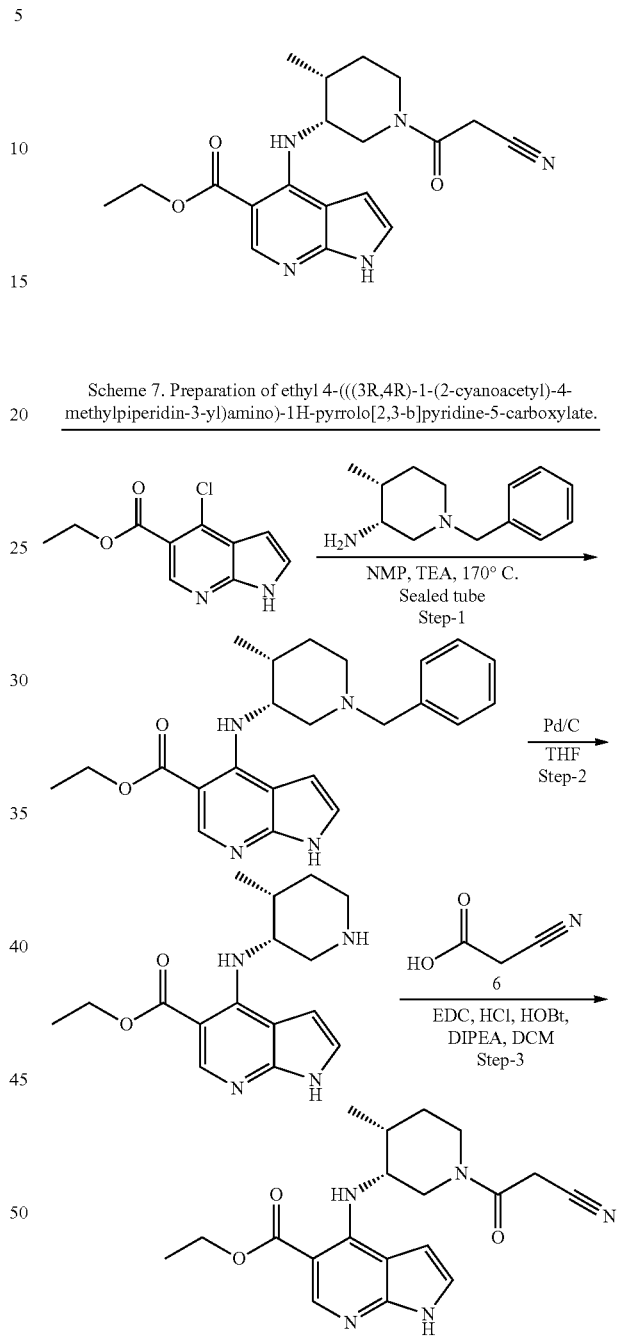

Preparation of (3R,4R)-1-benzyl-4-methylpiperidin-3-amine

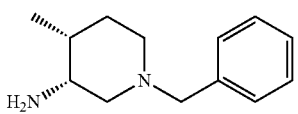

A solution of tert-butyl (3R,4R)-1-benzyl-4-methylpiperidin-3-yl)carbamate (2 g, 6.57 mmol) in HCl in dioxane (10 mL, 4M) was stirred at ambient temperature for 4 hours. The reaction mixture was concentrated in vacuo and neutralized with triethylamine (7 mL). The residue was quenched with water and extracted with dichloromethane. The organic layer was washed with water, brine and dried over anhydrous sodium sulfate. The solution was filtered and concentrated in vacuo to provide (3R, 4R)-1-benzyl-4-methylpiperidin-3-amine (1.3 g, crude): MS (ES) m/z 205.1 (M+H).

Step 1: Preparation of ethyl 4-(((3R,4R)-1-benzyl-4-methylpiperidin-3-yl)amino)-1H-pyrrolo[2,3-b]pyridine-5-carboxylate

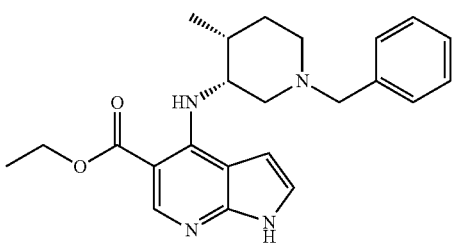 [SMILES: CCOC(=O)c1cnc2[nH]ccc2c1N[C@H]1CN(Cc2ccccc2)CC[C@H]1C]

To a solution of ethyl 4-chloro-1H-pyrrolo[2,3-b]pyridine-5-carboxylate (9 g, 40.17 mmol) in N-methyl-2-pyrrolidone (100 mL), was added (3R,4R)-1-benzyl-4-methylpiperidin-3-amine (9.8 g, 48.2 mmol) and triethylamine (4.5 mL) in a sealed tube and the mixture was heated to 170° C. for 16 hours. After cooling to room temperature, the reaction mixture was quenched with water and extracted with ethyl acetate. The organic layer was washed with water, brine and dried over anhydrous sodium sulfate. The solution was filtered and concentrated in vacuo. The crude material was purified using flash chromatography (50% ethyl acetate/hexane) to provide ethyl 4-(((3R,4R)-1-benzyl-4-methylpiperidin-3-yl)amino)-1H-pyrrolo[2,3-b]pyridine-5-carboxylate as a semi solid (10 g, 64% yield): MS (ES) m/z 393.4 (M+H).

Step 2: Preparation of ethyl 4-(((3R, 4R)-4-methylpiperidin-3-yl) amino)-1H-pyrrolo[2,3-b]pyridine-5-carboxylate

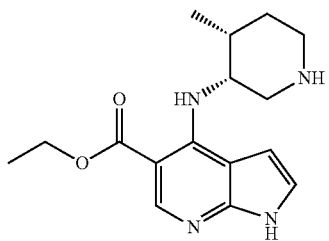

To a solution of ethyl 4-(((3R,4R)-1-benzyl-4-methylpiperidin-3-yl)amino)-1H-pyrrolo[2,3-b]pyridine-5-carboxylate (10 g, 25.5 mmol) in tetrahydrofuran (120 mL) was added palladium on carbon (30 g, 50% wet w/w) and the mixture was stirred under a hydrogen atmosphere using a Parr-shaker (70 psi) at ambient temperature for 30 hours. The reaction mixture was partitioned between 50% methanol/ethyl acetate and filtered through celite. The filtrate was concentrated to provide ethyl 4-(((3R,4R)-4-methylpiperidin-3-yl)amino)-1H-pyrrolo[2,3-b]pyridine-5-carboxylate (4.7 g, 95% yield): MS (ES) m/z 303.1 (M+H).

Step 3: Preparation of ethyl 4-(((3R,4R)-1-(2-cyanoacetyl)-4-methylpiperidin-3-yl)amino)-1H-pyrrolo[2,3-b]pyridine-5-carboxylate

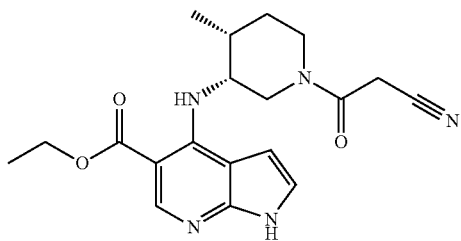 [SMILES: CCOC(=O)c1cnc2[nH]ccc2c1N[C@H]1CN(C(=O)CC#N)CC[C@H]1C]

To a solution of ethyl 4-(((3R,4R)-1-(2-cyanoacetyl)-4-methylpiperidin-3-yl)amino)-1H-pyrrolo[2,3-b]pyridine-5-carboxylate (4.7 g, 15.8 mmol) in dichloromethane (50 mL) was added N-(3-dimethylaminopropyl)-N'-ethylcarbodiimide HCl (4.9 g, 31.6 mmol), 1-hydroxybenzotriazole (4.2 g, 31.7 mmol), N,N-diisopropylethylamine (12.2 mL, 31.6 mmol) and cyanoacetic acid (2.7 g, 31.7 mmol) and the mixture was stirred at ambient temperature for 16 hours. The reaction was quenched with water and extracted with dichloromethane. The organic layer was washed with water, brine and dried over anhydrous sodium sulfate. The solution was filtered and concentrated in vacuo. The crude material was purified by using flash chromatography (6% methanol/dichloromethane) to provide ethyl 4-(((3R,4R)-1-(2-cyanoacetyl)-4-methylpiperidin-3-yl)amino)-1H-pyrrolo[2,3-b]pyridine-5-carboxylate (3.8 g, 66% yield): $^1$H NMR (400 MHz, DMSO-d$_6$ at 90° C.) δ 11.49 (s, 1H), 8.79-8.81 (m, 1H), 8.56 (s, 1H), 7.16 (s, 1H) 6.64 (s, 1H) 4.27-4.36 (m, 4H), 3.91 (m, 1H), 3.70 (m, 1H), 3.42 (m, 1H), 3.15 (m, 1H), 2.88 (m, 1H), 2.14 (br s, 2H), 1.64 (m, 1H), 1.30-1.33 (t, J=8.75 Hz, 3H), 0.95 (b s, 3H); MS (ES) m/z 370.3 (M+H).

Synthesis of Example 21: Preparation of 2-methoxyethyl 4-(((3R,4R)-1-(2-cyanoacetyl)-4-methylpiperidin-3-yl)amino)-1H-pyrrolo[2,3-b]pyridine-5-carboxylate

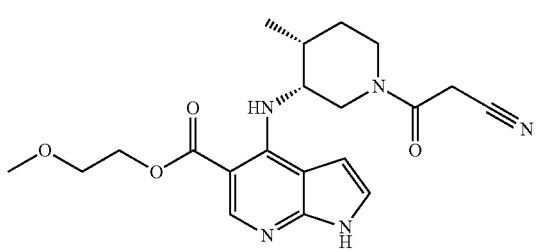 [SMILES: COCCOC(=O)c1cnc2[nH]ccc2c1N[C@H]1CN(C(=O)CC#N)CC[C@H]1C]

Scheme 8. Preparation of 2-methoxyethyl 4-(((3R,4R)-1-(2-cyanoacetyl)-4-methylpiperidin-3-yl)amino)-1H-pyrrolo[2,3-b]pyridine-5-carboxylate

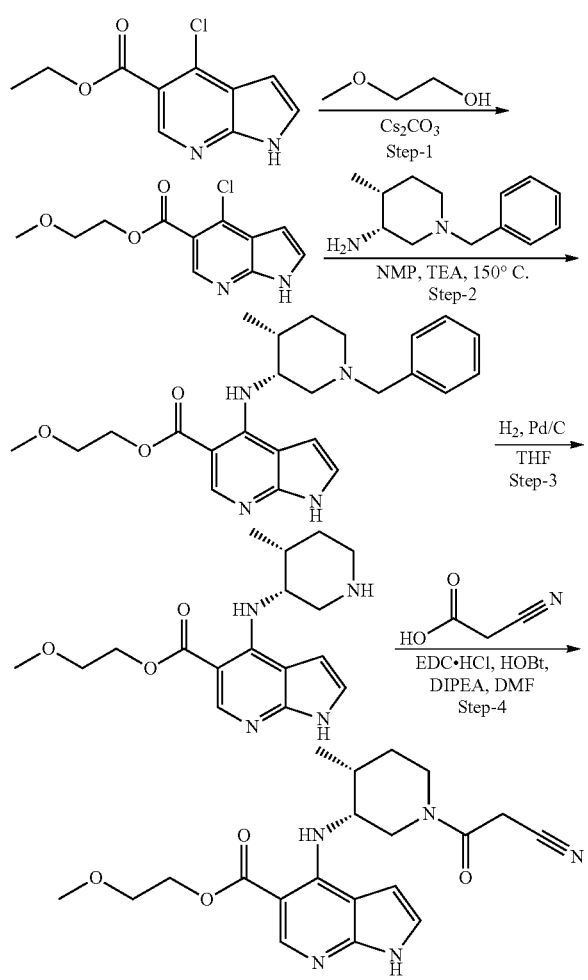

Step 1: Preparation of 2-methoxyethyl 4-chloro-1H-pyrrolo[2,3-b]pyridine-5-carboxylate

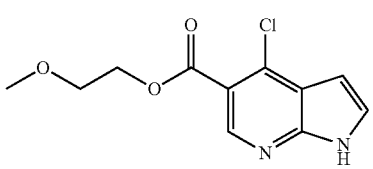 [SMILES: COCCOC(=O)c1cnc2[nH]ccc2c1Cl]

To a solution of ethyl 4-chloro-1H-pyrrolo[2,3-b]pyridine-5-carboxylate (4.0 g, 17.80 mmol) in methoxyethanol (40 mL) was added cesium carbonate (29.0 g, 89.0 mmol) and the mixture was stirred at ambient temperature for 16 hours. The reaction was quenched with water and extracted with ethyl acetate. The organic layer was washed with water, brine and dried over anhydrous sodium sulfate. The solution was filtered and concentrated in vacuo. The crude material was purified using flash chromatography (40% ethyl acetate/hexane) to provide 2-methoxyethyl 4-chloro-1H-pyrrolo[2,3-b]pyridine-5-carboxylate as a white solid (2.6 g, 57% yield): MS (ES) m/z 255 (M+H).

Step 2: Preparation of 2-methoxyethyl 4-(((3R,4R)-1-benzyl-4-methylpiperidin-3-yl)amino)-1H-pyrrolo[2,3-b]pyridine-5-carboxylate

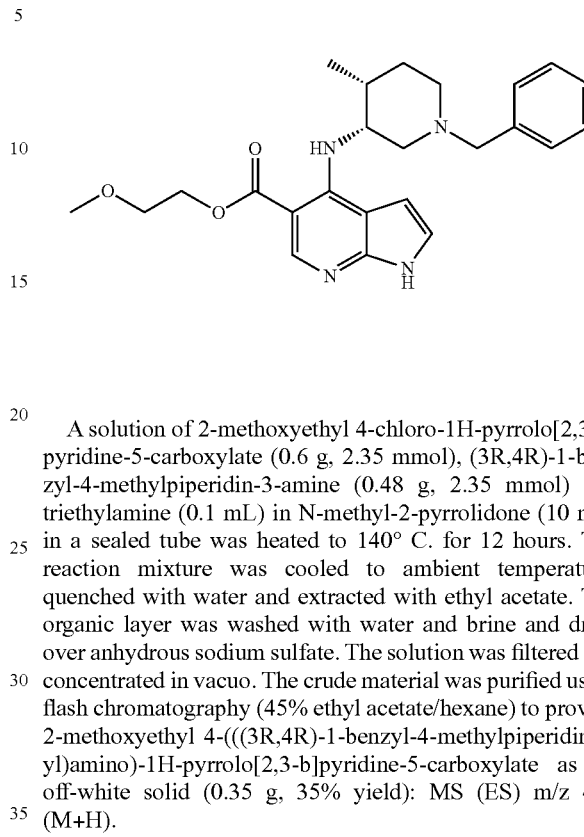

A solution of 2-methoxyethyl 4-chloro-1H-pyrrolo[2,3-b]pyridine-5-carboxylate (0.6 g, 2.35 mmol), (3R,4R)-1-benzyl-4-methylpiperidin-3-amine (0.48 g, 2.35 mmol) and triethylamine (0.1 mL) in N-methyl-2-pyrrolidone (10 mL) in a sealed tube was heated to 140° C. for 12 hours. The reaction mixture was cooled to ambient temperature, quenched with water and extracted with ethyl acetate. The organic layer was washed with water and brine and dried over anhydrous sodium sulfate. The solution was filtered and concentrated in vacuo. The crude material was purified using flash chromatography (45% ethyl acetate/hexane) to provide 2-methoxyethyl 4-(((3R,4R)-1-benzyl-4-methylpiperidin-3-yl)amino)-1H-pyrrolo[2,3-b]pyridine-5-carboxylate as an off-white solid (0.35 g, 35% yield): MS (ES) m/z 423 (M+H).

Step 3: Preparation of 2-methoxyethyl 4-(((3R,4R)-4-methylpiperidin-3-yl)amino)-1H-pyrrolo[2,3-b]pyridine-5-carboxylate

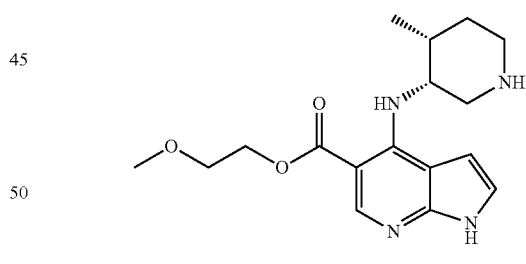

To a solution of 2-methoxyethyl 4-(((3R,4R)-1-benzyl-4-methylpiperidin-3-yl)amino)-1H-pyrrolo[2,3-b]pyridine-5-carboxylate (0.35 g, 0.82 mmol) in tetrahydrofuran (10 mL) was added palladium on carbon (0.3 g, 50% wet w/w) and the mixture was stirred under a hydrogen atmosphere at ambient temperature for 48 hours. The reaction mixture was filtered through celite. The filtrate was concentrated in vacuo to provide 2-methoxyethyl 4-(((3R,4R)-4-methylpiperidin-3-yl)amino)-1H-pyrrolo[2,3-b]pyridine-5-carboxylate (crude 0.16 g 58% yield): MS (ES) m/z 333 (M+H).

Step 4: Preparation of 2-methoxyethyl 4-(((3R,4R)-1-(2-cyanoacetyl)-4-methylpiperidin-3-yl)amino)-1H-pyrrolo[2,3-b]pyridine-5-carboxylate

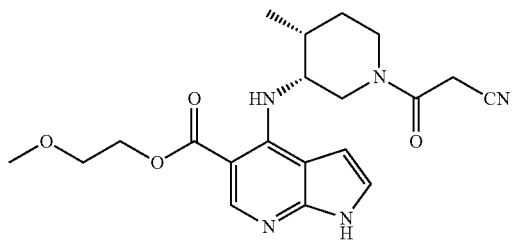 [SMILES: COCCOC(=O)c1cnc2[nH]ccc2c1N[C@H]1CN(C(=O)CC#N)CC[C@H]1C]

To a solution of 2-methoxyethyl 4-(((3R,4R)-4-methylpiperidin-3-yl)amino)-1H-pyrrolo[2,3-b]pyridine-5-carboxylate (0.16 g, 0.48 mmol) in N,N-dimethylformamide (10 mL) was added 1-ethyl-3-(3-dimethylamino propyl)carbodiimide.HCl (0.14 g, 0.96 mmol), 1-hydroxybenzotriazole (0.13 g, 0.96 mmol), N,N-diisopropylethylamine (0.25 mL, 1.44 mmol) and cyanoacetic acid (0.08 g, 0.96 mmol) and the mixture was stirred at ambient temperature for 24 hours. The reaction mixture was partitioned between ethyl acetate and water and the organic layer was separated. The organic layer was washed with water, brine and dried over anhydrous sodium sulfate. The solution was filtered and concentrated in vacuo. The crude material was purified using flash chromatography (5% methanol/dichloromethane) to provide 2-methoxyethyl 4-(((3R,4R)-1-(2-cyanoacetyl)-4-methylpiperidin-3-yl)amino)-1H-pyrrolo[2,3-b]pyridine-5-carboxylate (0.03 g, 16% yield): $^1$H NMR (400 MHz, DMSO-$d_6$, at 80° C.) δ 11.52 (s, 1H), 8.74 (s, 1H), 8.57 (s, 1H), 7.16 (s, 1H) 6.65 (s, 1H) 4.34-4.36 (m, 3H), 4.24 (m, 1H), 3.91 (m, 2H), 3.65-3.67 (m, 3H), 3.32 (s, 3H), 3.14 (m, 1H), 2.15 (m, 1H), 1.56-1.65 (m, 3H), 0.95 (br s, 3H); MS (ES) m/z 400 (M+H).

Synthesis of Example 24: Preparation of ethyl 4-(((3R,4R)-1-(2-cyanoethyl)-4-methylpiperidin-3-yl)amino)-1H-pyrrolo[2,3-b]pyridine-5-carboxylate

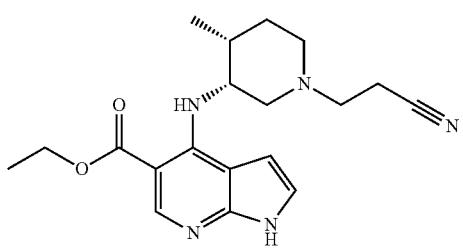 [SMILES: CCOC(=O)c1cnc2[nH]ccc2c1N[C@H]1CN(CCC#N)CC[C@H]1C]

Scheme 9. Preparation of ethyl 4-(((3R,4R)-1-(2-cyanoethyl)-4-methylpiperidin-3-yl)amino)-1H-pyrrolo[2,3-b]pyridine-5-carboxylate

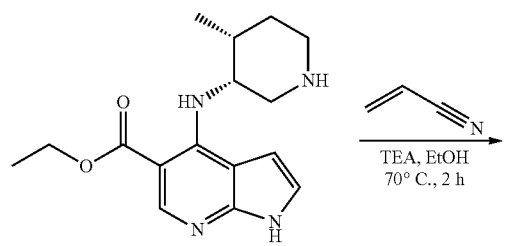

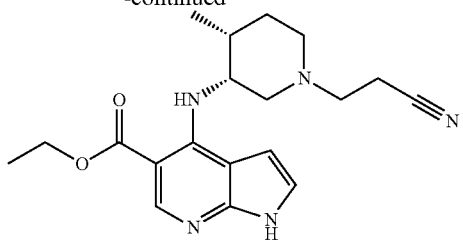

A solution of ethyl 4-(((3R,4R)-4-methylpiperidin-3-yl)amino)-1H-pyrrolo[2,3-b]pyridine-5-carboxylate (0.1 g, 0.311 mmol), acrylonitrile (0.035 g, 0.66 mmol) and triethylamine (0.13 mL, 0.99 mmol) in ethanol (10 mL) was heated at 70° C. for 2 hours. After cooling to ambient temperature, the reaction mixture was concentrated in vacuo and crude material purified using flash chromatography (50% ethyl acetate/hexane) to provide ethyl 4-(((3R,4R)-1-(2-cyanoethyl)-4-methylpiperidin-3-yl)amino)-1H-pyrrolo[2,3-b]pyridine-5-carboxylate (0.07 g, 63% yield): $^1$H NMR (400 MHz, DMSO-$d_6$) δ 11.61 (br s, 1H), 9.08 (d, J=9.2 Hz, 1H), 8.52 (s, 1H), 7.13 (s, 1H), 6.62 (s, 1H), 4.37 (br s, 1H), 4.24-4.25 (m, 2H), 2.79 (d, J=8.8 Hz, 2H), 2.43-2.60 (m, 4H), 2.02 (br s, 1H), 1.87 (br s, 1H), 1.70-1.55 (br s, 2H), 1.22-1.31 (m, 4H), 0.85 (d, J=6.0 Hz, 3H); MS (ES) m/z 356.2 (M+H).

Synthesis of Example 34: Preparation of ethyl (R)-4-((1-acryloylpiperidin-3-yl)amino)-1H-pyrrolo[2,3-b]pyridine-5-carboxylate

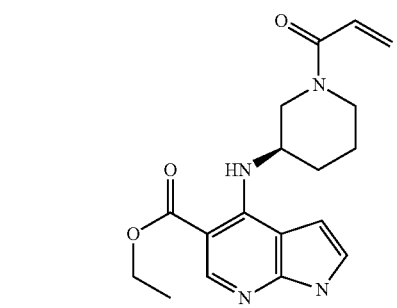 [SMILES: C=CC(=O)N1CCC[C@@H](Nc2c(C(=O)OCC)cnc3[nH]ccc23)C1]

Scheme 10. Preparation of ethyl (R)-4-((1-acryloylpiperidin-3-yl)amino)-1H-pyrrolo[2,3-b]pyridine-5-carboxylate

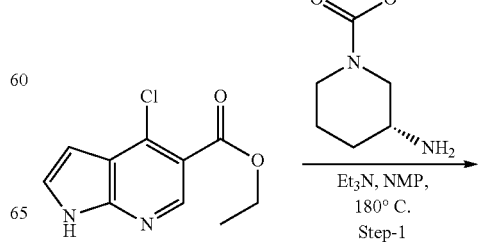

147

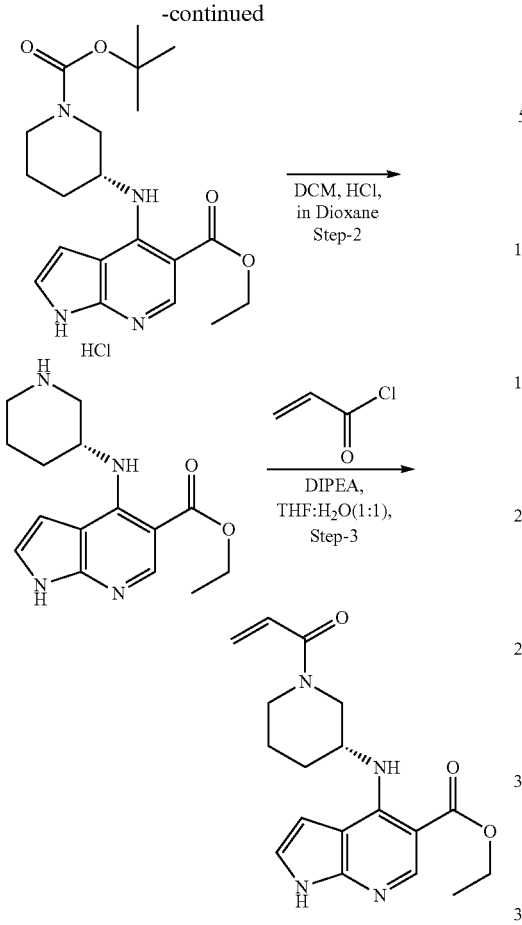

Step-1: Preparation of ethyl (R)-4-((1-(tert-butoxy-carbonyl)piperidin-3-yl)amino)-1H-pyrrolo[2,3-b]pyridine-5-carboxylate

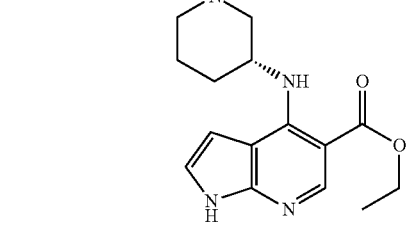

A solution of ethyl 4-chloro-1H-pyrrolo[2,3-b]pyridine-5-carboxylate (0.5 g, 2.23 mmol), tert-butyl (R)-3-aminopiperidine-1-carboxylate (0.53 g, 2.67 mmol) and triethylamine (0.3 mL) in N-methyl-2-pyrrolidone (10 mL) was subjected to microwave irradiation at 180° C. for 2 hours. After cooling to ambient temperature, the reaction mixture was quenched with water and extracted with ethyl acetate. The organic layer was dried over anhydrous sodium sulfate. The solution was concentrated in vacuo. The crude material was purified by using flash chromatography (50% ethyl acetate/hexane) to provide ethyl (R)-4-((1-(tert-butoxycarbonyl)piperidin-3-yl)amino)-1H-pyrrolo[2,3-b]pyridine-5-carboxylate as an off-white solid (0.6 g, 35% yield): MS (ES) m/z: 389.2 (M+H).

Step 2: Preparation of ethyl (R)-4-(piperidin-3-ylamino)-1H-pyrrolo[2,3-b]pyridine-5-carboxylate hydrochloride Salt

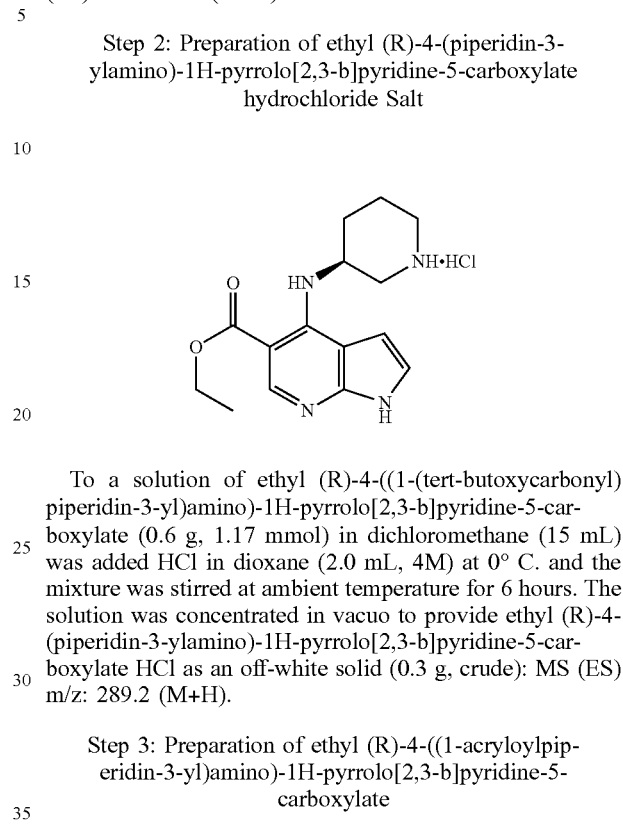

To a solution of ethyl (R)-4-((1-(tert-butoxycarbonyl)piperidin-3-yl)amino)-1H-pyrrolo[2,3-b]pyridine-5-carboxylate (0.6 g, 1.17 mmol) in dichloromethane (15 mL) was added HCl in dioxane (2.0 mL, 4M) at 0° C. and the mixture was stirred at ambient temperature for 6 hours. The solution was concentrated in vacuo to provide ethyl (R)-4-(piperidin-3-ylamino)-1H-pyrrolo[2,3-b]pyridine-5-carboxylate HCl as an off-white solid (0.3 g, crude): MS (ES) m/z: 289.2 (M+H).

Step 3: Preparation of ethyl (R)-4-((1-acryloylpiperidin-3-yl)amino)-1H-pyrrolo[2,3-b]pyridine-5-carboxylate

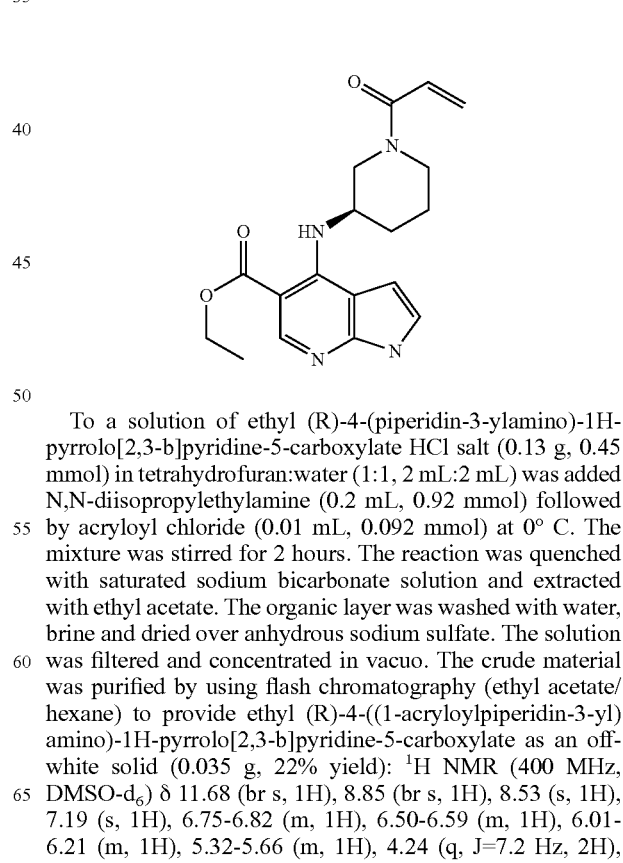

To a solution of ethyl (R)-4-(piperidin-3-ylamino)-1H-pyrrolo[2,3-b]pyridine-5-carboxylate HCl salt (0.13 g, 0.45 mmol) in tetrahydrofuran:water (1:1, 2 mL:2 mL) was added N,N-diisopropylethylamine (0.2 mL, 0.92 mmol) followed by acryloyl chloride (0.01 mL, 0.092 mmol) at 0° C. The mixture was stirred for 2 hours. The reaction was quenched with saturated sodium bicarbonate solution and extracted with ethyl acetate. The organic layer was washed with water, brine and dried over anhydrous sodium sulfate. The solution was filtered and concentrated in vacuo. The crude material was purified by using flash chromatography (ethyl acetate/hexane) to provide ethyl (R)-4-((1-acryloylpiperidin-3-yl)amino)-1H-pyrrolo[2,3-b]pyridine-5-carboxylate as an off-white solid (0.035 g, 22% yield): $^1$H NMR (400 MHz, DMSO-$d_6$) δ 11.68 (br s, 1H), 8.85 (br s, 1H), 8.53 (s, 1H), 7.19 (s, 1H), 6.75-6.82 (m, 1H), 6.50-6.59 (m, 1H), 6.01-6.21 (m, 1H), 5.32-5.66 (m, 1H), 4.24 (q, J=7.2 Hz, 2H), 4.11 (m, 1H), 3.72-3.84 (m, 1H) 3.57 (m, 1H), 2.06 (m, 1H), 1.70 (m, 2H), 1.58 (m, 1H), 1.31 (t, J=6.8 Hz, 3H), 1.22-1.25 (m, 1H), 0.82-1.09 (m, 1H); MS (ES) m/z: 343.2 (M+H).

Synthesis of Examples 68A and 68B: Preparation of enantiomers of (trans)-ethyl 4-((3-hydroxycyclopentyl)(methyl)amino)-1H-pyrrolo[2,3-b]pyridine-5-carboxylate 68A and 68B

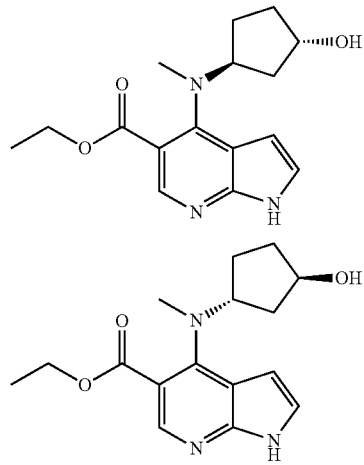

Scheme 11. Preparation of enantiomers of (trans)-ethyl 4-((3-hydroxycyclopentyl)(methyl)amino)-1H-pyrrolo[2,3-b]pyridine-5-carboxylate

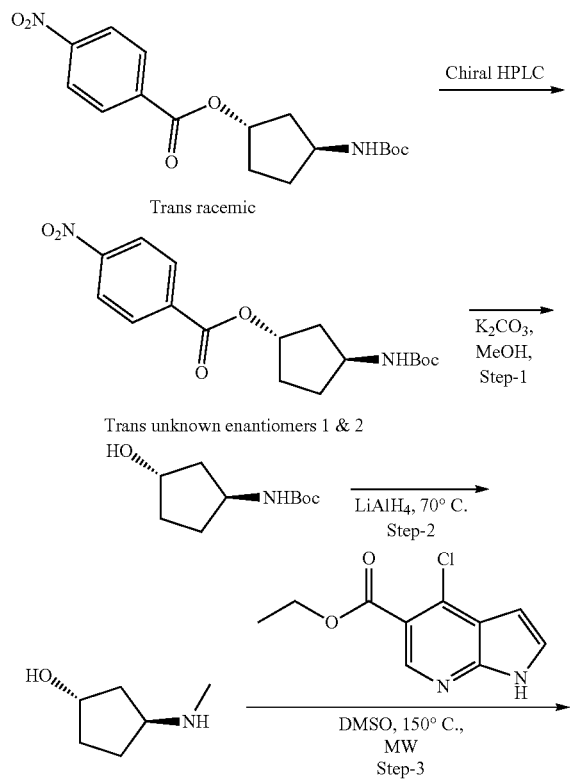

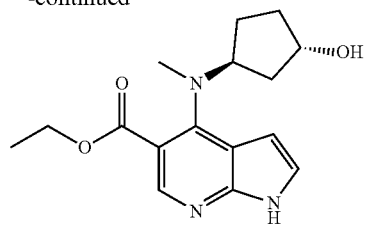

Trans unknown enantiomers 1 & 2

Chiral separation of (trans)-(rac)-3-((tert-butoxycarbonyl)amino)cyclopentyl 4-nitrobenzoate The enantiomers of (trans)-(rac)-3-((tert-butoxycarbonyl)amino)cyclopentyl 4-nitrobenzoate were separated by chiral chromatography.
Analytical Conditions:
Column: CHIRALPAK IA (250 mm×4.6 mm×51 m)
Mobile phase: nHexane:Ethanol with 0.1% DEA (50:50)
Flow rate: 1.0 mL/min
Enantiomer 1: Rentention time 4.161 min.
Enantiomer 2: Retention time 5.296 min.

Step 1: Preparation of (trans)-tert-butyl-(3-hydroxycyclopentyl)carbamate

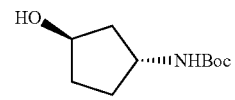 [SMILES: CC(C)(C)OC(=O)N[C@@H]1CC[C@@H](O)C1]

To a solution of one of the enantiomers of (trans)-3-((tert-butoxycarbonyl)amino)cyclopentyl 4-nitrobenzoate (1.2 g, 3.42 mmol) in methanol (30 mL) was added potassium carbonate (0.71 g, 5.14 mmol) and the mixture stirred at ambient temperature for 6 hours. The reaction mixture was concentrated in vacuo and the residue was dissolved in water and extracted with ethyl acetate. The organic layer was washed with water, brine and dried over anhydrous sodium sulfate. The solution was filtered and concentrated in vacuo. The crude material was purified by flash chromatography (30% ethyl acetate/hexane) to provide tert-butyl-(3-hydroxycyclopentyl) carbamate as an off-white solid (0.42 g, 60.95% yield): $^1$H NMR (400 MHz, DMSO-d$_6$) δ 6.72 (br s, 1H), 4.37 (d, J=3.6 Hz, 1H), 4.09-4.10 (m, 1H), 3.89-3.91 (m, 1H), 1.75-1.91 (m, 2H), 1.66-1.70 (m, 1H), 1.44-1.51 (m, 1H), 1.35 (s, 9H), 1.19-1.31 (m, 2H).

Step 2: Preparation of (trans)-3-(methylamino)cyclopentan-1-ol

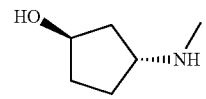

To a solution of one of the enantiomers of (trans)-tert-butyl-(3-hydroxycyclopentyl)carbamate (0.15 g, 0.74 mmol) in tetrahydrofuran (5 mL) and was added lithium aluminium hydride (2.23 mL, 2.23 mmol, (1.0M solution in tetrahydrofuran) dropwise at 0° C. and the mixture was heated at 70° C. for 4 hours. After cooling, the reaction mixture was quenched with aqueous sodium hydroxide solution and ethyl acetate and the suspension was filtered through celite. The organic layer was separated, washed with water and dried over anhydrous sodium sulphate. The filtrate was concentrated in vacuo to provide 3-(methylamino) cyclopentan-1-ol as a yellow oil (0.1 g, 80% yield): MS (ES) m/z 116 (M+H).

Step 3: Preparation of (trans)-ethyl 4-((3-hydroxy-cyclopentyl)(methyl)amino)-1H-pyrrolo [2,3-b] pyridine-5-carboxylate

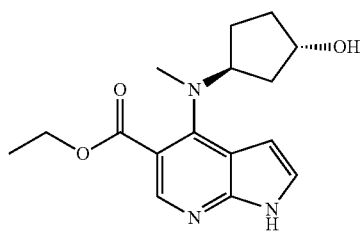 [SMILES: CCOC(=O)c1cnc2[nH]ccc2c1N(C)[C@H]1CC[C@H](O)C1]

A solution of ethyl 4-chloro-1H-pyrrolo[2,3-b]pyridine-5-carboxylate (0.15 g, 0.66 mmol) and one of the enantiomers of 3-(methylamino)cyclopentan-1-ol (0.092 g, 0.8 mmol) in dimethyl sulfoxide (3 mL) was heated under microwave irradiation for 2 hours. After cooling to ambient temperature, the reaction mixture was quenched with water and extracted with ethyl acetate. The organic layer was washed with water, brine and dried over anhydrous sodium sulfate. The solution was filtered and concentrated in vacuo. The crude material was purified by flash chromatography (9% methanol/dichloromethane) to obtain ethyl 4-((3-hydroxycyclopentyl)(methyl)amino)-1H-pyrrolo[2,3-b]pyridine-5-carboxylate as a brown solid (0.015 g, 7.42% yield).

Example 68A: (trans)-Ethyl 4-((-3-hydroxycyclopentyl)(methyl)amino)-1H-pyrrolo[2,3-b] pyridine-5-carboxylate, enantiomer 1

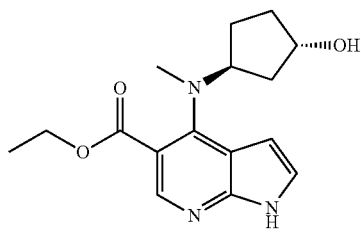 [SMILES: CCOC(=O)c1cnc2[nH]ccc2c1N(C)[C@H]1CC[C@H](O)C1]

$^1$H NMR (400 MHz, DMSO-d$_6$) δ 11.59 (s, 1H), 8.20 (m, 1H), 7.24-7.26 (m, 1H), 6.57-6.58 (m, 1H), 4.66-4.80 (m, 1H), 4.57 (m, 1H), 4.06-4.27 (m, 3H), 2.82 (s, 3H), 1.78-1.96 (m, 3H), 1.60-1.76 (m, 2H), 1.48-1.50 (m, 1H), 1.30 (t, J=8.8 Hz, 3H); MS (ES) m/z 304 (M+H).

Example 68B: (trans)-Ethyl 4-((-3-hydroxycyclopentyl)(methyl)amino)-1H-pyrrolo[2,3-b]pyridine-5-carboxylate, enantiomer 2

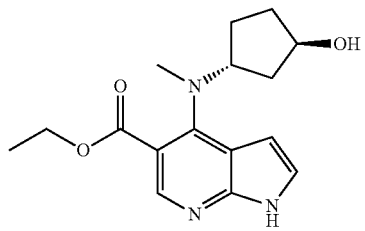 [SMILES: CCOC(=O)c1cnc2[nH]ccc2c1N(C)[C@@H]1CC[C@@H](O)C1]

$^1$H NMR (400 MHz, DMSO-d$_6$) δ 11.59 (br s, 1H), 8.20 (m, 1H), 7.24-7.26 (m, 1H), 6.57-6.58 (m, 1H), 4.66-4.74 (m, 1H), 4.54-4.55 (m, 1H), 4.20-4.27 (m, 3H), 2.78 (s, 3H), 1.80-1.94 (m, 3H), 1.71-1.78 (m, 2H), 1.48-1.51 (m, 1H), 1.31 (t, J=8.8 Hz, 3H).

Synthesis of Example 69: Isolation of Trans enantiomer-2, (trans)-ethyl 4-((3-(2-cyanoacetoxy)cyclopentyl)(methyl)amino)-1H-pyrrolo[2,3-b]pyridine-5-carboxylate

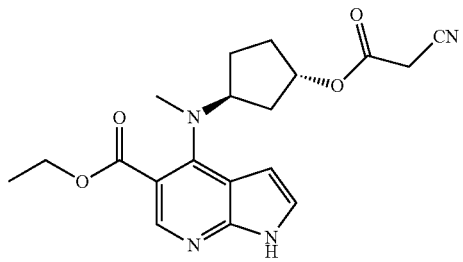

Trans enantiomer-2

$^1$H NMR (400 MHz, DMSO-d$_6$) δ 11.64 (s, 1H), 8.24 (s, 1H), 7.26-7.28 (m, 1H), 6.55-6.56 (m, 1H), 5.21-5.22 (m, 1H), 4.57-4.61 (m, 1H), 4.26 (q, J=6.8 Hz 2H), 3.94 (s, 2H), 2.84 (s, 3H), 2.11-2.20 (m, 2H), 1.92-2.0 (m, 3H), 1.83-1.86 (m, 1H), 1.29 (t, J=7.6 Hz, 3H). Retention time: 21.666 min.

Synthesis of Example 70: Isolation of Trans enantiomer-1, (trans)-ethyl 4-((3-(2-cyanoacetoxy)cyclopentyl)(methyl)amino)-1H-pyrrolo[2,3-b]pyridine-5-carboxylate

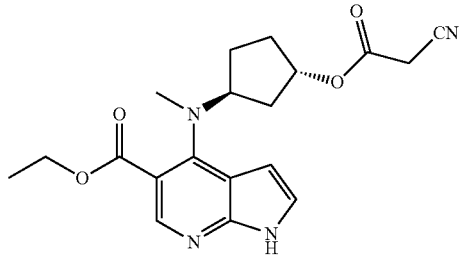

Trans enantiomer-1

¹H NMR (400 MHz, DMSO-d₆) δ 11.64 (s, 1H), 8.24 (s, 1H), 7.26-7.28 (m, 1H), 6.55-6.56 (m, 1H), 5.21-5.22 (m, 1H), 4.57-4.61 (m, 1H), 4.25 (q, J=6.8 Hz, 2H), 3.94 (s, 2H), 2.82 (s, 3H), 2.10-2.11 (m, 2H), 1.85-1.96 (m, 3H), 1.68-1.70 (m, 1H), 1.27 (t, J=7.2 Hz, 3H); Retention time: 19.434 min.

Synthesis of Examples 72-75: Preparation of enantiomers of (trans)-ethyl 4-((3-hydroxycyclopentyl)amino)-1H-pyrrolo[2,3-b]pyridine-5-carboxylate: 72 and 75 and (trans)-ethyl 4-((3-(2-cyanoacetoxy)cyclopentyl)amino)-1H-pyrrolo[2,3-b]pyridine-5-carboxylate: 73 and 74

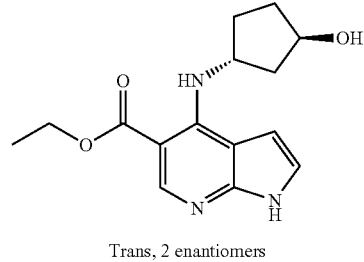

Trans, 2 enantiomers

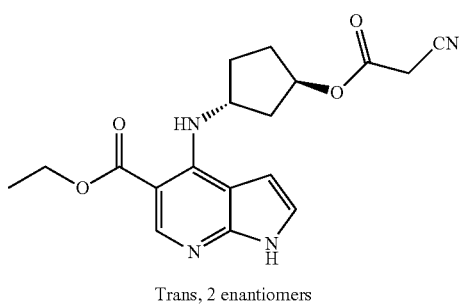

Trans, 2 enantiomers

Scheme 13. Preparation of enantiomers of (trans)-ethyl 4-((3-hydroxycyclopentyl)amino)-1H-pyrrolo[2,3-b]pyridine-5-carboxylate and (trans)-ethyl 4-((3-(2-cyanoacetoxy)cyclopentyl)amino)-1H-pyrrolo[2,3-b]pyridine-5-carboxylate

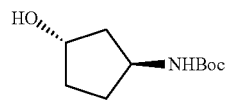

4M HCl in Dioxane, DCM
Step-1

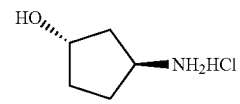

TEA, DMSO, 160° C.,
Step-2

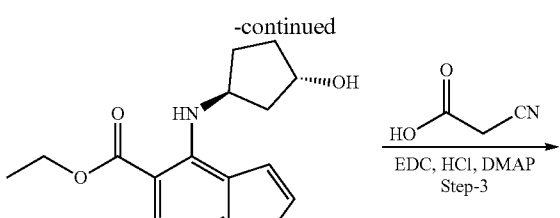

Trans enantiomers 1 & 2

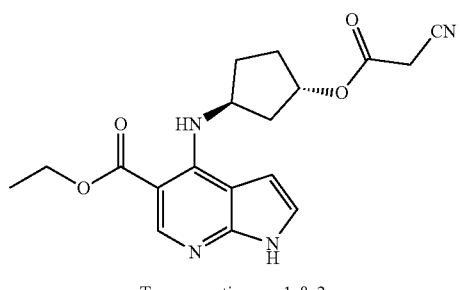

Trans enantiomers 1 & 2

Step-1: Preparation of (trans)-(rac)-3-aminocyclopentan-1-ol hydrochloride Salt

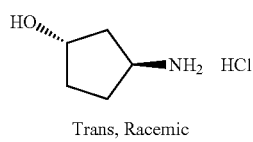

Trans, Racemic

To a solution of (trans)-(rac)-tert-butyl-(3-hydroxycyclopentyl)carbamate (0.27 g, 1.34 mmol) in dichloromethane (5 mL) at 0° C. was added HCl in dioxane (4M, 5 mL) and the solution warmed to ambient temperature and stirred for 5 hours. The reaction mixture was concentrated in vacuo and the residue washed with diethylether to provide 3-aminocyclopentan-1-ol hydrochloride salt as a yellow oil (0.18 g, 96% yield): MS (ES) m/z 102 (M+H).

Step-2: Preparation of (trans)-ethyl 4-((3-hydroxycyclopentyl) amino)-1H-pyrrolo[2,3-b]pyridine-5-carboxylate

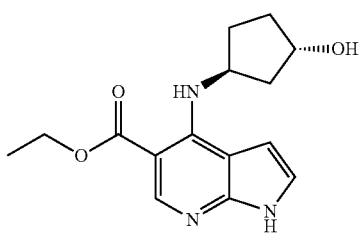

Trans, Racemic

A solution of (trans)-(rac)-ethyl 4-chloro-1H-pyrrolo[2,3-b]pyridine-5-carboxylate (0.05 g, 0.22 mmol), 3-amino cyclopentan-1-ol HCl (0.036 g, 0.26 mmol) and triethylamine (0.15 mL, 1.11 mmol) in dimethyl sulfoxide (3 mL) was heated under microwave irradiation at 150° C. for 1 hour. After cooling to ambient temperature, the reaction mixture was quenched with water and extracted with ethyl acetate. The organic layer was washed with water, brine and dried over anhydrous sodium sulfate. The solution was filtered and concentrated in vacuo. The crude material was purified by flash chromatography (9% methanol/dichloromethane) to provide ethyl 4-((3-hydroxycyclopentyl) amino)-1H-pyrrolo [2,3-b]pyridine-5-carboxylate as an off-white solid (0.01 g, 17% yield): MS (ES) m/z 290 (M+H).

Step 3: Preparation of (trans)-(rac)-ethyl 4-((3-(2-cyanoacetoxy)cyclopentyl)amino)-1H-pyrrolo[2,3-b]pyridine-5-carboxylate

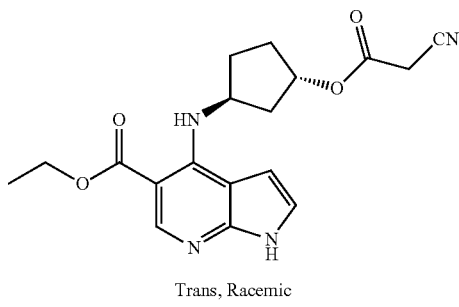 [SMILES: CCOC(=O)c1cnc2[nH]ccc2c1N[C@H]1CC[C@H](OC(=O)CC#N)C1]

Trans, Racemic

To a solution of (trans)-(rac)-ethyl 4-((3-hydroxycyclopentyl)amino)-1H-pyrrolo[2,3-b]pyridine-5-carboxylate (0.14 g, 0.48 mmol) in dichloromethane (10 mL) was added 2-cyanoacetic acid (0.062 g, 0.72 mmol), 4-dimethylaminopyridine (0.06 g, 0.48 mmol) and 1-ethyl-3-(3-dimethylaminopropyl)carbodiimide HCl (0.14 g, 0.72 mmol) and the mixture stirred at ambient temperature for 16 hours. The reaction mixture was quenched with water and extracted with dichloromethane. The organic layer was washed with water, brine and dried over anhydrous sodium sulfate. The solution was filtered and concentrated in vacuo. The crude material was purified by flash chromatography (5% methanol/dichloromethane) to provide ethyl 4-((3-(2-cyanoacetoxy)cyclopentyl)amino)-1H-pyrrolo[2,3-b]pyridine-5-carboxylate as an off-white solid (0.035 g, 20% yield): MS (ES) m/z 357 (M+H).

Synthesis of Example 72: Isolation of Trans enantiomer-2, (trans)-ethyl 4-((3-hydroxycyclopentyl)amino)-1H-pyrrolo [2,3-b]pyridine-5-carboxylate

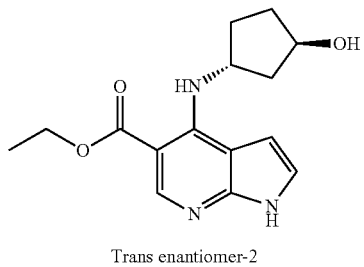 [SMILES: CCOC(=O)c1cnc2[nH]ccc2c1N[C@@H]1CC[C@@H](O)C1]

Trans enantiomer-2

$^1$H NMR (400 MHz, DMSO-d$_6$) δ 11.66 (br s, 1H), 8.82 (d, J=7.6 Hz, 1H), 8.52 (s, 1H), 7.17-7.18 (m, 1H), 6.67 (s, 1H), 4.61-4.63 (m, 2H), 4.21-4.26 (m, 3H), 1.98-2.37 (m, 3H), 1.68-1.69 (m, 1H), 1.53 (m, 2H), 1.29 (t, J=7.2 Hz, 3H). Retention time: 7.625 min.
Analytical Conditions:
Column: CHIRALPAK IA (250 mm×4.6 mm×51 m)
Mobile methanol with 0.1% DEA (50:50)
Flow rate: 0.5 mL/min Synthesis of Example 73: Isolation of Trans enantiomer-1, (trans)-ethyl 4-((3-(2-cyanoacetoxy)cyclopentyl)amino)-1H-pyrrolo [2,3-b]pyridine-5-carboxylate

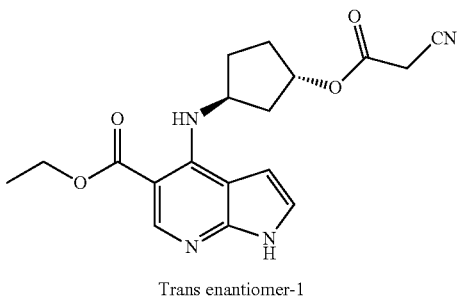 [SMILES: CCOC(=O)c1cnc2[nH]ccc2c1N[C@H]1CC[C@H](OC(=O)CC#N)C1]

Trans enantiomer-1

$^1$H NMR (400 MHz, DMSO-d$_6$) δ 11.67 (s, 1H), 8.81 (d, J=3.8 Hz, 1H), 8.53 (s, 1H), 7.17 (s, 11H), 6.65 (s, 1H), 5.30 (br, 1H), 4.63-4.66 (m, 1H), 4.25 (q, J=6.8 Hz, 2H), 3.99 (s, 2H), 2.05-2.31 (m, 3H), 1.93-2.0 (m, 1H), 1.79-1.81 (m, 1H), 1.60-1.67 (m, 1H), 1.30 (t, J=6.8 Hz, 3H). Retention time: 9.484 min.
Analytical Conditions:
Column: CHIRALPAK IA (250 mm×4.6 mm×51 m)
Mobile methanol with 0.1% DEA (50:50)
Flow rate: 0.5 mL/min Synthesis of Example 74: Isolation of Trans enantiomer-2, (trans)-ethyl 4-((3-(2-cyanoacetoxy)cyclopentyl)amino)-1H-pyrrolo[2,3-b]pyridine-5-carboxylate

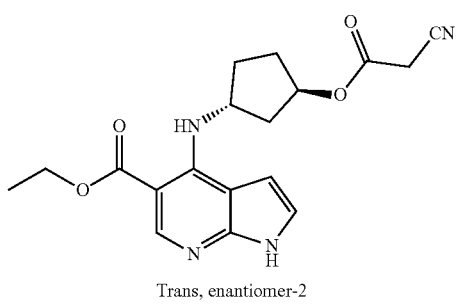 [SMILES: CCOC(=O)c1cnc2[nH]ccc2c1N[C@@H]1CC[C@@H](OC(=O)CC#N)C1]

Trans, enantiomer-2

$^1$H NMR (400 MHz, DMSO-d$_6$) 11.70 (br s, 1H), 8.84 (d, J=7.2 Hz, 1H), 8.53 (s, 1H), 7.18 (s, 1H), 6.65 (s, 1H), 5.25 (br s, 1H), 4.63-4.67 (m, 1H), 4.24 (q, J=7.2 Hz, 2H), 3.99 (s, 2H), 2.14-2.31 (m, 3H), 1.93-2.00 (m, 1H), 1.80 (m, 1H), 1.63-1.65 (m, 1H), 1.33 (t, J=7.2 Hz, 3H). Retention time 4.846 min.
Analytical Conditions:
Column: CHIRALPAK IA (250 mm×4.6 mm×51 m)
Mobile methanol with 0.1% DEA (50:50)
Flow rate: 0.5 mL/min Synthesis of Example 75: Isolation of Trans enantiomer-1, (trans)-ethyl 4-((3-hydroxycyclopentyl)amino)-1H-pyrrolo[2,3-b]pyridine-5-carboxylate

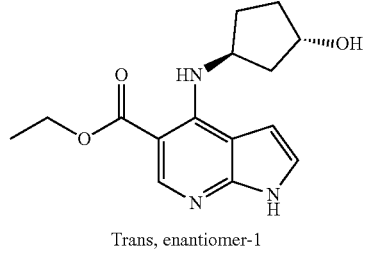 [SMILES: CCOC(=O)c1cnc2[nH]ccc2c1N[C@H]1CC[C@H](O)C1]

Trans, enantiomer-1

$^1$H NMR (400 MHz, DMSO-d$_6$) δ 11.65 (s, 1H), 8.80 (d, J=7.6 Hz 1H), 8.51 (s, 1H), 7.17 (s, 1H), 6.66 (s, 1H), 4.59-4.66 (m, 2H), 4.21-4.26 (m, 3H), 2.23-2.31 (m, 1H), 2.05-2.10 (m, 1H), 1.93-2.04 (m, 1H), 1.64-1.69 (m, 1H), 1.46-1.58 (m, 2H), 1.27 (t, J=7.6 Hz, 3H). Retention time: 7.540 min.

Analytical Conditions:

Column: CHIRALPAK IA (250 mm×4.6 mm×51 m)

Mobile methanol with 0.1% DEA (50:50)

Flow rate: 0.5 mL/min

Synthesis of Example 92: Preparation of ethyl 4-(((1r,4r)-4-((N-methylsulfamoyl)methyl)cyclohexyl)amino)-1H-pyrrolo[2,3-b]pyridine-5-carboxylate

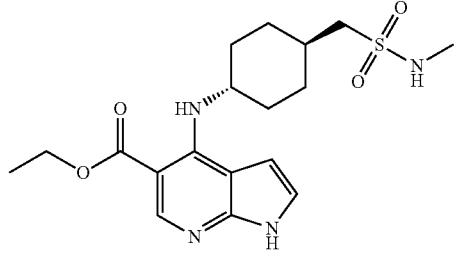 [SMILES: CCOC(=O)c1cnc2[nH]ccc2c1N[C@H]1CC[C@H](CS(=O)(=O)NC)CC1]

Scheme 14. Preparation of ethyl 4-(((1r,4r)-4-((N-methylsulfamoyl)methyl)cyclohexyl)amino)-1H-pyrrolo[2,3-b]pyridine-5-carboxylate

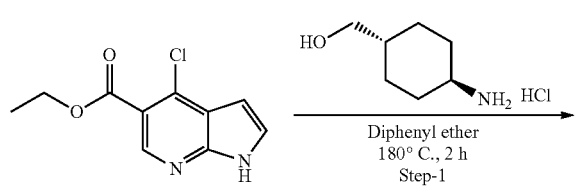

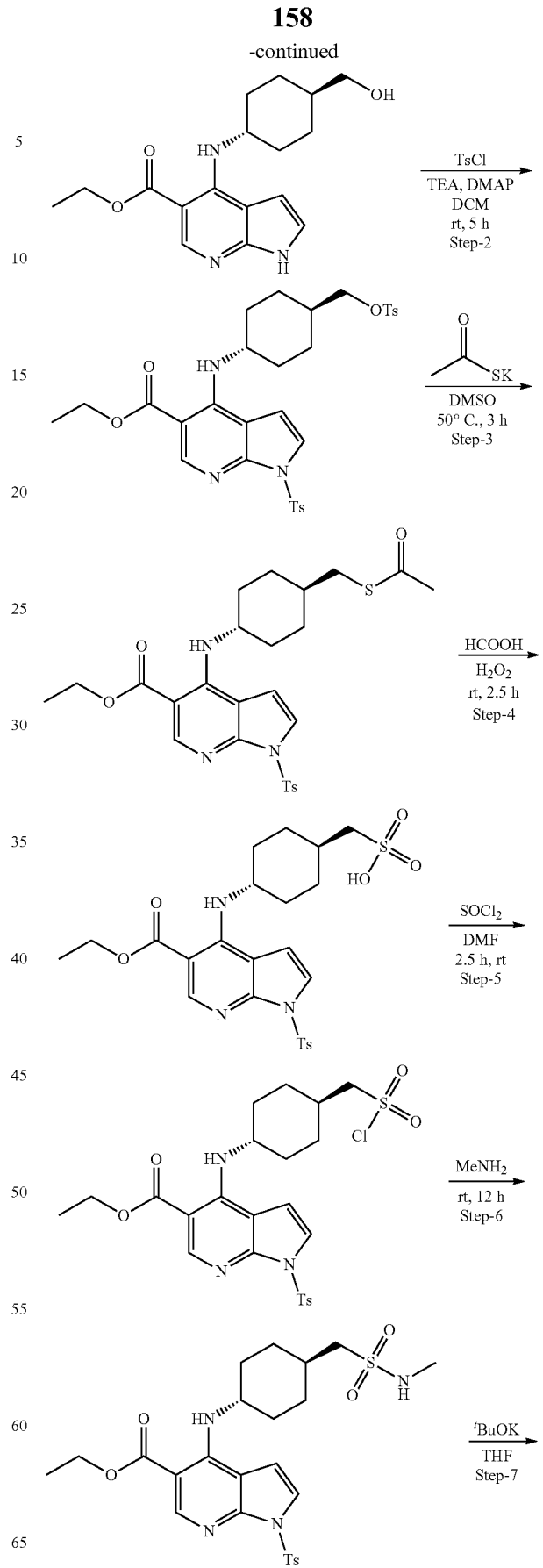

-continued

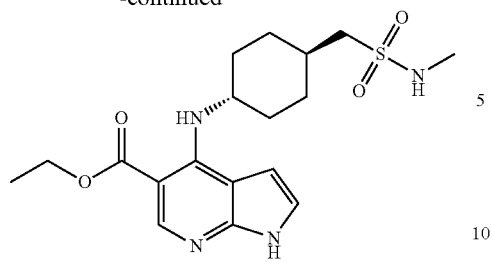

Preparation of
(((1r,4r)-4-Aminocyclohexyl)methanol hydrochloride

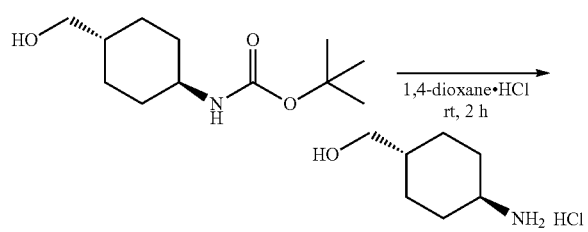

To a stirred solution of tert-butyl ((1r,4r)-4-(hydroxymethyl)cyclohexyl)carbamate (1 g, 17.47 mmol) in dioxane (5 mL) was added 1,4-dioxane•hydrochloride (10 mL) at 0° C. and the solution was stirred for 2 hours. The reaction was concentrated in vacuo to provide crude (1r,4r)-4-aminocyclohexyl)methanol hydrochloride as a semi solid (0.6 g crude).

Step 1: Preparation of ethyl 4-(((1r,4r)-4-(hydroxymethyl)cyclohexyl)amino)-1H-pyrrolo [2,3-b]pyridine-5-carboxylate

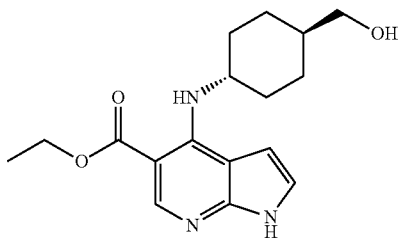 [SMILES: CCOC(=O)c1cnc2[nH]ccc2c1N[C@H]1CC[C@H](CO)CC1]

To a stirred solution of ethyl 4-chloro-1H-pyrrolo[2,3-b]pyridine-5-carboxylate (3 g, 13.39 mmol) in N-methylpyrrolidine (10 mL) was added triethylamine (0.3 mL) and ((1r,4r)-4-aminocyclohexyl)methanol hydrochloride (2.59 g, 19.9 mmol). The solution was heated in a sealed tube at 160° C. for 2 hours. After cooling to ambient temperature, the reaction mixture was quenched with water and extracted with dichloromethane. The organic layer was washed with brine, dried over anhydrous sodium sulphate and concentrated in vacuo. The crude material was purified by using flash chromatography (55% ethyl acetate/hexane) to provide ethyl 4-(((1r,4r)-4-(hydroxymethyl)cyclohexyl)amino)-1H-pyrrolo[2,3-b]pyridine-5-carboxylate as a brown solid (3 g, 71% yield): MS (ES) m/z 318.1 (M+H).

Step 2: Preparation of ethyl 1-tosyl-4-(((1r,4r)-4-((tosyloxy)methyl)cyclohexyl)amino)-1H-pyrrolo[2,3-b]pyridine-5-carboxylate

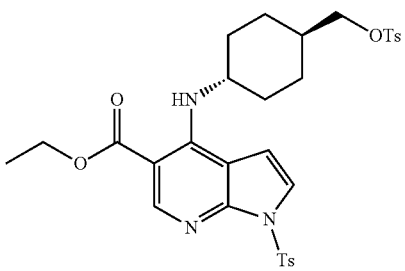 [SMILES: CCOC(=O)c1cnc2c(ccn2S(=O)(=O)c2ccc(C)cc2)c1N[C@H]1CC[C@H](COS(=O)(=O)c2ccc(C)cc2)CC1]

To a solution of ethyl 4-(((1r,4r)-4-(hydroxymethyl)cyclohexyl)amino)-1H-pyrrolo[2,3-b]pyridine-5-carboxylate (1.5 g, 4.73 mmol) in dichloromethane (20 mL) were added triethylamine (1.2 mL, 12.08 mmol), 4-dimethylaminopyridine (0.28 g, 2.36 mmol) and 4-toluenesulfonyl chloride (2.7 g, 14.19 mmol) at 0° C. The mixture was stirred at room temperature for 12 hours at which time the reaction was quenched with water and extracted with dichloromethane. The organic layer was washed with brine, dried over anhydrous sodium sulphate and concentrated in vacuo. The crude material was purified by using flash chromatography (55% ethyl acetate/hexane) to provide ethyl 1-tosyl-4-(((1r,4r)-4-((tosyloxy)methyl)cyclohexyl)amino)-1H-pyrrolo[2,3-b]pyridine-5-carboxylate as an off-white solid (1.6 g, 55% yield): MS (ES) m/z 626.1 (M+H).

Step-3: Preparation of ethyl 4-(((1r,4r)-4-((acetylthio)methyl)cyclohexyl)amino)-1-tosyl-1H-pyrrolo[2,3-b]pyridine-5-carboxylate

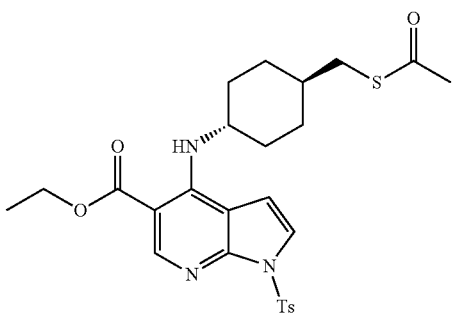 [SMILES: CCOC(=O)c1cnc2c(ccn2S(=O)(=O)c2ccc(C)cc2)c1N[C@H]1CC[C@H](CSC(C)=O)CC1]

To a solution of ethyl 1-tosyl-4-(((1r,4r)-4-((tosyloxy)methyl)cyclohexyl)amino)-1H-pyrrolo[2,3-b]pyridine-5-carbo-xylate (1.6 g, 2.56 mmol) in dimethyl sulfoxide (5 mL) was added potassium ethanethioate (0.33 g, 2.89 mmol) and the mixture was stirred at 50° C. for 3 hours. The reaction mixture was cooled to ambient temperature and quenched with ice water. The obtained solid was filtered, washed with water and dried to provide ethyl 4-(((1r,4r)-4-((acetylthio)methyl)cyclohexyl)amino)-1-tosyl-1H-pyrrolo[2,3-b]pyridine-5-carboxylate as a white solid (1.6 g, 74%): MS (ES) m/z 530.1 (M+H).

Step 4: Preparation of (((1r,4r)-4-((5-(ethoxycarbonyl)-1-tosyl-1H-pyrrolo [2,3-b]pyridin-4-yl) amino) cyclohexyl) methanesulfonic acid

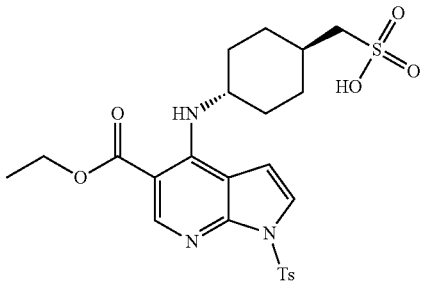 [SMILES: CCOC(=O)c1cnc2c(ccn2S(=O)(=O)c2ccc(C)cc2)c1N[C@H]1CC[C@H](CS(=O)(=O)O)CC1]

A solution of ethyl 4-(((1r,4r)-4-((acetylthio)methyl)cyclohexyl)amino)-1-tosyl-1H-pyrrolo[2,3-b]pyridine-5-carboxylate (0.3 g, 0.56 mmol) in hydrogen peroxide (0.15 mL) was treated with formic acid (0.8 mL) at 0° C. and the solution was stirred at room temperature for 2.5 hours. The reaction mixture was quenched with ice water, the obtained solid was filtered, washed with water and dried to provide ((1r,4r)-4-((5-(ethoxycarbonyl)-1-tosyl-1H-pyrrolo[2,3-b]pyridin-4-yl)amino)cyclohexyl)methanesulfonic acid as a white solid (0.21 g, 66% yield): MS (ES) m/z 535.1 (M+H).

Step 5: Preparation of ethyl 4-(((1r,4r)-4-((chlorosulfonyl)methyl)cyclohexyl)amino)-1-tosyl-1H-pyrrolo[2,3-b]pyridine-5-carboxylate

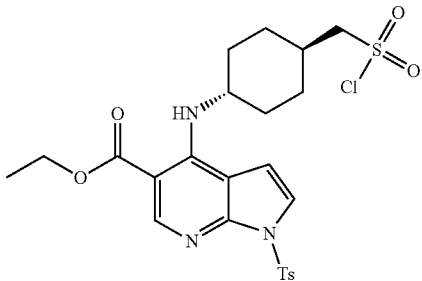 [SMILES: CCOC(=O)c1cnc2c(ccn2S(=O)(=O)c2ccc(C)cc2)c1N[C@H]1CC[C@H](CS(=O)(=O)Cl)CC1]

To a stirred solution of ((1r,4r)-4-((5-(ethoxycarbonyl)-1-tosyl-1H-pyrrolo[2,3-b]pyridin-4-yl)amino)cyclohexyl)methanesulfonic acid (0.21 g, 0.39 mmol) in N,N-dimethylformamide (0.1 mL) was added thionyl chloride (2.0 mL) at 0° C. and the solution stirred at room temperature for 2.5 hours. The reaction mixture was concentrated in vacuo to provide ethyl 4-(((1r,4r)-4-((chlorosulfonyl)methyl)cyclohexyl)amino)-1-tosyl-1H-pyrrolo[2,3-b]pyridine-5-carboxylate as a pale yellow solid (0.35 g crude).

Step 6: Preparation of ethyl 4-(((1r,4r)-4-((N-methylsulfamoyl)methyl)cyclohexyl)amino)-1-tosyl-1H-pyrrolo[2,3-b]pyridine-5-carboxylate

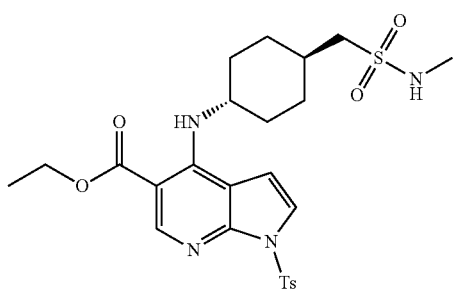 [SMILES: CCOC(=O)c1cnc2c(ccn2S(=O)(=O)c2ccc(C)cc2)c1N[C@H]1CC[C@H](CS(=O)(=O)NC)CC1]

To a solution of ethyl 4-(((1r,4r)-4-((chlorosulfonyl)methyl)cyclohexyl)amino)-1-tosyl-1H-pyrrolo[2,3-b]pyridine-5-carboxylate (0.21 g, 0.37 mmol) in tetrahydrofuran (10 mL) was added methylamine (15 mL, 2.0 M in tetrahydrofuran) and the solution was stirred in a sealed tube at room temperature 12 hours. The reaction mixture was quenched with water and extracted with ethyl acetate which was washed with brine, dried over anhydrous sodium sulphate, filtered and concentrated in vacuo. The crude material was purified by flash column chromatography (40% ethyl acetate/hexane) to provide ethyl 4-(((1r,4r)-4-((N-methylsulfamoyl)methyl)cyclohexyl)amino)-1-tosyl-1H-pyrrolo[2,3-b]pyridine-5-carboxylate as a brown solid (0.07 g, 70% yield): MS (ES) m/z 548.1 (M+H).

Step 7: Preparation of ethyl 4-(((1r,4r)-4-((N-methylsulfamoyl)methyl)cyclohexyl)amino)-1H-pyrrolo[2,3-b]pyridine-5-carboxylate

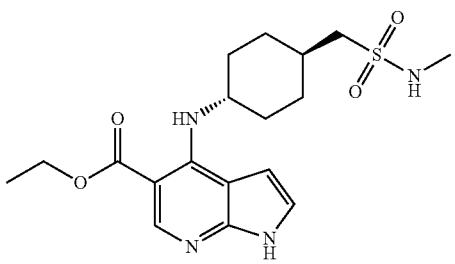 [SMILES: CCOC(=O)c1cnc2[nH]ccc2c1N[C@H]1CC[C@H](CS(=O)(=O)NC)CC1]

To a solution of ethyl 4-(((1r,4r)-4-((N-methylsulfamoyl)methyl)cyclohexyl)amino)-1-tosyl-1H-pyrrolo[2,3-b]pyridine-5-carboxylate (0.14 g, 0.25 mmol) in tetrahydrofuran (1 mL) was added potassium tert-butoxide (0.07 g, 0.63 mmol) and the solution was stirred at room temperature for 2.5 hours. The reaction mixture was quenched with water, extracted with ethyl acetate, washed with brine, dried over anhydrous sodium sulphate, filtered and concentrated in vacuo. The crude material was purified by flash column chromatography (40% ethyl acetate/hexane) to provide ethyl 4-(((1r,4r)-4-((N-methylsulfamoyl)methyl)cyclohexyl)amino)-1H-pyrrolo[2,3-b]pyridine-5-carboxylate as an off white solid (0.07 g, 37% yield): $^1$H NMR (400 MHz, DMSO-$d_6$) δ 11.63 (br s, 1H), 8.71-8.73 (m, 1H), 8.51 (s, 1H), 7.16 (s, 1H), 6.85 (s, 1H), 6.51 (s, 1H), 4.22-4.24 (m, 2H), 3.87 (br s, 1H), 2.92-2.93 (m, 2H), 2.55 (m, 3H), 2.11 (m, 2H), 1.97 (m, 2H), 1.84 (m, 2H), 1.29-1.30 (m, 6H); MS (ES) m/z 382.1 (M+H).

Synthesis of Example 94: Preparation of ethyl 4-(methyl((1r,4r)-4-((N-methylsulfamoyl)methyl)cyclohexyl)amino)-1H-pyrrolo[2,3-b]pyridine-5-carboxylate

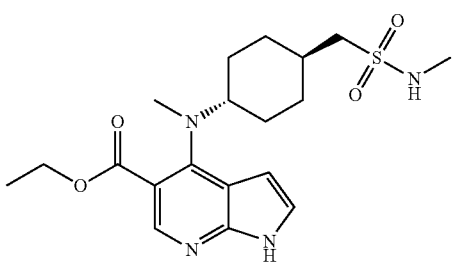 [SMILES: CCOC(=O)c1cnc2[nH]ccc2c1N(C)[C@H]1CC[C@H](CS(=O)(=O)NC)CC1]

Scheme 15: Preparation of ethyl 4-(methyl((1r,4r)-4-((N-methylsulfamoyl)methyl)cyclohexyl)amino)-1H-pyrrolo[2,3-b]pyridine-5-carboxylate

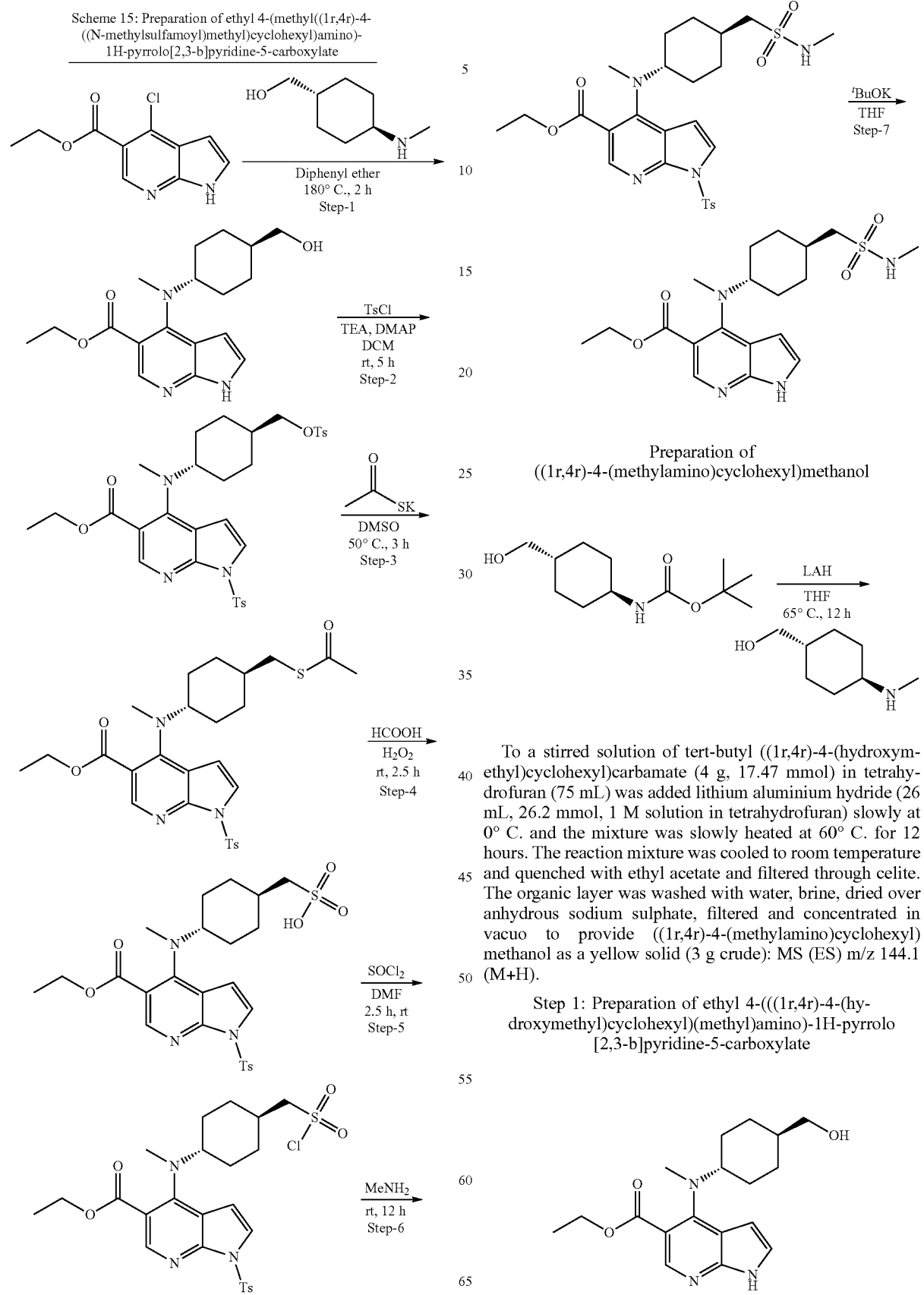

Preparation of ((1r,4r)-4-(methylamino)cyclohexyl)methanol

To a stirred solution of tert-butyl ((1r,4r)-4-(hydroxymethyl)cyclohexyl)carbamate (4 g, 17.47 mmol) in tetrahydrofuran (75 mL) was added lithium aluminium hydride (26 mL, 26.2 mmol, 1 M solution in tetrahydrofuran) slowly at 0° C. and the mixture was slowly heated at 60° C. for 12 hours. The reaction mixture was cooled to room temperature and quenched with ethyl acetate and filtered through celite. The organic layer was washed with water, brine, dried over anhydrous sodium sulphate, filtered and concentrated in vacuo to provide ((1r,4r)-4-(methylamino)cyclohexyl)methanol as a yellow solid (3 g crude): MS (ES) m/z 144.1 (M+H).

Step 1: Preparation of ethyl 4-(((1r,4r)-4-(hydroxymethyl)cyclohexyl)(methyl)amino)-1H-pyrrolo[2,3-b]pyridine-5-carboxylate To a solution of ethyl 4-chloro-1H-pyrrolo[2,3-b]pyridine-5-carboxylate (3 g, 13.39 mmol) in diphenyl ether (10 mL) was added ((1r,4r)-4-(methylamino)cyclohexyl)methanol (3.4 g, 24.10 mmol) and the solution was subjected to microwave irradiation at 180° C. for 2 hours. The reaction mixture was cooled to ambient temperature, quenched with water and extracted with dichloromethane. The organic layer was washed with brine, dried over sodium sulphate, filtered and concentrated in vacuo. The crude material was purified by using flash chromatography (55% ethyl acetate/hexane) to provide ethyl 4-(((1r,4r)-4-(hydroxymethyl)cyclohexyl)(methyl)amino)-1H-pyrrolo[2,3-b]pyridine-5-carboxylate as a brown solid (1 g, 27% yield): MS (ES) m/z 332.2 (M+H).

Step 2: Preparation of ethyl 4-(methyl((1r,4r)-4-((tosyloxy)methyl)cyclohexyl)amino)-1-tosyl-1H-pyrrolo[2,3-b]pyridine-5-carboxylate

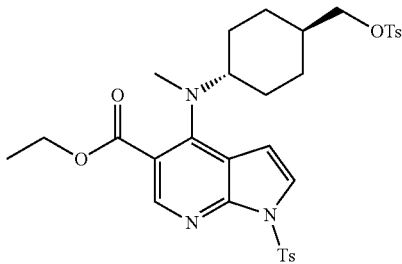 [SMILES: CCOC(=O)c1cnc2c(ccn2S(=O)(=O)c2ccc(C)cc2)c1N(C)[C@H]1CC[C@H](COS(=O)(=O)c2ccc(C)cc2)CC1]

To a stirred solution of ethyl 4-(((1r,4r)-4-(hydroxymethyl)cyclohexyl)(methyl)amino)-1H-pyrrolo[2,3-b]pyridine-5-carboxylate (1.0 g, 3.02 mmol) in dichloromethane (20 mL) was added triethylamine (1.2 mL, 12.08 mmol) at 0° C., followed by 4-dimethylaminopyridine (0.18 g, 1.51 mmol) and 4-toluenesulfonyl chloride (1.7 g, 9.06 mmol). The mixture was stirred under a N$_2$ atmosphere at room temperature for 12 hours. The reaction mixture was quenched with water and extracted with dichloromethane. The organic layer was washed with brine, dried over anhydrous sodium sulphate, filtered and concentrated in vacuo. The crude material was purified by using flash chromatography (20% ethyl acetate/hexane) to provide ethyl 4-(methyl((1r,4r)-4-((tosyloxy)methyl)cyclohexyl)amino)-1-tosyl-1H-pyrrolo[2,3-b]pyridine-5-carboxylate as an off-white solid (1.4 g, 73% yield): MS (ES) m/z 640.2 (M+H).

Step 3: Preparation of ethyl 4-(((1r,4r)-4-((acetylthio)methyl)cyclohexyl)(methyl)amino)-1-tosyl-1H-pyrrolo[2,3-b]pyridine-5-carboxylate

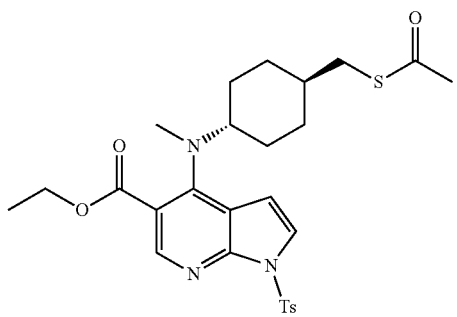 [SMILES: CCOC(=O)c1cnc2c(ccn2S(=O)(=O)c2ccc(C)cc2)c1N(C)[C@H]1CC[C@H](CSC(C)=O)CC1]

To a stirred solution of ethyl 4-(methyl((1r,4r)-4-((tosyloxy)methyl)cyclohexyl)amino)-1-tosyl-1H-pyrrolo[2,3-b]pyridine-5-carboxylate (1.4 g, 2.18 mmol) in dimethyl sulfoxide (30 mL) was added potassium ethanethioate (0.28 g, 2.47 mmol) and the mixture was stirred at 50° C. for 3 hours. The reaction mixture was quenched with ice water, the obtained solid was filtered, washed with water and dried to provide ethyl 4-(((1r,4r)-4-((acetylthio)-methyl)cyclohexyl)(methyl)amino)-1-tosyl-1H-pyrrolo[2,3-b]pyridine-5-carboxylate as a brown colour solid (1.0 g, 84% yield): MS (ES) m/z 544.2 (M+H).

Step 4: Preparation of ((1r,4r)-4-((5-(ethoxycarbonyl)-1-tosyl-1H-pyrrolo[2,3-b]pyridin-4-yl)(methyl)amino)cyclohexyl) methanesulfonic acid

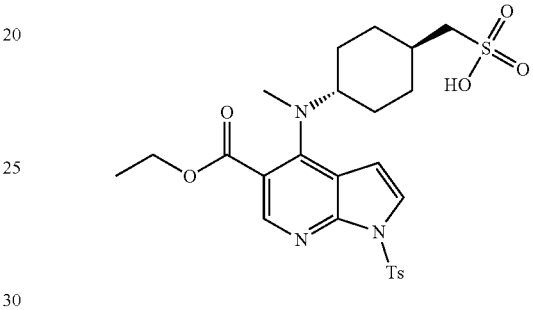

A stirred solution of ethyl 4-(((1r,4r)-4-((acetylthio)methyl)cyclohexyl)(methyl)amino)-1-tosyl-1H-pyrrolo[2,3-b]pyridine-5-carboxylate (1.1 g, 2.02 mmol) in hydrogen peroxide (1 mL) was treated with formic acid (9 mL) at 0° C. and the solution was stirred at room temperature for 2.5 hours. The reaction mixture was quenched with ice water, the obtained solid was filtered, washed with water and dried to obtain ((1r,4r)-4-((5-(ethoxycarbonyl)-1-tosyl-1H-pyrrolo[2,3-b]pyridin-4-yl)(methyl)amino)cyclohexyl)methanesulfonic acid as an off-white solid (0.55 g, 50% yield): $^1$HNMR (400 MHz, DMSO-d$_6$) δ 8.21 (s, 1H), 7.9 (d, J=7.6 Hz, 2H), 7.7 (d, J=5.2 Hz, 1H), 7.39 (d, J=8 Hz, 2H), 6.67 (d, J=3.2 Hz, 1H), 4.25-4.18 (q, 2H), 3.64-3.60 (m, 2H), 2.75 (s, 3H), 2.37-02.32 (m, 5H), 2.06-2.03 (m, 2H), 1.75-1.70 (m, 5H), 1.29 (t, J=6.8 Hz, 3H), 1.06-0.96 (m, 2H).

Step 5: Preparation of ethyl 4-(((1r,4r)-4-((chlorosulfonyl)methyl)cyclohexyl)(methyl)amino)-1-tosyl-1H-pyrrolo[2,3-b]pyridine-5-carboxylate

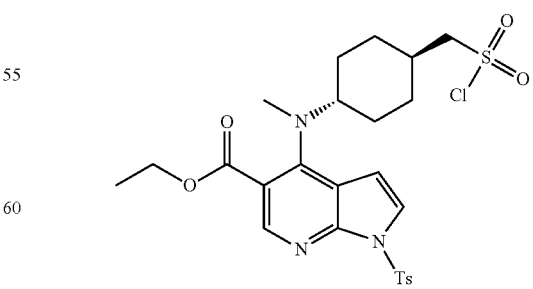

To a solution of ((1r,4r)-4-((5-(ethoxycarbonyl)-1-tosyl-1H-pyrrolo[2,3-b]pyridin-4-yl)(methyl)amino)cyclohexyl)-methanesulfonic acid (0.5 g, 0.9 mmol) in N,N-dimethylformamide (0.5 mL) was added thionyl chloride (5 mL) at 0° C. and the solution stirred for 2.5 hours. The reaction mixture was concentrated in vacuo to provide ethyl 4-(((1r,4r)-4-((chlorosulfonyl)methyl)cyclohexyl)(methyl)amino)-1-tosyl-1H-pyrrolo[2,3-b]pyridine-5-carboxylate as a colorless liquid (0.35 g crude): MS (ES) m/z 568.2 (M+H).

Step 6: Preparation of ethyl 4-(methyl((1r,4r)-4-((N-methylsulfamoyl)methyl)cyclohexyl)amino)-1-tosyl-1H-pyrrolo[2,3-b]pyridine-5-carboxylate

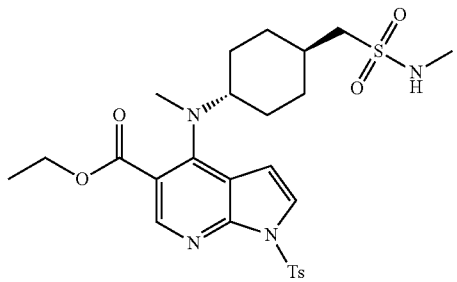 [SMILES: CCOC(=O)c1cnc2c(ccn2S(=O)(=O)c2ccc(C)cc2)c1N(C)[C@H]1CC[C@H](CS(=O)(=O)NC)CC1]

To a stirred solution of ethyl 4-(((1r,4r)-4-((chlorosulfonyl)methyl)cyclohexyl)(methyl)amino)-1-tosyl-1H-pyrrolo[2,3-b]pyridine-5-carboxylate (0.35 g, 0.61 mmol) in tetrahydrofuran (10 mL) was added methylamine (15 mL, 2.0 M in tetrahydrofuran) and the solution was stirred for 12 hours at room temperature. The reaction mixture was quenched with water and extracted with ethyl acetate, brine, dried over anhydrous sodium sulphate and concentrated in vacuo. The crude material was purified by using flash chromatography (40% ethyl acetate/hexane) to provide ethyl 4-(methyl((1r,4r)-4-((N-methylsulfamoyl)methyl)cyclohexyl)amino)-1-tosyl-1H-pyrrolo[2,3-b]pyridine-5-carboxylate as a yellow solid (0.300 g, 87%): MS (ES) m/z 563.2 (M+H).

Step 7: Preparation of ethyl 4-(methyl((1r,4r)-4-((N-methylsulfamoyl)methyl)cyclohexyl)amino)-1H-pyrrolo[2,3-b]pyridine-5-carboxylate

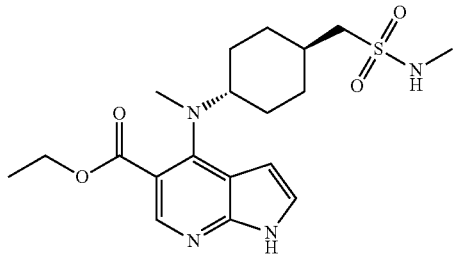 [SMILES: CCOC(=O)c1cnc2[nH]ccc2c1N(C)[C@H]1CC[C@H](CS(=O)(=O)NC)CC1]

To a stirred solution of ethyl 4-(methyl((1r,4r)-4-((N-methylsulfamoyl)methyl)cyclohexyl)amino)-1-tosyl-1H-pyrrolo[2,3-b]pyridine-5-carboxylate (0.3 g, 0.53 mmol) in tetrahydrofuran (8 mL) was added potassium tert-butoxide (0.15 g, 1.33 mmol) and the solution was stirred at room temperature for 1.5 hours. The reaction mixture was quenched with water and extracted with ethyl acetate. The organic layer was washed with brine, dried over anhydrous sodium sulphate and concentrated in vacuo. The crude material was purified by using flash chromatography (45% ethyl acetate/hexane) to provide ethyl 4-(methyl((1r,4r)-4-((N-methylsulfamoyl)methyl)cyclohexyl)amino)-1H-pyrrolo[2,3-b]pyridine-5-carboxylate as an off-white solid (0.08 g, 37% yield): $^1$H NMR (400 MHz, DMSO-$d_6$): δ 11.64 (s, 1H), 8.18 (s, 1H), 7.25 (s, 1H), 6.85 (d, J=4.8 Hz, 1H), 6.40 (s, 1H), 4.25-4.20 (q, 2H), 3.81 (bs, 1H), 2.90 (d, J=5.6 Hz, 2H), 2.80 (s, 3H), 2.55 (d, J=4.8 Hz, 3H), 2.05-2.02 (m, 2H), 1.81-1.76 (m, 5H), 1.29 (t, J=6.8 Hz, 3H), 1.21-1.19 (m, 2H); MS (ES) m/z 409.0 [M+H].

Synthesis of Example 113: Preparation of ethyl 4-((3-(2-cyanoethoxy)cyclopentyl)amino)-1H-pyrrolo[2,3-b]pyridine-5-carboxylate

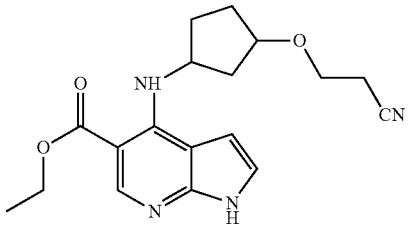 [SMILES: CCOC(=O)c1cnc2[nH]ccc2c1NC1CCC(OCCC#N)C1]

Scheme 16. Preparation of ethyl 4-((3-(2-cyanoethoxy)cyclopentyl)amino)-1H-pyrrolo[2,3-b]pyridine-5-carboxylate.

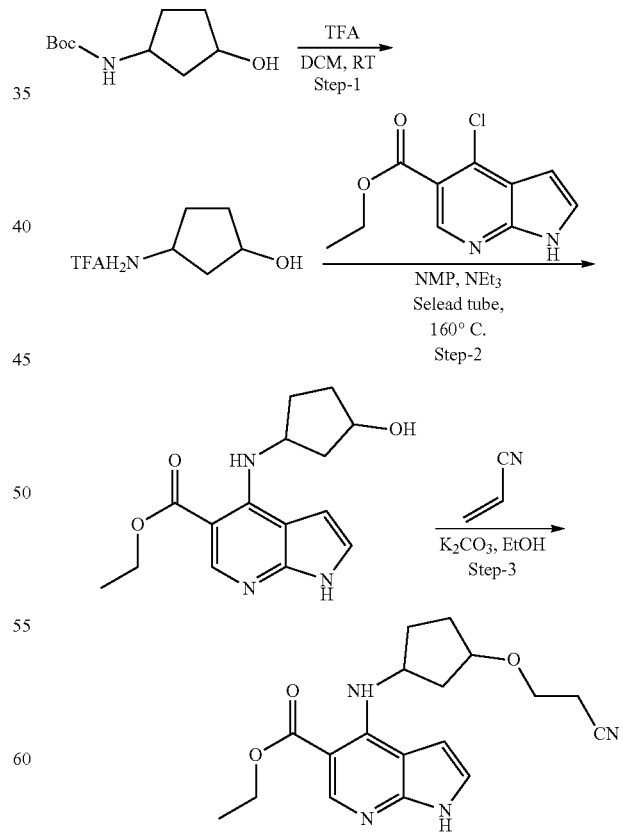

Step 1: Preparation of 3-aminocyclopentan-1-ol trifluoroacetic acid Salt

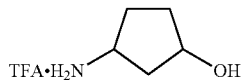

To a solution of tert-butyl (3-hydroxycyclopentyl)carbamate (1.0 g, 5.47 mmol) in dichloromethane (5 mL) was added trifluoroacetic acid (5 mL). The solution was stirred at ambient temperature for 5 hours and then concentrated in vacuo to dryness to provide 3-aminocyclopentan-1-ol trifluoroacetic acid salt (1.17 g, crude).

Step 2: Preparation of ethyl 4-((3-hydroxycyclopentyl)amino)-1H-pyrrolo[2,3-b]pyridine-5-carboxylate

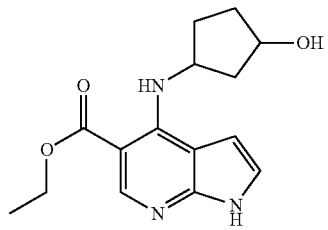 [SMILES: CCOC(=O)c1cnc2[nH]ccc2c1NC1CCC(O)C1]

A stirred solution of ethyl 4-chloro-1H-pyrrolo[2,3-b]pyridine-5-carboxylate (1.27 g, 5.44 mmol), 3-aminocyclopentan-1-ol trifluoroacetic acid salt (1.17 g, 5.44 mmol), triethylamine (2.27 g, 16.3 mmol) in N-methyl-2-pyrrolidone (10 mL) was heated in a sealed tube at 160° C. for 12 hours. After cooling to ambient temperature, the reaction mixture was partitioned between ethyl acetate and water. The organic layer was washed with water, brine and dried over anhydrous sodium sulfate. The solution was filtered and concentrated in vacuo. The crude material was purified using flash chromatography (10% methanol/dichloromethane) to provide ethyl 4-((3-hydroxycyclopentyl)amino)-1H-pyrrolo[2,3-b]pyridine-5-carboxylate as a colorless gum (0.82 g, 50% yield): MS (ES) m/z 290.1 (M+H).

Step 3: Preparation of ethyl 4-((3-(2-cyanoethoxy)cyclopentyl)amino)-1H-pyrrolo[2,3-b]pyridine-5-carboxylate

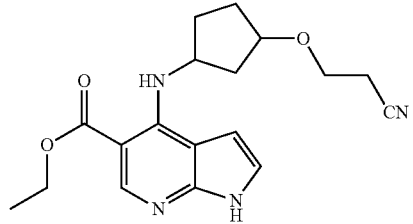 [SMILES: CCOC(=O)c1cnc2[nH]ccc2c1NC1CCC(OCCC#N)C1]

To a suspension of potassium carbonate (0.86 g, 6.25 mmol) in ethanol (10 mL) was added ethyl 4-((3-hydroxycyclopentyl)amino)-1H-pyrrolo[2,3-b]pyridine-5-carboxylate (0.74 g, 2.56 mmol) and the mixture was stirred at ambient temperature for 0.5 hours. Then acrylonitrile (1.35 g, 25.6 mmol) was added and the mixture was stirred for 15 hours. The solvent was concentrated in vacuo and residue was partitioned between ethyl acetate and water. The organic layer was washed with water, brine and dried over anhydrous magnesium sulfate. The solution was filtered and concentrated in vacuo. The crude material was purified by reverse phase preparative HPLC (0.1% ammonia in water: acetonitrile) to provide ethyl 4-((3-(2-cyanoethoxy)cyclopentyl)amino)-1H-pyrrolo[2,3-b]pyridine-5-carboxylate (0.05 g, 6% yield): $^1$H NMR (400 MHz, DMSO-$d_6$) δ 11.61 (br s, 1H), 8.95 (d, J=7.6 Hz, 1H), 8.50 (s, 1H), 7.14 (s, 1H), 6.58 (s, 1H), 4.59-4.5 (m, 1H), 4.25 (q, J=7.2 Hz, 2H), 4.02-4.10 (m, 1H), 3.56-0.351 (m, 2H), 2.73 (t, J=6.4 Hz, 2H), 2.26-2.19 (m, 1H), 2.15-2.07 (m, 1H), 1.90-1.82 (m, 2H), 1.73-1.69 (m, 2H), 1.29 (t, J=6.2 Hz, 3H); MS (ES) m/z 343.1 (M+H).

Prep HPLC Analytical Conditions
Column: Inertsil ODS 3V (250 mm×4.6 mm×5 mic)
Mobile phase (A): 0.1% Ammonia in water
Mobile phase (B): ACN
Flow rate: 1.0 mL/min
Retention time: 12.61 min.

Synthesis of Example 117: Preparation of ethyl (R)-4-((1-(2-cyanoacetyl)piperidin-3-yl)amino)-1H-pyrrolo[2,3-b]pyridine-5-carboxylate

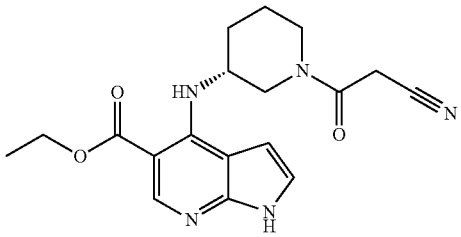 [SMILES: CCOC(=O)c1cnc2[nH]ccc2c1N[C@@H]1CCCN(C(=O)CC#N)C1]

Scheme 17. Preparation of ethyl (R)-4-((1-(2-cyanoacetyl)piperidin-3-yl)amino)-1H-pyrrolo[2,3-b]pyridine-5-carboxylate

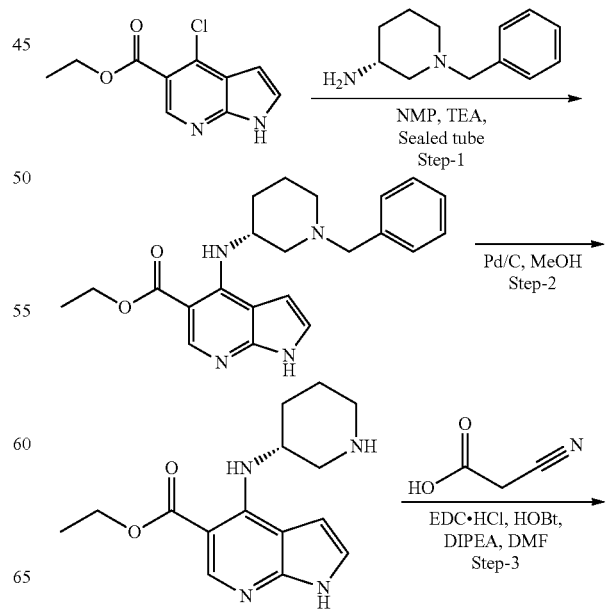

-continued

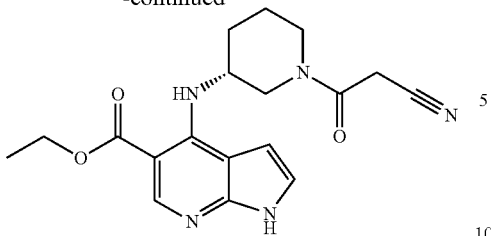

Step 1: Preparation of ethyl (R)-4-((1-benzylpiperidin-3-yl)amino)-1H-pyrrolo[2,3-b]pyridine-5-carboxylate

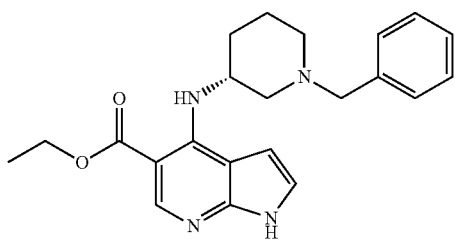 [SMILES: CCOC(=O)c1cnc2[nH]ccc2c1N[C@@H]1CCCN(Cc2ccccc2)C1]

To a solution of ethyl 4-chloro-1H-pyrrolo[2,3-b]pyridine-5-carboxylate (5 g, 22.3 mmol) in N-methyl-2-pyrrolidone (35 mL), was added (R)-1-benzylpiperidin-3-amine (8.48 g, 44.6 mmol) and triethylamine (1 mL) in a sealed tube. The mixture was heated to 170° C. for 16 hours. After cooling to room temperature the reaction mixture was quenched with water to precipitate a solid which was filtered and washed with water, dried and concentrated in vacuo to provide ethyl (R)-4-((1-((benzyloxy)carbonyl)piperidin-3-yl)amino)-1H-pyrrolo[2,3-b]pyridine-5-carboxylate as a brown solid (8 g, 95% yield): MS (ES) m/z 379.1 (M+H).

Step 2: Preparation of ethyl (R)-4-(piperidin-3-ylamino)-1H-pyrrolo[2,3-b]pyridine-5-carboxylate

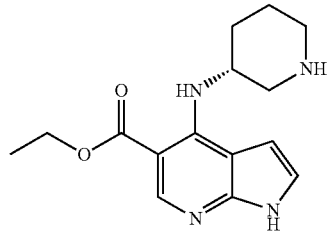 [SMILES: CCOC(=O)c1cnc2[nH]ccc2c1N[C@@H]1CCCNC1]

To a solution of ethyl (R)-4-((1-((benzyloxy)carbonyl)piperidin-3-yl)amino)-1H-pyrrolo[2,3-b]pyridine-5-carboxylate (0.25 g, 0.66 mmol) in methanol (5 mL) was added 10% palladium on carbon (0.3 g, 50% wet w/w) and the mixture was stirred under a hydrogen atmosphere at ambient temperature for 12 hours. The reaction mixture was partitioned between 50% methanol/ethyl acetate and filtered through celite. The filtrate was concentrated in vacuo to provide ethyl (R)-4-(piperidin-3-ylamino)-1H-pyrrolo[2,3-b]pyridine-5-carboxylate as an off-white solid (0.1 g, 90% yield): MS (ES) m/z 289.3 (M+H).

Step 3: Preparation of ethyl (R)-4-((1-(2-cyanoacetyl)piperidin-3-yl)amino)-1H-pyrrolo[2,3-b]pyridine-5-carboxylate

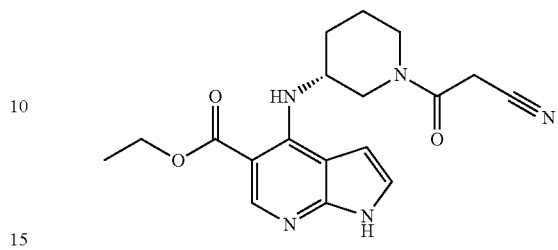

To a solution of ethyl (R)-4-(piperidin-3-ylamino)-1H-pyrrolo[2,3-b]pyridine-5-carboxylate (9 g, 31.3 mmol) in dichloromethane (50 mL) was added N-(3-dimethylaminopropyl)-N'-ethylcarbodiimide HCl (9.7 g, 62.5 mmol), 1-hydroxybenzotriazole (8.43 g, 62.5 mmol), N,N-diisopropylethylamine (11.3 mL, 62.5 mmol) and cyanoacetic acid (0.76 g, 9.0 mmol) and the mixture was stirred at ambient temperature for 18 hours. The reaction mixture was quenched with water and extracted with dichloromethane. The organic layer was washed with water, brine and dried over anhydrous sodium sulfate. The solution was filtered and concentrated in vacuo. The crude material was purified by using flash chromatography (5% methanol/dichloromethane) to provide ethyl (R)-4-((1-(2-cyanoacetyl)piperidin-3-yl)amino)-1H-pyrrolo[2,3-b]pyridine-5-carboxylate (7.5 g, 68% yield): $^1$H NMR (400 MHz, DMSO-$d_6$) δ 11.68 (br s, 1H), 8.86-8.79 (m, 1H), 8.54 (s, 1H), 7.20 (s, 1H), 6.67 (s, 1H), 4.17-4.44 (m, 3H), 3.70-4.05 (m, 4H), 3.45-3.48 (m, 1H), 3.11-3.24 (m, 1H), 2.06 (br s, 1H), 1.57-1.72 (m, 3H), 1.28-1.32 (t, J=7.2 Hz, 3H); MS (ES) m/z 356.1 (M+H).

Synthesis of Example 118: Preparation of methyl 4-(((3R,4R)-1-(2-cyanoacetyl)-4-methylpiperidin-3-yl)amino)-1H-pyrrolo[2,3-b]pyridine-5-carboxylate

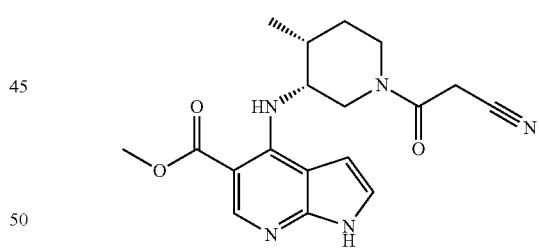

Scheme 18. Preparation of methyl 4-(((3R,4R)-1-(2-cyanoacetyl)-4-methylpiperidin-3-yl)amino)-1H-pyrrolo[2,3-b]pyridine-5-carboxylate.

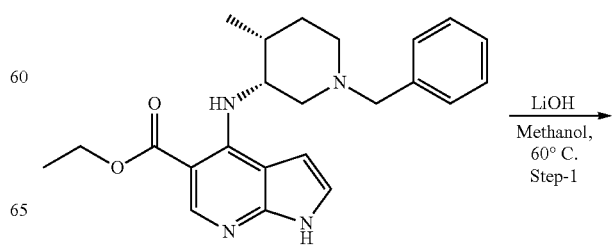

-continued

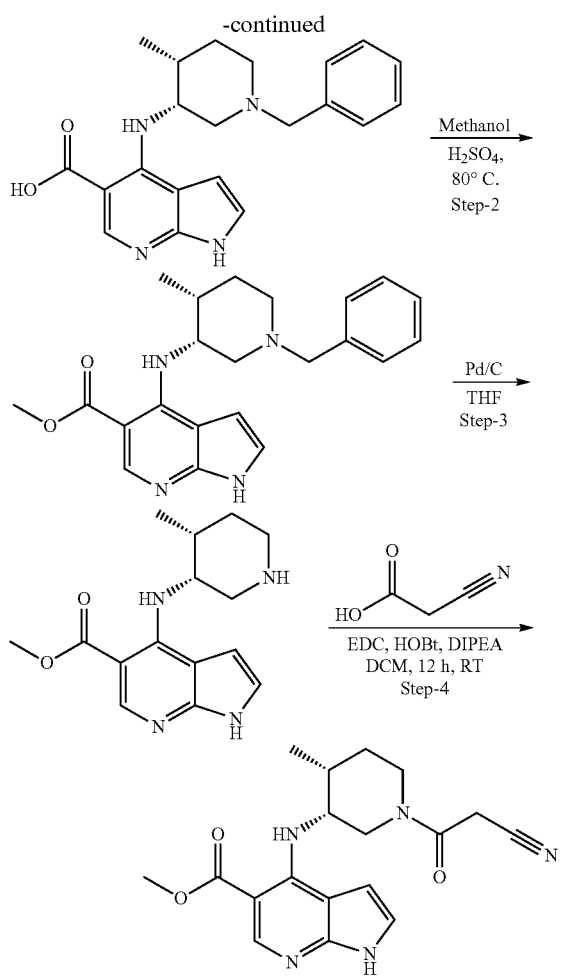

Step 1: Preparation of 4-(((3R,4R)-1-benzyl-4-methylpiperidin-3-yl)amino)-1H-pyrrolo[2,3-b]pyridine-5-carboxylic acid To a solution of ethyl 4-(((3R,4R)-1-benzyl-4-methylpiperidin-3-yl)amino)-1H-pyrrolo[2,3-b]pyridine-5-carboxylate (0.1 g, 0.25 mmol) in methanol (10 mL) was added lithium hydroxide (0.017 g, 0.75 mmol) and the mixture was heated to 60° C. for 10 hours. After cooling to ambient temperature, the reaction mixture was concentrated in vacuo to dryness. The residue was dissolved in water and acidified with 2N hydrochloric acid and the aqueous mixture was extracted with ethyl acetate. The organic layer was washed with water, brine and dried over anhydrous sodium sulfate. The solution was filtered and concentrated in vacuo to provide 4-(((3R,4R)-1-benzyl-4-methylpiperidin-3-yl)amino)-1H-pyrrolo[2,3-b]pyridine-5-carboxylic acid (0.085 g, 91% yield): MS (ES) m/z 365.2 (M+H)

Step 2: Preparation of ethyl 4-(((3R,4R)-1-benzyl-4-methylpiperidin-3-yl)amino)-1H-pyrrolo[2,3-b]pyridine-5-carboxylate

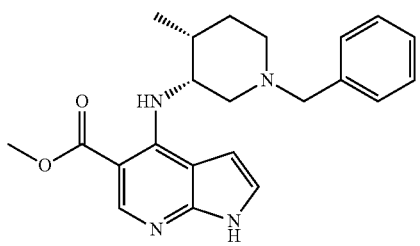 [SMILES: COC(=O)c1cnc2[nH]ccc2c1N[C@H]1CN(Cc2ccccc2)CC[C@H]1C]

To a solution of 4-(((3R,4R)-1-benzyl-4-methylpiperidin-3-yl)amino)-1H-pyrrolo[2,3-b]pyridine-5-carboxylic acid (0.08 g, 0.22 mmol) in methanol (10 mL) was added sulfuric acid (1.0 mL) and the solution was heated to 80° C. for 48 hours. After cooling to ambient temperature, the reaction was quenched with saturated bicarbonate solution and extracted with ethyl acetate. The organic layer was washed with water, brine and dried over anhydrous sodium sulfate. The solution filtered and concentrated in vacuo to provide methyl 4-(((3R,4R)-1-benzyl-4-methylpiperidin-3-yl)amino)-1H-pyrrolo[2,3-b]pyridine-5-carboxylate (0.1 g, crude): MS (ES) m/z 379.1 (M+H).

Step 3: Preparation of methyl 4-(((3R,4R)-4-methylpiperidin-3-yl)amino)-1H-pyrrolo[2,3-b]pyridine-5-carboxylate

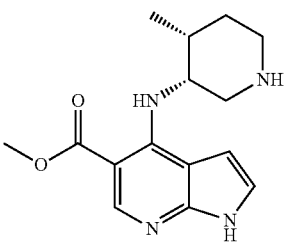 [SMILES: COC(=O)c1cnc2[nH]ccc2c1N[C@H]1CNCC[C@H]1C]

To a solution of methyl 4-(((3R,4R)-1-benzyl-4-methylpiperidin-3-yl)amino)-1H-pyrrolo[2,3-b]pyridine-5-carboxylate (0.1 g, 0.34 mmol) in tetrahydrofuran (5 mL), was added palladium on carbon (0.5 g, 50% wet w/w) and the mixture was stirred under a hydrogen atmosphere at ambient temperature for 12 hours. The resulting solution was partitioned between 50% methanol/ethyl acetate and filtered through celite. The filtrate was concentrated in vacuo to provide methyl 4-(((3R,4R)-4-methylpiperidin-3-yl)amino)-1H-pyrrolo[2,3-b]pyridine-5-carboxylate (0.09 g, 93% yield): MS (ES) m/z 289.2 (M+H).

Step 4: Preparation of methyl 4-(((3R,4R)-1-(2-cyanoacetyl)-4-methylpiperidin-3-yl)amino)-1H-pyrrolo [2,3-b]pyridine-5-carboxylate

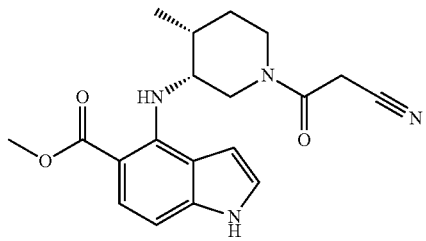

To a solution of methyl 4-(((3R,4R)-4-methylpiperidin-3-yl)amino)-1H-pyrrolo[2,3-b]pyridine-5-carboxylate (0.1 g, 0.34 mmol) in dichloromethane (5 mL) was added N-(3-dimethylaminopropyl)-N'-ethylcarbodiimide HCl (0.10 g, 0.69 mmol), 1-hydroxybenzotriazole (0.09 g, 0.69 mmol), N,N-diisopropylethylamine (0.89 g, 6.94 mmol) and cyanoacetic acid (0.04 g, 0.52 mmol) and the mixture was stirred at ambient temperature for 12 hours. The reaction mixture was quenched with water and extracted with dichloromethane. The organic layer was washed with water, brine and dried over anhydrous sodium sulfate. The solution was filtered and concentrated in vacuo. The crude material was purified using flash chromatography (6% methanol/dichloromethane) to provide methyl 4-(((3R,4R)-1-(2-cyanoacetyl)-4-methy piperidin-3-yl)amino)-1H-pyrrolo[2,3-b]pyridine-5-carboxylate (0.06 g, 49% yield). 1H NMR (400 MHz, DMSO-d6) δ 11.73 (m, 1H), 8.82-8.91 (m, 1H), 8.52-8.55 (m, 1H), 7.19-7.22 (m, 1H), 6.65-6.70 (m, 1H), 4.26-4.42 (m, 2H), 4.06 (s, 1H), 3.85 (s, 1H), 3.65-3.68 (m, 1H), 3.38-3.42 (m, 1H), 3.04-3.19 (m, 2H), 2.18-2.88 (m, 1H), 2.12 (br s, 1H), 1.35-1.64 (m, 3H), 0.88-0.96 (m, 3H); MS (ES) m/z 356 (M+H).

Examples 119 and 120: Preparation of tert-butyl 4-(((3R,4R)-1-(2-cyanoacetyl)-4-methylpiperidin-3-yl)amino)-1H-pyrrolo[2,3-b]pyridine-5-carboxylate and 4-(((3R,4R)-1-(2-cyanoacetyl)-4-methylpiperidin-3-yl)amino)-1H-pyrrolo[2,3-b]pyridine-5-carboxylic acid trifluoroacetic acid Salt

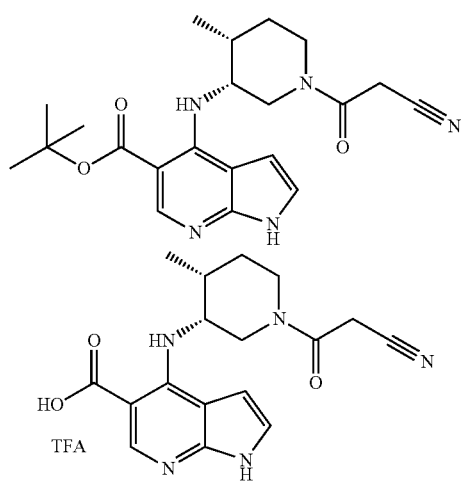

Scheme 19. Preparation of tert-butyl 4-(((3R,4R)-1-(2-cyanoacetyl)-4-methylpiperidin-3-yl)amino)-1H-pyrrolo[2,3-b]pyridine-5-carboxylate and 4-(((3R,4R)-1-(2-cyanoacetyl)-4-methylpiperidin-3-yl)amino)-1H-pyrrolo[2,3-b]pyridine-5-carboxylic acid trifluoroacetic acid salt

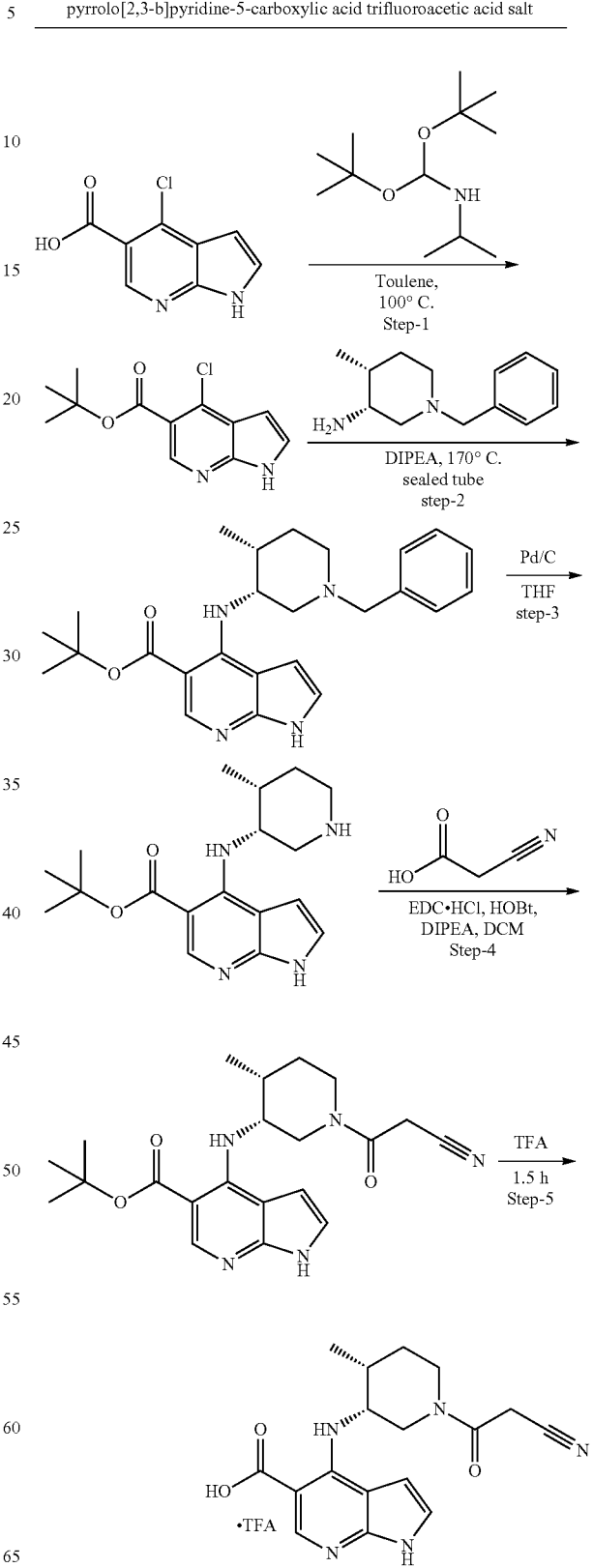

Step 1: Preparation of tert-butyl 4-chloro-1H-pyrrolo[2,3-b]pyridine-5-carboxylate

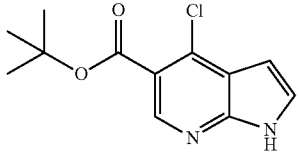 [SMILES: CC(C)(C)OC(=O)c1cnc2[nH]ccc2c1Cl]

To a solution of 4-chloro-H-pyrrolo[2,3-b]pyridine-5-carboxylic acid (3.5 g, 17.8 mmol) in toluene (20 mL), was added N-(di-tert-butoxymethyl)propan-2-amine (14.5 g, 71.4 mmol) and the mixture was heated to 100° C. for 1 hour and then stirred at ambient temperature for 12 hours. The reaction mixture was quenched with water and extracted with ethyl acetate. The organic layer was washed with water, brine and dried over anhydrous sodium sulfate. The solution was filtered and concentrated in vacuo to provide tert-butyl 4-chloro-1H-pyrrolo[2,3-b]pyridine-5-carboxylate (3.1 g, 63% yield): MS (ES) m/z 253.1 (M+H).

Step 2: Preparation of tert-butyl 4-(((3R,4R)-1-benzyl-4-methylpiperidin-3-yl)amino)-1H-pyrrolo[2,3-b]pyridine-5-carboxylate

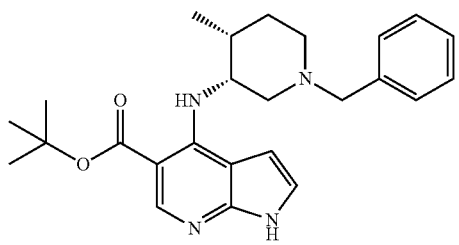 [SMILES: C[C@@H]1CCN(Cc2ccccc2)C[C@@H]1Nc1c(C(=O)OC(C)(C)C)cnc2[nH]ccc12]

To a solution of tert-butyl 4-chloro-1H-pyrrolo[2,3-b]pyridine-5-carboxylate (0.9 g, 3.57 mmol) in N-methylpyrrolidine (2 mL), was added (3R,4R)-1-benzyl-4-methylpiperidin-3-amine (0.72 g, 3.57 mmol) and triethylamine (0.2 mL) in a sealed tube and the mixture heated at 170° C. for 16 hours. After cooling to ambient temperature, the reaction mixture was quenched with water to precipitate a solid. The solid was filtered, washed with water and dried to provide tert-butyl 4-(((3R,4R)-1-benzyl-4-methylpiperidin-3-yl)amino)-1H-pyrrolo[2,3-b]pyridine-5-carboxylate as a brown solid (1 g, 67% yield): MS (ES) m/z 421.2 (M+H).

Step 3: Preparation of tert-butyl 4-(((3R,4R)-4-methylpiperidin-3-yl)amino)-1H-pyrrolo[2,3-b]pyridine-5-carboxylate

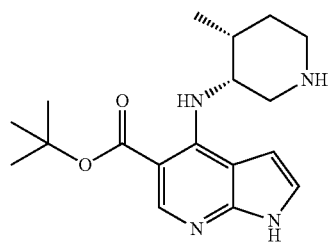 [SMILES: C[C@@H]1CCNC[C@@H]1Nc1c(C(=O)OC(C)(C)C)cnc2[nH]ccc12]

To a solution of tert-butyl 4-(((3R,4R)-1-benzyl-4-methylpiperidin-3-yl)amino)-1H-pyrrolo[2,3-b]pyridine-5-carboxylate (0.4 g, 0.95 mmol) in tetrahydrofuran (1 mL) was added palladium on carbon (1 g, 50% wet w/w) and the mixture was stirred under a hydrogen atmosphere at ambient temperature for 24 hours. The reaction was partitioned between 50% methanol/ethyl acetate and filtered through celite. The filtrate was concentrated in vacuo to provide tert-butyl 4-(((3R,4R)-4-methylpiperidin-3-yl)amino)-1H-pyrrolo[2,3-b]pyridine-5-carboxylate (0.4 g, crude): MS (ES) m/z 331.2 (M+H).

Step 4: Preparation of Example 119: tert-butyl 4-(((3R,4R)-1-(2-cyanoacetyl)-4-methylpiperidin-3-yl)amino)-1H-pyrrolo[2,3-b]pyridine-5-carboxylate

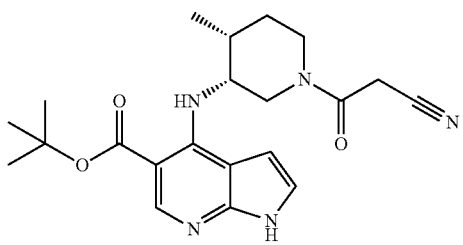 [SMILES: C[C@@H]1CCN(C(=O)CC#N)C[C@@H]1Nc1c(C(=O)OC(C)(C)C)cnc2[nH]ccc12]

To a solution of tert-butyl 4-(((3R,4R)-4-methylpiperidin-3-yl)amino)-1H-pyrrolo[2,3-b]pyridine-5-carboxylate (0.4 g, 1.2 mmol) in dichloromethane (10 mL) was added N-(3-dimethylaminopropyl)-N'-ethylcarbodiimide HCl (0.37 g, 2.4 mmol), 1-hydroxyl benzotriazole (0.32 g, 2.4 mmol), N,N-diisopropylethylamine (0.31 g, 0.24 mmol) and cyanoacetic acid (0.2 g, 2.4 mmol) and the mixture was stirred at ambient temperature for 12 hours. The reaction mixture was quenched with water and extracted with dichloromethane. The organic layer was washed with water, brine and dried over anhydrous sodium sulfate. The solution was filtered and concentrated in vacuo. The crude material was purified using flash chromatography (10% methanol/dichloromethane) to provide tert-butyl 4-(((3R,4R)-1-(2-cyanoacetyl)-4-methylpiperidin-3-yl)amino)-1H-pyrrolo[2,3-b]pyridine-5-carboxylate (0.2 g, 41% yield).

$^1$H NMR (400 MHz, DMSO-$d_6$) δ 11.65-11.71 (m, 1H), 8.91-8.93 (m, 1H), 8.48-8.52 (m, 1H), 7.17-7.20 (m, 1H) 6.63-6.69 (s, 1H) 4.21-4.43 (m, 2H), 3.84-4.07 (m, 2H), 3.60-3.70 (s, 1H), 3.38-3.41 (m, 1H), 3.07-3.20 (m, 2H), 2.13 (br s, 1H), 1.61-1.68 (m, 1H), 1.54 (s, 9H), 0.90-0.96 (m, 3H); MS (ES) m/z 398.2 (M+H).

Step 5: Preparation of Example 120: 4-(((3R,4R)-1-(2-cyanoacetyl)-4-methylpiperidin-3-yl)amino)-1H-pyrrolo[2,3-b]pyridine-5-carboxylic acid trifluoroacetic acid Salt

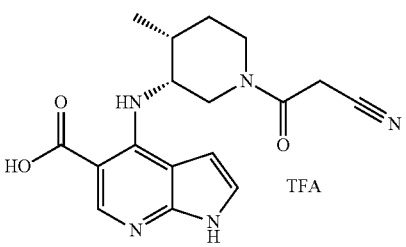 [SMILES: C[C@@H]1CCN(C(=O)CC#N)C[C@@H]1Nc1c(C(=O)O)cnc2[nH]ccc12]

To a solution of tert-butyl 4-(((3R,4R)-1-(2-cyanoacetyl)-4-methylpiperidin-3-yl)amino)-1H-pyrrolo[2,3-b]pyridine-5-carboxylate (0.055 g, 1.2 mmol) was added trifluoroacetic acid (1 mL) and the mixture was stirred at ambient temperature for 1.5 hours. The reaction was concentrated in vacuo and crude material was purified by reverse phase preparative HPLC to provide 4-(((3R,4R)-1-(2-cyanoacetyl)-4-methylpiperidin-3-yl)amino)-1H-pyrrolo[2,3-b]pyridine-5-carboxylic acid.trifluoroacetic acid salt (0.03 g, 47.6% yield). $^1$H NMR (400 MHz, DMSO-$d_6$) δ 12.37 (br s, 1H), 9.94 (br s, 1H), 8.62 (s, 1H), 7.38 (m, 1H) 6.93 (m, 1H) 4.31-4.54 (m, 2H), 3.69-4.11 (m, 2H), 3.69-3.73 (m, 1H), 3.41-3.49 (m, 1H), 3.10-3.19 (m, 1H), 2.15 (br s, 1H), 1.62-1.70 (m, 1H), 1.46-1.49 (m, 1H), 1.21-1.36 (m, 1H), 0.85-0.94 (m, 3H); MS (ES) m/z 342.3 (M+H). Retention time: 4.603 min.

Analytical Conditions:

Column: Inertsil ODS 3V (250 mm×4.6 mm×5 mic)

Mobile phase (A): 0.1% TFA in water

Mobile phase (B): ACN,

Flow rate: 1.0 mL/min

Synthesis of Example 121: Preparation of (R)-4-((1-(2-cyanoacetyl)piperidin-3-yl)amino)-1H-pyrrolo[2,3-b]pyridine-5-carboxylic acid trifluoroacetic acid Salt

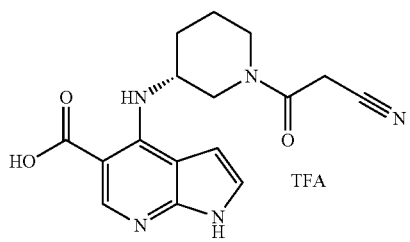 [SMILES: N#CCC(=O)N1CCC[C@@H](Nc2c(C(=O)O)cnc3[nH]ccc23)C1]

Scheme 20. Preparation of (R)-4-((1-(2-cyanoacetyl)piperidin-3-yl)amino)-1H-pyrrolo[2,3-b]pyridine-5-carboxylic acid trifluoroacetic acid salt.

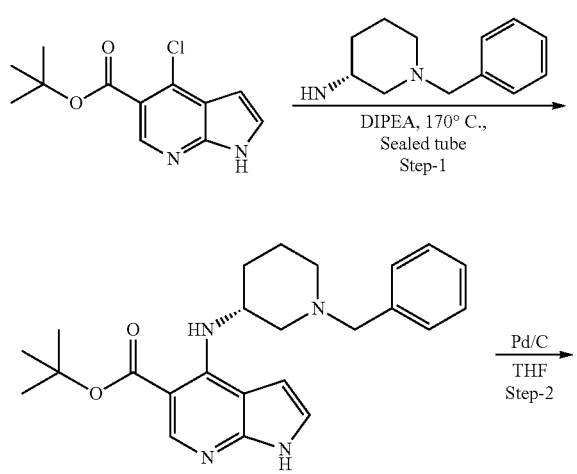

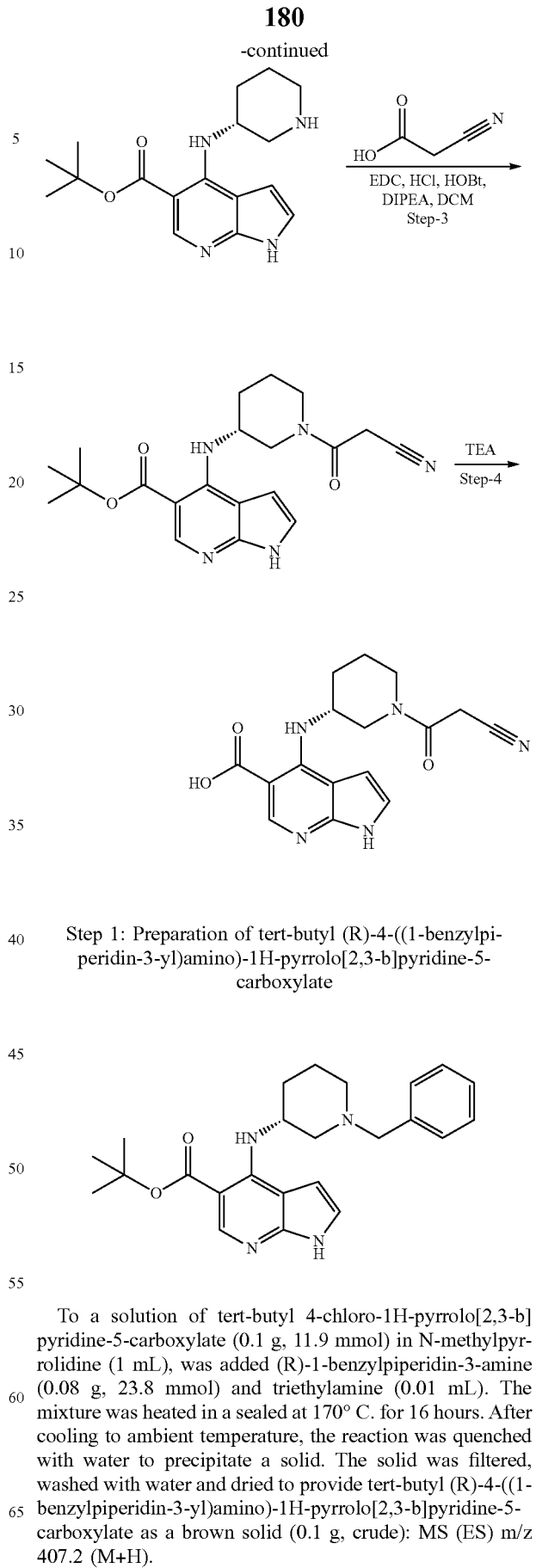

Step 1: Preparation of tert-butyl (R)-4-((1-benzylpiperidin-3-yl)amino)-1H-pyrrolo[2,3-b]pyridine-5-carboxylate To a solution of tert-butyl 4-chloro-1H-pyrrolo[2,3-b]pyridine-5-carboxylate (0.1 g, 11.9 mmol) in N-methylpyrrolidine (1 mL), was added (R)-1-benzylpiperidin-3-amine (0.08 g, 23.8 mmol) and triethylamine (0.01 mL). The mixture was heated in a sealed at 170° C. for 16 hours. After cooling to ambient temperature, the reaction was quenched with water to precipitate a solid. The solid was filtered, washed with water and dried to provide tert-butyl (R)-4-((1-benzylpiperidin-3-yl)amino)-1H-pyrrolo[2,3-b]pyridine-5-carboxylate as a brown solid (0.1 g, crude): MS (ES) m/z 407.2 (M+H).

Step 2: Preparation of tert-butyl (R)-4-(piperidin-3-ylamino)-1H-pyrrolo[2,3-b]pyridine-5-carboxylate

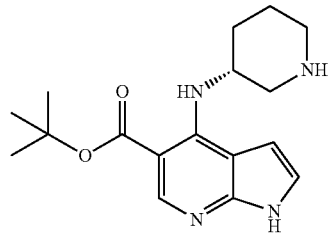 [SMILES: CC(C)(C)OC(=O)c1cnc2[nH]ccc2c1N[C@@H]1CCCNC1]

To a solution tert-butyl (R)-4-((1-benzylpiperidin-3-yl)amino)-1H-pyrrolo[2,3-b]pyridine-5-carboxylate (3.1 g, 7.63 mmol) in methanol (10 mL) was added palladium on carbon (2 g, 50% wet w/w) and the mixture was stirred under a hydrogen atmosphere using Parr-shaker (70 psi) at ambient temperature for 30 hours. The reaction mixture was filtered through celite and washed with 50% methanol/ethyl acetate (200 mL). The filtrate was concentrated in vacuo to provide tert-butyl (R)-4-(piperidin-3-ylamino)-1H-pyrrolo[2,3-b]pyridine-5-carboxylate (2.0 g crude): MS (ES) m/z 317.1 (M+H)

Step 3: Preparation of tert-butyl (R)-4-((1-(2-cyanoacetyl)piperidin-3-yl)amino)-1H-pyrrolo [2,3-b]pyridine-5-carboxylate

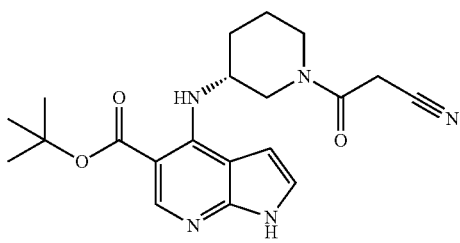 [SMILES: CC(C)(C)OC(=O)c1cnc2[nH]ccc2c1N[C@@H]1CCCN(C(=O)CC#N)C1]

To a stirred solution of tert-butyl (R)-4-(piperidin-3-ylamino)-1H-pyrrolo[2,3-b]pyridine-5-carboxylate (2.0 g, 6.32 mmol) in dichloromethane (20 mL) was added N-(3-dimethylaminopropyl)-N'-ethylcarbodiimide HCl (1.07 g, 12.6 mmol), 1-hydroxybenzotriazole (1.70 g, 12.6 mmol), N,N-diisopropylethylamine (2.4 g, 18.9 mmol) and cyanoacetic acid (1.70 g, 12.6 mmol) and mixture was stirred at ambient temperature for 12 hours. The reaction mixture was quenched with water and extracted with dichloromethane. The organic layer was washed with water, brine and dried over anhydrous sodium sulfate. The solution was filtered and concentrated in vacuo. The crude material was purified using flash chromatography (10% methanol/dichloromethane) to provide tert-butyl (R)-4-((1-(2-cyanoacetyl) piperidin-3-yl)amino)-1H-pyrrolo[2,3-b]pyridine-5-carboxylate (1.4 g, 58% yield): MS (ES) m/z 384.1 (M+H).

Step 4: Preparation of (R)-4-((1-(2-cyanoacetyl)piperidin-3-yl)amino)-1H-pyrrolo[2,3-b]pyridine-5-carboxylic acid trifluoroacetic acid Salt

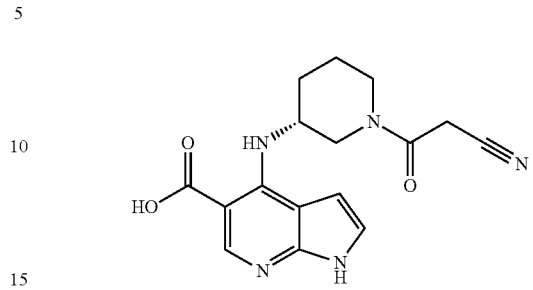

To tert-butyl (R)-4-((1-(2-cyanoacetyl)piperidin-3-yl)amino)-1H-pyrrolo[2,3-b]pyridine-5-carboxylate (1 g, 2.6 mmol) was added trifluoroacetic acid (5 mL) and the mixture was stirred at ambient temperature for 1.5 hours. The reaction was concentrated in vacuo and crude material was purified using reverse phase preparative HPLC (0.1% trifluoroacetic acid in water/methanol) to provide (R)-4-((1-(2-cyanoacetyl) piperidin-3-yl) amino)-1H-pyrrolo[2,3-b]pyridine-5-carboxylic acid trifluoroacetic acid salt (0.72 g, 63% yield): $^1$H NMR (400 MHz, D$_2$O, DMSO-d$_6$) δ 8.59 (s, 1H), 7.32-7.34 (m, 1H) 6.81-6.86 (m, 1H) 4.40 (m, 1H), 4.23 (m, 1H), 3.90-4.05 (m, 2H), 3.33-3.48 (m, 2H), 2.04 (m, 1H), 1.57-1.78 (m, 3H), 1.18-1.21 (m, 1H); MS (ES) m/z 328.1 (M+H).

Analytical Conditions:
Column: Inertsil ODS 3V (250 mm×4.6 mm×5 mic);
Mobile phase (A): 0.1% TFA in water
Mobile phase (B): Methanol;
Flow rate: 1.0 mL/min

Synthesis of Example 123: Preparation of ethyl (R)-4-((1-(2-cyanoethyl)piperidin-3-yl)amino)-1H-pyrrolo[2,3-b]pyridine-5-carboxylate

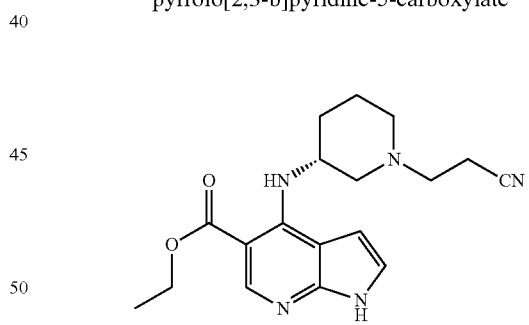

Scheme 21. Preparation of ethyl (R)-4-((1-(2-cyanoethyl)-piperidin-3-yl)amino)-1H-pyrrolo[2,3-b]pyridine-5-carboxylate.

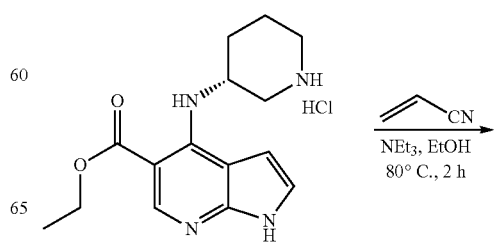

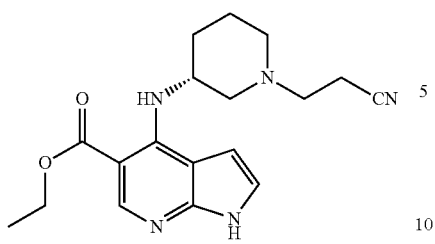
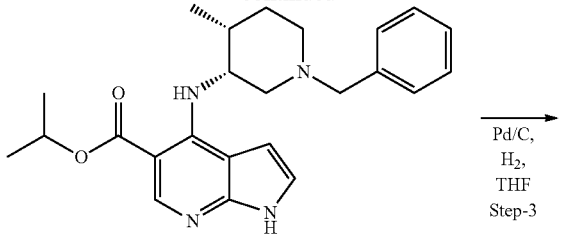

A solution of ethyl (R)-4-(piperidin-3-ylamino)-1H-pyrrolo[2,3-b]pyridine-5-carboxylate HCl (0.07 g, 0.21 mmol), acrylonitrile (0.11 g, 2.16 mmol) and triethylamine (0.06 mL, 0.42 mmol) in ethanol (3 mL) was heated to 80° C. for 2 hours. After cooling to ambient temperature, the solvent was concentrated in vacuo and the crude material purified using flash chromatography (5% methanol/dichloromethane) to provide ethyl (R)-4-((1-(2-cyanoethyl)piperidin-3-yl)amino)-1H-pyrrolo[2,3-b]pyridine-5-carboxylate as an off-white solid (0.025 g, 34% yield): $^1$H NMR (400 MHz, DMSO-$d_6$) δ 11.64 (s, 1H), 8.93 (b, 1H), 8.52 (s, 1H), 7.15 (s, 1H), 6.55 (s, 1H), 4.16-4.25 (m, 3H), 2.90-2.88 (m, 1H), 2.64 (s, 3H), 2.53-2.61 (m, 2H), 2.31-2.38 (m, 2H), 1.83-1.92 (m, 1H), 1.63-1.75 (m, 1H), 1.43-1.62 (m, 2H), 1.28-1.38 (m, 3H); MS (ES) m/z 342.1 (M+H).

Synthesis of Example 124: Preparation of isopropyl 4-(((3R,4R)-1-(2-cyanoacetyl)-4-methylpiperidin-3-yl)amino)-1H-pyrrolo[2,3-b]pyridine-5-carboxylate

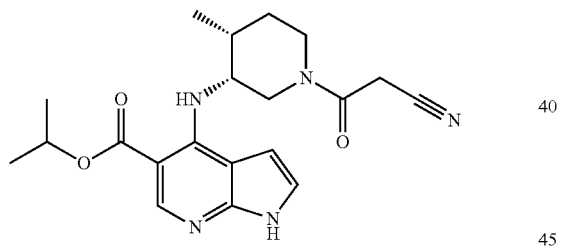

Scheme 22. Preparation of isopropyl 4-(((3R,4R)-1-(2-cyanoacetyl)-4-methylpiperidin-3-yl)amino)-1H-pyrrolo[2,3-b]pyridine-5-carboxylate.

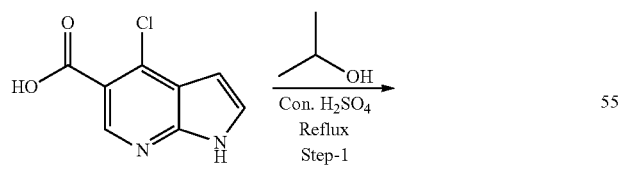

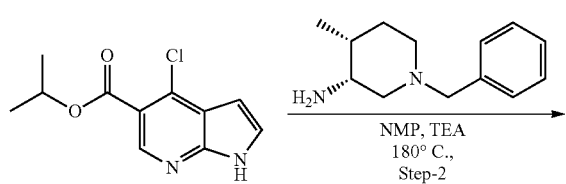

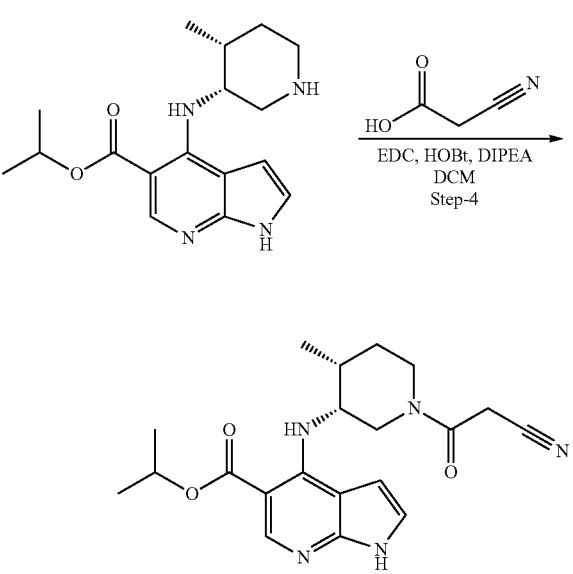

Step 1: Preparation of isopropyl 4-chloro-1H-pyrrolo[2,3-b]pyridine-5-carboxylate

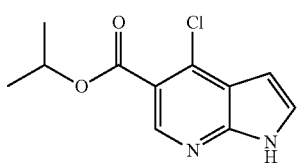 [SMILES: CC(C)OC(=O)c1cnc2[nH]ccc2c1Cl]

To a solution of 4-chloro-1H-pyrrolo[2,3-b]pyridine-5-carboxylic acid (0.5 g, 2.55 mmol) in isopropyl alcohol (20 mL) was added concentrated sulfuric acid (0.2 mL) at 0° C. and the mixture heated at reflux for 10 hours. After cooling to ambient temperature, the reaction was concentrated in vacuo and the residue was quenched with saturated sodium bicarbonate and extracted with ethyl acetate. The organic layer was washed with water, brine and dried over anhydrous sodium sulfate. The solution was filtered and concentrated in vacuo to provide isopropyl 4-chloro-1H-pyrrolo[2,3-b]pyridine-5-carboxylate as a white solid (0.45 g, crude): MS (ES) m/z: 239.1 (M+H).

Step 2: Preparation of isopropyl 4-(((3R,4R)-1-benzyl-4-methylpiperidin-3-yl)amino)-1H-pyrrolo[2,3-b] pyridine-5-carboxylate

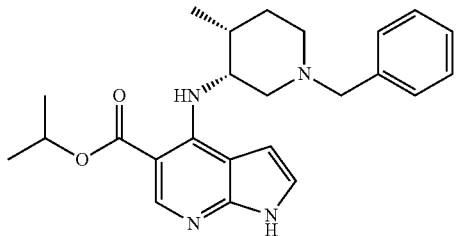 [SMILES: CC(C)OC(=O)c1cnc2[nH]ccc2c1N[C@H]1CN(Cc2ccccc2)CC[C@H]1C]

A solution of isopropyl 4-chloro-1H-pyrrolo[2,3-b]pyridine-5-carboxylate (0.4 g, 1.68 mmol), (3R,4R)-1-benzyl-4-methylpiperidin-3-amine (0.41 g, 2.01 mmol) and triethylamine (0.5 mL) in N-methyl-2-pyrrolidone (5 mL) was subjected to microwave irradiation at 180° C. for 2 hours. After cooling to room temperature, the reaction mixture was quenched with water and extracted with ethyl acetate. The organic layer was washed with brine, dried over anhydrous sodium sulfate. The solution was filtered and concentrated in vacuo. The crude material was purified by using flash chromatography (ethyl acetate/hexane) to provide isopropyl 4-(((3R,4R)-1-benzyl-4-methylpiperidin-3-yl)amino)-1H-pyrrolo[2,3-b]pyridine-5-carboxylate as a liquid (0.6 g, 88% yield): MS (ES) m/z: 407.1 (M+H).

Step 3: Preparation of isopropyl 4-(((3R,4R)-4-methylpiperidin-3-yl)amino)-1H-pyrrolo[2,3-b]pyridine-5-carboxylate

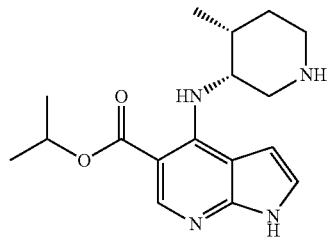 [SMILES: CC(C)OC(=O)c1cnc2[nH]ccc2c1N[C@H]1CNCC[C@H]1C]

To a solution of isopropyl 4-(((3R,4R)-1-benzyl-4-methylpiperidin-3-yl)amino)-1H-pyrrolo[2,3-b]pyridine-5-carboxylate (0.6 g, 1.47 mmol) in tetrahydrofuran (30 mL) was added palladium on carbon (0.9 g, 50% wet w/w) and the mixture was stirred under hydrogen atmosphere (70 psi) by using Parr-shaker at ambient temperature for 16 hours. The reaction mixture was filtered through celite and filtrate was concentrated in vacuo to provide isopropyl 4-(((3R,4R)-4-methylpiperidin-3-yl) amino)-1H-pyrrolo[2,3-b]pyridine-5-carboxylate (0.45 g crude): MS (ES) hn/z: 317.1 (M+H).

Step 4: Preparation of isopropyl 4-(((3R,4R)-1-(2-cyanoacetyl)-4-methylpiperidin-3-yl)amino)-1H-pyrrolo[2,3-b]pyridine-5-carboxylate

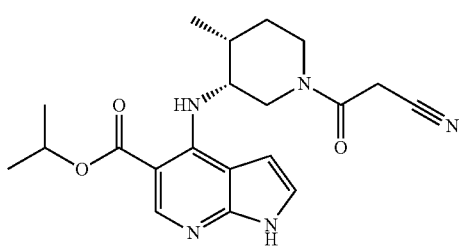

To a solution of isopropyl 4-(((3R,4R)-4-methylpiperidin-3-yl)amino)-1H-pyrrolo[2,3-b]pyridine-5-carboxylate (0.2 g, 0.63 mmol) in dichloromethane (6 mL) was added N-(3-dimethylaminopropyl)-N'-ethylcarbodiimide HCl (0.14 g, 0.75 mmol), 1-hydroxybenzotriazole (0.1 g, 0.75 mmol), N,N-diisopropylethylamine (0.3 mL, 1.58 mmol) and cyanoacetic acid (0.08 g, 0.94 mmol) and the mixture was stirred at ambient temperature for 6 hours. The reaction mixture was quenched with water and extracted with dichloromethane. The organic layer was washed with brine, dried over anhydrous sodium sulfate. The solution was filtered and concentrated in vacuo. The crude material was purified by using flash chromatography (ethyl acetate/hexane) to provide isopropyl 4-(((3R,4R)-1-(2-cyanoacetyl)-4-methyl piperidin-3-yl)amino)-1H-pyrrolo[2,3-b]pyridine-5-carboxylate as a pale yellow solid (0.05 g, 21% yield). $^1$H NMR (400 MHz, DMSO-$d_6$, at 90° C.) δ 11.54 (br s, 1H), 8.85 (d, J=8.4 Hz, 1H), 8.54 (s, 1H), 7.17 (s, 1H), 6.64 (br s, 1H), 5.12-5.18 (m, 1H), 4.25-4.42 (m, 2H), 3.88-4.00 (m, 1H), 3.68-3.79 (m, 1H), 3.28-3.44 (m, 1H), 2.65-2.87 (m, 1H), 2.07-2.17 (m, 1H), 1.57-1.66 (m, 2H), 1.43-1.48 (m, 1H), 1.32 (t, J=6.4 Hz, 6H), 0.96 (br s, 3H); MS (ES) m/z 384.3 (M+H).

Synthesis of Example 125: Preparation of propyl 4-(((3R,4R)-1-(2-cyanoacetyl)-4-methylpiperidin-3-yl)amino)-1H-pyrrolo[2,3-b]pyridine-5-carboxylate

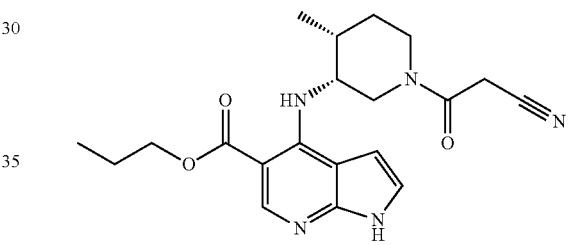

Scheme 23. Preparation of propyl 4-(((3R,4R)-1-(2-cyanoacetyl)-4-methylpiperidin-3-yl)amino)-1H-pyrrolo[2,3-b]pyridine-5-carboxylate.

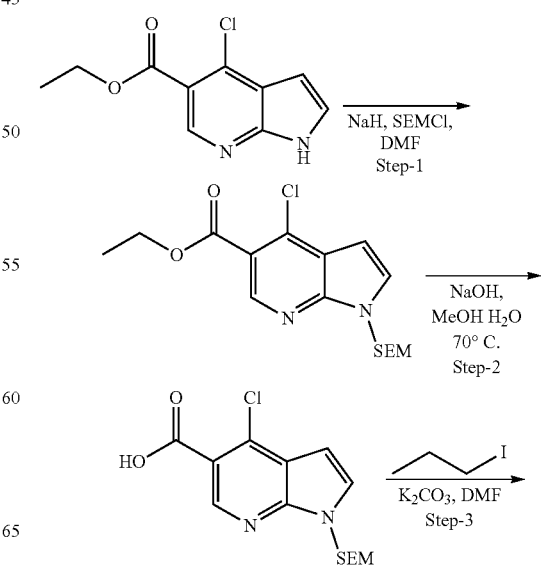

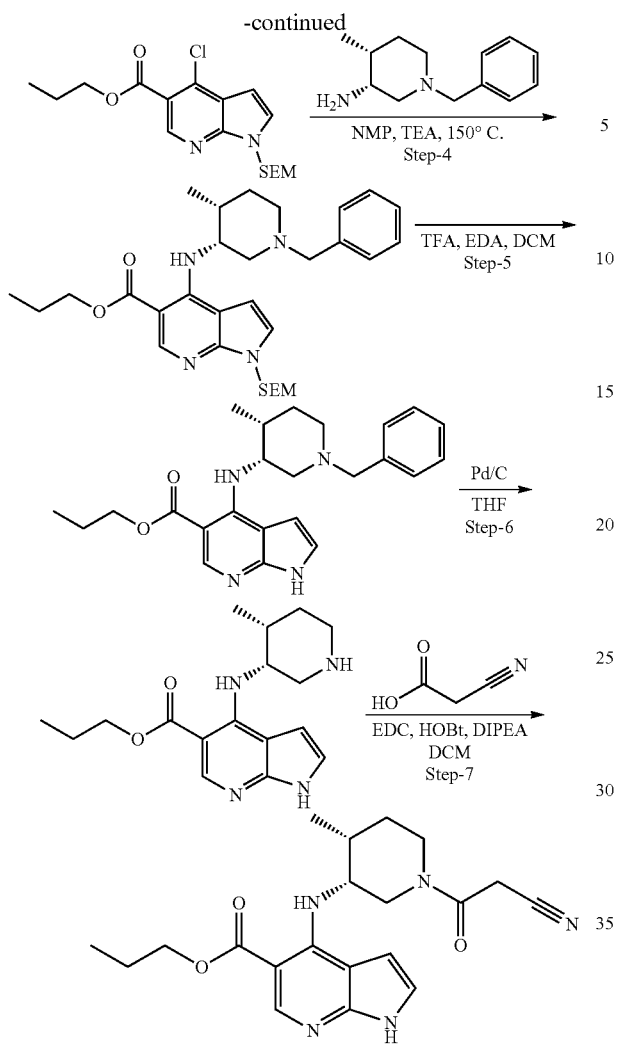

Step 1: Preparation of ethyl 4-chloro-1-((2-(trimethylsilyl)ethoxy)methyl)-1H-pyrrolo[2,3-b]pyridine-5-carboxylate

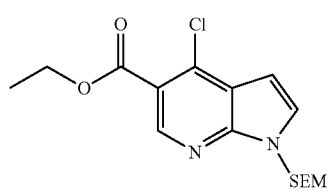 [SMILES: CCOC(=O)c1cnc2c(ccn2COCC[Si](C)(C)C)c1Cl]

To a suspension of sodium hydride (0.53 g, 13.39 mmol) in dimethylformamide (30 mL) was added ethyl 4-chloro-1H-pyrrolo[2,3-b]pyridine-5-carboxylate (2.0 g, 8.92 mmol) at 0° C. and the mixture was stirred for 30 minutes. Then 2-(trimethylsilyl)ethoxymethyl chloride (1.9 mL, 10.7 mmol) was added at 0° C. and the mixture stirred for 2 hours. The reaction mixture was quenched with ice water and extracted with ethyl acetate. The combined organic layer was washed with water, brine and dried over sodium sulfate. The solution was filtered and concentrated in vacuo. The crude material was purified by using flash chromatography (ethyl acetate/hexane) to provide ethyl 4-chloro-1-((2-(trimethylsilyl)ethoxy)methyl)-1H-pyrrolo[2,3-b]pyridine-5-carboxylate as a liquid (2.0 g, 64% yield): MS (ES) m/z 355.1 (M+H).

Step 2: Preparation of 4-chloro-1-((2-(trimethylsilyl)ethoxy)methyl)-1H-pyrrolo[2,3-b]pyridine-5-carboxylic acid

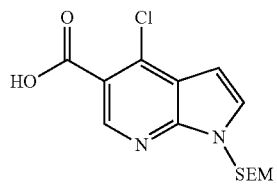 [SMILES: C[Si](C)(C)CCOCn1ccc2c(Cl)c(C(=O)O)cnc21]

To a solution of ethyl 4-chloro-1-((2-(trimethylsilyl)ethoxy)methyl)-1H-pyrrolo[2,3-b]pyridine-5-carboxylate (1.8, 5.07 mmol) in methanol:water (8:2, 30 mL) at 0° C. was added sodium hydroxide (0.45 g, 10.1 mmol). The mixture was then heated at 70° C. for 10 hours. After cooling to ambient temperature, the reaction mixture was concentrated in vacuo and residue was dissolved in water and acidified with 3N HCl. The aqueous layer was extracted with ethyl acetate. The organic layer was washed with water, brine and dried over anhydrous sodium sulfate. The solution was filtered and concentrated in vacuo to provide 4-chloro-1-((2-(trimethylsilyl)ethoxy)methyl)-1H-pyrrolo[2,3-b]pyridine-5-carboxylic acid as an off-white solid (1.5 g, crude): MS (ES) m/z: 327.1 (M+H).

Step 3: Preparation of propyl 4-chloro-1-((2-(trimethylsilyl)ethoxy)methyl)-1H-pyrrolo[2,3-b]pyridine-5-carboxylate

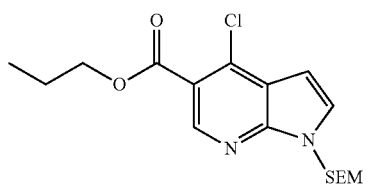 [SMILES: CCCOC(=O)c1cnc2c(ccn2COCC[Si](C)(C)C)c1Cl]

To a solution of 4-chloro-1-((2-(trimethylsilyl)ethoxy)methyl)-H-pyrrolo[2,3-b]pyridine-5-carboxylic acid (0.5 g, 1.53 mmol) in N,N dimethylformamide (10 mL) was added potassium carbonate (0.42 g, 3.06 mmol) and 1-iodopropane (0.3 mL, 6.12) and the mixture was stirred at room temperature for 16 hours. The reaction was quenched with ice water and extracted with ethyl acetate. The organic layer was washed with water, brine and dried over sodium sulfate. The solution was filtered and concentrated in vacuo to provide propyl 4-chloro-1-((2-(trimethylsilyl)ethoxy)methyl)-1H-pyrrolo[2,3-b]pyridine-5-carboxylate as a liquid (0.6 g, crude): MS (ES) m/z: 369.1 (M+H).

Step 4: Preparation of propyl 4-(((3R,4R)-1-benzyl-4-methylpiperidin-3-yl)amino)-1-((2-(trimethylsilyl)ethoxy)methyl)-1H-pyrrolo[2,3-b]pyridine-5-carboxylate

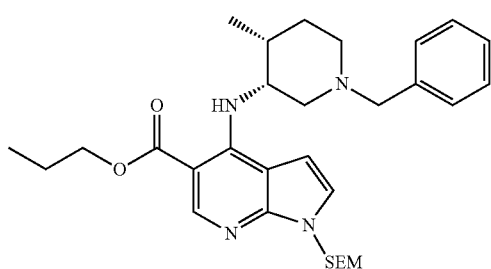 [SMILES: CCCOC(=O)c1cnc2c(ccn2COCC[Si](C)(C)C)c1N[C@H]1CN(Cc2ccccc2)CC[C@H]1C]

A mixture of propyl 4-chloro-1-((2-(trimethylsilyl)ethoxy)methyl)-1H-pyrrolo[2,3-b]pyridine-5-carboxylate (0.2 g, 0.54 mmol), (3R,4R)-1-benzyl-4-methylpiperidin-3-amine (0.13 g, 0.65 mmol) and triethylamine (0.1 mL, xx mmol) in N-methyl-2-pyrrolidone (6.0 mL) was heated in a sealed tube for 12 hours. After cooling to ambient temperature, the reaction was quenched with water and extracted with ethyl acetate. The organic layer was washed with water, brine and dried over sodium sulfate. The solution was filtered and concentrated in vacuo. The crude material was purified using flash chromatography (ethyl acetate/hexane) to provide propyl 4-(((3R,4R)-1-benzyl-4-methylpiperidin-3-yl)amino)-1-((2-(trimethylsilyl)ethoxy)methyl)-1H-pyrrolo[2,3-b]pyridine-5-carboxylate as a liquid (0.8 g, 69% yield): MS (ES) m/z: 537.3 (M+H).

Step 5: Preparation of propyl 4-(((3R, 4R)-1-benzyl-4-methylpiperidin-3-yl)amino)-1H-pyrrolo[2,3-b]pyridine-5-carboxylate

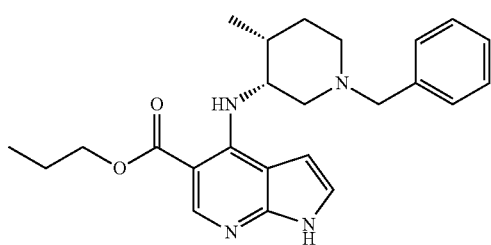 [SMILES: CCCOC(=O)c1cnc2[nH]ccc2c1N[C@H]1CN(Cc2ccccc2)CC[C@H]1C]

To a solution of propyl 4-(((3R,4R)-1-benzyl-4-methylpiperidin-3-yl)amino)-1-((2-(trimethylsilyl)ethoxy)methyl)-1H-pyrrolo[2,3-b]pyridine-5-carboxylate (0.8 g, 1.49 mmol) in dichloromethane (10 mL) was added trifluoroacetic acid (10 mL) and the mixture was stirred at ambient temperature for 3 hours. The volatiles were removed in vacuo and residue was dissolved dichloromethane (10 mL) and ethylenediamine (10 mL) was added. The reaction was stirred at ambient temperature for 3 hours. The reaction mixture was quenched with water and extracted with ethyl acetate. The organic layer was dried over anhydrous sodium sulfate and concentrated in vacuo. The crude material was purified by using flash chromatography (ethyl acetate/hexane) to provide propyl 4-(((3R,4R)-1-benzyl-4-methylpiperidin-3-yl)amino)-1H-pyrrolo[2,3-b]pyridine-5-carboxylate as a pale yellow solid (0.45 g, 75% yield): MS (ES) m/z: 407.3 (M+H).

Step 6: Preparation of propyl 4-(((3R,4R)-4-methylpiperidin-3-yl)amino)-1H-pyrrolo[2,3-b]pyridine-5-carboxylate

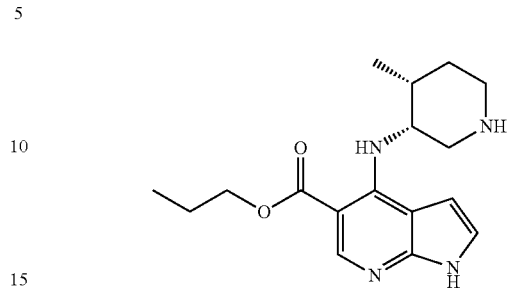

To a solution of propyl 4-(((3R,4R)-1-benzyl-4-methylpiperidin-3-yl)amino)-1H-pyrrolo[2,3-b]pyridine-5-carboxylate (0.45 g, 1.18 mmol) in tetrahydrofuran (50 mL) was added palladium on carbon (0.5 g, 50% wet w/w) and the mixture was stirred under a hydrogen atmosphere at ambient temperature for 10 hours. The reaction mixture was filtered through celite. The filtrate was concentrated in vacuo to provide propyl 4-(((3R,4R)-4-methylpiperidin-3-yl)amino)-1H-pyrrolo[2,3-b]pyridine-5-carboxylate as an off-white solid (0.3 g, crude): MS (ES) m/z: 317.4 (M+H).

Step 7: Preparation of propyl 4-(((3R,4R)-1-(2-cyanoacetyl)-4-methylpiperidin-3-yl)amino)-1H-pyrrolo[2,3-b]pyridine-5-carboxylate

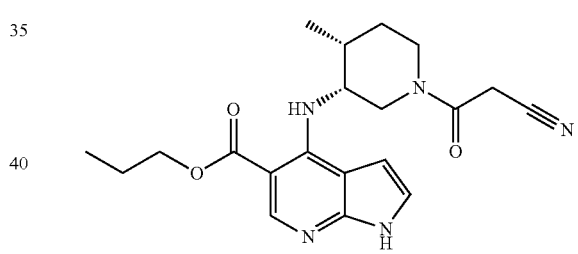

To a solution of propyl 4-(((3R,4R)-4-methylpiperidin-3-yl)amino)-1H-pyrrolo[2,3-b]pyridine-5-carboxylate (0.15 g, 0.47 mmol) in dichloromethane (5 mL) was added N-(3-dimethylaminopropyl)-N'-ethylcarbodiimide HCl (0.108 g, 0.56 mmol), 1-hydroxybenzotriazole (0.08 g, 0.56 mmol), N,N-diisopropylethylamine (0.2 mL, 1.18 mmol), cyanoacetic acid (0.06 g, 0.71 mmol) and the mixture was stirred at ambient temperature for 16 hours. The reaction was quenched with water and extracted with dichloromethane. The organic layer was washed with water, brine and dried over anhydrous sodium sulfate. The solution was filtered and concentrated in vacuo. The crude material was purified using flash chromatography (ethyl acetate/hexane) to provide propyl 4-(((3R,4R)-1-(2-cyanoacetyl)-4-methylpiperidin-3-yl)amino)-1H-pyrrolo[2,3-b]pyridine-5-carboxylate as a pale yellow solid (0.07 g, 42% yield): $^1$H NMR (400 MHz, DMSO-$d_6$, at 90° C.) δ 11.47 (br s, 1H), 8.81 (d, J=6.8 Hz, 1H), 8.57 (s, 1H), 7.16 (s, 1H), 6.64 (br s, 1H), 4.38 (m, 1H), 4.20-4.21 (m, 3H), 3.70-3.84 (m, 2H), 3.38-3.40 (m, 1H), 3.16 (m, 1H), 2.15 (m, 1H), 1.68-1.77 (m, 3H), 1.52-1.64 (m, 1H), 1.07-1.24 (m, 1H), 0.95-0.99 (br s, 6H); MS (ES) m/z: 384 (M+H).

Synthesis of Example 126: Preparation of ethyl 4-(((3R,4R)-1-(1-cyanocyclopropane-1-carbonyl)-4-methylpiperidin-3-yl)amino)-1H-pyrrolo[2,3-b]pyridine-5-carboxylate

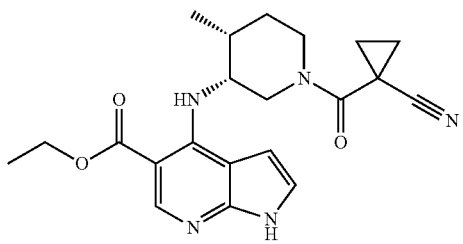 [SMILES: CCOC(=O)c1cnc2[nH]ccc2c1N[C@H]1CN(C(=O)C2(C#N)CC2)CC[C@H]1C]

Scheme 24. Preparation of ethyl 4-(((3R,4R)-1-(1-cyanocyclopropane-1-carbonyl)-4-methylpiperidine-3-yl)amino)-1H-pyrrolo[2,3-b]pyridine-5-carboxylate.

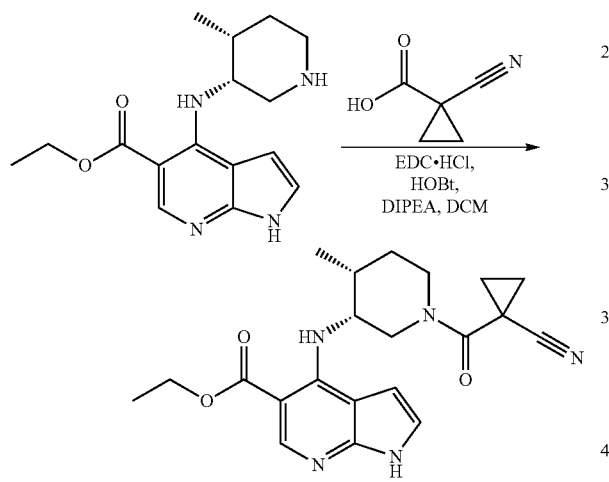

To a solution of ethyl 4-(((3R,4R)-4-methylpiperidin-3-yl)amino)-1H-pyrrolo[2,3-b]pyridine-5-carboxylate (0.15 g, 0.49 mmol) in dichloromethane (6 mL) was added N-(3-dimethylaminopropyl)-N'-ethylcarbodiimide HCl (0.142 g, 0.74 mmol), 1-hydroxybenzotriazole (0.1 g, 0.74 mmol), N,N-diisopropylethylamine (0.3 mL, 1.48 mmol), 1-cyanocyclopropane-1-carboxylic acid (0.08 g, 0.74 mmol) and the mixture was stirred at room temperature for 10 hours. The reaction was quenched with water and extracted with dichloromethane. The organic layer was washed with water, brine and dried over anhydrous sodium sulfate. The solution was filtered and concentrated in vacuo. The crude material was purified by using flash chromatography (10% methanol/dichloromethane) to provide ethyl 4-(((3R,4R)-1-(1-cyanocyclopropane-1-carbonyl)-4-methyl piperidin-3-yl)amino)-1H-pyrrolo[2,3-b] pyridine-5-carboxylate as an off-white solid (0.05 g, 26% yield): $^1$H NMR (400 MHz, DMSO-$d_6$) δ 11.69 (br s, 1H), 8.87 (d, J=8.4 Hz, 1H), 8.52 (s, 1H), 7.19 (s, 1H), 6.68 (br s, 1H), 4.41 (m, 2H), 4.20-4.28 (m, 3H), 3.28 (s, 3H), 2.16 (m, 1H), 1.68 (m, 1H), 1.46 (m, 3H), 1.21-1.29 (m, 4H), 0.93 (d, J=5.6 Hz, 3H); MS (ES) m/z: 396 (M+H).

Synthesis of Example 127: Preparation of ethyl 4-(((3R,4R)-1-(2-cyanopropanoyl)-4-methylpiperidin-3-yl)amino)-1H-pyrrolo[2,3-b]pyridine-5-carboxylate

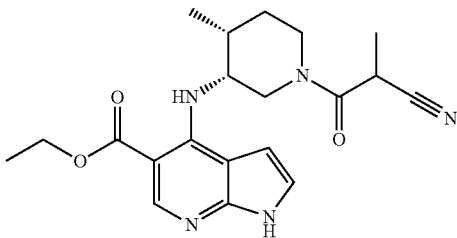 [SMILES: CCOC(=O)c1cnc2[nH]ccc2c1N[C@H]1CN(C(=O)C(C)C#N)CC[C@H]1C]

Scheme 25. Preparation of ethyl 4-(((3R,4R)-1-(2-cyanopropanoyl)-4-methypiperidin-3-yl)amino)-1H-pyrrolo[2,3-b]pyridine-5-carboxylate.

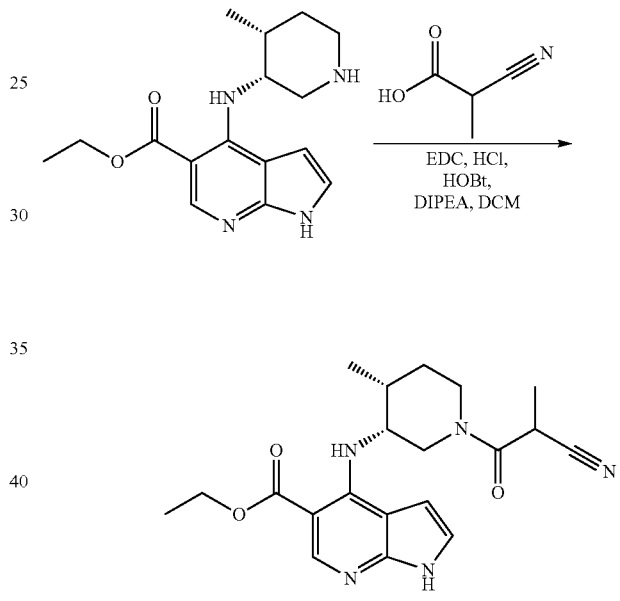

To a solution of ethyl 4-(((3R,4R)-4-methylpiperidin-3-yl)amino)-1H-pyrrolo[2,3-b]pyridine-5-carboxylate (0.15 g, 0.49 mmol) in dichloromethane (6 mL) was added N-(3-dimethylaminopropyl)-N'-ethylcarbodiimide HCl (0.142 g, 0.74 mmol), 1-hydroxybenzotriazole (0.1 g, 0.74 mmol), N,N-diisopropylethylamine (0.3 mL, 1.48 mmol) and 2-cyanopropanoic acid (0.075 g, 0.74 mmol) and the mixture was stirred at room temperature for 10 hours. The reaction mixture was quenched with water and extracted with dichloromethane. The organic layer was washed with water, brine and dried over anhydrous sodium sulfate. The solution was filtered and concentrated in vacuo. The crude material was purified by using flash chromatography (ethyl acetate/hexane) to provide ethyl 4-(((3R,4R)-1-(2-cyanopropanoyl)-4-methylpiperidin-3-yl)amino)-1H-pyrrolo[2,3-b]pyridine-5-carboxylate as an off-white solid (0.038 g, 20% yield): $^1$H NMR (400 MHz, DMSO-$d_6$, at 90° C.) δ 11.47 (br s, 1H), 8.82 (d, J=8.4 Hz, 1H), 8.55 (s, 1H), 7.15 (s, 1H), 6.65 (br s, 1H), 4.40 (m, 2H), 4.27 (m, 3H), 3.89 (m, 1H), 3.0-3.31 (m, 2H), 2.15 (m, 1H), 1.67 (m, 1H), 1.49 (m, 1H), 1.24-1.32 (m, 6H), 0.94 (d, J=6.0 Hz, 3H); MS (ES) m/z: 384.4 (M+H).

Synthesis of Example 128: Preparation of ethyl (R)-4-((1-(1-cyanocyclopropane-1-carbonyl)piperidin-3-yl)amino)-1H-pyrrolo[2,3-b]pyridine-5-carboxylate

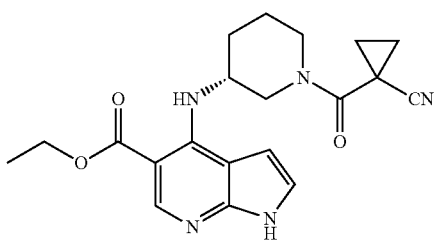 [SMILES: CCOC(=O)c1cnc2[nH]ccc2c1N[C@@H]1CCCN(C(=O)C2(C#N)CC2)C1]

Scheme 26. Preparation of ethyl (R)-4-((1-(1-cyanocyclopropane-1-carbonyl)piperidin-3-yl)amino)-1H-pyrrolo[2,3-b]pyridine-5-carboxylate.

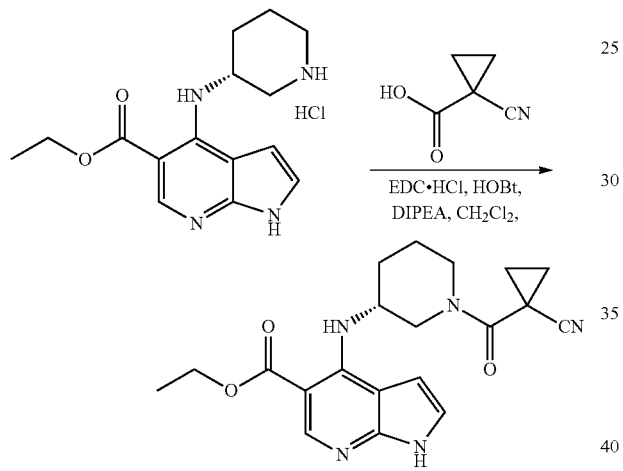

To a solution of ethyl (R)-4-(piperidin-3-ylamino)-1H-pyrrolo[2,3-b]pyridine-5-carboxylate HCl (0.07 g, 0.24 mmol) in dichloromethane (5 mL) was added diisopropylethylamine (0.12 mL, 0.72 mmol), 1-ethyl-3-(3-dimethylaminopropyl)carbodiimide.HCl (0.06 g, 0.36 mmol), 1-hydroxybenzotriazole (0.04 g, 0.36 mmol) and 1-cyanocyclopropane-1-carboxylic acid (0.04 g, 0.36 mmol) and the mixture was stirred at ambient temperature for 12 hours. The reaction mixture was quenched with water and extracted with dichloromethane. The combined organic layers were washed with water, brine and dried over anhydrous sodium sulfate. The solution was filtered and concentrated in vacuo. The crude material was purified using flash chromatography (100% ethyl acetate/hexane). The impure product was further purified by prep HPLC to provide ethyl (R)-4-((1-(1-cyanocyclopropane-1-carbonyl)piperidin-3-yl)amino)-1H-pyrrolo[2,3-b]pyridine-5-carboxylate as an off-white solid (0.022 g, 26% yield): $^1$H NMR (400 MHz, DMSO-$d_6$) δ 11.69 (s, 1H), 8.86 (d, J=6.8 Hz, 1H), 8.54 (s, 1H), 7.20 (s, 1H), 6.68 (s, 1H), 4.24 (d, J=6.8 Hz, 3H), 3.96 (d, J=11.2 Hz, 1H), 3.69 (br s, 3H), 2.06 (br s, 1H), 1.76 (br s, 3H), 1.55 (br s, 3H), 1.22-1.31 (m, 4H); MS (ES) m/z 382.3 (M+H).
Retention time: 13.605 min.

Analytical Conditions:
Column: Inertsil ODS 3V (250 mm×4.6 mm×5 mic);
Mobile phase (A): 0.1% Ammonia in water;
Mobile phase (B): ACN; Flow rate: 1.0 mL/min.

Synthesis of Example 129: Preparation of ethyl 4-(((3R)-1-(2-cyanopropanoyl)piperidin-3-yl)amino)-1H-pyrrolo[2,3-b]pyridine-5-carboxylate

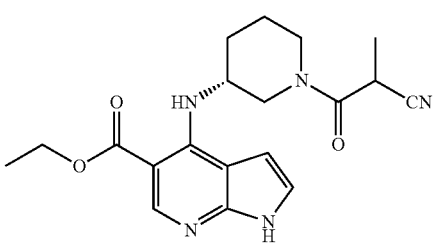 [SMILES: CCOC(=O)c1cnc2[nH]ccc2c1N[C@@H]1CCCN(C(=O)C(C)C#N)C1]

Scheme 27. Preparation of ethyl 4-(((3R)-1-(2-cyanopropanoyl)piperidin-3-yl)amino)-1H-pyrrolo[2,3-b]pyridine-5-carboxylate.

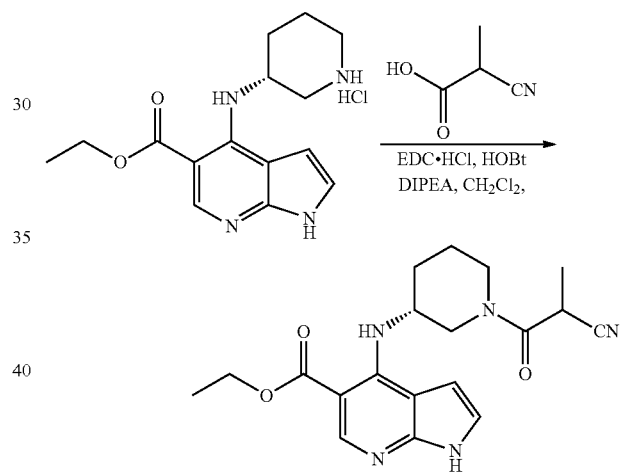

To a solution of ethyl (R)-4-(piperidin-3-ylamino)-1H-pyrrolo[2,3-b]pyridine-5-carboxylate HCl (0.06 g, 0.20 mmol) in dichloromethane (5 mL) was added diisopropylethylamine (0.10 mL, 0.62 mmol), 1-ethyl-3-(3-dimethylaminopropyl)carbodiimide.HCl (0.059 g, 0.31 mmol), 1-hydroxybenzotriazole (0.042 g, 0.31 mmol) and 2-cyanopropanoic acid (0.030 g, 0.31 mmol). The mixture was stirred at ambient temperature for 12 hours. The reaction was quenched with water and extracted with dichloromethane. The combined organic layers were washed with water, brine and dried over anhydrous sodium sulfate. The solution was filtered and concentrated in vacuo. The crude material was further purified by prep HPLC to provide ethyl 4-(((3R)-1-(2-cyanopropanoyl)piperidin-3-yl)amino)-1H-pyrrolo[2,3-b]pyridine-5-carboxylate as an off-white solid (0.016 g, 23% yield): $^1$H NMR (400 MHz, DMSO-$d_6$) δ 11.68 (s, 1H), 8.83-8.89 (m, 1H), 8.53 (s, 1H), 7.19 (s, 1H), 6.66 (s, 1H), 4.37-4.42 (m, 1H), 4.17-4.24 (m, 2H), 4.09-4.11 (m, 2H), 3.77-3.79 (m, 1H), 3.42-3.58 (m, 3H), 2.04 (br s, 1H), 1.51-1.71 (m, 3H), 1.38-1.40 (m, 2H), 1.27-1.33 (m, 3H); MS (ES) m/z 370.2 (M+H).
Retention time: 9.050 min Analytical Conditions:
Column: Inertsil ODS 3V (250 mm×4.6 mm×5 mic);
Mobile phase (A): 0.1% Ammonia in water
Mobile phase (B): ACN; Flow rate: 1.0 mL/min.

Synthesis of Example 130: Preparation of propyl (R)-4-((1-(2-cyanoacetyl)piperidin-3-yl)amino)-1H-pyrrolo[2,3-b]pyridine-5-carboxylate

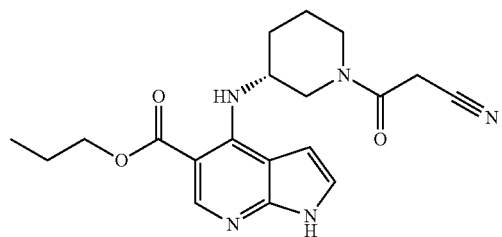 [SMILES: CCCOC(=O)c1cnc2[nH]ccc2c1N[C@@H]1CCCN(C(=O)CC#N)C1]

Scheme 28. Preparation of propyl (R)-4-((1-(2-cyanoacetyl)piperidin-3-yl)amino-1H-pyrrolo[2,3-b]pyridine-5-carboxylate.

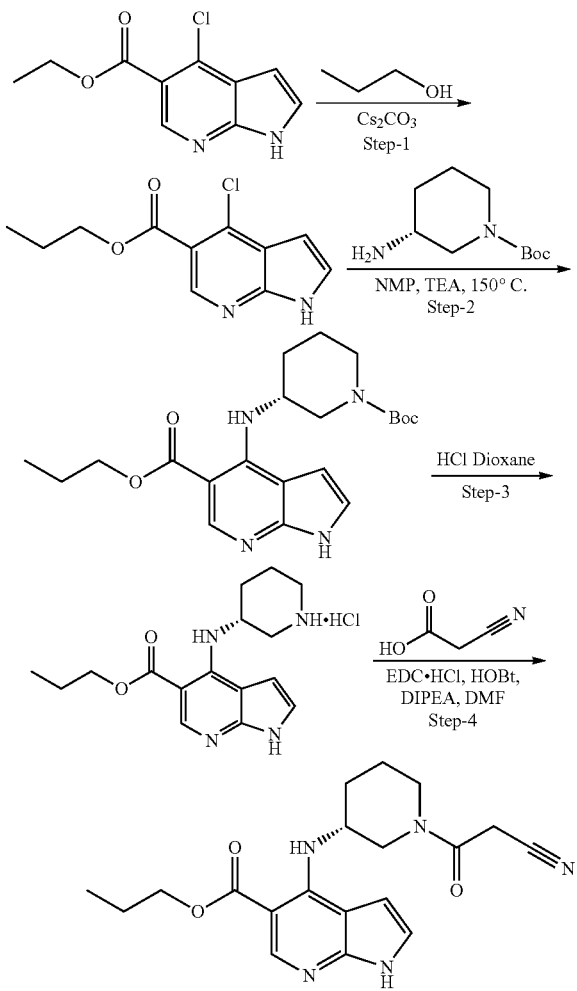

Step 1: Preparation of propyl 4-chloro-1H-pyrrolo[2,3-b]pyridine-5-carboxylate

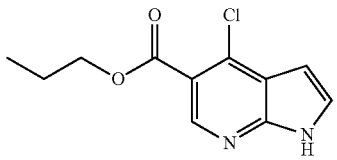 [SMILES: CCCOC(=O)c1cnc2[nH]ccc2c1Cl]

To a solution of ethyl 4-chloro-1H-pyrrolo[2,3-b]pyridine-5-carboxylate (10.0 g, 44.51 mmol) in propanol (100 mL), was added cesium carbonate (43.4 g, 133.5 mmol) and the mixture was stirred at ambient temperature for 16 hours. The reaction mixture was concentrated in vacuo, the residue was dissolved in water and extracted with ethyl acetate. The organic layer was washed with water, brine and dried over anhydrous sodium sulfate. The solution was filtered and concentrated in vacuo. The crude material was purified using flash chromatography (40% ethyl acetate/hexane) to provide propyl 4-chloro-1H-pyrrolo[2,3-b]pyridine-5-carboxylate as a white solid (10 g, 96% yield): MS (ES) m/z 239 (M+H).

Step 2: Preparation of propyl (R)-4-((1-(tert-butoxycarbonyl)piperidin-3-yl)amino)-1H-pyrrolo[2,3-b]pyridine-5-carboxylate

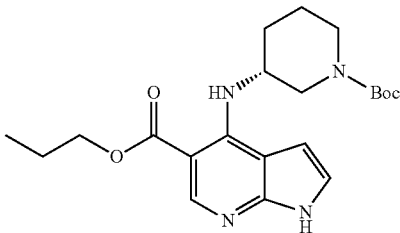 [SMILES: CCCOC(=O)c1cnc2[nH]ccc2c1N[C@@H]1CCCN(C(=O)OC(C)(C)C)C1]

A solution of propyl 4-chloro-1H-pyrrolo[2,3-b]pyridine-5-carboxylate (0.5 g, 2.09 mmol), tert-butyl (R)-3-aminopiperidine-1-carboxylate (0.418 g, 2.09 mmol) and triethylamine (0.1 mL, 0.7 mmol) in N-methyl-2-pyrrolidone (10 mL) in sealed tube was heated to 140° C. for 5 hours. After cooling to room temperature, the reaction was quenched with water and extracted with ethyl acetate. The organic layer was washed with water, brine and dried over anhydrous sodium sulfate. The solution was filtered and concentrated in vacuo. The crude material was purified using flash chromatography (50% ethyl acetate/hexane) to provide propyl (R)-4-((1-(tert-butoxycarbonyl)piperidin-3-yl)amino)-1H-pyrrolo[2,3-b]pyridine-5-carboxylate as a yellow solid (0.2 g, 23% yield): MS (ES) m/z 403 (M+H)

Step 3: Preparation of propyl (R)-4-(piperidin-3-ylamino)-1H-pyrrolo[2,3-b]pyridine-5-carboxylate hydrochloride Salt

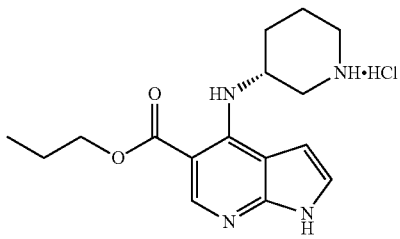

To a solution of propyl (R)-4-((1-(tert-butoxycarbonyl)piperidin-3-yl)amino)-1H-pyrrolo[2,3-b]pyridine-5-carboxylate (0.2 g, 0.49 mmol) in dioxane (5 mL) was added 4M HCl in dioxane (5 mL) at 0° C. and the reaction was allowed to warm to ambient temperature and stir for 5 hours. The solution was concentrated in vacuo and the residue was washed with diethyl ether to provide propyl (R)-4-(piperidin-3-ylamino)-1H-pyrrolo[2,3-b]pyridine-5-carboxylate HCl as an off-white solid (0.15 g, 90% yield): MS (ES) m/z 303 (M+H).

Step 4: Preparation of propyl (R)-4-((1-(2-cyanoacetyl)piperidin-3-yl)amino)-1H-pyrrolo[2,3-b]pyridine-5-carboxylate

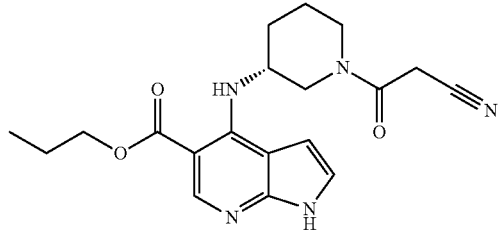 [SMILES: CCCOC(=O)c1cnc2[nH]ccc2c1N[C@@H]1CCCN(C(=O)CC#N)C1]

To a solution of propyl (R)-4-(piperidin-3-ylamino)-1H-pyrrolo[2,3-b]pyridine-5-carboxylate HCl (0.15 g, 0.44 mmol) in dichloromethane (10 mL), was added 1-ethyl-3-(3-dimethylaminopropyl)carbodiimide HCl (0.13 g, 0.88 mmol), 1-hydroxybenzotriazole (0.12 g, 0.88 mmol), N,N-diisopropylethylamine (0.23 mL, 1.32 mmol), cyanoacetic acid (0.07 g, 0.88 mmol) and the mixture stirred at ambient temperature for 16 hours. The reaction mixture was partitioned between dichloromethane and water. The organic layer was washed with water, brine and dried over anhydrous sodium sulfate. The solution was filtered and concentrated in vacuo. The crude material was purified using flash chromatography (5% methanol/dichloromethane) to provide propyl (R)-4-((1-(2-cyanoacetyl)piperidin-3-yl)amino)-1H-pyrrolo[2,3-b]pyridine-5-carboxylate (0.037 g, 23% yield). $^1$H NMR (400 MHz, DMSO-d$_6$ at 80° C.) δ 11.47 (s, 1H), 8.74 (s, 1H), 8.56 (s, 1H), 7.16 (s, 1H), 6.66 (s, 1H), 4.18-4.19 (m, 3H), 3.94 (m, 2H), 3.73 (m, 1H), 3.52 (m, 1H), 3.27 (m, 2H), 2.08 (m, 1H), 1.67-1.88 (m, 5H), 0.97 (t, J=7.6 Hz, 3H); MS (ES) m/z 370 (M+H).
Retention time: 10.27 min Analytical Conditions:
Column: Inertsil ODS 3V (250 mm×4.6 mm×5 mic)
Mobile phase (A): 0.1% ammonia in water
Mobile phase (B): ACN
Flow rate: 1.0 mL/min

Synthesis of Example 131: Preparation of 2-methoxyethyl (R)-4-((1-(2-cyanoacetyl)piperidin-3-yl)amino)-1H-pyrrolo[2,3-b]pyridine-5-carboxylate

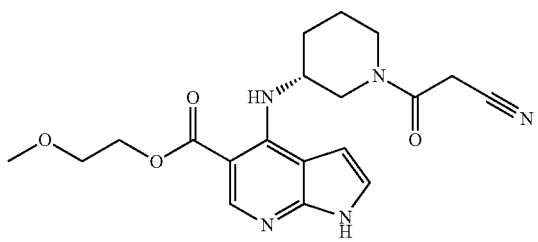 [SMILES: COCCOC(=O)c1cnc2[nH]ccc2c1N[C@@H]1CCCN(C(=O)CC#N)C1]

Scheme 29. Preparation of 2-methoxyethyl (R)-4-((1-(2-cyanoacetyl)piperidin-3-yl)amino)-1H-pyrrolo[2,3-b]pyridine-5-carboxylate.

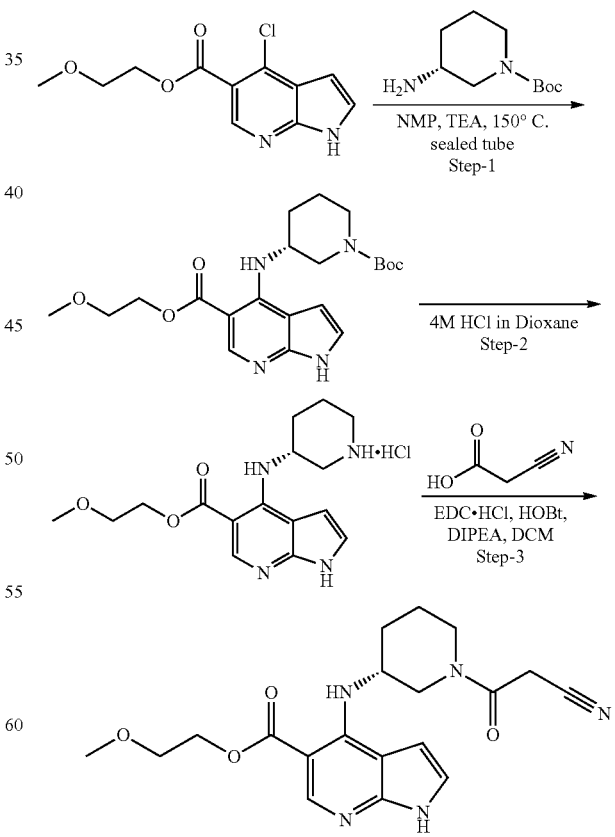

Step 1: Preparation of 2-methoxyethyl (R)-4-((1-(tert-butoxycarbonyl)piperidin-3-yl)amino)-1H-pyrrolo[2,3-b]pyridine-5-carboxylate

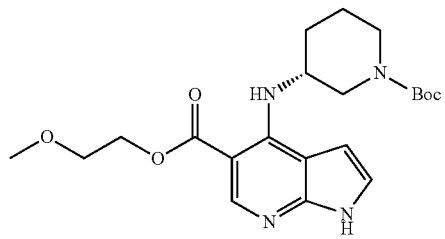 [SMILES: COCCOC(=O)c1cnc2[nH]ccc2c1N[C@@H]1CCCN(C(=O)OC(C)(C)C)C1]

A solution of 2-methoxyethyl 4-chloro-1H-pyrrolo[2,3-b]pyridine-5-carboxylate (0.45 g, 1.76 mmol), tert-butyl (R)-3-aminopiperidine-1-carboxylate (0.35 g, 1.76 mmol) and triethylamine (0.1 mL) in N-methyl-2-pyrrolidone (10 mL) was heated to 120° C. in a sealed tube for 12 hours. After cooling to ambient temperature, the reaction mixture was quenched with water and extracted with ethyl acetate. The organic layer was washed with water, brine and dried over anhydrous sodium sulfate. The solution was filtered and concentrated in vacuo. The crude material was purified using flash chromatography (70% ethyl acetate/hexane) to provide 2-methoxyethyl (R)-4-((1-(tert-butoxycarbonyl)piperidin-3-yl)amino)-1H-pyrrolo[2,3-b]pyridine-5-carboxylate as an off-white solid (0.5 g, 68% yield): MS (ES) m/z 419 (M+H)

Step 2: Preparation of 2-methoxyethyl (R)-4-(piperidin-3-ylamino)-1H-pyrrolo[2,3-b]pyridine-5-carboxylate HCl Salt

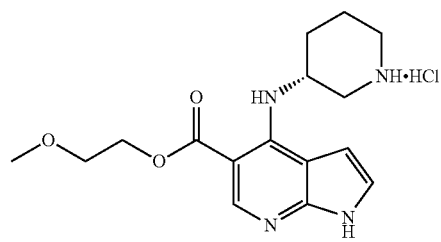

To a solution of 2-methoxyethyl (R)-4-((1-(tert-butoxycarbonyl)piperidin-3-yl)amino)-1H-pyrrolo[2,3-b]pyridine-5-carboxylate (0.5 g, 1.19 mmol) in dioxane (5 mL) was added HCl in dioxane (8 mL, 4M) at 0° C. The reaction was allowed to warm to ambient temperature and the mixture was stirred for 16 hours. The solution was concentrated in vacuo. The residue was washed with diethyl ether to provide 2-methoxyethyl (R)-4-(piperidin-3-ylamino)-1H-pyrrolo[2,3-b]pyridine-5-carboxylate HCl salt as an off-white solid (0.4 g, 94% yield): MS (ES) m/z 319 (M+H)

Step 3: Preparation of 2-methoxyethyl (R)-4-((1-(2-cyanoacetyl)piperidin-3-yl)amino)-1H-pyrrolo[2,3-b]pyridine-5-carboxylate

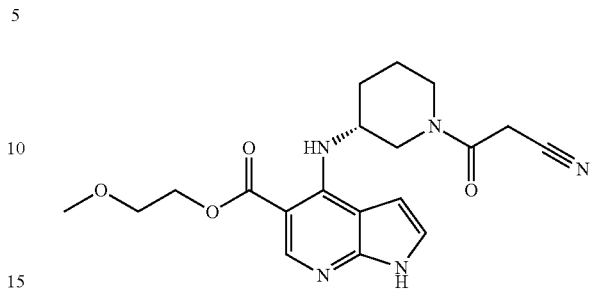

To a solution 2-methoxyethyl (R)-4-(piperidin-3-ylamino)-1H-pyrrolo[2,3-b]pyridine-5-carboxylate HCl salt (0.4 g, 1.12 mmol) in dichloromethane (10 mL) was added 1-ethyl-3-(3-dimethylaminopropyl)carbodiimide HCl (0.35 g, 2.26 mmol), 1-hydroxybenzotriazole (0.305 g, 2.26 mmol), N,N-diisopropylethylamine (0.58 mL, 3.39 mmol) and cyanoacetic acid (0.19 g, 2.26 mmol) and the mixture stirred at ambient temperature for 16 hours. The reaction mixture was partitioned between dichloromethane and water. The organic layer was washed with water, brine and dried over anhydrous sodium sulfate. The solution was filtered and concentrated in vacuo. The crude material was purified by using flash chromatography (5% methanol/dichloromethane) to provide 2-methoxyethyl (R)-4-((1-(2-cyanoacetyl)piperidin-3-yl)amino)-1H-pyrrolo[2,3-b]pyridine-5-carboxylate as an off-white solid (0.1 g, 23% yield): $^1$H NMR (400 MHz, DMSO-$d_6$ at 80° C.) δ 11.49 (s, 1H), 8.66 (br s, 1H), 8.56 (s, 1H), 7.17 (s, 1H), 6.66 (s, 1H), 4.35 (t, J=7.6 Hz, 2H), 4.16 (m, 2H), 3.94 (m, 2H), 3.66 (t, J=7.6 Hz, 2H), 3.53 (m, 1H), 3.32 (s, 3H), 3.31 (m, 1H), 2.08 (m, 1H), 1.66-1.69 (m, 4H); MS (ES) m/z 386 (M+H).

Synthesis of Example 132: Preparation of ethyl 4-((3-(2-cyanoethyl)cyclohexyl)amino)-1H-pyrrolo[2,3-b]pyridine-5-carboxylate

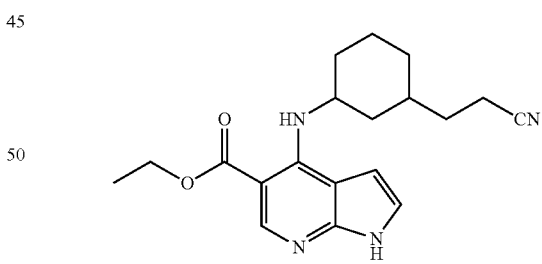

Scheme 30. Preparation of ethyl 4-((3-(2-cyanoethyl)cyclohexyl)amino)-1H-pyrrolo[2,3-b]pyridine-5-carboxylate.

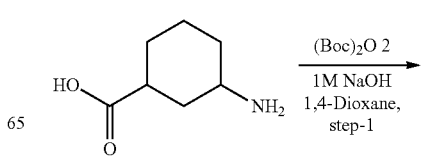

-continued

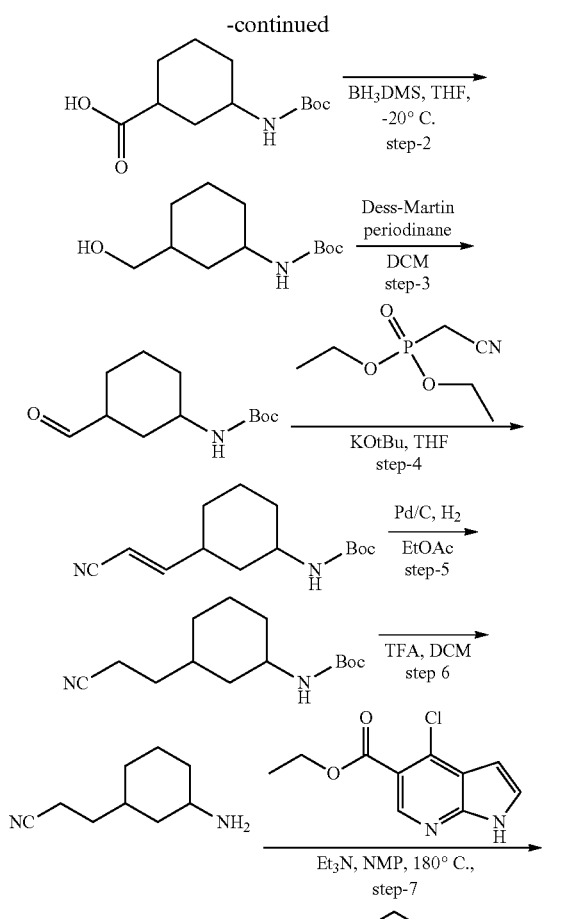

Step 1: Preparation of 3-((tert-butoxycarbonyl)amino)cyclohexane-1-carboxylic acid

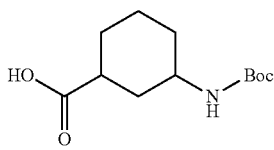

To a stirred solution of 3-aminocyclohexane-1-carboxylic acid (5 g, 34.91 mmol) in 1,4-dioxane (50 mL) was added 1N sodium hydroxide solution (2.1 g, 52.4 mmol) and the solution stirred at ambient temperature for 10 minutes. At this time di-tert-butyldicarbonate (10.4 mL, 45.4 mmol) was added and the mixture was stirred at ambient temperature for 15 hours. The solvent was concentrated in vacuo and the residue diluted with water and the mixture acidified (pH 4.0) with saturated potassium bisulfate solution. The aqueous solution was extracted with dichloromethane. The combined organic layers were washed with water, brine and dried over anhydrous sodium sulfate. The solution was filtered and concentrated in vacuo to provide 3-((tert-butoxycarbonyl)amino)cyclohexane-1-carboxylic acid as an off-white solid (8 g, 94% yield): MS (ES) m/z 242.1 (M−H).

Step 2: Preparation of tert-butyl (3-(hydroxymethyl)cyclohexyl)carbamate

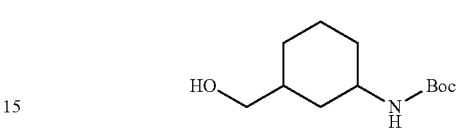

To a solution of 3-((tert-butoxycarbonyl)amino)cyclohexane-1-carboxylic acid (6 g, 24.6 mmol) in dry tetrahydrofuran (60 mL) was added borane-dimethylsulfide (3.51 mL, 36.98 mmol, xM) at −20° C. and the resulting mixture was stirred at ambient temperature for 15 hours. The reaction was cooled to 0° C. and quenched by adding methanol dropwise and the mixture was stirred for 30 minutes. The solvent was concentrated in vacuo and the crude material purified by column chromatography (methanol/dichloromethane) to provide tert-butyl (3-(hydroxymethyl)cyclohexyl)carbamate as a colorless oil (4.3 g, 76% yield): MS (ES) m/z 130.2 (M+H).

Step-3: Preparation of tert-butyl (3-formylcyclohexyl)carbamate

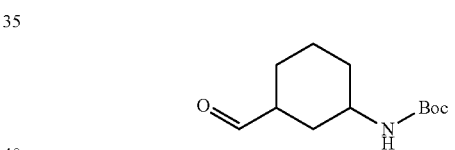

To a solution of tert-butyl (3-(hydroxymethyl)cyclohexyl)carbamate (3 g, 13.1 mmol) in dry dichloromethane (30 mL) was added Dess-Martin periodinane (7.21 g, 17.0 mmol) at 0° C. and the mixture stirred at ambient temperature for 2 hours. The reaction was cooled to 0° C. and quenched with saturated aqueous sodium bicarbonate solution and a pinch of sodium thiosulphate was added. The mixture was stirred at 0° C. for 30 minutes. The emulsion was filtered through celite and washed with dichloromethane. The organic layer was separated, washed with water, brine and dried over anhydrous sodium sulfate. The solution was filtered and concentrated in vacuo to provide tert-butyl (3-formylcyclohexyl)carbamate and carried to next step without further purification (3 g, crude).

Step 4: Preparation of tert-butyl (E)-(3-(2-cyanovinyl)cyclohexyl)carbamate

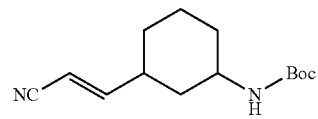 [SMILES: CC(C)(C)OC(=O)NC1CCCC(/C=C/C#N)C1]

To a suspension of potassium tert-butoxide (2.32 g, 19.8 mmol) in dry tetrahydrofuran (30 mL) was added diethyl (cyanomethyl)phosphonate (3 mL, 18.5 mmol) at 0° C. The mixture was stirred for 1 hour and then a solution of tert-butyl (3-formylcyclohexyl)carbamate (3 g, 13.2 mmol) in dry tetrahydrofuran (10 mL) was added. The mixture was stirred at ambient temperature for 12 hours. The reaction mixture was quenched with water and extracted with ethyl acetate. The combined organic layers were washed with water, brine and dried over anhydrous sodium sulfate. The solution was filtered and concentrated in vacuo. The crude material was purified using flash chromatography (1% methanol/dichloromethane) to provide tert-butyl (E)-(3-(2-cyanovinyl)cyclohexyl)carbamate as a colorless semisolid (1.2 g, 36% yield): MS (ES) m/z 151.2 (M+H).

Step 5: Preparation of tert-butyl (3-(2-cyanoethyl)cyclohexyl)carbamate

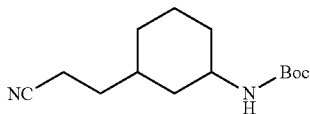 [SMILES: CC(C)(C)OC(=O)NC1CCCC(CCC#N)C1]

To a stirred solution of tert-butyl (E)-(3-(2-cyanovinyl) cyclohexyl)carbamate (1.1 g, 4.39 mmol) in ethyl acetate (15 mL) was added palladium on carbon (0.1 g, 50% wet w/w) under an argon atmosphere. The suspension was stirred at ambient temperature under a hydrogen atmosphere for 2 hours. The reaction was filtered through celite and washed with ethyl acetate. The filtrate was concentrated in vacuo to provide tert-butyl (3-(2-cyanoethyl)cyclohexyl) carbamate (1.2 g, crude): MS (ES) m/z 153.2 (M+H).

Step 6: Preparation of 3-(3-aminocyclohexyl)propanenitrile

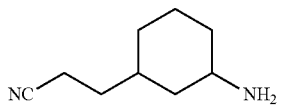 [SMILES: N#CCCC1CCCC(N)C1]

To a solution of tert-butyl (3-(2-cyanoethyl)cyclohexyl) carbamate (1.2 g, 4.75 mmol) in dry dichloromethane (20 mL) was added trifluoroacetic acid (1.1 mL, 14.3 mmol) at 0° C. and the mixture was stirred at ambient temperature for 15 hours. The solvent was concentrated in vacuo, the residue diluted with ethyl acetate and basified using triethylamine at 0° C. The organic layer was washed with water, brine and dried over anhydrous sodium sulfate. The solution was filtered and concentrated in vacuo to provide 3-(3-amino-cyclohexyl)propanenitrile as a colorless oil (0.6 g, 48% yield): MS (ES) m/z 153.2 (M+H).

Step 7: Preparation of ethyl 4-((3-(2-cyanoethyl) cyclohexyl)amino)-1H-pyrrolo[2,3-b]pyridine-5-carboxylate as a mixture of stereoisomers

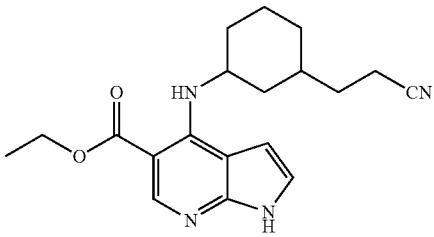 [SMILES: CCOC(=O)c1cnc2[nH]ccc2c1NC1CCCC(CCC#N)C1]

To a solution of 3-(3-aminocyclohexyl)propanenitrile (0.25 g, 1.64 mmol) in N-methyl-2-pyrrolidone (10 mL) was added ethyl 4-chloro-1H-pyrrolo[2,3-b]pyridine-5-carboxylate (0.44 g, 1.97 mmol) and triethylamine (0.7 mL, 4.93 mmol) at room temperature. The mixture was subjected to microwave irradiation at 170° C. for 1 hour. The reaction mixture was cooled to room temperature, quenched with water and extracted with ethyl acetate. The organic layer was washed with water, brine and dried over sodium sulfate. The solution was filtered and concentrated in vacuo. The crude material was purified using flash chromatography (ethyl acetate/n-hexane) to provide ethyl 4-((3-(2-cyanoethyl)cy-clohexyl)amino)-1H-pyrrolo[2,3-b]pyridine-5-carboxylate as an off-white solid (0.22 g): MS (ES) m/z 341.2 (M+H).

Scheme 31. Separation of steriosomers of Example 132.

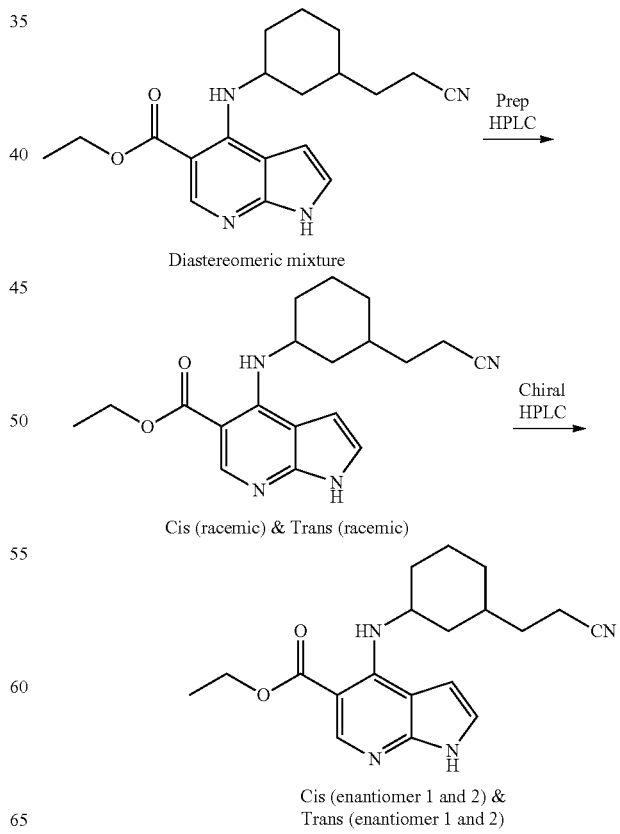

Ethyl 4-((3-(2-cyanoethyl)cyclohexyl)amino)-1H-pyrrolo[2,3-b]pyridine-5-carboxylate (Example 132) was subjected to prep.HPLC and two diastereomers were separated by the following method.

Analytical Conditions:
Column: Inertsil ODS 3V (250 mm×4.6 mm×5 mic)
Mobile phase (A): 0.1% Ammonia in water
Mobile phase (B): ACN
Flow rate: 1.0 mL/min(50:50)

Synthesis of Example 133: (rac)-(cis)-ethyl 4-((3-(2-cyanoethyl)cyclohexyl)amino)-1H-pyrrolo[2,3-b]pyridine-5-carboxylate

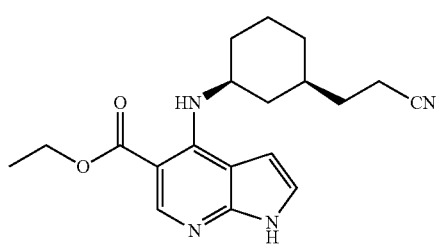 [SMILES: CCOC(=O)c1cnc2[nH]ccc2c1N[C@H]1CCC[C@@H](CCC#N)C1]

$^1$H NMR (400 MHz, DMSO-$d_6$) δ 11.62 (s, 1H), 9.08 (d, J=8.4 Hz, 1H), 8.53 (s, 1H), 7.15 (t, J=2.8 Hz, 1H), 6.57 (s, 1H), 4.43 (d, J=3.6 Hz, 1H), 4.25 (q, J=7.2 Hz, 2H), 2.48 (s, 1H), 1.98 (d, J=8.0 Hz, 1H), 1.60-1.85 (m, 5H), 1.42-1.55 (m, 4H), 1.30 (t, J=7.2 Hz, 3H), 1.21 (s, 1H), 1.0-1.08 (m, 1H); MS (ES) m/z 341.0 (M+H). Retention time: 4.93 min.

Analytical Conditions:
Column: CHIRALPAK IC (100 mm×4.6 mm×3 mic)
Mobile phase: nHexane:Ethanol with (70:30)
Flow rate: 1.0 ml/min Synthesis of Example 134: (rac)-(trans)-Ethyl 4-((3-(2-cyanoethyl)cyclohexyl)amino)-1H-pyrrolo[2,3-b]pyridine-5-carboxylate

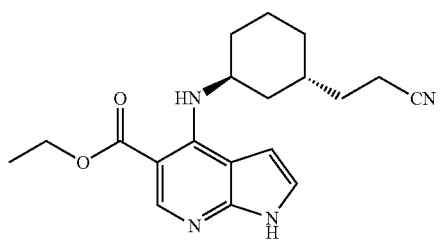

$^1$H NMR (400 MHz, DMSO-$d_6$) δ 11.63 (s, 1H), 8.74 (d, J=8.0 Hz, 1H), 8.52 (s, 1H), 7.15 (s, 1H), 6.53 (s, 1H), 4.23 (q, J=7.2 Hz, 2H), 3.93 (d, J=8.0 Hz, 1H), 2.48 (s, 1H), 2.12 (m, 2H), 1.75 (m, 2H), 1.41-1.60 (m, 4H), 1.29 (t, J=6.8 Hz, 3H), 1.12-1.21 (m, 2H), 0.88-1.00 (m, 2H); MS (ES) m/z 341.0 (M+H). Retention time: 6.953 min.

Analytical Conditions:
Column: CHIRALPAK IC (100 mm×4.6 mm×3 mic)
Mobile phase: n-Hexane:Ethanol with (70:30)
Flow rate: 1.0 mL/min Synthesis of Example 135: (cis) ethyl 4-((3-(2-cyanoethyl)cyclohexyl)amino)-1H-pyrrolo[2,3-b]pyridine-5-carboxylate, enantiomer 1

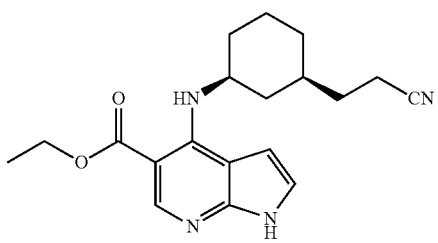

Cis isomer, single enantiomer $^1$H NMR (400 MHz, DMSO-$d_6$) δ 11.62 (s, 1H), 9.08 (d, J=8.4 Hz, 1H), 8.53 (s, 1H), 7.15 (s, 1H), 6.57 (s, 1H), 4.42 (br s, 1H), 4.25 (q, J=6.8 Hz, 2H), 2.48 (s, 1H), 1.97-2.00 (m, 1H), 1.83 (m, 1H), 1.60-1.75 (m, 5H), 1.42-1.55 (m, 4H), 1.30 (t, J=7.2 Hz, 3H), 1.0-1.08 (m, 1H); MS (ES) m/z 341.4 (M+H). Retention time 3.43 min.

Analytical Conditions:
Column: CHIRALPAK IC (100 mm×4.6 mm×3 mic)
Mobile phase: n-hexane:Ethanol with (50:50)
Flow rate: 1.0 mL/min Synthesis of Example 136: (cis) ethyl 4-((3-(2-cyanoethyl)cyclohexyl)amino)-1H-pyrrolo[2,3-b]pyridine-5-carboxylate, enantiomer 2

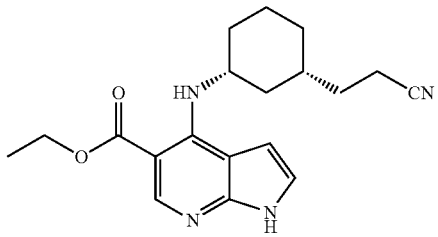

Cis isomer, single enantiomer
absolute configuration not known $^1$H NMR (400 MHz, DMSO-$d_6$) δ 11.62 (s, 1H), 9.08 (d, J=7.6 Hz, 1H), 8.53 (s, 1H), 7.15 (s, 1H), 6.57 (s, 1H), 4.42 (br s, 1H), 4.25 (q, J=6.8 Hz, 2H), 2.48 (s, 1H), 1.97-2.01 (m, 1H), 1.83 (m, 1H), 1.64-1.70 (m, 5H), 1.45-1.55 (m, 4H), 1.30 (t, J=7.2 Hz, 3H), 1.02-1.05 (m, 1H); MS (ES) m/z 341.4 (M+H). Retention time 6.24 min.

Analytical Conditions:
Column: CHIRALPAK IC (100 mm×4.6 mm×3 mic)
Mobile phase: n-hexane:ethanol with (50:50)
Flow rate: 1.0 mL/min Synthesis of Example 137: (trans) ethyl 4-((3-(2-cyanoethyl)cyclohexyl)amino)-1H-pyrrolo[2,3-b]pyridine-5-carboxylate enantiomer 1

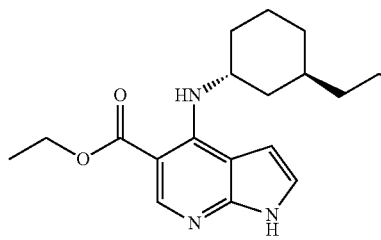

Trans isomer, single enantiomer $^1$H NMR (400 MHz, DMSO-$d_6$) δ 11.65 (s, 1H), 8.74 (d, J=8.0 Hz, 1H), 8.52 (s, 1H), 7.16 (s, 1H), 6.52 (s, 1H), 4.23 (q, J=6.8 Hz, 2H), 3.92 (br s, 1H), 2.12 (m, 2H), 1.98 (t, J=7.6 Hz, 1H), 1.74 (m, 3H), 1.36-1.58 (m, 4H), 1.29 (t, J=6.8 Hz, 3H), 1.21 (s, 2H), 0.67-1.00 (m, 1H); MS (ES) m/z 341.4 (M+H). Retention time: 3.489 min.

Analytical Conditions:
Column: CHIRALPAK IC (100 mm×4.6 mm×3 mic)
Mobile phase: n-hexane:ethanol with (50:50)
Flow rate: 1.0 mL/min Synthesis of Example 138: (trans)-ethyl 4-((3-(2-cyanoethyl)cyclohexyl)amino)-1H-pyrrolo[2,3-b]pyridine-5-carboxylate, enantiomer 2

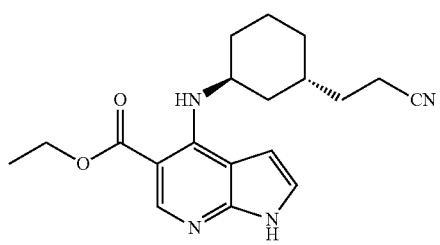 [SMILES: CCOC(=O)c1cnc2[nH]ccc2c1N[C@H]1CCC[C@H](CCC#N)C1]

Trans isomer, single enantiomer $^1$H NMR (400 MHz, DMSO-$d_6$): δ 11.63 (s, 1H), 8.74 (d, J=8.0 Hz, 1H), 8.52 (s, 1H), 7.15 (s, 1H), 6.60 (s, 1H), 4.23 (q, J=7.2 Hz, 2H), 4.92-4.94 (m, 1H), 2.12 (m, 2H), 1.97-2.00 (m, 1H), 1.75 (m, 2H), 1.37-1.60 (m, 4H), 1.29 (t, J=6.8 Hz, 3H), 1.21 (s, 2H), 0.68-1.00 (m, 2H); MS (ES) m/z 341.4 (M+H). Retention time: 6.472 min.

Analytical Conditions:
Column: CHIRALPAK IC (100 mm×4.6 mm×3 mic)
Mobile phase: n-hexane:ethanol with (50:50)
Flow rate: 1.0 mL/min Synthesis of Examples 139 and 140: Preparation of cis and trans (rac)-propyl 4-((3-(2-cyanoethyl)cyclohexyl)amino)-1H-pyrrolo[2,3-b]pyridine-5-carboxylate Example 139 and 140

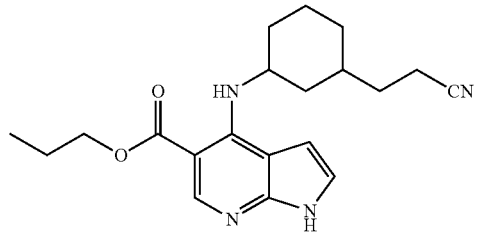 [SMILES: CCCOC(=O)c1cnc2[nH]ccc2c1NC1CCCC(CCC#N)C1]

Cis (racemic) & Trans (racemic)

Scheme 32. Preparation of cis- and trans- (rac)-propyl 4-((3-(2-cyanoethyl)cyclohexyl)amino)-1H-pyrrolo[2,3-b]pyridine-5-carboxylate.

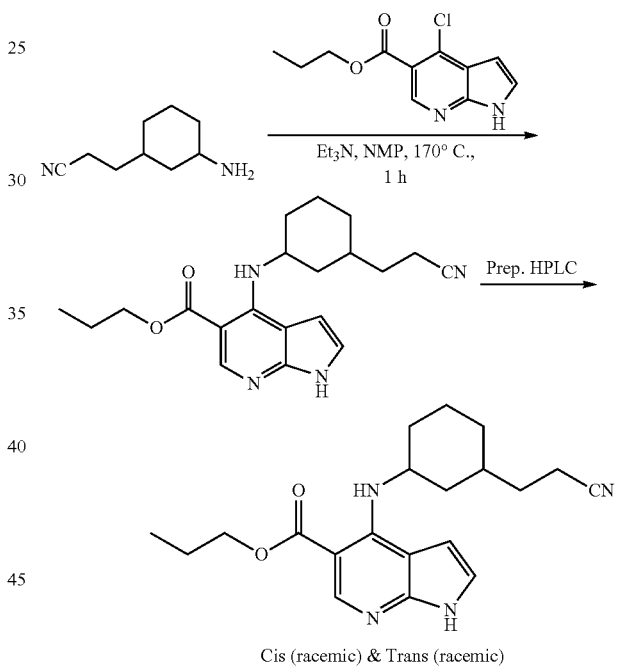

Step 1: Preparation of propyl 4-((3-(2-cyanoethyl)cyclohexyl)amino)-1H-pyrrolo[2,3-b]pyridine-5-carboxylate

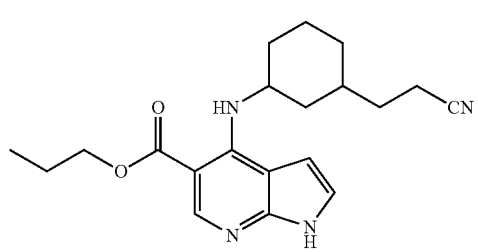

To a solution of 3-(3-aminocyclohexyl)propanenitrile (0.3 g, 1.97 mmol) in N-methyl-2-pyrrolidone (13 mL) was added propyl 4-chloro-1H-pyrrolo[2,3-b]pyridine-5-carboxylate (0.56 g, 2.36 mmol) and triethylamine (0.9 mL, 5.91 mmol) at ambient temperature. The mixture was subjected to microwave irradiation at 170° C. for 1 hour. After cooling to ambient temperature, the reaction mixture was quenched with water and extracted with ethyl acetate. The organic layer was washed with water, brine and dried over anhydrous sodium sulfate. The solution was filtered and concentrated in vacuo. The crude material was purified using flash chromatography (10% methanol/dichloromethane) to provide propyl 4-((3-(2-cyanoethyl)cyclohexyl)amino)-1H-pyrrolo[2,3-b]pyridine-5-carboxylate as a brown oil (0.65 g crude): MS (ES) m/z 130.2 (M+H). The cis and trans isomers were separated using the following chromatographic conditions:

Analytical Conditions:
Column: Inertsil ODS 3V (250 mm×4.6 mm×5 mic)
Mobile phase (A): 0.1% ammonia in water
Mobile phase (B): ACN
Flow rate: 1.0 mL/min(50:50)

Synthesis of Example 139: (rac) (cis) propyl 4-((3-(2-cyanoethyl)cyclohexyl)amino)-1H-pyrrolo[2,3-b]pyridine-5-carboxylate

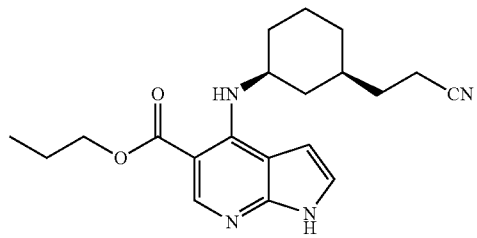 [SMILES: CCCOC(=O)c1cnc2[nH]ccc2c1N[C@H]1CCC[C@@H](CCC#N)C1]

$^1$H NMR (400 MHz, DMSO-d$_6$) δ 11.63 (s, 1H), 9.08 (d, J=8.0 Hz, 1H), 8.54 (s, 1H), 7.15 (s, 1H), 6.57 (s, 1H), 4.42 (br s, 1H), 4.17 (t, J=6.0 Hz, 2H), 2.48 (br s, 3H), 1.97-2.17 (m, 1H), 1.61-1.85 (m, 7H), 1.42-1.55 (m, 3H), 1.03-1.14 (m, 1H), 0.96 (t, J=7.6 Hz, 3H); MS (ES) m/z 355.1 (M+H). Retention time 26.226 min Synthesis of Example 140: (rac)-(trans)-propyl 4-((3-(2-cyanoethyl)cyclohexyl)amino)-1H-pyrrolo[2,3-b]pyridine-5-carboxylate $^1$H NMR (400 MHz, DMSO-d$_6$) δ 11.64 (s, 1H), 8.73 (d, J=8.0 Hz, 1H), 8.53 (s, 1H), 7.16 (t, J=2.8 Hz, 1H), 6.53 (s, 1H), 4.15 (t, J=6.8 Hz, 2H), 3.92-3.94 (m, 1H), 2.48 (s, 3H), 2.12 (t, J=12.4 Hz, 2H), 1.67-1.79 (m, 4H), 1.42-1.56 (m, 4H), 1.07-1.30 (m, 2H), 0.96 (t, J=7.6 Hz, 3H): MS (ES) m/z 355.4 (M+H). Retention time 30.787 min.

Synthesis of Example 141: Preparation of ethyl 4-((3-hydroxycyclohexyl)amino)-1H-pyrrolo[2,3-b]pyridine-5-carboxylate

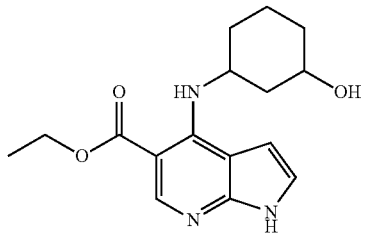 [SMILES: CCOC(=O)c1cnc2[nH]ccc2c1NC1CCCC(O)C1]

Step 1: Preparation of tert-butyl (3-hydroxycyclohexyl)carbamate

To a solution tert-butyl (3-oxocyclohexyl)carbamate (1 g, 4.69 mmol) in methanol (20 mL) was added sodium borohydride (0.26 g, 7.04 mmol) and the mixture was stirred at ambient temperature for 1 hour. The reaction was quenched with water and methanol was removed in vacuo. The residue was extracted with ethyl acetate. The organic layer was washed with water, brine and dried over sodium sulfate and concentrated in vacuo to provide tert-butyl (3-hydroxycyclohexyl)carbamate as a colorless liquid (1 g, 100% yield): MS (ES) m/z 160.1 (M-56).

Step 2: Preparation of 3-aminocyclohexan-1-ol, HCl Salt

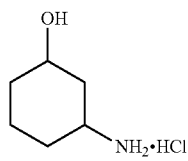

To a solution of tert-butyl (3-hydroxycyclohexyl)carbamate (1 g, 4.65 mmol) in dichloromethane (20 mL) and was added dioxane.HCl (1M, 20 mL) and the mixture stirred at ambient temperature for 12 hours. The mixture was concentrated in vacuo to provide 3-aminocyclohexan-1-ol HCl salt (0.65 g, crude): MS (ES) m/z 116 (M+H)

Step-3: Preparation of ethyl 4-((3-hydroxycyclohexyl)amino)-1H-pyrrolo[2,3-b]pyridine-5-carboxylate

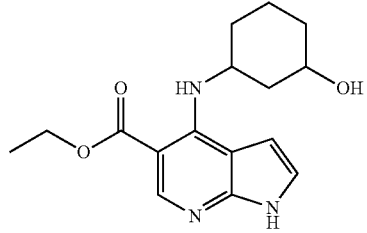 [SMILES: CCOC(=O)c1cnc2[nH]ccc2c1NC1CCCC(O)C1]

To a stirred solution of ethyl 4-chloro-1H-pyrrolo[2,3-b]pyridine-5-carboxylate (0.96 g, 4.30 mmol) in N-methyl-2-pyrrolidone (2 mL) was added 3-aminocyclohexan-1-ol HCl salt (0.65 g, 4.30 mmol) and triethylamine (0.3 mL). The solution was heated in a sealed tube at 170° C. for 16 hours. After cooling to ambient temperature, the reaction was quenched with water and extracted with dichloromethane. The organic layer was washed with water, brine and dried over anhydrous sodium sulfate. The solution was filtered and concentrated in vacuo. The crude material was purified by chiral HPLC purification to provide ethyl 4-((3-hydroxycyclohexyl)amino)-1H-pyrrolo[2,3-b]pyridine-5-carboxylate as an off-white solid as a mixture of stereoisomers. (0.01 g): $^1$H NMR (400 MHz, DMSO-$d_6$) δ 11.62 (br s, 1H), 8.77 (d, J=8.0 Hz, 1H), 8.51 (s, 1H), 7.16 (s, 1H), 6.51 (s, 1H) 4.65 (d, J=4.4 Hz, 1H), 4.21-4.26 (m, 2H), 3.92-3.99 (m, 1H), 3.56-3.62 (m, 1H) 2.25 (m, 1H), 1.98 (m, 1H), 1.82 (m, 1H), 1.69-1.73 (m, 1H), 1.29 (t, J=7.2 Hz, 3H), 1.12-1.20 (m, 4H); MS (ES) m/z 304.2 (M+H).
Retention time: 6.959 min.
Column: CHIRALPAK IC (100 mm×4.6 mm×3 mic)
mobile phase: MTBE:IPA with 0.1% DEA (90:10)
Flow rate: 1.0 mL/minute Synthesis of Example 142: Preparation of ethyl 4-((3-(cyanomethyl)-4-hydroxycyclohexyl)amino)-1H-pyrrolo[2,3-b]pyridine-5-carboxylate

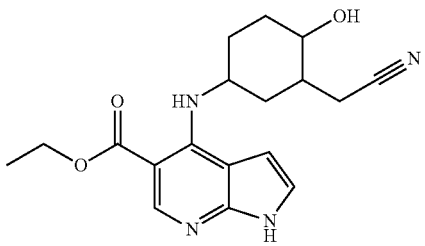 [SMILES: CCOC(=O)c1cnc2[nH]ccc2c1NC1CCC(O)C(CC#N)C1]

Scheme 34: Preparation of ethyl 4-((3-(cyanomethyl)-4-hydroxycyclohexyl)amino)-1H-pyrrolo[2,3-b]pyridine-5-carboxylate.

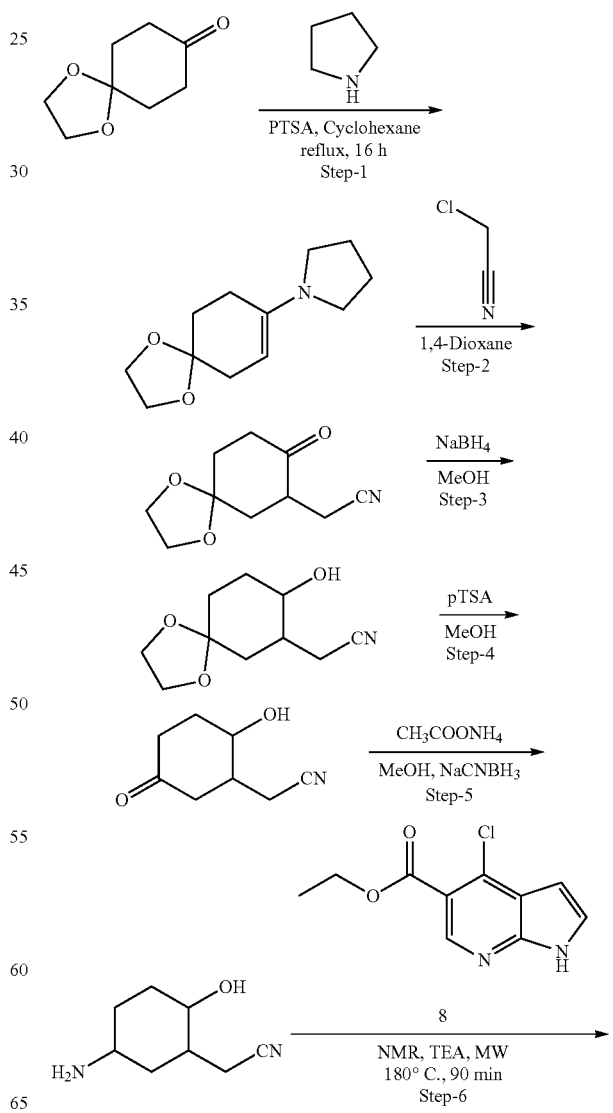

-continued

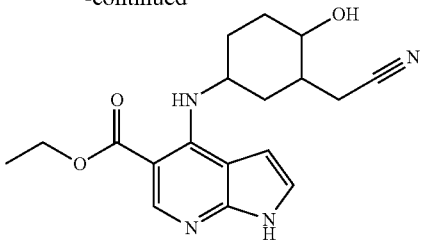

Step 1: Preparation of 1-(1,4-dioxaspiro[4.5]dec-7-en-8-yl)pyrrolidine

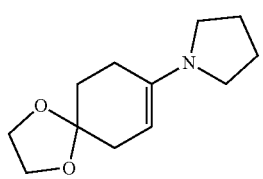 [SMILES: C1=C(N2CCCC2)CCC2(C1)OCCO2]

To a stirred solution of 1,4-dioxaspiro[4.5]decan-8-one (10 g, 64.1 mmol) in cyclohexane (200 mL) was added pyrrolidine (5.8 mL, 70.25 mmol) and p-toluenesulfonic acid (0.24 g, 1.28 mmol). The solution was heated to reflux in a Dean-Stark apparatus for 3 hours. After cooling the solution to ambient temperature, the reaction was concentrated in vacuo to remove cyclohexane and traces of pyrrolidine. The crude product was used for the next step without further purification (13.4 g).

Step 2: Preparation of 2-(8-oxo-1,4-dioxaspiro[4.5]decan-7-yl)acetonitrile

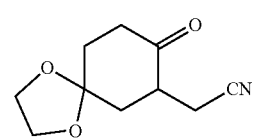 [SMILES: N#CCC1CC2(CCC1=O)OCCO2]

A stirred solution of 1-(1,4-dioxaspiro[4.5]dec-7-en-8-yl)pyrrolidine (13.4 g, 64.11 mmol) and 2-chloroacetonitrile (4.8 mL, 76.48) in 1,4-dioxane (250 mL) was heated to reflux for 5 hours. The reaction mixture was cooled to ambient temperature and concentrated in vacuo. The crude material was purified by using flash chromatography (30% ethyl acetate/hexane) to provide 2-(8-oxo-1,4-dioxaspiro[4.5]decan-7-yl)acetonitrile as a yellow oil (4.72 g, 37% yield): MS (ES) m/z 196.1 (M+H).

Step 3: Preparation of 2-(8-hydroxy-1,4-dioxaspiro[4.5]decan-7-yl)acetonitrile

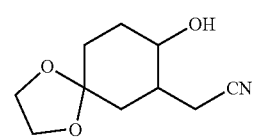 [SMILES: N#CCC1CC2(CCC1O)OCCO2]

To a stirred solution of 2-(8-oxo-1,4-dioxaspiro[4.5]decan-7-yl)acetonitrile (4.7 g, 24.1 mmol) in methanol (50 mL) was added sodium borohydride (91.37 g, 36.5 mmol) in portions at 0° C., and the solution was stirred at ambient temperature for 2 hours. The reaction mixture was concentrated in vacuo and the residue was dissolved in ethyl acetate, washed with water, brine and dried over anhydrous sodium sulfate. The solution was filtered and concentrated in vacuo to provide 2-(8-hydroxy-1,4-dioxaspiro[4.5]decan-7-yl)acetonitrile as a colourless oil (4.57 g, 76% yield): MS (ES) m/z 198.1 (M+H).

Step 4: Preparation of 2-(2-hydroxy-5-oxocyclohexyl)acetonitrile

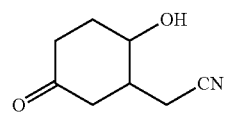

A solution of hydroxy-1,4-dioxaspiro[4.5]decan-7-yl)acetonitrile (3.5 g, 17.94 mmol) and p-toluenesulfonic acid monohydrate (1.0 g, 5.38 mmol) in acetone:water (30:10 mL) was heated to 100° C. for 2 hours. After cooling to ambient temperature, the reaction mixture was concentrated in vacuo and the residue was dissolved in ethyl acetate which was washed with water, brine and dried over anhydrous sodium sulfate. The solution was filtered and concentrated in vacuo to provide 2-(2-hydroxy-5-oxocyclohexyl)acetonitrile as a brown coloured oil (2.25 g, 83% yield): MS (ES) m/z 154.1 (M+H).

Step 5: Preparation of 2-(5-amino-2-hydroxycyclohexyl)acetonitrile

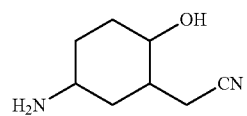 [SMILES: N#CCC1CC(N)CCC1O]

To a stirred solution of 2-(2-hydroxy-5-oxocyclohexyl)acetonitrile (2.24 g, 14.64 mmol) in methanol (50 mL) was added ammonium acetate (2.25 g, 29.28 mmol) and sodium borohydride (1.38 g, 21.96 mmol) and the mixture was stirred at ambient temperature for 15 hours. The reaction mixture was concentrated in vacuo to provide 2-(5-amino-2-hydroxycyclohexyl)acetonitrile as a colourless gummy solid (10 g, crude): MS (ES) m/z 155.1 (M+H).

Step 6: Preparation of ethyl 4-((3-(cyanomethyl)-4-hydroxycyclohexyl)amino)-1H-pyrrolo[2,3-b]pyridine-5-carboxylate

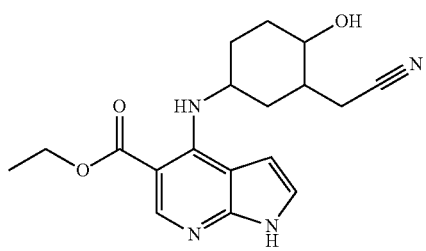 [SMILES: CCOC(=O)c1cnc2[nH]ccc2c1NC1CCC(O)C(CC#N)C1]

A solution of ethyl 4-chloro-1H-pyrrolo[2,3-b]pyridine-5-carboxylate (2.0 g, 8.93 mmol), 2-(5-amino-2-hydroxycyclohexyl)acetonitrile (2.0 g, 13.4 mmol), and a catalytic amount of triethylamine in N-methylpyrrolidine (40 mL) was subjected to microwave irradiation at 180° C. for 2 hours. After cooling the reaction mixture was quenched with water and extracted with ethyl acetate. The organic layer was washed with water, brine, dried over anhydrous sodium sulphate, filtered and concentrated in vacuo. The crude material was purified using flash chromatography (5% methanol/dichloromethane) to provide ethyl 4-((3-(cyanomethyl)-4-hydroxycyclohexyl)amino)-1H-pyrrolo[2,3-b]pyridine-5-carboxylate as an off-white solid (0.06 g, 2% yield): $^1$HNMR (400 MHz, DMSO-$d_6$, at 90° C.) δ 11.61 (br s, 1H), 8.93 (d, J=8 Hz, 1H), 8.52 (s, 1H), 7.14 (s, 1H), 6.55 (s, 1H), 4.50 (br s, 1H), 4.25 (q, J=6.8 Hz, 2H), 4.09 (br s, 1H), 3.65 (br s, 1H), 2.1-2.2 (m, 2H), 1.64-1.74 (m, 3H), 1.51-1.59 (m, 3H), 1.27-1.31 (m, 4H); MS (ES) m/z 304.1 (M+H).

Synthesis of Example 143: Preparation of ethyl (S)-4-((1-(2-cyanoacetyl)piperidin-3-yl)amino)-1H-pyrrolo[2,3-b]pyridine-5-carboxylate

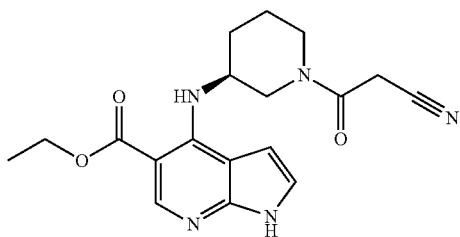 [SMILES: CCOC(=O)c1cnc2[nH]ccc2c1N[C@H]1CCCN(C(=O)CC#N)C1]

Scheme 35: Preparation of ethyl (S)-4-((1-(2-cyanoacetyl)piperidin-3-yl)amino)-1H-pyrrolo[2,3-b]pyridine-5-carboxylate.

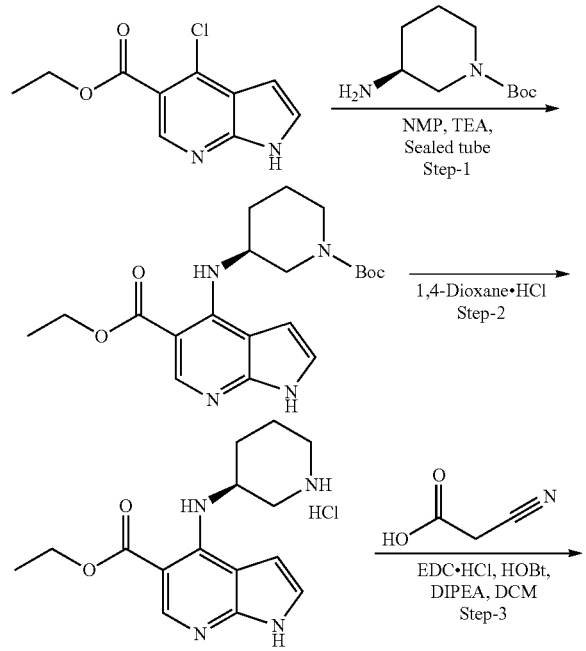

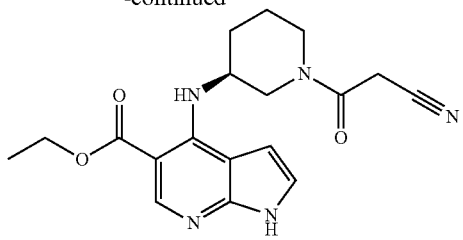

Step 1: Preparation of ethyl (S)-4-((1-benzylpiperidin-3-yl)amino)-1H-pyrrolo[2,3-b]pyridine-5-carboxylate

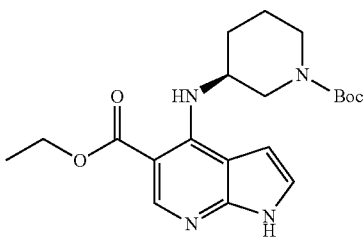 [SMILES: CCOC(=O)c1cnc2[nH]ccc2c1N[C@H]1CCCN(C(=O)OC(C)(C)C)C1]

To a stirred solution of ethyl 4-chloro-1H-pyrrolo[2,3-b]pyridine-5-carboxylate (7 g, 31.2 mmol) in N-methyl-2-pyrrolidone (40 mL) was added tert-butyl (S)-3-aminopiperidine-1-carboxylate (12.5 g, 62.5 mmol) and triethylamine (0.4 mL) in a sealed tube. The mixture was heated to 170° C. for 5 hours. After cooling to ambient temperature, the reaction mixture was quenched with water and extracted with ethyl acetate. The organic layer was washed with water, brine and dried over anhydrous sodium sulfate. The solution was filtered and concentrated in vacuo. The crude material was purified by flash chromatography (50% ethyl acetate/hexane) to provide ethyl (S)-4-((1-(tert-butoxycarbonyl)piperidin-3-yl)amino)-1H-pyrrolo[2,3-b]pyridine-5-carboxylate as a colourless oil (7 g, 57% yield): MS (ES) m/z 389.2 (M+H).

Step 2: Preparation of ethyl (S)-4-(piperidin-3-ylamino)-1H-pyrrolo[2,3-b]pyridine-5-carboxylate hydrochloride

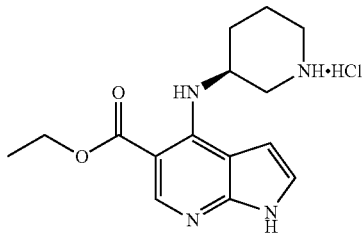

To a stirred solution of ethyl (S)-4-((1-(tert-butoxycarbonyl)piperidin-3-yl)amino)-1H-pyrrolo[2,3-b]pyridine-5-carboxylate (7 g, 18.0 mmol) in 1,4-dioxane (10 mL) was added (4M) hydrochloride in 1,4-dioxane (15 mL) and the mixture was stirred under a nitrogen atmosphere at ambient temperature for 12 hours. The reaction mixture was concentrated in vacuo to provide ethyl (S)-4-(piperidin-3-ylamino)-1H-pyrrolo[2,3-b]pyridine-5-carboxylate hydrochloride as an off-white solid (4 g, crude): MS (ES) m/z 289.3 (M+H).

Step 3—Preparation of ethyl (S)-4-((1-(2-cyanoacetyl)piperidin-3-yl)amino)-1H-pyrrolo[2,3-b]pyridine-5-carboxylate

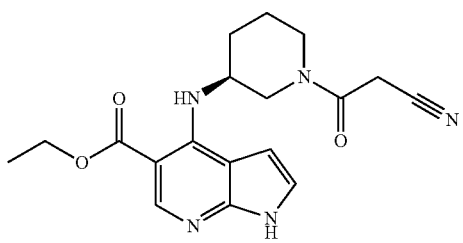 [SMILES: CCOC(=O)c1cnc2[nH]ccc2c1N[C@H]1CCCN(C(=O)CC#N)C1]

To a stirred solution of ethyl (S)-4-(piperidin-3-ylamino)-1H-pyrrolo[2,3-b]pyridine-5-carboxylate hydrochloride (2.5 g, 8.68 mmol) in N,N-dimethylformamide (25 mL) were added N-(3-dimethylaminopropyl)-N'-ethylcarbodiimide hydrochloride (2.6 g, 17.3 mmol), 1-hydroxybenzotriazole (2.3 g, 17.3 mmol), N,N-diisopropylethylamine (2.2 g, 17.3 mmol) and cyanoacetic acid (1.4 g, 17.3 mmol). The mixture was then stirred at ambient temperature for 18 hours. The reaction mixture was quenched with water and extracted with dichloromethane. The organic layer was washed with water, brine and dried over anhydrous sodium sulfate. The solution was filtered and concentrated in vacuo. The crude material was purified by flash chromatography (5% methanol/dichloromethane) to provide ethyl (S)-4-((1-(2-cyanoacetyl)piperidin-3-yl)amino)-1H-pyrrolo[2,3-b]pyridine-5-carboxylate as a yellow solid (1.2 g, 40% yield): $^1$H NMR (400 MHz, DMSO-$d_6$) δ 11.7 (br s, 1H), 8.86-8.80 (m, 1H), 8.54 (s, 1H), 7.20 (s, 1H), 6.67 (s, 1H), 4.06-4.27 (m, 3H), 3.63-4.00 (m, 4H), 3.40-3.45 (m, 1H), 3.10-3.15 (m, 1H), 2.05 (br s, 1H), 1.64-1.71 (m, 3H), 1.28-1.31 (t, J=12 Hz, 3H); MS (ES) m/z 356.2 (M+H).

Synthesis of Example 144: Preparation of ethyl (R)-4-((1-(2-cyano-2-methylpropanoyl)piperidin-3-yl)amino)-1H-pyrrolo[2,3-b]pyridine-5-carboxylate

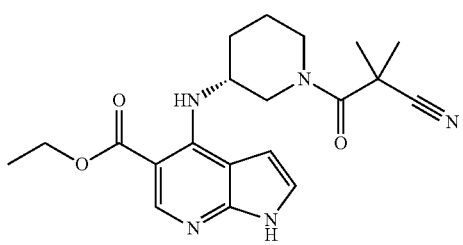 [SMILES: CCOC(=O)c1cnc2[nH]ccc2c1N[C@@H]1CCCN(C(=O)C(C)(C)C#N)C1]

Scheme 36: Preparation of ethyl (R)-4-((1-(2-cyano-2-methylpropanoyl)piperidin-3-yl)amino)-1H-pyrrolo[2,3-b]pyridine-5-carboxylate.

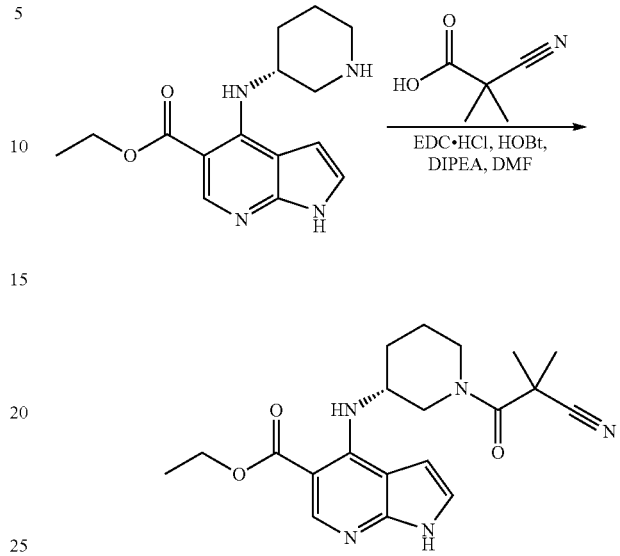

To a stirred solution of ethyl (R)-4-(piperidin-3-ylamino)-1H-pyrrolo[2,3-b]pyridine-5-carboxylate (0.1 g, 8.68 mmol) in dichloromethane (5 mL) was added N-(3-dimethylaminopropyl)-N'-ethylcarbodiimide.HCl (0.1 g, 0.69 mmol), 1-hydroxybenzotriazole (0.09 g, 0.69 mmol), N,N-diisopropylethylamine (0.09 g, 0.69 mmol) and cyanoacetic acid (0.08 g, 0.69 mmol). The mixture was stirred at ambient temperature for 18 hours. The reaction mixture was quenched with water and extracted with dichloromethane. The organic layer was washed with water, brine and dried over anhydrous sodium sulfate. The solution was filtered and concentrated in vacuo. The crude material was purified by flash chromatography (5% methanol/dichloromethane) to provide ethyl (R)-4-((1-(2-cyano-2-methyl-propanoyl)piperidin-3-yl)amino)-1H-pyrrolo[2,3-b]pyridine-5-carboxylate as a yellow solid (0.015 g, 40% yield): $^1$H NMR (400 MHz, DMSO-$d_6$) δ 11.67 (br s, 1H), 8.89-8.91 (m, 1H), 8.53 (s, 1H), 7.19 (s, 1H), 6.66 (s, 1H), 4.21-4.27 (m, 3H), 3.9-3.95 (m, 1H), 3.71 (m, 3H), 2.1-2.2 (br s, 1H), 1.85-1.6 (m, 3H), 1.50-1.54 (m, 6H), 1.28-1.31 (t, J=12 Hz, 3H); MS (ES) m/z 384.1 (M+H).

Synthesis of Example 145: Preparation of cyclopropylmethyl (R)-4-((1-(2-cyanoacetyl)piperidin-3-yl)amino)-1H-pyrrolo[2,3-b]pyridine-5-carboxylate

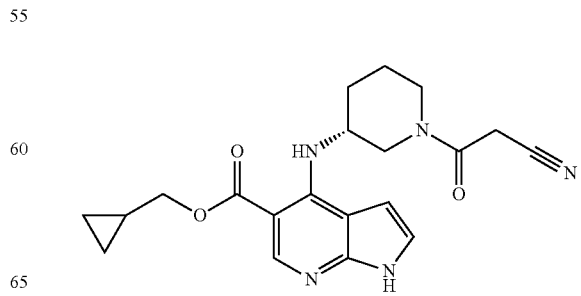

Scheme 37: Preparation of cyclopropylmethyl (R)-4-((1-(2-cyanoacetyl)piperidin-3-yl)amino)-1H-pyrrolo[2,3-b]pyridine-5-carboxylate.

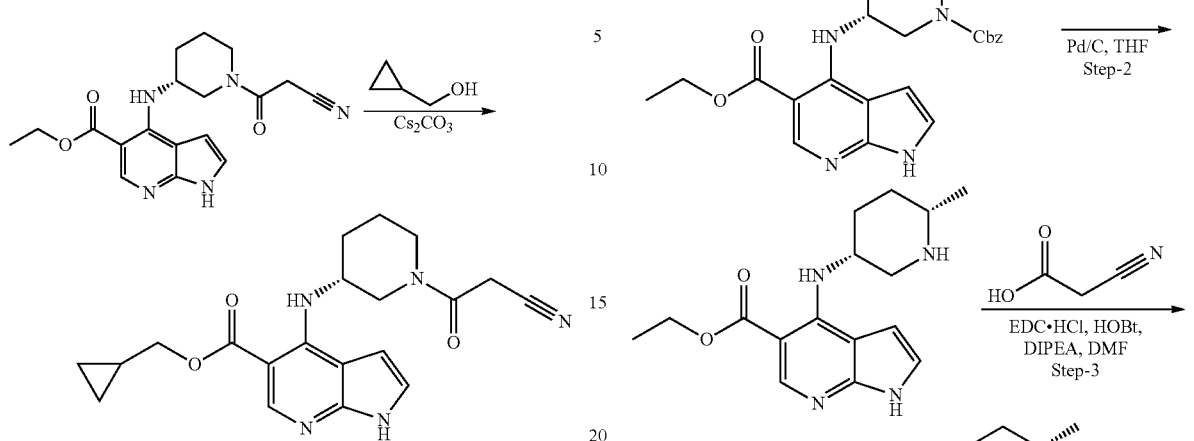

To a stirred solution of ethyl (R)-4-((1-(2-cyanoacetyl)piperidin-3-yl)amino)-1H-pyrrolo[2,3-b]pyridine-5-carboxylate (0.12 g, 0.33 mmol) in cyclopropylmethanol (5 mL) was added cesium carbonate (0.53 g, 1.65 mmol). The mixture was stirred at ambient temperature for 12 hours. The reaction mixture was concentrated in vacuo and the crude material was purified by flash chromatography (4% methanol/dichloromethane) to provide cyclopropylmethyl (R)-4-((1-(2-cyanoacetyl)piperidin-3-yl)amino)-1H-pyrrolo[2,3-b]pyridine-5-carboxylate as a brown solid (0.013 g, 10% yield): $^1$H NMR (400 MHz, DMSO-$d_6$) δ 11.70 (br s, 1H), 8.77-8.84 (m, 1H), 8.56 (s, 1H), 7.20 (s, 1H), 6.67 (s, 1H), 4.16-4.29 (m, 2H), 4.05-4.06 (m, 3H), 3.77-3.99 (m, 2H), 3.62-3.70 (m, 1H), 3.44 (m, 1H), 3.13-3.15 (m, 1H), 2.05 (m, 1H), 1.64 (m, 3H), 1.21-1.29 (m, 2H), 0.53-0.55 (m, 1H), 0.32-0.33 (m, 1H); MS (ES) m/z 382.1 (M+H).

Synthesis of Example 146: Preparation of ethyl 4-(((3R,6S)-1-(2-cyanoacetyl)-6-methylpiperidin-3-yl)amino)-1H-pyrrolo[2,3-b]pyridine-5-carboxylate

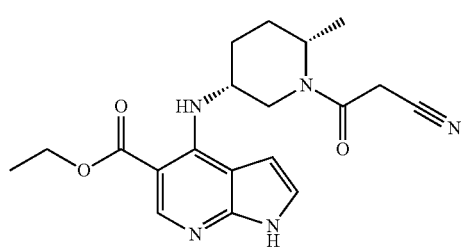 [SMILES: CCOC(=O)c1cnc2[nH]ccc2c1N[C@@H]1CC[C@H](C)N(C(=O)CC#N)C1]

Scheme 38: Preparation of ethyl 4-(((3R,6S)-1-(2-cyanoacetyl)-6-methylpiperidin-3-yl)amino)-1H-pyrrolo[2,3-b]pyridine-5-carboxylate.

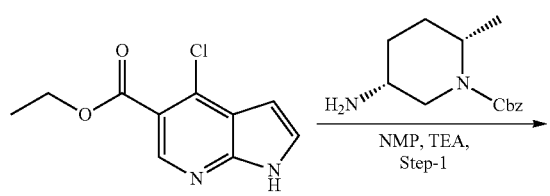

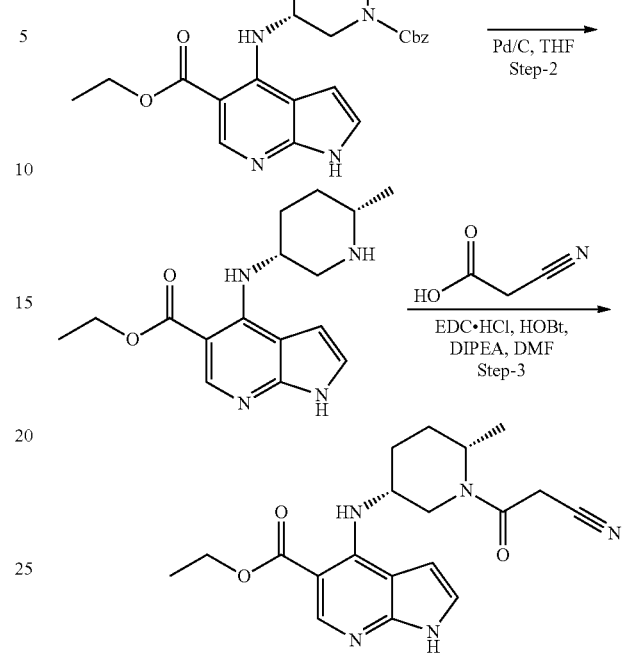

Step 1: Preparation of ethyl 4-(((3R,6S)-1-((benzyloxy)carbonyl)-6-methylpiperidin-3-yl)amino)-1H-pyrrolo[2,3-b]pyridine-5-carboxylate

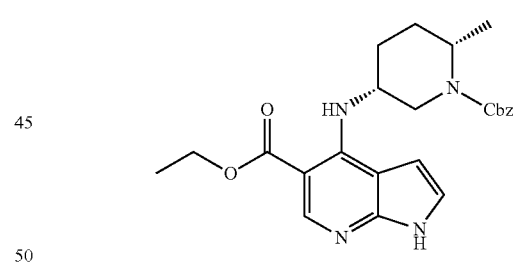

To a solution of ethyl 4-chloro-1H-pyrrolo[2,3-b]pyridine-5-carboxylate (0.35 g, 1.56 mmol) in N-methyl-2-pyrrolidone (5 mL) was added benzyl (2S,5R)-5-amino-2-methylpiperidine-1-carboxylate (0.65 g, 2.65 mmol) and triethylamine (0.5 mL). The mixture was heated to 180° C. under microwave irradiation for 1 hour. The reaction mixture was cooled to ambient temperature, quenched with water and extracted with ethyl acetate. The organic layer was washed with water, brine and dried over anhydrous sodium sulfate. The reaction mixture was filtered and concentrated in vacuo. The crude material was purified by flash chromatography (40% ethyl acetate/hexane) to provide ethyl 4-(((3R,6S)-1-((benzyloxy)-carbonyl)-6-methylpiperidin-3-yl)amino)-1H-pyrrolo[2,3-b]pyridine-5-carboxylate as a yellow solid (0.3 g, 44% yield).

221

Step 2: Preparation of ethyl 4-(((3R, 6S)-6-methylpiperidin-3-yl) amino)-1H-pyrrolo[2,3-b]pyridine-5-carboxylate

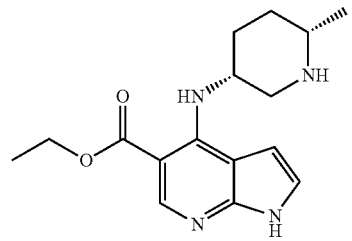 [SMILES: CCOC(=O)c1cnc2[nH]ccc2c1N[C@@H]1CC[C@H](C)NC1]

To a solution of ethyl 4-(((3R,6S)-1-((benzyloxy)carbonyl)-6-methylpiperidin-3-yl)amino)-1H-pyrrolo[2,3-b]pyridine-5-carboxylate (0.3 g, 0.68 mmol) in tetrahydrofuran (5 mL) was added palladium on carbon (0.3 g, 50% wet w/w). The reaction mixture was placed under a hydrogen atmosphere and stirred at room temperature for 12 hours. The reaction mixture was filtered through celite and washed with 50% methanol/ethyl acetate (100 mL). The filtrate was concentrated in vacuo to provide ethyl 4-(((3R, 6S)-6-methylpiperidin-3-yl) amino)-1H-pyrrolo[2,3-b]pyridine-5-carboxylate as an off-white solid (0.2 g, crude): MS (ES) m/z 303.2 (M+H).

Step 3: Preparation of ethyl 4-(((3R,6S)-1-(2-cyanoacetyl)-6-methylpiperidin-3-yl)amino)-1H-pyrrolo[2,3-b]pyridine-5-carboxylate

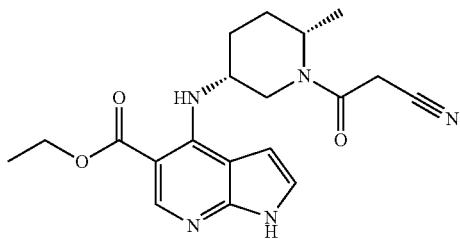 [SMILES: CCOC(=O)c1cnc2[nH]ccc2c1N[C@@H]1CC[C@H](C)N(C(=O)CC#N)C1]

To a solution of ethyl 4-(((3R, 6S)-6-methylpiperidin-3-yl)amino)-1H-pyrrolo[2,3-b]pyridine-5-carboxylate (0.2 g, 0.66 mmol) in N,N-dimethylformamide (2 mL) was added N-(3-dimethylaminopropyl)-N'-ethylcarbodiimide hydrochloride (0.11 g, 1.32 mmol), 1-hydroxybenzotriazole (0.17 g, 1.32 mmol), N,N-diisopropylethylamine (0.18 g, 1.32 mmol) and cyanoacetic acid (0.11 g, 1.32 mmol) and the mixture stirred at ambient temperature for 18 hours. The reaction mixture was quenched with water and extracted with dichloromethane. The organic layer was washed with water, brine and dried over anhydrous sodium sulfate. The solution was filtered and concentrated in vacuo. The crude material was purified by flash chromatography (5% methanol/dichloromethane) to provide ethyl (R)-4-((1-(2-cyano-2-methylpropanoyl)piperidin-3-yl)amino)-1H-pyrrolo[2,3-b]pyridine-5-carboxylate as a brown solid (0.07 g, 28% yield): $^1$H NMR (400 MHz, DMSO-$d_6$) δ 11.718 (br s, 1H), 8.75 (m, 1H), 8.54 (s, 1H), 7.20 (s, 1H), 6.63-6.66 (m, 1H), 4.67 (m, 1H), 3.84-4.28 (m, 6H), 1.62-1.97 (m, 5H), 1.11-1.32 (m, 6H); MS (ES) m/z 370.2 (M+H).

222

Synthesis of Example 147: Preparation of 4-(((1S,3R)-3-(2-cyanoethyl)cyclohexyl)amino)-1H-pyrrolo[2,3-b]pyridine-5-carboxylic acid

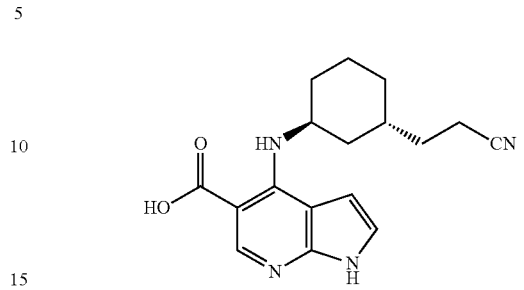

Scheme 39: Preparation of 4-(((1S,3R)-3-(2-cyanoethyl)cyclohexyl) amino)-1H-pyrrolo[2,3-b]pyridine-5-carboxylic acid.

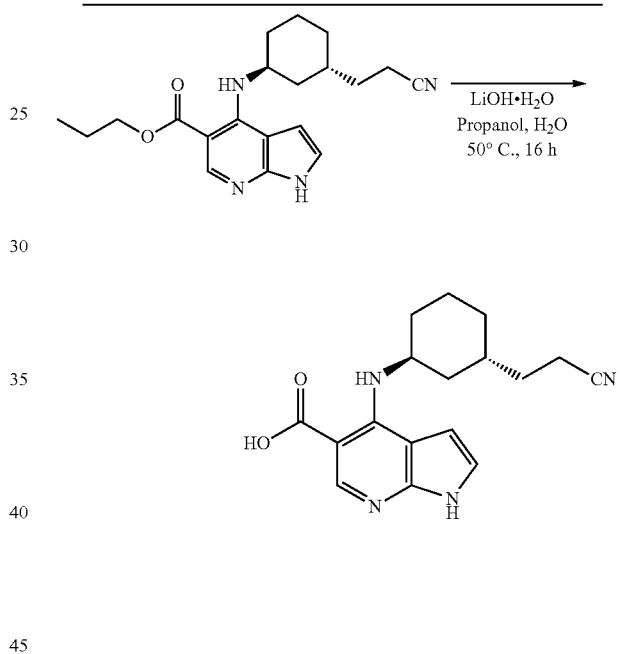

To a stirred solution of propyl 4-(((1S,3R)-3-(2-cyanoethyl)cyclohexyl)amino)-1H-pyrrolo[2,3-b]pyridine-5-carboxylate (0.04 g, 0.112 mmol) in n-propanol (6 mL) was added lithium hydroxide monohydrate (0.04 g, 1.12 mmol) at 0° C. and the mixture was heated at 50° C. for 32 hours. After cooling the reaction mixture was concentrated in vacuo and the residue was dissolved in water which was washed with diethyl ether. The aqueous layer was acidified to pH 2.0 with saturated potassium bisulphate solution at 0° C. and then extracted with 5% methanol/dichloromethane. The organic layer was dried over anhydrous sodium sulphate, filtered and concentrated in vacuo. The obtained crude product was triturated with n-pentane to provide 4-(((1S,3R)-3-(2-cyanoethyl)cyclohexyl)amino)-1H-pyrrolo[2,3-b]pyridine-5-carboxylic acid as an off-white solid (0.02 g, 50% yield): $^1$H NMR (400 MHz, DMSO-$d_6$): δ 12.20 (br s, 1H), 11.52 (s, 1H), 9.15 (br s, 1H), 8.49 (s, 1H), 7.12 (s, 1H), 6.50 (s, 1H), 3.91 (d, J=8.0 Hz, 1H), 2.52 (s, 1H), 2.11 (t, J=12.0 Hz, 2H), 1.74 (t, J=16.0 Hz, 2H), 1.41-1.57 (m, 4H), 1.11-1.21 (m, 2H), 0.79-0.98 (m, 2H); MS (ES) m/z 313.0 (M+H).

Synthesis of Examples 148-150. Preparation and separation of stereoisomers of 2-methoxyethyl 4-((3-(2-cyanoethyl)cyclohexyl)amino)-1H-pyrrolo[2,3-b]pyridine-5-carboxylate Scheme 40: Preparation and separation of stereoisomers of 2-methoxyethyl 4-((3-(2-cyanoethyl)cyclohexyl)amino)-1H-pyrrolo[2,3-b]pyridine-5-carboxylate.

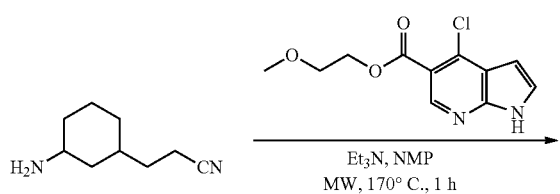

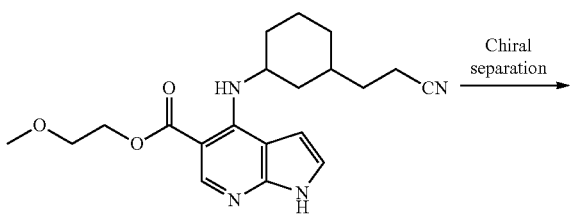

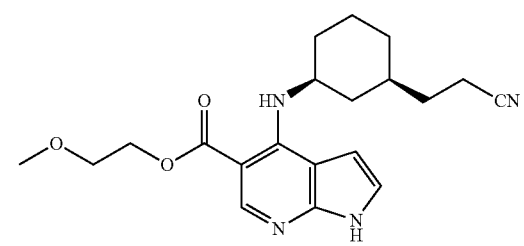 [SMILES: COCCOC(=O)c1cnc2[nH]ccc2c1N[C@H]1CCC[C@H](CCC#N)C1]

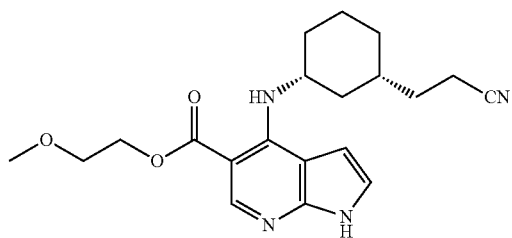

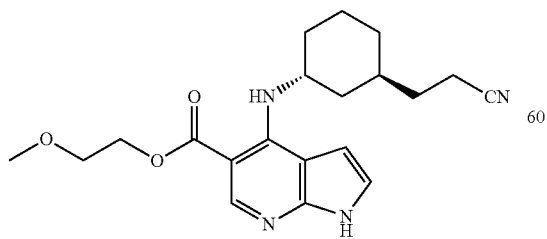

Preparation of 2-methoxyethyl 4-((3-(2-cyanoethyl)cyclohexyl)amino)-1H-pyrrolo[2,3-b]pyridine-5-carboxylate

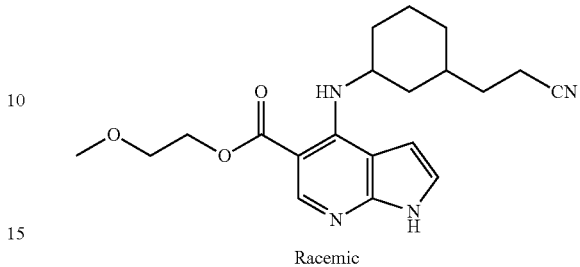

Racemic

To a stirred solution of 3-(3-aminocyclohexyl)propanenitrile (0.27 g, 1.77 mmol) in N-methyl-2-pyrrolidone (15 mL) was added 2-methoxyethyl 4-chloro-1H-pyrrolo[2,3-b]pyridine-5-carboxylate (0.54 g, 2.128 mmol) and triethylamine (0.74 mL, 5.31 mmol). The mixture was then subjected to a microwave irradiation at 170° C. for 1 hour. After cooling to ambient temperature, the reaction mixture was diluted with ethyl acetate and washed with water, brine, dried over sodium sulphate, filtered and concentrated in vacuo. The crude material was purified by flash chromatography (50% ethyl acetate/hexane) to provide crude racemic 2-methoxyethyl 4-((3-(2-cyanoethyl)cyclohexyl)amino)-1H-pyrrolo[2,3-b]pyridine-5-carboxylate an off-white solid (0.42 g, crude). Racemic 2-methoxyethyl 4-((3-(2-cyanoethyl)cyclohexyl)amino)-1H-pyrrolo[2,3-b]pyridine-5-carboxylate (0.42 g) was purified by prep HPLC using the following method to give 0.115 g of pure racemic compound as an off white solid.

Analytical Conditions:
Column: Inertsil ODS 3V (250 mm×4.6 mm×5 mic)
Mobile phase (A): 0.1% ammonia in water
Mobile phase (B): ACN
Flow rate: 1.0 mL/min
T/% B: 0/20, 10/70, 25/90, 27/20, 30/20
RT=12.927 min The stereoisomers of 2-methoxyethyl 4-((3-(2-cyanoethyl)cyclohexyl)amino)-1H-pyrrolo[2,3-b]pyridine-5-carboxylate were separated using the following chromatographic conditions.
Column: CHIRALPAK IA (100 mm×4.6 mm×3 mic)
Mobile phase: n-hexane:ethanol with 0.1% DEA (90:10)
Flow rate: 1.0 mL/min

Synthesis of Example 148: Isolation of racemic, trans-2-methoxyethyl 4-((3-(2-cyanoethyl)cyclohexyl)amino)-1H-pyrrolo[2,3-b]pyridine-5-carboxylate Isolated as an off-white solid (0.02 g, 17% yield): $^1$H NMR (400 MHz, DMSO-$d_6$) δ 11.66 (s, 1H), 9.03 (d, J=8.0 Hz, 1H), 8.53 (s, 1H), 7.15 (s, 1H), 6.57 (d, J=2.8 Hz, 1H), 4.42 (t, J=4.0 Hz, 1H), 4.32 (t, J=4.4 Hz, 2H), 3.64 (t, J=4.8 Hz, 2H), 3.29 (d, J=5.6 Hz, 3H), 2.44 (s, 2H), 1.81-1.84 (m, 1H), 1.70-1.74 (m, 3H), 1.60-1.67 (m, 2H); 1.41-1.55 (m, 4H); 1.00-1.08 (m, 1H); MS (ES) m/z 371.1 (M+H). Retention time 8.652 min.

Synthesis of Example 149: Isolation of one enantiomer of cis-2-methoxyethyl 4-((3-(2-cyanoethyl)cyclohexyl)amino)-1H-pyrrolo[2,3-b]pyridine-5-carboxylate, enantiomer 1

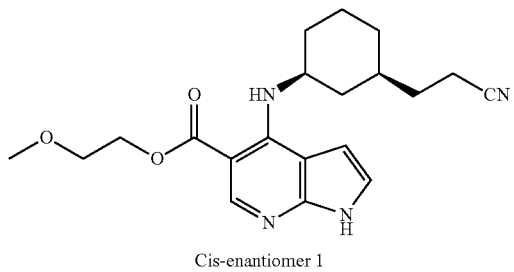 [SMILES: COCCOC(=O)c1cnc2[nH]ccc2c1N[C@H]1CCC[C@@H](CCC#N)C1]

Cis-enantiomer 1

Isolated as an off-white solid (0.03 g, 29% yield): $^1$H NMR (400 MHz, DMSO-$d_6$) δ 11.67 (s, 1H), 8.66 (d, J=8.0 Hz, 1H), 8.52 (s, 1H), 7.16 (s, 1H), 6.57 (s, 1H), 4.31 (t, J=4.4 Hz, 2H), 3.94 (t, J=3.6 Hz, 1H), 3.63 (t, J=4.4 Hz, 2H), 3.29 (d, J=4.8 Hz, 3H), 2.50-2.52 (m, 2H), 2.12 (t, J=12.0 Hz, 2H), 1.74 (t, J=16.0 Hz, 2H), 1.41-1.51 (m, 3H); 1.05-1.31 (m, 2H), 0.83-1.00 (m, 2H); MS (ES) m/z 371.1 (M+H). Retention time 10.04 min.

Synthesis of Example 150: Isolation of the opposite enantiomer of cis 2-methoxyethyl 4-((3-(2-cyanoethyl)cyclohexyl)amino)-1H-pyrrolo[2,3-b]pyridine-5-carboxylate, enantiomer 2

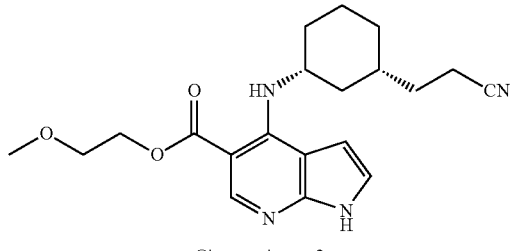

Cis-enantiomer 2

Isolated as an off-white solid (0.03 g, 28% yield); $^1$H NMR (400 MHz, DMSO-$d_6$) δ 11.67 (s, 1H), 8.66 (d, J=8.0 Hz, 1H), 8.52 (s, 1H), 7.16 (d, J=2.8 Hz 1H), 6.53 (d, J=3.2 Hz, 1H), 4.31-4.46 (m, 2H), 3.90-3.97 (m, 1H), 3.66 (d, J=20.0 Hz, 2H), 3.29 (s, 3H), 2.50 (s, 2H), 2.12 (t, J=12.0 Hz, 2H), 1.74 (t, J=15.6 Hz, 2H), 1.41-1.60 (m, 3H), 1.08-1.31 (m, 2H), 0.68-1.0 (m, 2H); MS (ES) m/z 371.1 (M+H). Retention time 13.39 min.

Synthesis of Example 151-152: Preparation of cis- and trans-racemic methyl 4-((3-(2-cyanoethyl)cyclohexyl)amino)-1H-pyrrolo[2,3-b]pyridine-5-carboxylate Scheme 41: Preparation of cis- and trans-racemic methyl 4-((3-(2-cyanoethyl)cyclohexyl)amino)-1H-pyrrolo[2,3-b]pyridine-5-carboxylate.

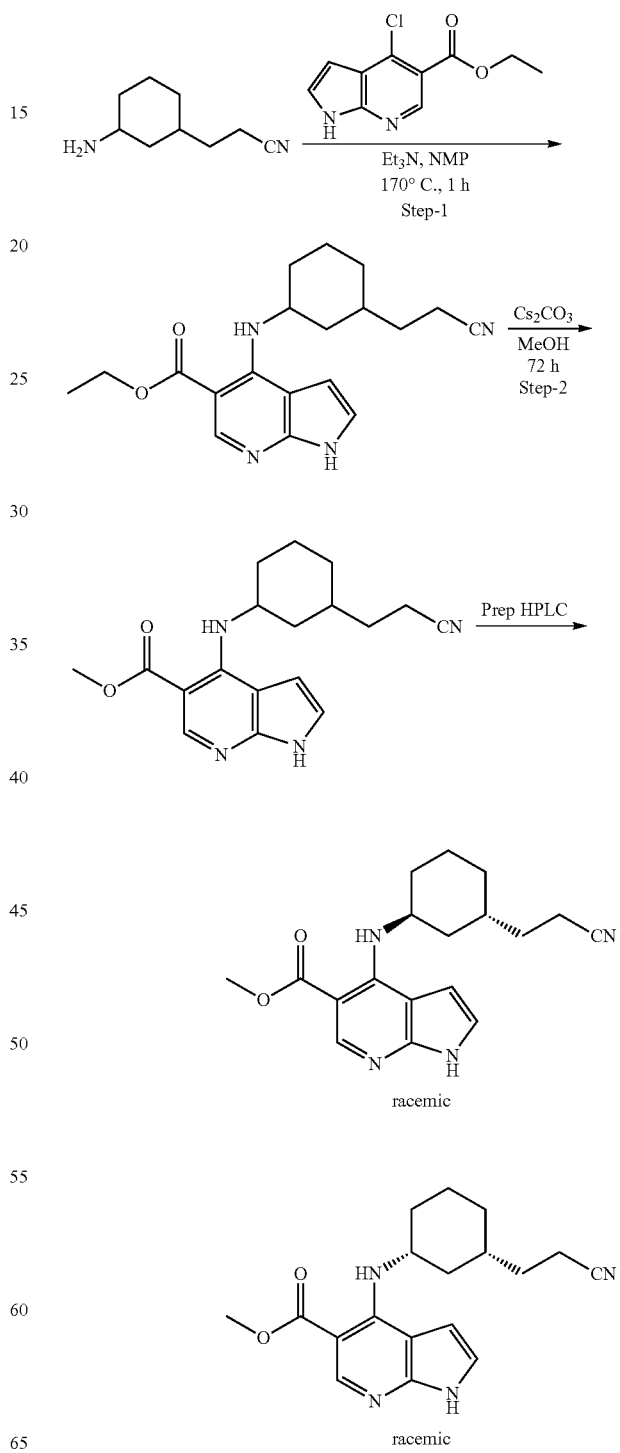

Step 1: Preparation of ethyl 4-((3-(2-cyanoethyl)cyclohexyl)amino)-1H-pyrrolo[2,3-b]pyridine-5-carboxylate

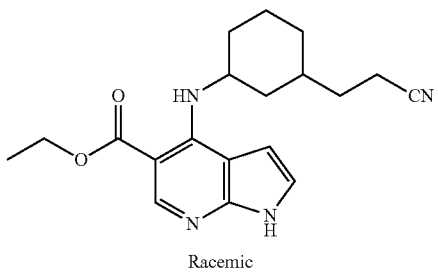 [SMILES: CCOC(=O)c1cnc2[nH]ccc2c1NC1CCCC(CCC#N)C1]

Racemic

To a stirred solution of 3-(3-aminocyclohexyl)propanenitrile (0.07 g, 0.459 mmol) in N-methyl-2-pyrrolidone (3 mL) was added ethyl 4-chloro-1H-pyrrolo[2,3-]pyridine-5-carboxylate (0.123 g, 0.551 mmol) and triethylamine (0.2 mL, 1.337 mmol). The mixture was subjected to a microwave irradiation at 170° C. for 1 hour. After cooling to ambient temperature, the reaction mixture was diluted with ethyl acetate and washed with water, brine, dried over anhydrous sodium sulphate, filtered and concentrated in vacuo. The crude material was purified by flash chromatography (50% ethyl acetate/hexane) to provide ethyl 4-((3-(2-cyanoethyl)cyclohexyl)amino)-1H-pyrrolo[2,3-b]pyridine-5-carboxylate as a yellow semisolid (0.38 g, 36% yield): MS (ES) m/z 341.1 (M+H).

Step 2: Preparation of methyl 4-((3-(2-cyanoethyl)cyclohexyl)amino)-1H-pyrrolo[2,3-b]pyridine-5-carboxylate

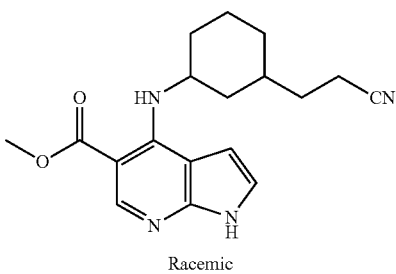 [SMILES: COC(=O)c1cnc2[nH]ccc2c1NC1CCCC(CCC#N)C1]

Racemic

To a stirred solution of ethyl 4-((3-(2-cyanoethyl)cyclohexyl)amino)-1H-pyrrolo[2,3-b]pyridine-5-carboxylate (0.2 g, 0.587 mmol) in dry methanol (8 mL) was added cesium carbonate (0.957 g, 2.937 mmol) at 0° C. and the resulting mixture was stirred at room temperature for 72 hours. The reaction mixture was concentrated in vacuo. The residue was diluted with water and extracted with dichloromethane. The organic layer was dried over anhydrous sodium sulphate, filtered and concentrated in vacuo. The crude product was purified by column chromatography (50% ethyl acetate/hexane) to provide methyl 4-((3-(2-cyanoethyl)cyclohexyl)amino)-1H-pyrrolo[2,3-b]pyridine-5-carboxylate as a colourless oil (0.08 g, 42% yield): MS (ES) m/z 327.1 (M+H).

The cis- and trans-diastereomers of methyl 4-((3-(2-cyanoethyl)cyclohexyl)amino)-1H-pyrrolo[2,3-b]pyridine-5-carboxylate were separated using the following chromatographic conditions:

Analytical Conditions:
Column: Inertsil ODS 3V (250 mm×4.6 mm×5 mic)
Mobile phase (A): 0.1% ammonia in water
Mobile phase (B): ACN
Flow rate: 1.0 mL/min (50:50)

Synthesis of Example 151: trans-racemic-methyl 4-((3-(2-cyanoethyl)cyclohexyl)amino)-1H-pyrrolo[2,3-b]pyridine-5-carboxylate

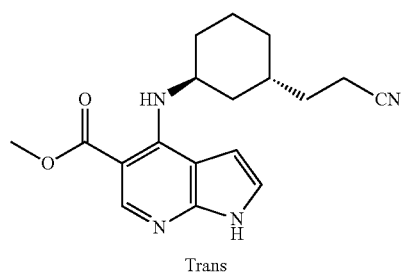 [SMILES: COC(=O)c1cnc2[nH]ccc2c1N[C@H]1CCC[C@H](CCC#N)C1]

Trans

Isolated as an off-white solid (0.01 g, 13% yield): $^1$H NMR (400 MHz, DMSO-$d_6$) δ 11.61 (s, 1H), 9.07 (d, J=8.4 Hz, 1H), 8.51 (s, 1H), 7.15 (t, J=2.8 Hz, 1H), 6.57 (d, J=1.2 Hz, 1H), 4.43 (t, J=3.6 Hz, 1H), 3.78 (s, 3H), 2.47 (s, 2H), 1.82-1.85 (m, 1H), 1.61-1.75 (m, 5H), 1.41-1.55 (m, 4H), 1.0-1.08 (m, 1H); MS (ES) m/z 327.2 (M+H). Retention time 12.729 min.

Synthesis of Example 152: cis-racemic-methyl 4-((3-(2-cyanoethyl)cyclohexyl)amino)-1H-pyrrolo[2,3-b]pyridine-5-carboxylate

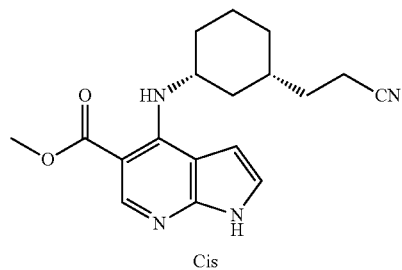 [SMILES: COC(=O)c1cnc2[nH]ccc2c1N[C@@H]1CCC[C@H](CCC#N)C1]

Cis

Isolated as an off-white solid (0.04 g, 50% yield): $^1$H NMR (400 MHz, DMSO-$d_6$) δ 11.63 (s, 1H), 8.72 (d, J=8.0 Hz, 1H), 8.50 (s, 1H), 7.15 (d, J=2.0 Hz, 1H), 6.53 (d, J 1.2 Hz, 1H), 3.90-3.98 (m, 1H), 3.77 (s, 3H), 2.50 (s, 2H), 2.12 (t, J=12.8 Hz, 2H), 1.75 (t, d, J=16.4 Hz, 2H), 1.41-1.60 (m, 4H), 1.13-1.21 (m, 1H), 0.85-1.0 (m, 2H); MS (ES) m/z 327.1 (M+H). Retention time: 14.252 min.

Synthesis of Examples 153-155: Preparation of stereoisomers ethyl 4-((3-(2-cyanoethyl)cyclopentyl)amino)-1H-pyrrolo[2,3-b]pyridine-5-carboxylate

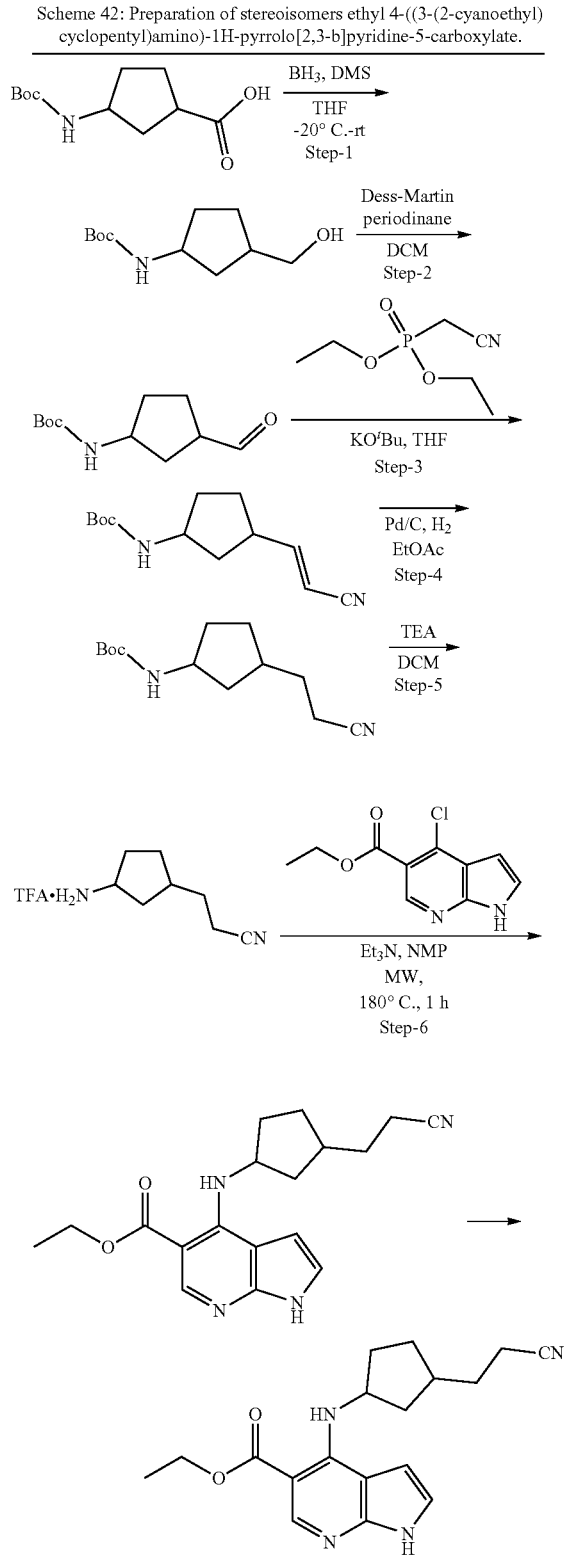

Step 1: Preparation of tert-butyl (3-(hydroxymethyl)cyclopentyl)carbamate

To a stirred solution of 3-((tert-butoxycarbonyl)amino)cyclopentane-1-carboxylic acid (2 g, 8.73 mmol) in dry tetrahydrofuran (30 mL) was added borane-dimethylsulfide (1.07 mL, 11.35 mmol) at 0° C. and the mixture was stirred at ambient temperature for 15 hours. The reaction mixture was cooled to 0° C., quenched with methanol and then stirred for 30 minutes. The reaction mixture was concentrated to provide tert-butyl (3-(hydroxymethyl)cyclopentyl)carbamate as a colourless liquid (2.5 g, crude): MS (ES) m/z 160.2 (M−56).

Step 2: Preparation of tert-butyl (3-formylcyclopentyl)carbamate

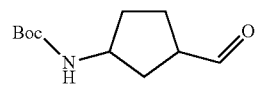

To a stirred solution of tert-butyl (3-(hydroxymethyl)cyclopentyl)carbamate (1 g, 4.65 mmol) in dry dichloromethane (30 mL) was added Dess-Martin periodinane (2.95 g, 6.97 mmol) at 0° C. The mixture was warmed to ambient temperature and stirred for 2 hours. The reaction mixture was cooled to 0° C. and quenched with saturated sodium bicarbonate. The organic layer was separated, washed with brine, dried over anhydrous sodium sulphate, filtered and concentrated in vacuo to provide tert-butyl (3-formylcyclopentyl)carbamate as a colourless liquid (1.1 g, crude).

Step 3: Preparation of tert-butyl (E)-(3-(2-cyanovinyl)cyclopentyl)carbamate

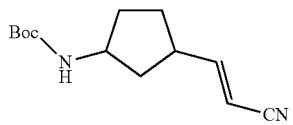 [SMILES: CC(C)(C)OC(=O)NC1CCC(/C=C/C#N)C1]

To a suspension of potassium tert-butoxide (0.86 g, 5.16 mmol) in dry tetrahydrofuran (30 mL) was added diethyl (cyanomethyl)phosphonate (1.16 mL, 7.23 mmol) at 0° C. and the mixture stirred for 1 hour. A solution of tert-butyl (3-formylcyclopentyl)carbamate (1.1 g crude, 5.16 mmol) in dry tetrahydrofuran (10 mL) was then added. The resulting mixture was stirred at ambient temperature for 12 hours. The reaction mixture was diluted with ethyl acetate and washed with water and brine. The organic layer was dried over anhydrous sodium sulphate, filtered and concentrated in vacuo. The crude material was purified by flash chromatography (20% ethyl acetate/hexane) provide tert-butyl (E)-(3-(2-cyanovinyl)cyclopentyl)carbamate as a colourless liquid (0.25 g, 21% yield): MS (ES) m/z 181.2 (M−56).

Step 4: Preparation of tert-butyl (3-(2-cyanoethyl)cyclopentyl)carbamate

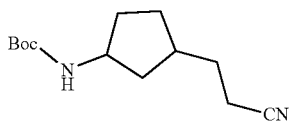

To a solution of tert-butyl (E)-(3-(2-cyanovinyl)cyclopentyl)carbamate (0.25 g, 1.05 mmol) in ethyl acetate (15 mL) was added palladium on carbon (0.2 g, 50% wet w/w) at room temperature under an argon atmosphere. The suspension was stirred at ambient temperature under a hydrogen atmosphere for 12 hours. The reaction mixture was filtered through celite, washed with ethyl acetate and the filtrate was concentrated in vacuo. The crude material was purified by flash chromatography (20% ethyl acetate/hexane) to provide tert-butyl (3-(2-cyanoethyl)cyclopentyl)carbamate as a colourless liquid (0.12 g, 48% yield): MS (ES) m/z 183.1 (M−56).

Step 5: Preparation of 3-(3-aminocyclopentyl)propanenitrile.trifluoroactic acid

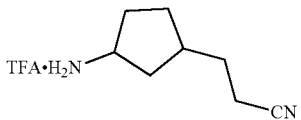

To a solution of tert-butyl (3-(2-cyanoethyl)cyclopentyl)carbamate (0.12 g, 0.54 mmol) in dichloromethane (20 mL) was added trifluoroacetic acid (0.5 mL) at 0° C. and the solution was stirred at ambient temperature for 3 hours. The reaction mixture was concentrated in vacuo to provide 3-(3-aminocyclopentyl)propanenitrile trifluoroactic acid as a colourless semi solid (0.1 g, crude): MS (ES) m/z 139.2 (M+H).

Step 6: Preparation of ethyl 4-((3-(2-cyanoethyl)cyclopentyl)amino)-1H-pyrrolo[2,3-b]pyridine-5-carboxylate

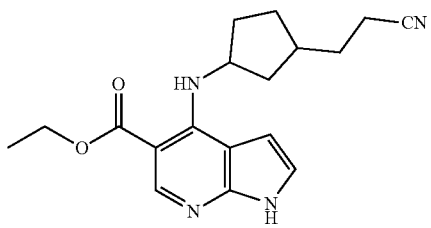 [SMILES: CCOC(=O)c1cnc2[nH]ccc2c1NC1CCC(CCC#N)C1]

To a stirred solution of 3-(3-aminocyclopentyl)propanenitrile trifluoroactic acid (0.1 g, 0.42 mmol) in N-methyl-2-pyrrolidone (1 mL) was added ethyl 4-chloro-1H-pyrrolo[2,3-b]pyridine-5-carboxylate (0.09 g, 0.42 mmol) and triethylamine (0.1 mL). The reaction mixture was then heated to 170° C. for 16 hours. The reaction mixture was diluted with ethyl acetate, washed with water and brine. The organic layer was dried over anhydrous sodium sulphate, filtered and concentrated in vacuo. The crude material was purified by flash chromatography (6% methanol/dichloromethane) to give ethyl 4-((3-(2-cyanoethyl)cyclopentyl)amino)-1H-pyrrolo[2,3-b]pyridine-5-carboxylate as an off white solid (0.08 g, 57% yield): MS (ES) m/z 327.1 (M+H).

Two of the stereoisomers of this compound could be isolated by chiral chromatography and the other 2 were isolated as a mixture using the following conditions.

Analytical Conditions:

Column: CHIRALPAK IC (100 mm×4.6 mm×3 mic)

Mobile phase: n-hexane:ethanol with 0.1% DEA (80:20)

Flow rate: 1.0 mL/min

Synthesis of Example 153: Ethyl 4-((3-(2-cyanoethyl)cyclopentyl)amino)-1H-pyrrolo[2,3-b]pyridine-5-carboxylate as a mixture of 2 stereoisomers

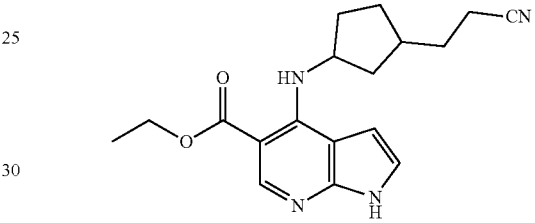

Isolated as an off-white solid (0.022 g, 27% yield): $^1$H NMR (400 MHz, DMSO-$d_6$) δ 11.63 (s, 1H), 8.81 (d, J=6.8 Hz, 1H), 8.51 (s, 1H), 7.15 (s, 1H), 6.65 (s, 1H), 4.54-4.48 (m, 1H), 4.23 (q, J=6.8 Hz, 2H), 2.48-2.30 (m, 1H), 2.22-2.08 (m, 2H), 1.92-1.81 (m, 2H), 1.66-1.31 (m, 4H), 1.29 (t, J=7.2 Hz, 3H), 1.23-1.17 (m, 2H); MS (ES) m/z 327.1 (M+H). Mixture of 2 stereoisomers with retention times 6.96 and 7.68 min.

Synthesis of Example 154: Ethyl 4-((3-(2-cyanoethyl)cyclopentyl)amino)-1H-pyrrolo[2,3-b]pyridine-5-carboxylate, single stereoisomer 1

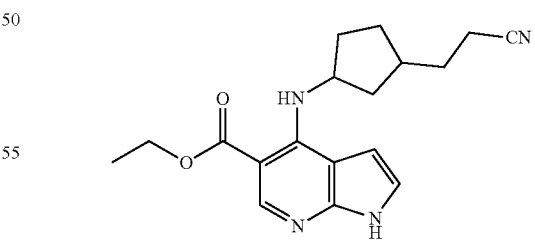

Isolated as an off-white solid (0.0056, 7% yield): $^1$H NMR (400 MHz, DMSO-$d_6$): δ 11.63 (br s, 1H), 8.82 (d, J=6.8 Hz, 1H), 8.51 (s, 1H), 7.15 (s, 1H), 6.65 (s, 1H), 4.49-4.47 (m, 1H), 4.23 (q, J=6.8 Hz, 2H), 2.41-2.37 (m, 1H), 2.17-2.03 (m, 3H), 1.95-1.89 (m, 2H), 1.67-1.62 (m, 3H), 1.29 (t, J=6.8 Hz, 3H), 1.27-1.12 (m, 2H); MS (ES) m/z 327.1 (M+H). Retention time 12.16 min.

Synthesis of Example 155: Ethyl 4-((3-(2-cyano-ethyl)cyclopentyl)amino)-1H-pyrrolo[2,3-b]pyridine-5-carboxylate, single stereoisomer 2

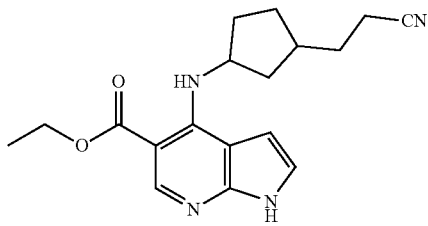 [SMILES: CCOC(=O)c1cnc2[nH]ccc2c1NC1CCC(CCC#N)C1]

Isolated as an off-white solid (0.0138 g, 17% yield): $^1$H NMR (400 MHz, DMSO-d$_6$) δ 11.63 (s, 1H), 8.81 (d, J=6.4 Hz, 1H), 8.51 (s, 1H), 7.15 (s, 1H), 6.64 (s, 1H), 4.54 (br s, 1H), 4.24 (q, J=7.2 Hz, 2H), 2.22-2.09 (m, 3H), 1.94-14.81 (m, 3H), 1.64-1.55 (m, 3H), 1.31 (t, J=6.8 Hz, 3H), 1.27-1.21 (m, 2H); MS (ES) m/z 327.1 (M+H). Retention time 14.02.

Synthesis of Example 156: Preparation of ethyl 4-(((R)-1-((S)-2,2-difluorocyclopropane-1-carbonyl)piperidin-3-yl)amino)-1H-pyrrolo[2,3-b]pyridine-5-carboxylate

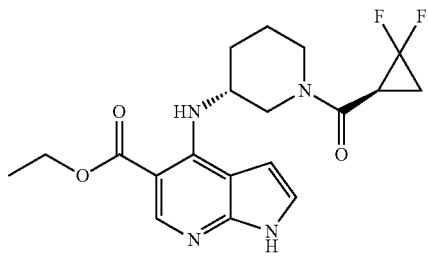 [SMILES: CCOC(=O)c1cnc2[nH]ccc2c1N[C@@H]1CCCN(C(=O)[C@@H]2CC2(F)F)C1]

Scheme 43: Preparation of ethyl 4-(((R)-1-((S)-2,2-difluorocyclopropane-1-carbonyl)piperidin-3-yl)amino-1H-pyrrolo[2,3-b]pyridine-5-carboxylate

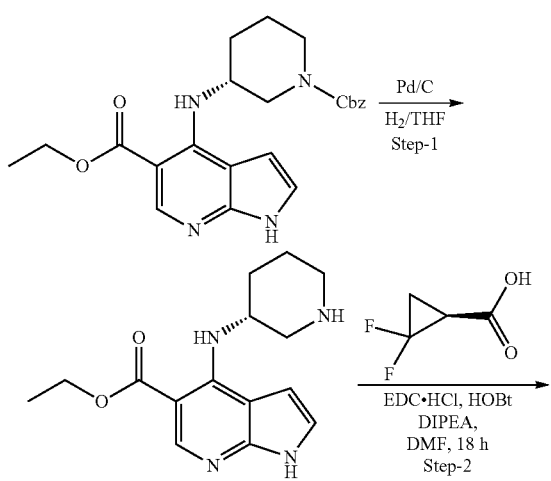

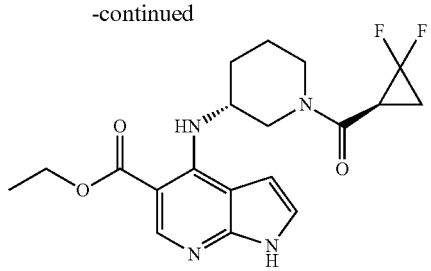

Step 1: Preparation of ethyl (R)-4-(piperidin-3-ylamino)-1H-pyrrolo[2,3-b]pyridine-5-carboxylate

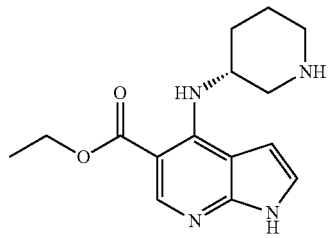 [SMILES: CCOC(=O)c1cnc2[nH]ccc2c1N[C@@H]1CCCNC1]

To a stirred solution of ethyl (R)-4-((1-((benzyloxy)carbonyl)piperidin-3-yl)amino)-1H-pyrrolo[2,3-b]pyridine-5-carboxylate (0.5 g, 1.18 mmol) in tetrahydrofuran (10 mL) was added Pd/C (0.05 g, 50% w/w wet) under argon atmosphere and the resulting mixture was stirred at ambient temperature under hydrogen atmosphere (balloon pressure) for 18 hours. The reaction mixture was filtered through celite and washed with methanol. The filtrate was concentrated in vacuo and the crude was triturated with diethyl ether to provide ethyl (R)-4-(piperidin-3-ylamino)-1H-pyrrolo[2,3-b]pyridine-5-carboxylate as a pale brown solid (0.21 g, 61% yield): MS (ES) m/z 289.2 (M+H).

Step 2: Preparation of ethyl 4-(((R)-1-((S)-2,2-difluorocyclopropane-1-carbonyl)piperidin-3-yl)amino)-1H-pyrrolo[2,3-b]pyridine-5-carboxylate

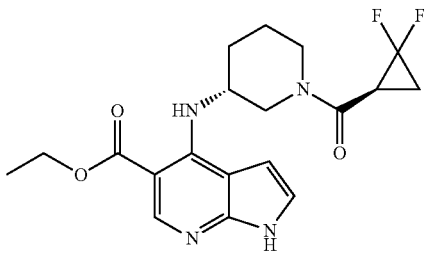

To a solution of ethyl (R)-4-(piperidin-3-ylamino)-1H-pyrrolo[2,3-b]pyridine-5-carboxylate (0.1 g, 0.35 mmol) in dry N,N-dimethyl formamide (7 mL) was added (S)-2,2-difluorocyclopropane-1-carboxylic acid (0.06 g, 0.52 mmol), N-(3-dimethylaminopropyl)-N'-ethylcarbodiimide hydrochloride (0.13 g, 0.69 mmol), hydroxybenzotriazole (0.09 g, 0.69 mmol) and N,N-diisopropylethylamine (0.18 mL, 1.038 mmol) at 0° C. The reaction mixture was stirred at ambient temperature for 18 hours. The reaction mixture was quenched with ice water and extracted with ethyl acetate. The organic layer was washed with brine, dried over sodium sulfate, filtered and concentrated in vacuo. The crude material was purified using flash chromatography (60% ethyl acetate/hexane) to provide ethyl 4-(((R)-1-((S)-2,2-difluorocyclopropane-1-carbonyl)piperidin-3-yl)amino)-1H-pyrrolo[2,3-b]pyridine-5-carboxylate as an off-white solid (0.04 g, 29% yield): $^1$H NMR (400 MHz, DMSO-d$_6$, at 60°): δ 11.54 (s, 1H), 8.79 (s, 1H), 8.54 (s, 1H), 7.16 (s, 1H), 6.65 (s, 1H), 4.25 (s, 3H), 3.70-4.12 (m, 2H), 3.49 (s, 2H), 2.10 (s, 1H), 1.57-1.82 (m, 6H), 1.30 (s, 3H). MS (ES) m/z 393.1 (M+H)

Synthesis of Example 157: Preparation of ethyl-4-(((R)-1-((R)-2,2-difluorocyclopropane-1-carbonyl)piperidin-3-yl)amino)-1H-pyrrolo[2,3-b]pyridine-5-carboxylate

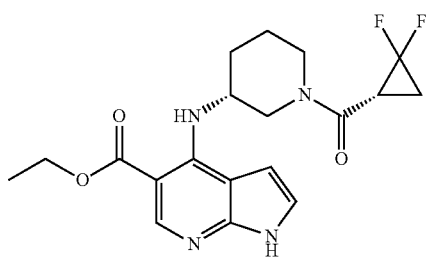

Scheme 44: Preparation of ethyl-4-(((R)-1-((R)-2,2-difluorocyclopropane-1-carbonyl)piperidin-3-yl)amino)-1H-pyrrolo[2,3-b]pyridine-5-carboxylate

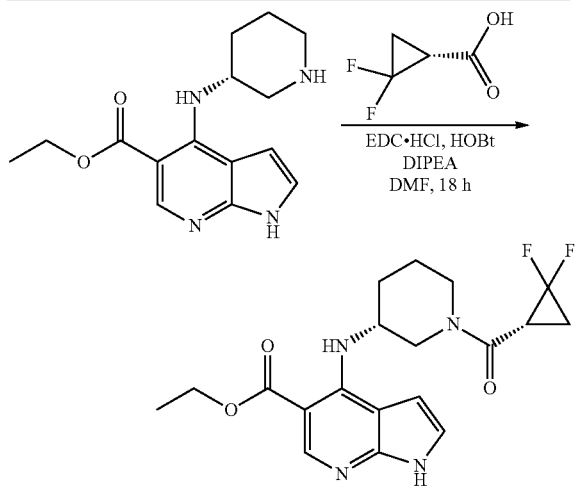

To a solution of ethyl (R)-4-(piperidin-3-ylamino)-1H-pyrrolo[2,3-b]pyridine-5-carboxylate (0.1 g, 0.35 mmol) in dry N,N-dimethyl formamide (7 mL) was added (S)-2,2-difluorocyclopropane-1-carboxylic acid (0.06 g, 0.52 mmol), N-(3-dimethylaminopropyl)-N'-ethylcarbodiimide hydrochloride (0.13 g, 0.69 mmol), hydroxybenzotriazole (0.09 g, 0.69 mmol) and N,N-diisopropylethylamine (0.18 mL, 1.038 mmol) at 0° C. The reaction mixture was stirred at ambient temperature for 18 hours. The reaction mixture was quenched with ice water and extracted with ethyl acetate. The organic layer was washed with brine, dried over sodium sulfate, filtered and concentrated in vacuo. The crude material was purified using flash chromatography (60% ethyl acetate/hexane) to provide ethyl-4-(((R)-1-((R)-2,2-difluorocyclopropane-1-carbonyl)piperidin-3-yl)amino)-1H-pyrrolo[2,3-b]pyridine-5-carboxylate as an off-white solid (0.05 g, 40% yield): $^1$HNMR at 70° C. (400 MHz, DMSO-d$_6$ at 70°): δ 11.49 (s, 1H), 8.78 (s, 1H), 8.55 (s, 1H), 7.14 (s, 1H), 6.61 (s, 1H), 4.26-4.27 (m, 3H), 3.79-3.93 (m, 2H), 3.40-3.54 (m, 2H), 2.11 (brs, 1H), 1.73-1.96 (m, 6H), 1.31 (s, 3H); MS (ES) m/z 393.1 (M+H).

Biological Activity Assay

JAK1 and JAK3 Enzyme Activity Assays

The activity of JAK3 (a.a. 781-1124, ThermoFisher) was quantified by measuring the phosphorylation of SRCtide (FAM-GEEPLYWSFPAKKK-NH$_2$). Kinase reactions were run in a 384-well Greiner plate with 2% final DMSO concentration under the buffer conditions of 20 mM HEPES, pH 7.5, 10 mM MgCl$_2$, 0.01% BSA, and 0.0005% Tween-20. The kinase reaction components were 2.5 nM JAK3, 1 μM SRCtide peptide and 1 uM ATP. Examples were tested in dose-response starting at 2 μM (11 concentrations, 3-fold serial dilution, duplicate reactions). The reactions were incubated at room temperature for 40 minutes, then stopped by adding a 1:1 volume of 30 mM EDTA in 20 mM HEPES, pH 7.5 (15 mM EDTA final). After the reaction was stopped, the phosphorylated and unphosphorylated peptides were separated and quantified using a Caliper LC3000/EZ-Reader system and HTS Well Analyzer Software (Caliper, A PerkinElmer Company, Hopkinton, Mass.). GraFit (Erithacus Software Ltd., Horley, U.K.) was used to calculate inhibitor potency by fitting dose-response data to the 4-parameter logistical IC$_{50}$ equation.

The inhibitory potency of candidate compounds of JAK1 done at Thermo Fisher Scientific in their Selectscreen using a Z-lyte assay. The 2×JAK1/Tyr 06 mixture is prepared in 50 mM HEPES pH 6.5, 0.01% BRIJ-35, 10 mM MgCl2, 1 mM EGTA, 0.02% NaN$_3$. The final 10 μL of the Kinase Reaction consists of 21.2-91.5 ng JAK1 and 2 μM Tyr 06 in 50 mM HEPES pH 7.0, 0.01% BRIJ-35, 10 mM MgCl$_2$, 1 mM EGTA, 0.01% NaN$_3$. After the 1 hour Kinase Reaction incubation, 5 μL of a 1:128 dilution of Development Reagent is added.

Background signal is defined in the absence of enzyme and uninhibited signal is defined in the presence of vehicle (2% DMSO) alone. Compounds were evaluated in an 11 point dose-response ranging from 20 mM to 0.34 nM. IC$_{50}$ values of compounds are determined using a 4 parameter logistical fit of emission ratio as a function of the concentration of compound. The results are shown in Table 2.

TABLE 2

| Example No | JAK1 Inhibition IC$_{50}$<br>+++ indicates ≤ 0.01 μM<br>++ indicates 0.01-0.1 μM<br>+ indicates 0.1-1 μM<br>− indicates > 1 μM | JAK3 Inhibition IC$_{50}$<br>+++ indicates ≤ 0.01 μM<br>++ indicates 0.01-0.1 μM<br>+ indicates 0.1-1 μM<br>− indicates > 1 μM |
|---|---|---|
| 1 | ++ | ++ |
| 3 | +++ | +++ |
| 21 | ++ | +++ |
| 24 | +++ | +++ |
| 34 | + | + |
| 68A | + | + |
| 68B | + | ++ |
| 69 | + | + |
| 70 | ++ | + |
| 72 | ++ | ++ |
| 73 | +++ | ++ |

TABLE 2-continued

| Example No | JAK1 Inhibition IC$_{50}$<br>+++ indicates ≤ 0.01 μM<br>++ indicates 0.01-0.1 μM<br>+ indicates 0.1-1 μM<br>− indicates > 1 μM | JAK3 Inhibition IC$_{50}$<br>+++ indicates ≤ 0.01 μM<br>++ indicates 0.01-0.1 μM<br>+ indicates 0.1-1 μM<br>− indicates > 1 μM |
|---|---|---|
| 74 | ++ | ++ |
| 75 | ++ | ++ |
| 92 | +++ | +++ |
| 94 | Not Determined | ++ |
| 113 | ++ | ++ |
| 117 | +++ | +++ |
| 118 | +++ | ++ |
| 119 | + | + |
| 120 | + | + |
| 121 | + | + |
| 123 | +++ | +++ |
| 123 | +++ | +++ |
| 124 | ++ | ++ |
| 125 | +++ | +++ |
| 126 | ++ | ++ |
| 127 | +++ | ++ |
| 128 | ++ | +++ |
| 129 | +++ | +++ |
| 130 | +++ | +++ |
| 131 | ++ | ++ |
| 132 | +++ | +++ |
| 133 | +++ | +++ |
| 134 | +++ | +++ |
| 135 | +++ | +++ |
| 136 | ++ | ++ |
| 137 | +++ | +++ |
| 138 | ++ | +++ |
| 139 | +++ | +++ |
| 140 | +++ | +++ |
| 141 | ++ | ++ |
| 142 | +++ | ++ |
| 143 | + | ++ |
| 144 | ++ | ++ |
| 145 | +++ | ++ |
| 146 | +++ | +++ |
| 147 | + | + |
| 148 | ++ | +++ |
| 149 | + | ++ |
| 150 | +++ | +++ |
| 151 | +++ | +++ |
| 152 | +++ | +++ |
| 153 | +++ | +++ |
| 154 | + | ++ |
| 155 | + | ++ |
| 156 | Not Determined | ++ |

JAK Cellular Target Modulation Assays

Target modulation was based upon the ability of a compound to inhibit JAK isoform specific phosphorylation of selected substrates. IL-2 stimulated STAT5 phosphorylation on Tyr694 was used to assess JAK1/3 compound selectivity. GM-CSF stimulated STAT5 phosphorylation on Tyr694 was used to assess JAK2 compound selectivity. IFNγ stimulated STAT1 phosphorylation on Tyr701 was used to assess JAK1/2 compound selectivity. For all three assays, human PBMC from frozen stocks were thawed, pelleted, resuspended in complete media (90% RPMI, 10% heat inactivated FBS, 10 mM HEPES, 47 μM 2-ME, pen/strep) and placed in wells of a 96 well V-bottom plate at 200,000 per well in 120 μl complete media. Compounds were added as 15 μl per well of 10× working stock solutions in complete media with 1% DMSO (or medium with 1% DMSO for controls) and placed on a plate shaker in a 37° C. incubator with 5% CO$_2$ for 1 hour with gentle shaking (setting of 3). Stimulation used the addition of soluble cytokines. For the JAK1/3 phospho-STAT5 assay, 15 μl of 10× working stock recombinant human IL-2 was added to a final concentration of 25 ng/ml. For the JAK2 phospho-STAT5 assay, 15 μl of 10× working stock recombinant human GM-CSF was added to a final concentration of 5 ng/ml. For the JAK1/2 phospho-STAT1 assay, 15 μl of 10× working stock of recombinant human IFNγ was added to a final concentration of 10 ng/ml. Plates were then placed back on the plate shaker in the incubator for an additional 5, 5 and 10 minutes respectively upon which the plates were removed from the incubator, sealed with a plate sealer and the cells pelleted at 400×g for 5 minutes. After pelleting, the media was removed by aspiration and the cells were lysed in ELISA specific cell lysis buffer. The levels of phospho-STAT5 were determined using a Phospho (Tyr694)/Total STAT5a,b Whole Cell Lysate kit from Meso Scale Discovery. Levels of phospho-STAT1 were determined using a CST-PathScan Phospho-STAT1 (Tyr701) Sandwich ELISA kit. The results are shown in Table 3.

TABLE 3

| Example No | IL2-STAT5 Inhibition IC$_{50}$<br>++ indicates ≤ 0.1 μM<br>+ indicates 0.1-1 μM<br>− indicates > 1 μM | Infγ-STAT1 IC$_{50}$<br>++ indicates ≤ 0.1 μM<br>+ indicates 0.1-1 μM<br>− indicates > 1 μM |
|---|---|---|
| 1 | + | − |
| 3 | ++ | + |
| 21 | + | − |
| 24 | ++ | + |
| 34 | + | − |
| 68A | − | Not Determined |
| 68B | − | Not Determined |
| 69 | − | Not Determined |
| 70 | + | − |
| 72 | + | − |
| 73 | ++ | ++ |
| 74 | + | − |
| 75 | + | − |
| 92 | ++ | + |
| 113 | + | − |
| 117 | ++ | ++ |
| 118 | ++ | + |
| 119 | − | Not Determined |
| 120 | − | Not Determined |
| 121 | − | Not Determined |
| 123 | ++ | + |
| 124 | + | − |
| 125 | ++ | + |
| 126 | + | − |
| 127 | ++ | + |
| 128 | ++ | − |
| 129 | ++ | + |
| 130 | + | + |
| 131 | + | + |
| 132 | ++ | + |
| 133 | ++ | + |
| 134 | ++ | + |
| 135 | ++ | ++ |
| 136 | + | − |
| 137 | ++ | + |
| 138 | + | + |
| 139 | + | − |
| 140 | + | + |
| 141 | + | − |
| 142 | ++ | + |
| 143 | − | Not Determined |
| 144 | + | + |
| 145 | ++ | + |
| 146 | ++ | ++ |
| 147 | + | − |
| 148 | + | + |
| 149 | + | − |
| 150 | ++ | + |
| 151 | ++ | + |
| 152 | ++ | + |

TABLE 3-continued

| Example No | IL2-STAT5 Inhibition IC$_{50}$<br>++ indicates ≤ 0.1 μM<br>+ indicates 0.1-1 μM<br>− indicates > 1 μM | Infγ-STAT1 IC$_{50}$<br>++ indicates ≤ 0.1 μM<br>+ indicates 0.1-1 μM<br>− indicates > 1 μM |
|---|---|---|
| 153 | ++ | + |
| 154 | + | − |
| 155 | + | − |
| 156 | + | Not Determined |

All references, patents or applications, U.S. or foreign, cited in the application are hereby incorporated by reference as if written herein in their entireties. Where any inconsistencies arise, material literally disclosed herein controls.

From the foregoing description, one skilled in the art can easily ascertain the essential characteristics of this invention, and without departing from the spirit and scope thereof, can make various changes and modifications of the invention to adapt it to various usages and conditions.

What is claimed is:

1. A compound, or a pharmaceutically acceptable salt, hydrate or solvate thereof, of Formula (I):

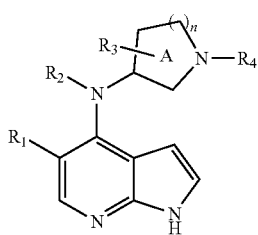

(I)

wherein:
$R_1$ is selected from —CO$_2$R$_5$, —C$_1$-C$_5$alkyl-CO$_2$R$_5$, —C$_3$-C$_6$-cycloalkyl-CO$_2$R$_5$, —NHCO$_2$R$_5$, —N(C$_1$-C$_5$ alkyl)-CO$_2$R$_5$, —O—CO$_2$R$_5$, or —C$_1$-C$_5$alkyl-O—CO$_2$R$_5$;
$R_2$ is selected from H, —C$_1$-C$_4$alkyl, —C$_3$-C$_6$cycloalkyl, or —C$_1$-C$_2$alkyl-C$_3$-C$_6$cycloalkyl, wherein the alkyl or cycloalkyl groups are optionally substituted with one or more groups selected from halogen, —OH, or —O—C$_1$-C$_5$alkyl;
n is 0, 1 or 2;
Ring A is substituted at one or more carbons with one, two, or three $R_3$ substituents wherein each $R_3$ group is independently selected from H, halogen, —C$_1$-C$_4$alkyl, —C$_3$-C$_6$cycloalkyl, —OH, or —O—C$_1$-C$_5$alkyl wherein each alkyl or cycloalkyl group is optionally substituted with one or more groups selected from: halogen, —OH, —C$_1$-C$_5$alkylalkoxy, or —O—C$_1$-C$_5$alkyl;
Two $R_3$ groups on the same or different carbon atoms of the ring A may be optionally joined to form a spirocyclic or bicyclic ring system with ring A;
$R_4$ is selected from —C(O)—R$_6$, —CH$_2$R$_6$, —C(O)—CH═CH$_2$, —C(O)—C(CH$_2$OCH$_3$)═CH$_2$, —C(O)—CH═CHCH$_3$, —C(O)—CH═CHCH$_2$NR$_7$R$_8$, —C(O)—C$_1$-C$_5$alkyl, or —C(O)—C$_3$-C$_6$cycloalkyl, wherein the alkyl or cycloalkyl groups may be optionally substituted with one or more groups selected from —OH, halogen, alkyne, or —CN;
$R_5$ is selected from —C$_1$-C$_5$alkyl, or —C$_3$-C$_6$cycloalkyl wherein the alkyl or cycloalkyl groups may be optionally substituted by one or more groups selected from halogen, —OH, or —O—C$_1$-C$_5$alkyl;
$R_6$ is selected from —C$_1$-C$_5$alkyl, —C$_3$-C$_6$cycloalkyl, —C$_1$-C$_5$alkyl-C$_3$-C$_6$cycloalkyl, —NR$_7$R$_8$, —O-aryl, —O-heteroaryl, or heteroaryl wherein the alkyl, cycloalkyl, or heteroaryl groups can be optionally substituted by one or more groups selected from halogen, —CN, alkyne, —OH, trifluoromethyl, —O—C$_1$-C$_5$alkyl, or —O—C$_3$-C$_6$cycloalkyl;
$R_7$ and $R_8$ are independently selected from H, —C$_1$-C$_5$ alkyl, —C$_1$-C$_5$ alkoxy, or —C$_3$-C$_5$ cycloalkyl wherein the alkyl groups may be optionally substituted by one or more groups selected from halogen, —OH, or —CN; and
$R_7$ and $R_8$ may be optionally joined to form a ring to form a heterocycle or with another heteroatom to form a ring.

2. The compound of claim 1, or a pharmaceutically acceptable salt, hydrate or solvate thereof, wherein:
$R_1$ is —CO$_2$R$_5$.

3. The compound of claim 1, or a pharmaceutically acceptable salt, hydrate or solvate thereof, wherein:
$R_1$ is —C$_1$-C$_5$-alkyl-CO$_2$R$_5$.

4. The compound of claim 1, or a pharmaceutically acceptable salt, hydrate or solvate thereof, wherein:
$R_1$ is —C$_3$-C$_6$-cycloalkyl-CO$_2$R$_5$.

5. The compound of claim 1, or a pharmaceutically acceptable salt, hydrate or solvate thereof, wherein:
$R_1$ is —NHCO$_2$R$_5$.

6. The compound of claim 1, or a pharmaceutically acceptable salt, hydrate or solvate thereof, wherein:
$R_1$ is —N(C$_1$-C$_5$ alkyl)-CO$_2$R$_5$.

7. The compound of claim 1, or a pharmaceutically acceptable salt, hydrate or solvate thereof, wherein:
$R_1$ is —O—CO$_2$R$_5$.

8. The compound of claim 1, or a pharmaceutically acceptable salt, hydrate or solvate thereof, wherein:
$R_1$ is —C$_1$-C$_5$alkyl-O—CO$_2$R$_5$.

9. A compound, or a pharmaceutically acceptable salt, hydrate or solvate thereof, of Formula (III):

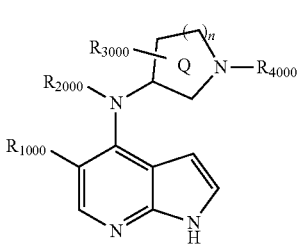

(III)

wherein:
$R_{1000}$ is selected from —CO$_2$R$_{5000}$, —C$_1$-C$_5$alkyl-CO$_2$R$_{5000}$, —C$_3$-C$_6$-cycloalkyl-CO$_2$R$_{5000}$, —NHCO$_2$R$_{5000}$, —N(C$_1$-C$_5$ alkyl)-CO$_2$R$_{5000}$, —O—CO$_2$R$_{5000}$, or —C$_1$-C$_5$alkyl-O—CO$_2$R$_{5000}$;
$R_{2000}$ is selected from H, —C$_1$-C$_4$alkyl, —C$_3$-C$_6$cycloalkyl, or —C$_1$-C$_2$alkyl-C$_3$-C$_6$cycloalkyl, wherein the alkyl or cycloalkyl groups are optionally substituted with one or more groups selected from halogen, —OH, or —O—C$_1$-C$_5$alkyl;
n is 0, 1 or 2;
Ring Q is substituted at one or more carbons with one, two, or three $R_{3000}$ substituents wherein each $R_{3000}$ group is independently selected from H, halogen, —C$_1$-C$_4$alkyl, —C$_3$-C$_6$cycloalkyl, —OH, or —O—C$_1$-

$C_5$alkyl wherein each alkyl or cycloalkyl group is optionally substituted with one or more groups selected from: halogen, —OH, —$C_1$-$C_5$alkylalkoxy, or —O—$C_1$-$C_5$alkyl;

Two $R_{3000}$ groups on the same or different carbon atoms of the ring Q may be optionally joined to form a spirocyclic or bicyclic ring system with ring Q;

$R_{4000}$ is selected from —C(O)—$R_{6000}$, —$CH_2R_{6000}$, —C(O)—CH=$CH_2$, —C(O)—C($CH_2OCH_3$)=$CH_2$, —C(O)—CH=$CHCH_3$, —C(O)—CH=$CHCH_2NR_{7000}R_{8000}$, —C(O)—$C_1$-$C_5$alkyl, or —C(O)—$C_3$-$C_6$cycloalkyl, wherein the alkyl or cycloalkyl groups may be optionally substituted with one or more groups selected from —OH, halogen, alkyne, or —CN;

$R_{5000}$ is selected from H, —$C_1$-$C_5$alkyl, and —$C_3$-$C_6$cycloalkyl wherein the alkyl or cycloalkyl groups may be optionally substituted by one or more groups selected from halogen, —OH, —$C_3$-$C_5$ cycloalkyl, or —O—$C_1$-$C_5$alkyl;

$R_{6000}$ is selected from —$C_1$-$C_5$alkyl, —$C_3$-$C_6$cycloalkyl, —$C_1$-$C_5$alkyl-$C_3$-$C_6$cycloalkyl, —$NR_{7000}R_{8000}$, —O-aryl, —O-heteroaryl, or heteroaryl wherein the alkyl, cycloalkyl, or heteroaryl groups can be optionally substituted by one or more groups selected from halogen, —CN, alkyne, —OH, trifluoromethyl, —O—$C_1$-$C_5$alkyl, or —O—$C_3$-$C_6$cycloalkyl;

$R_{7000}$ and $R_{8000}$ are independently selected from H, —$C_1$-$C_5$ alkyl, —$C_1$-$C_5$ alkoxy, or —$C_3$-$C_5$ cycloalkyl where the alkyl groups may be optionally substituted by one or more groups selected from halogen, —OH, —CN, or —$C_3$-$C_5$ cycloalkyl;

$R_{7000}$ and $R_{8000}$ may be optionally joined to form a ring to form a heterocycle or with another heteroatom to form a ring.

10. The compound of claim 1, wherein the compound is selected from the group consisting of:

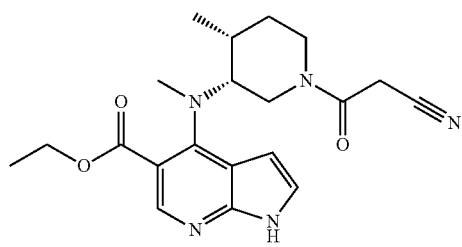

ethyl 4-(((3R,4R)-1-(2-cyanoacetyl)-4-methylpiperidin-3-yl)(methyl)amino)-1H-pyrrolo[2,3-b]pyridine-5-carboxylate,

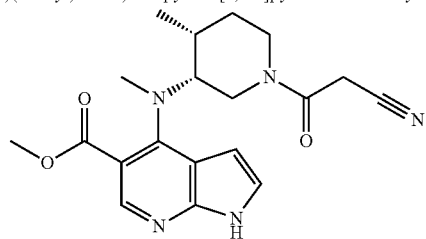

methyl 4-(((3R,4R)-1-(2-cyanoacetyl)-4-methylpiperidin-3-yl)(methyl)amino)-1H-pyrrolo[2,3-b]pyridine-5-carboxylate,

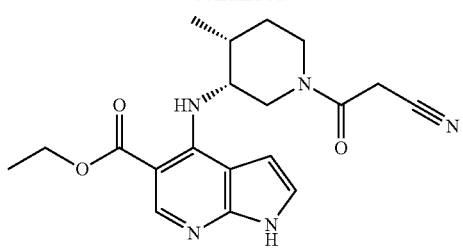

ethyl 4-(((3R,4R)-1-(2-cyanoacetyl)4-methylpiperidin-3-yl)amino)-1H-pyrrolo[2,3-b]pyridine-5-carboxylate,

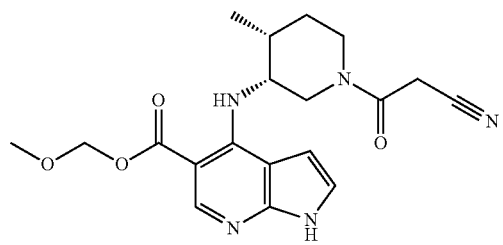

methoxymethyl 4-(((3R,4R)-1-(2-cyanoacetyl)-4-methylpiperidin-3-yl)amino)-1H-pyrrolo[2,3-b]pyridine-5-carboxylate,

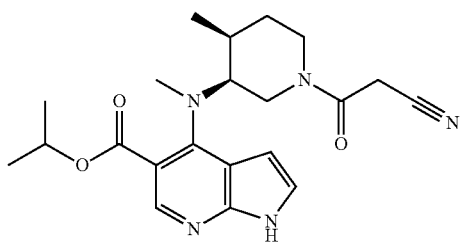

isopropyl 4-(((3S,4S)-1-(2-cyanoacetyl)-4-methylpiperidin-3-yl)(methyl)amino)-1H-pyrrolo[2,3-b]pyridine-5-carboxylate,

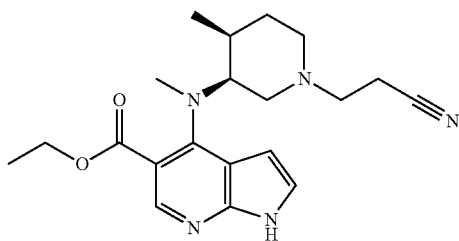

ethyl 4-(((3S,4S)-1-(2-cyanoethyl)-4-methylpiperidin-3-yl)(methyl)amino)-1H-pyrrolo[2,3-b]pyridine-5-carboxylate,

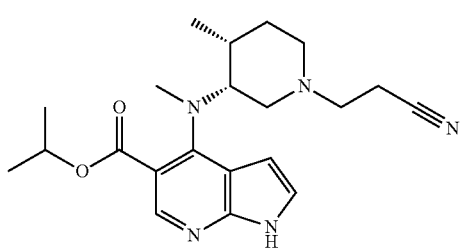

isopropyl 4-(((3R,4R)-1-(2-cyanoethyl)-4-methylpiperidin-3-yl)(methyl)amino)-1H-pyrrolo[2,3-b]pyridine-5-carboxylate,

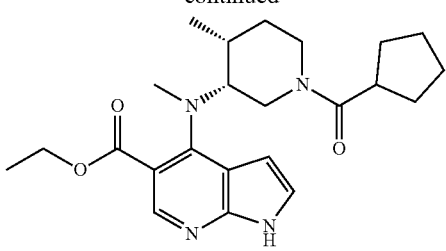

ethyl 4-(((3R,4R)-1-(cyclopentanecarbonyl)-4-methylpiperidin-3-yl)(methyl)amino)-1H-pyrrolo[2,3-b]pyridine-5-carboxylate,

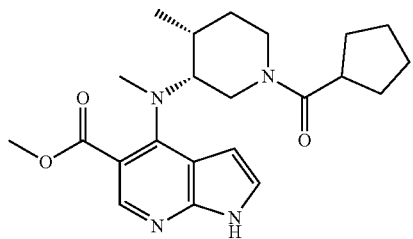

methyl 4-(((3R,4R)-1-(cyclopentanecarbonyl)-4-methylpiperidin-3-yl)(methyl)amino)-1H-pyrrolo[2,3-b]pyridine-5-carboxylate,

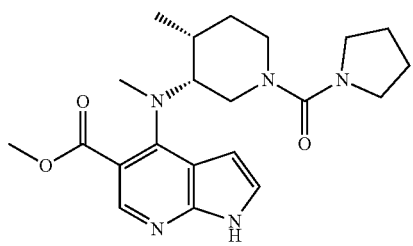

methyl 4-(methyl(3R,4R)-4-methyl-1-(pyrrolidine-1-carbonyl)piperidin-3-yl)amino)-1H-pyrrolo[2,3-b]pyridine-5-carboxylate,

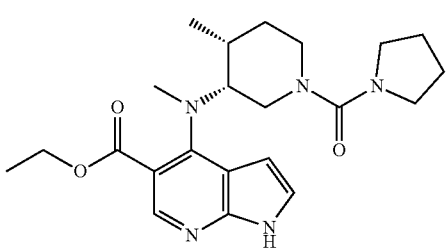

ethyl 4-(methyl(3R,4R)-4-methyl-1-(pyrrolidine-1-carbonyl)piperidin-3-yl)amino)-1H-pyrrolo[2,3-b]pyridine-5-carboxylate,

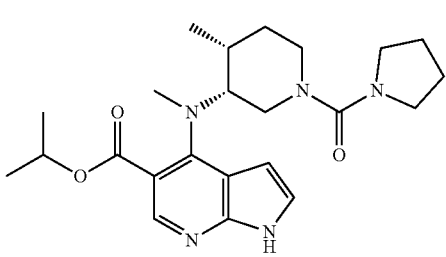

isopropyl 4-(methyl(3R,4R)-4-methyl-1-(pyrrolidine-1-carbonyl)piperidin-3-yl)amino)-1H-pyrrolo[2,3-b]pyridine-5-carboxylate,

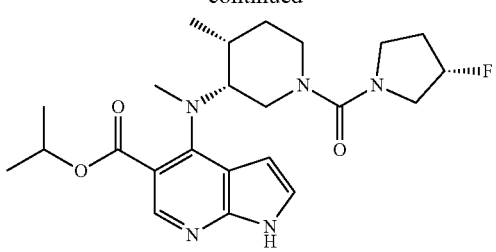

isopropyl 4-(((3R,4R)-1-((S)-3-fluoropyrrolidine-1carbony)-4-methylpiperidin-3-yl)(methyl)amino)-1H-pyrrolo[2,3-b]pyridine-5-carboxylate,

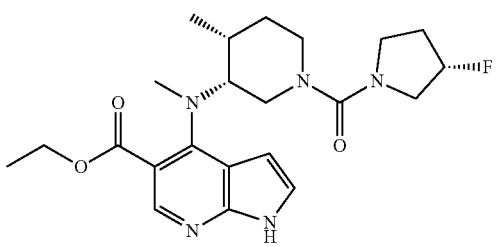

ethyl 4-(((3R,4R)-1-((S)-3-fluoropyrrolidine-1-carbonyl)-4-methylpiperidin-3-yl)(methyl)amino)-1H-pyrrolo[2,3-b]pyridine-5-carboxylate,

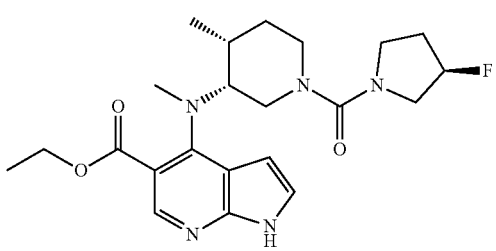

ethyl 4-(((3R,4R)-1-((R)-3-fluoropyrrolidine-1-carbonyl)-4-methylpiperidin-3-yl)(methyl)amino)-1H-pyrrolo[2,3-b]pyridine-5-carboxylate,

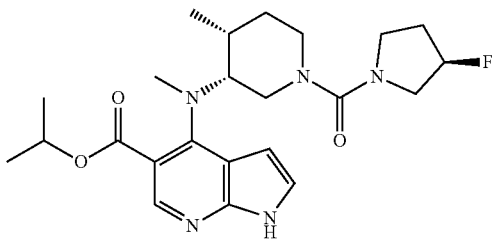

isopropyl 4-(((3R,4R)-1-((R)-3-fluoropyrrolidine-1-carbonyl)-4-methylpiperidin-3-yl)(methyl)amino)-1H-pyrrolo[2,3-b]pyridine-5-carboxylate,

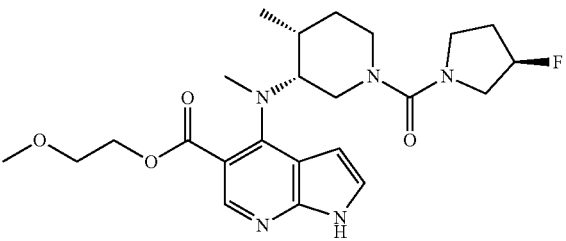

2-methoxyethyl 4-(((3R,4R)-1-((R)-3-fluoropyrrolidine-1-carbonyl)-4-methylpiperidin-3-yl)(methyl)amino)-1H-pyrrolo[2,3-b]pyridine-5-carboxylate,

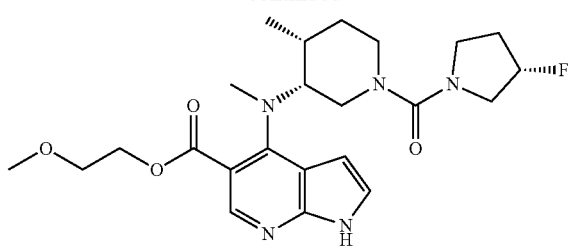

2-methoxyethyl 4-(((3R,4R)-1-((S)-3-fluoropyrrolidine-1-carbonyl)-4-methylpiperidin-3-yl)(methyl)amino)-1H-pyrrolo[2,3-b]pyridine-5-carboxylate,

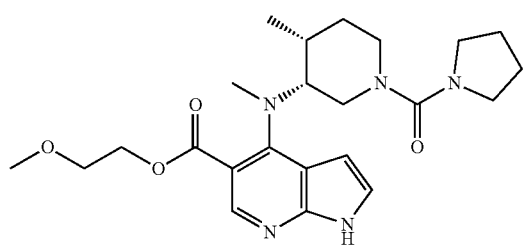

2-methoxyethyl 4-(methyl((3R,4R)-4-methyl-1-(pyrrolidine-1-carbonyl)piperidin-3-yl)amino)-1H-pyrrolo[2,3-b]pyridine-5-carboxylate,

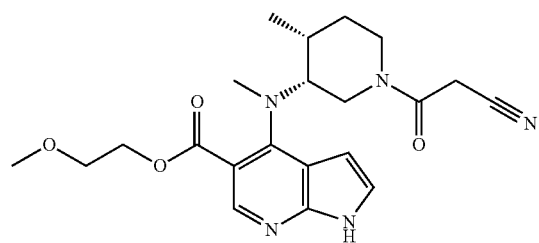

2-methoxyethyl 4-(((3R,4R)-1-(2-cyanoacetyl)-4-methylpiperidin-3-yl)(methyl)amino)-1H-pyrrolo[2,3-b]pyridine-5-carboxylate,

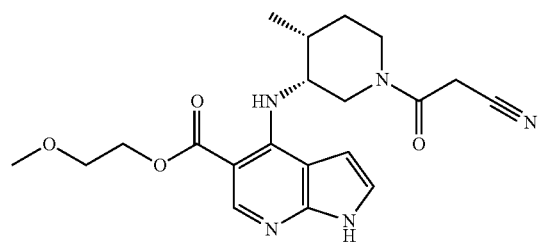

2-methoxyethyl 4-(((3R,4R)-1-(2-cyanoacetyl)-4-methylpiperidin-3-yl)amino)-1H-pyrrolo[2,3-b]pyridine-5-carboxylate,

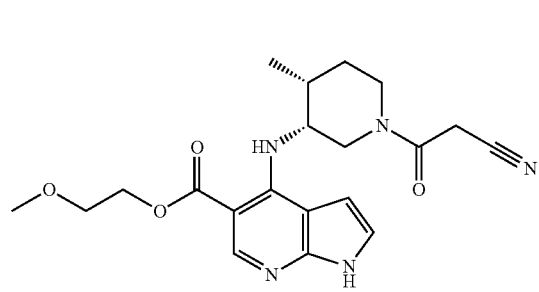

2-methoxyethyl 4-(((3R,4R)-1-(2-cyanoethyl)-4-methylpiperidin-3-yl)amino)-1H-pyrrolo[2,3-b]pyridine-5-carboxylate,

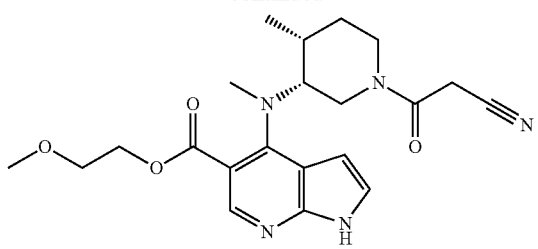

2-methoxyethyl 4-(((3R,4R)-1-(2-cyanoethyl)-4-methylpiperidin-3-yl)(methyl)amino)-1H-pyrrolo[2,3-b]pyridine-5-carboxylate,

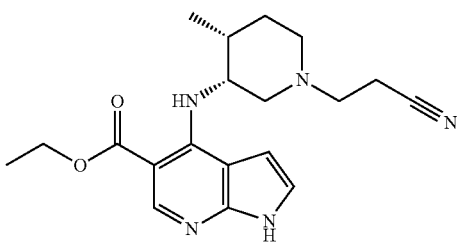

ethyl 4-(((3R,4R)-1-(2-cyanoethyl)-4-methylpiperidin-3-yl)amino)-1H-pyrrolo[2,3-b]pyridine-5-carboxylate,

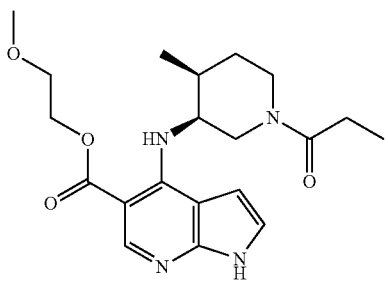

2-methoxyethyl 4-(((3RS,4S)-4-methyl-1-propionylpiperidin-3-yl)amino)-1H-pyrrolo[2,3-b]pyridine-5-carboxylate,

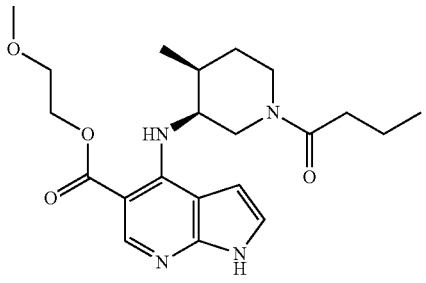

2-methoxyethyl 4-(((3S,4S)-1-butyryl-4-methylpiperidin-3-yl)amino)-1H-pyrrolo[2,3-b]pyridine-5-carboxylate,

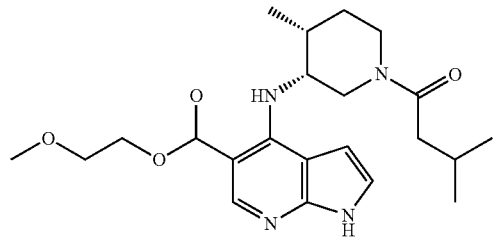

2-methoxyethyl 4-(((3R,4R)-4-methyl-1-(3-methylbutanoyl)piperidin-3-yl)amino)-1H-pyrrolo[2,3-b]pyridine-5-carboxylate,

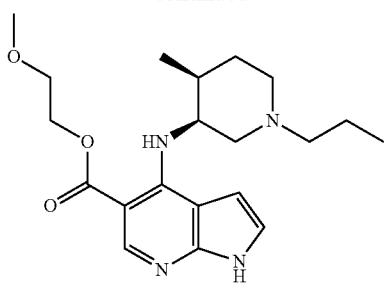

2-methoxyethyl 4-(((3S,4S)-4-methyl-1-propylpiperidin-3-yl)amino)-1H-pyrrolo[2,3-b]pyridine-5-carboxylate,

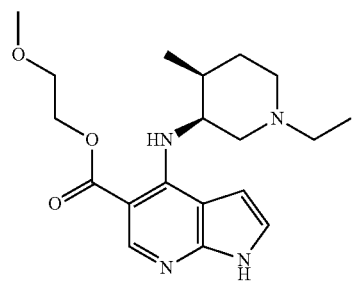

2-methoxyethyl 4-(((3S,4S)-1-ethyl-4-methylpiperidin-3-yl)amino)-1H-pyrrolo[2,3-b]pyridine-5-carboxylate,

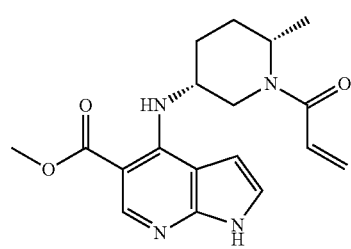

methyl 4-(((3R,6S)-1-acryloyl-6-methylpiperidin-3-yl)amino)-1H-pyrrolo[2,3-b]pyridine-5-carboxylate,

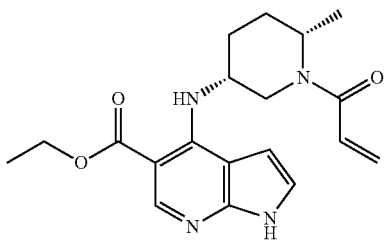

ethyl 4-(((3R,6S)-1-acryloyl-6-methylpiperidin-3-yl)amino)-1H-pyrrolo[2,3-b]pyridine-5-carboxylate,

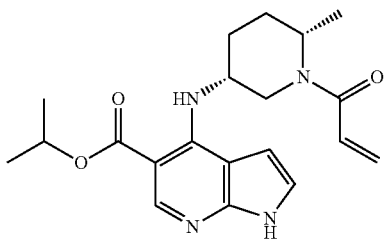

isopropyl 4-(((3R,6S)-1-acryloyl-6-methylpiperidin-3-yl)amino)-1H-pyrrolo[2,3-b]pyridine-5-carboxylate,

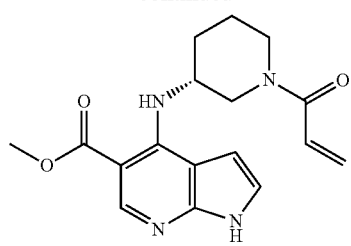

methyl (R)-4-((1-acryloylpiperidin-3-yl)amino)-1H-pyrrolo[2,3-b]pyridine-5-carboxylate,

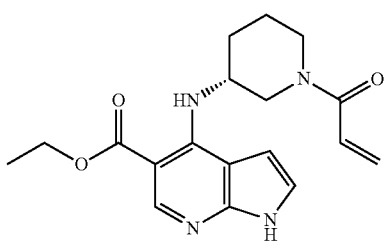

ethyl (R)-4-((1-acryloylpiperidin-3-yl)amino)-1H-pyrrolo[2,3-b]pyridine-5-carboxylate,

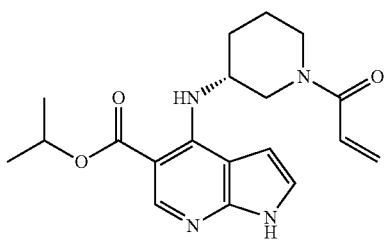

isopropyl) (R)-4-((1-acryloylpiperidin-3-yl)amino)-1H-pyrrolo[2,3-b]pyridine-5-carboxylate,

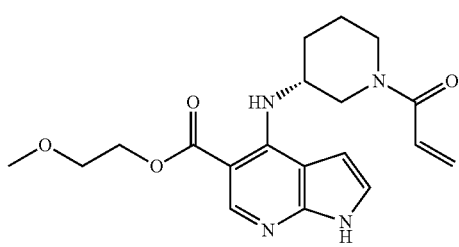

2-methoxyethyl (R)-4-((1-acryloylpiperidin-3-yl)amino)-1H-pyrrolo[2,3-b]pyridine-5-carboxylate,

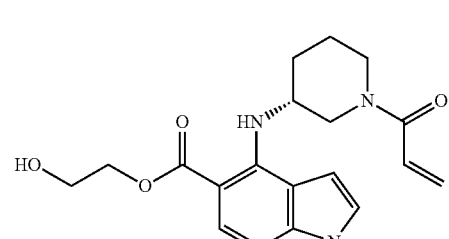

2-hydroxyethyl (R)-4-((1-acryloylpiperidin-3-yl)amino)-1H-pyrrolo[2,3-b]pyridine-5-carboxylate, -continued

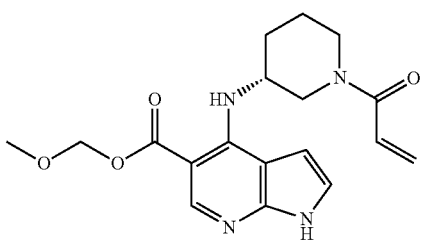

methoxymethyl (R)-4-((1-acryloylpiperidin-3-yl)amino)-1H-pyrrolo[2,3-b]pyridine-5-carboxylate,

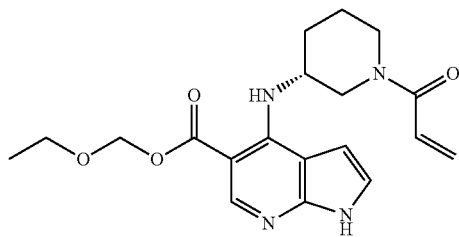

ethoxymethyl (R)-4-((1-acryloylpiperidin-3-yl)amino)-1H-pyrrolo[2,3-b]pyridine-5-carboxylate,

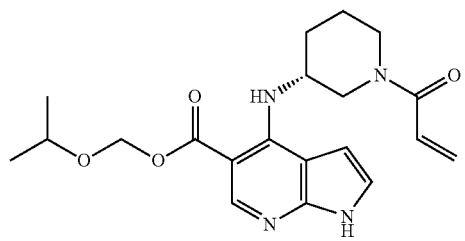

isopropoxymethyl (R)-4-((1-acryloylpiperidin-3-yl)amino)-1H-pyrrolo[2,3-b]pyridine-5-carboxylate,

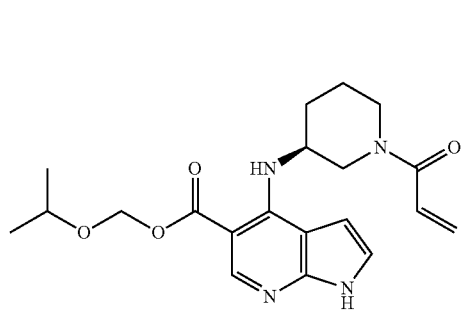

isopropoxymethyl (S)-4-((1-acryloylpiperidin-3-yl)amino)-1H-pyrrolo[2,3-b]pyridine-5-carboxylate,

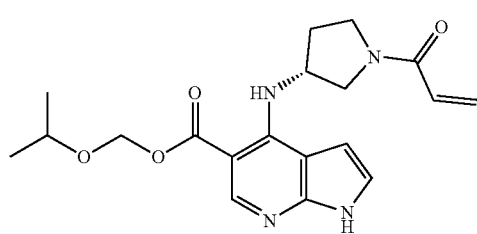

isopropoxymethyl (R)-4-((1-acryloylpyrrolidin-3-yl)amino)-1H-pyrrolo[2,3-b]pyridine-5-carboxylate, -continued

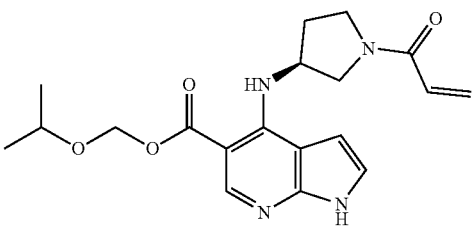

isopropoxymethyl (S)-4-((1-acryloylpyrrolidin-3-yl)amino)-1H-pyrrolo[2,3-b]pyridine-5-carboxylate,

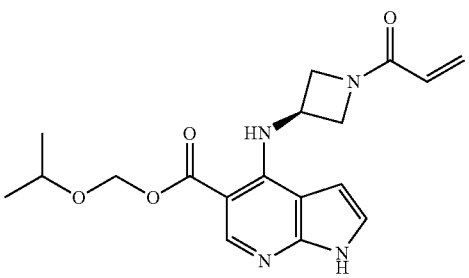

isopropoxymethyl 4-((1-acryloylazetidin-3-yl)amino)-1H-pyrrolo[2,3-b]pyridine-5-carboxylate,

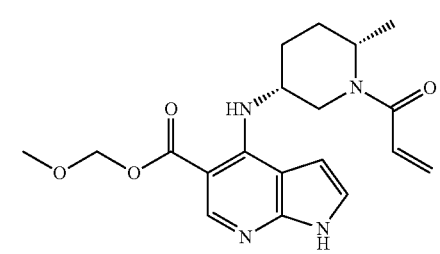

methoxymethyl 4-(((3R,6S)-1-acryloyl-6-methylpiperidin-3-yl)amino)-1H-pyrrolo[2,3-b]pyridine-5-carboxylate,

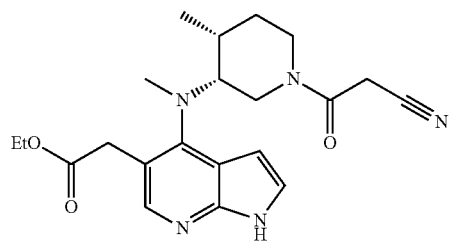

ethyl 2-(4-(((3R,4R)-1-(2-cyanoacetyl)-4-methylpiperidin-3-yl)(methyl)amino)-1H-pyrrolo[2,3-b]pyridin-5-carboxylate,

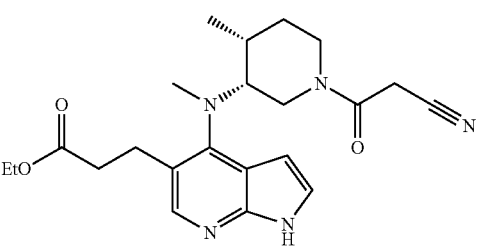

ethyl 3-(4-(((3R,4R)-1-(2-cyanoacetyl)-4-methylpiperidin-3-yl)(methyl)amino)-1H-pyrrolo[2,3-b]pyridin-5-yl)propanoate

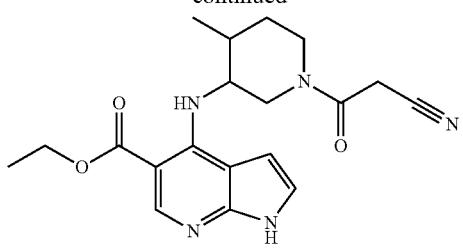

ethyl 4-((1-(2-cyanoacetyl)-4-methylpiperidin-3-yl)amino)-1H-pyrrolo[2,3-b]pyridine-5-carboxylate,

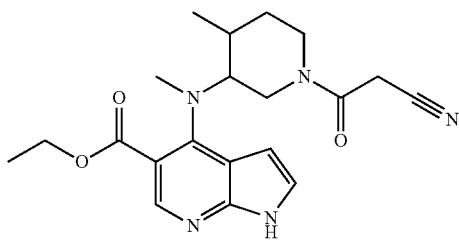

ethyl 4-((1-(2-cyanoacetyl)-4-methylpiperidin-3-yl)(methyl)amino)-1H-pyrrolo[2,3-b]pyridine-5-carboxylate,

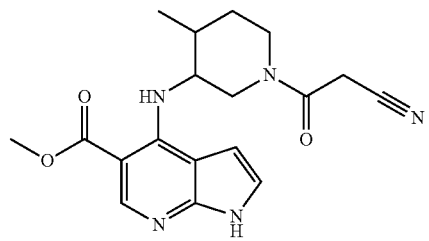

methyl 4-((1-(2-cyanoacetyl)-4-methylpiperidin-3-yl)amino)-1H-pyrrolo[2,3-b]pyridine-5-carboxylate,

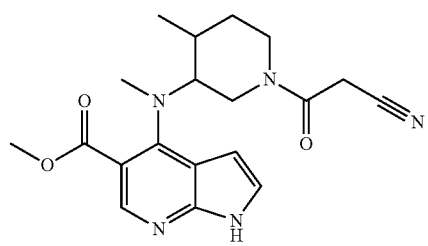

methyl 4-((1-(2-cyanoacetyl)-4-methylpiperidin-3-yl)(methyl)amino)-1H-pyrrolo[2,3-b]pyridine-5-carboxylate,

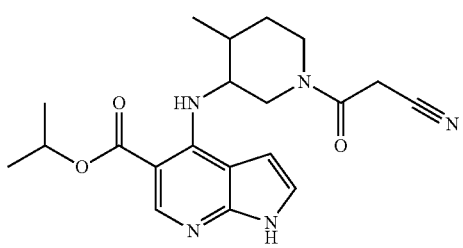

isopropyl 4-((1-(2-cyanoacetyl)-4-methylpiperidin-3-yl)amino)-1H-pyrrolo[2,3-b]pyridine-5-carboxylate,

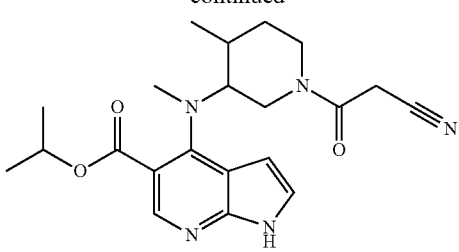

isopropyl 4-((1-(2-cyanoacetyl)-4-methylpiperidin-3-yl)methyl)amino)-1H-pyrrolo[2,3-b]pyridine-5-carboxylate,

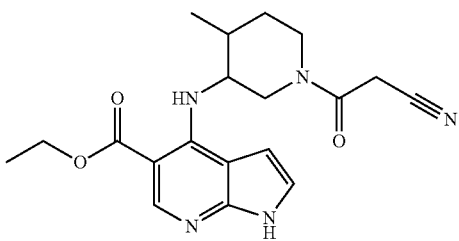

ethyl 4-((1-(2-cyanoethyl)-4-methylpiperidin-3-yl)amino)-1H-pyrrolo[2,3-b]pyridine-5-carboxylate,

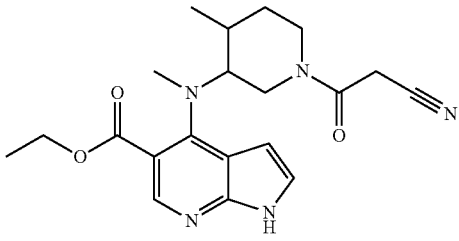

ethyl 4-((1-(2-cyanoethyl)-4-methylpiperidin-3-yl)(methyl)amino)-1H-pyrrolo[2,3-b]pyridine-5-carboxylate,

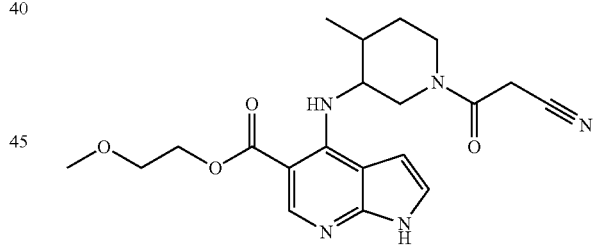

2-methoxyethyl 4-((1-(2-cyanoethyl)-4-methylpiperidin-3-yl)amino)-1H-pyrrolo[2,3-b]pyridine-5-carboxylate,

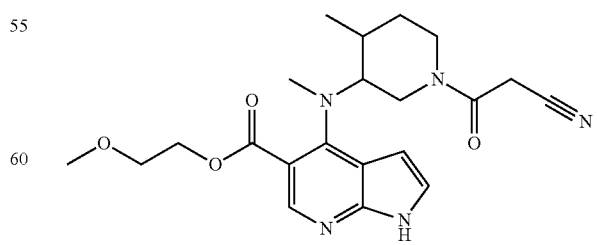

2-methoxyethyl 4-((1-(2-cyanoethyl)-4-methylpiperidin-3-yl)amino)-1H-pyrrolo[2,3-b]pyridine-5-carboxylate,

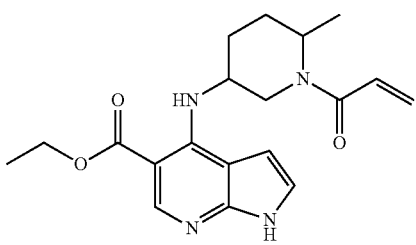

ethyl 4-((1-acryloyl-6-methylpiperidin-3-yl)amino)-1H-pyrrolo[2,3-b]pyridine-5-carboxylate,

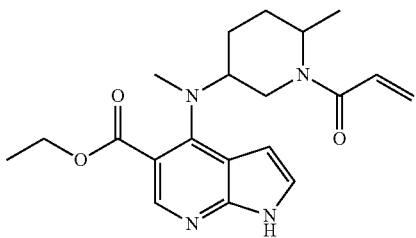

ethyl 4-((1-acryloyl-6-methylpiperidin-3-yl)(methyl)amino)-1H-pyrrolo[2,3-b]pyridine-5-carboxylate,

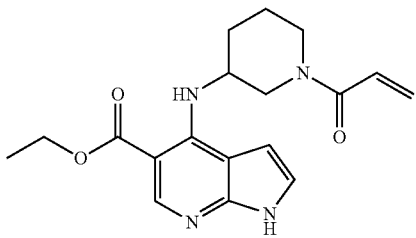

ethyl 4-((1-acryloylpiperidin-3-yl)amino)-1H-pyrrolo[2,3-b]pyridine-5-carboxylate,

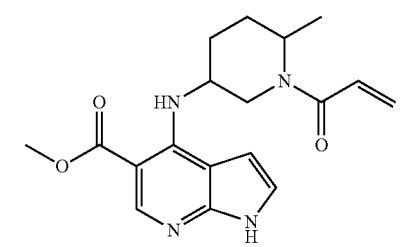

methyl 4-((1-acryloyl-6-methylpiperidin-3-yl)amino)-1H-pyrrolo[2,3-b]pyridine-5-carboxylate,

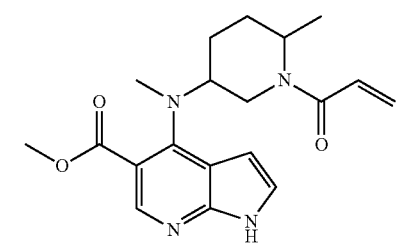

methyl 4-((1-acryloyl-6-methylpiperidin-3-yl)(methyl)amino)-1H-pyrrolo[2,3-b]pyridine-5-carboxylate,

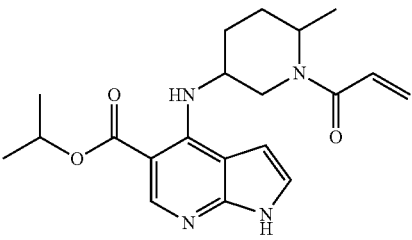

isopropyl 4-((1-acryloyl-6-methylpiperidin-3-yl)amino)-1H-pyrrolo[2,3-b]pyridine-5-carboxylate,

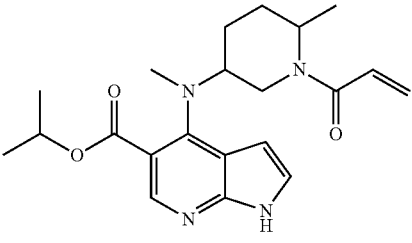

isopropyl 4-((1-acryloyl-6-methylpiperidin-3-yl)(methyl)amino)-1H-pyrrolo[2,3-b]pyridine-5-carboxylate,

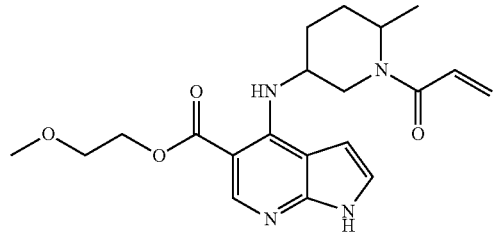

2-methoxyethyl 4-((1-acryloyl-6-methylpiperidin-3-yl)amino)-1H-pyrrolo[2,3-b]pyridine-5-carboxylate,

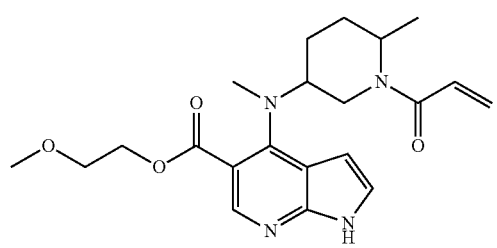

2-methoxyethyl 4-((1-acryloyl-6-methylpiperidin-3-yl)(methyl)amino)-1H-pyrrolo[2,3-b]pyridine-5-carboxylate,

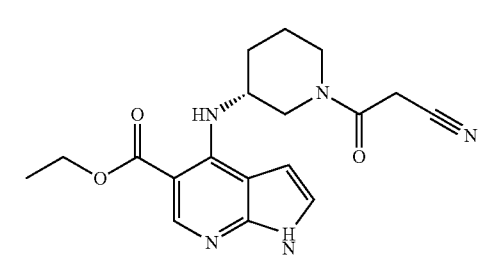

ethyl (R)-4-((1-(2-cyanoacetyl)piperidin-3-yl)amino)-1H-pyrrolo[2,3-b]pyridine-5-carboxylate, -continued

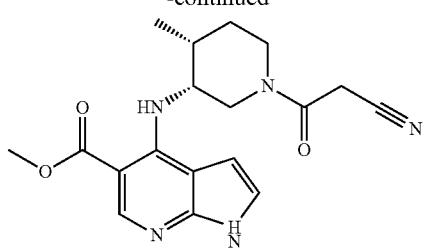

methyl 4-(((3R,4R)-1-(2-cyanoacetyl)-4-methylpiperidin-3-yl)amino)-1H-pyrrolo[2,3-b]pyridine-5-carboxylate,

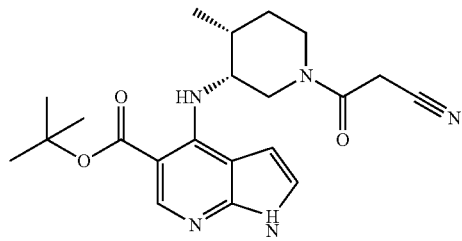

tert-butyl 4-(((3R,4R)-1-(2-cyanoacetyl)-4-methylpiperidin-3-yl)amino)-1H-pyrrolo[2,3-b]pyridine-5-carboxylate,

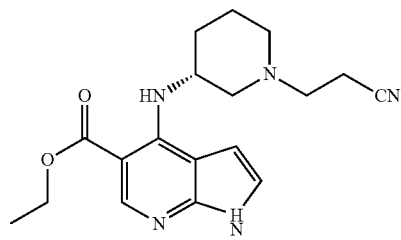

ethyl (R)-4-((1-(2-cyanoacetyl)piperidin-3-yl)amino)-1H-pyrrolo[2,3-b]pyridine-5-carboxylate,

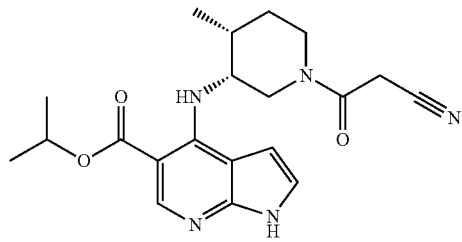

isopropyl 4-(((3R,4R)-1-(2-cyanoacetyl)-4-methylpiperidin-3-yl)amino)-1H-pyrrolo[2,3-b]pyridine-5-carboxylate,

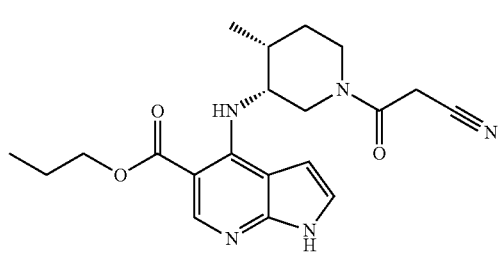

propyl 4-(((3R,4R)-1-(2-cyanoacetyl)-4-methylpiperidin-3-yl)amino)-1H-pyrrolo[2,3-b]pyridine-5-carboxylate, -continued

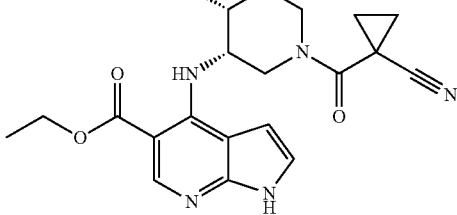

ethyl 4-(((3R,4R)-1-(2-cyanocyclopropane-1-carbonyl)-4-methylpiperidin-3-yl)amino)-1H-pyrrolo[2,3-b]pyridine-5-carboxylate,

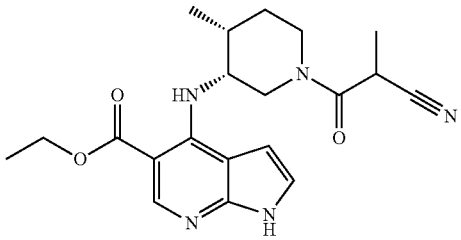

ethyl 4-(((3R,4R)-1-(2-cyanopropanoyl)-4-methylpiperidin-3-yl)amino)-1H-pyrrolo[2,3-b]pyridine-5-carboxylate,

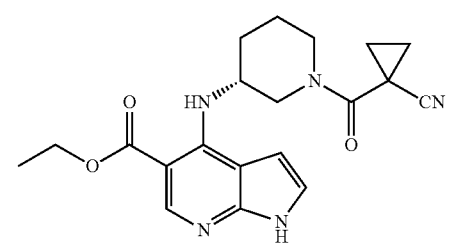

ethyl (R)-4-((1-(1-cyanocyclopropane)-1-carbonyl)piperidin-3-yl)amino)-1H-pyrrolo[2,3-b]pyridine-5-carboxylate,

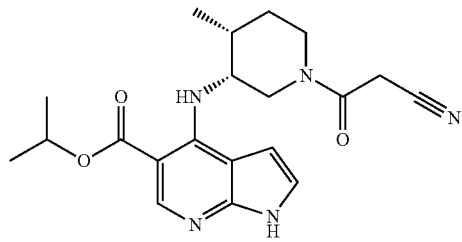

ethyl 4-(((3R)-1-(2-cyanopropanoyl)piperidin-3-yl)amino)-1H-pyrrolo[2,3-b]pyridine-5-carboxylate,

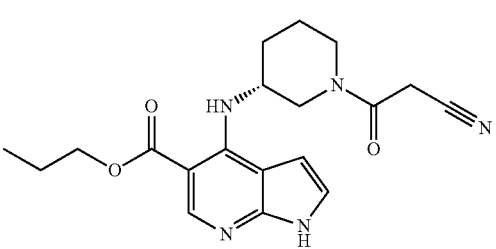

proyl (R)-4-((1-(2-cyanoacetyl)piperidin-3-yl)amino)-1H-pyrrolo[2,3-b]pyridine-5-carboxylate,

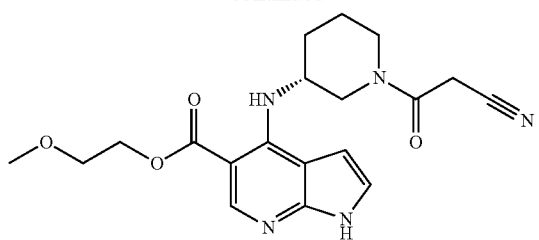

2-methoxyethyl (R)-4-((1-(2-cyanoacetyl)piperidin-3-yl)amino)-1H-pyrrolo[2,3-b]pyridine-5-carboxylate,

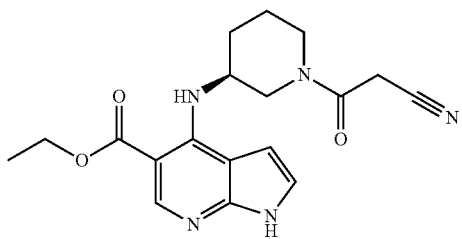

ethyl (S)-4-((1-(2-cyanoacetyl)piperidin-3-yl)amino)-1H-pyrrolo[2,3-b]pyridine-5-carboxylate,

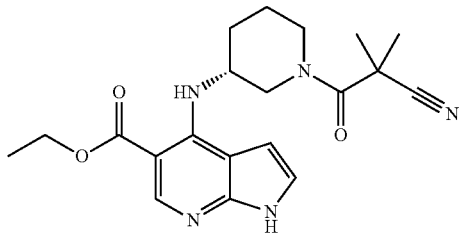

ethyl (R)-4-((1-(2-cyano-2-methylpropanoyl)piperidin-3-yl)amino)-1H-pyrrolo[2,3-b]pyridine-5-carboxylate,

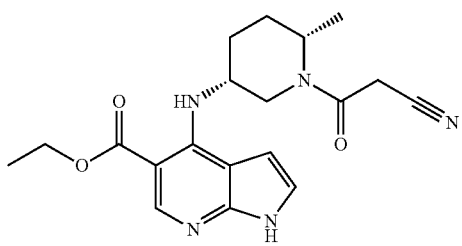

ethyl 4-(((3R,6S)-1-(2-cyanoacetyl)-6-methylpiperidin-3-yl)amino)-1H-pyrrolo[2,3-b]pyridine-5-carboxylate,

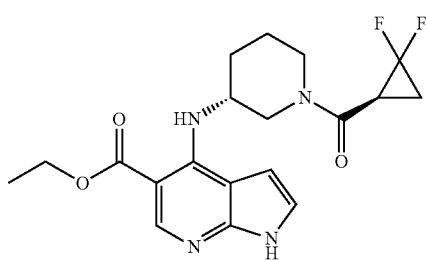 [SMILES: CCOC(=O)c1cnc2[nH]ccc2c1N[C@@H]1CCCN(C(=O)[C@@H]2CC2(F)F)C1]

ethyl 4-(((R)-1-((S)-2,2-difluorocyclopropane-1-carbonyl)piperidin-3-yl)amino)-1H-pyrrolo[2,3-b]pyridine-5-carboxylate,

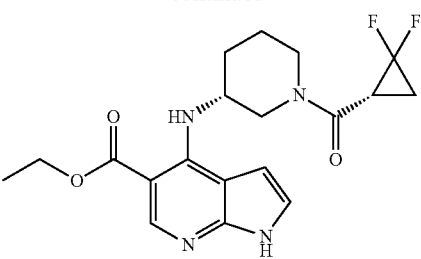 [SMILES: CCOC(=O)c1cnc2[nH]ccc2c1N[C@@H]1CCCN(C(=O)[C@H]2CC2(F)F)C1]

ethyl-4-(((R)-1-((R)-2,2-difluorocyclopropane-1-carbonyl)piperidin-3-yl)amino)-1H-pyrrolo[2,3-b]pyridine-5-carboxylate,

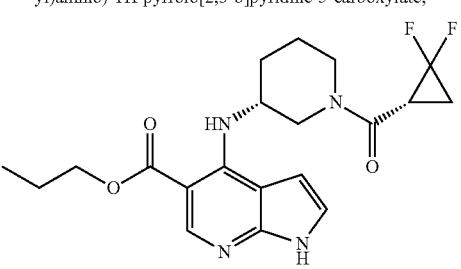

propyl 4-(((R)-1-((R)-2,2-difluorocyclopropane-1-carbonyl)piperidin-3-yl)amino)-1H-pyrrolo[2,3-b]pyridine-5-carboxylate,

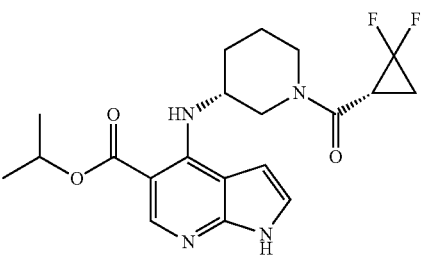

isopropyl 4-(((R)-1-((R)-2,2-difluorocyclopropane-1-carbonyl)piperidin-3-yl)amino)-1H-pyrrolo[2,3-b]pyridine-5-carboxylate,

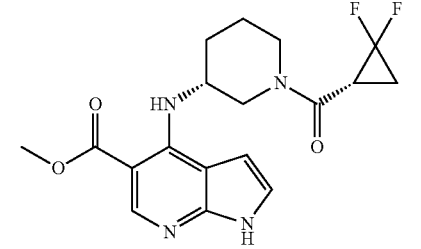

methyl 4-(((R)-1-((R)-2,2-difluorocyclopropane-1-carbonyl)piperidin-3-yl)amino)-1H-pyrrolo[2,3-b]pyridine-5-carboxylate,

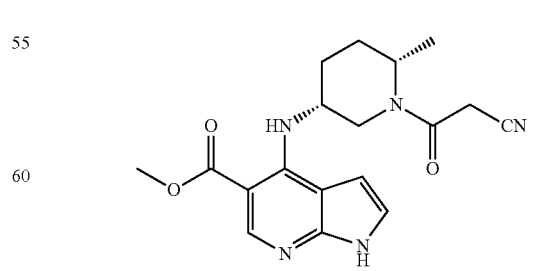

methyl 4-(((3R,6S)-1-(2-cyanoacetyl)-6-methylpiperidin-3-yl)amino)-1H-pyrrolo[2,3-b]pyridine-5-carboxylate,

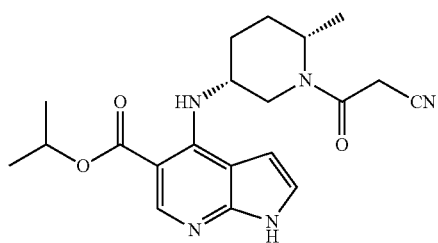

isopropyl 4-(((3R,6S)-1-(2-cyanoacetyl)-6-methylpiperidin-3-yl)amino)-
1H-pyrrolo[2,3-b]pyridine-5-carboxylate,

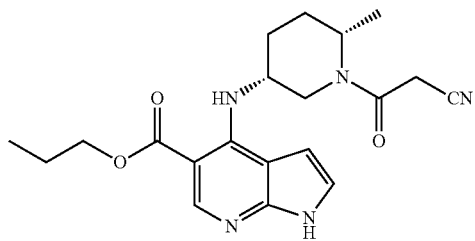

propyl 4-(((3R,6S)-1-(2-cyanoacetyl)-6-methylpiperidin-3-yl)amino)-
1H-pyrrolo[2,3-b]pyridine-5-carboxylate,

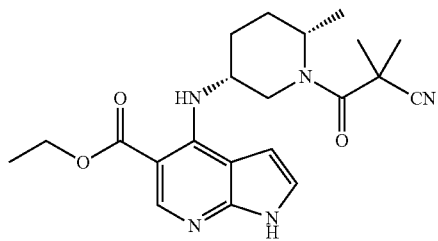

ethyl 4-(((3R,6S)-1-(2-cyano-2-methylpropanoyl)-6-methylpiperidin-3-
yl)amino)-1H-pyrrolo[2,3-b]pyridine-5-carboxylate,

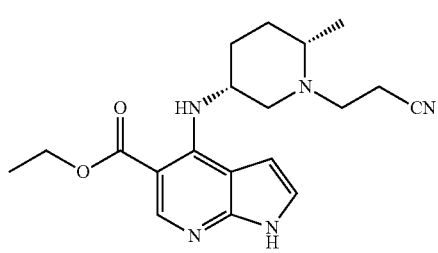

ethyl 4-(((3R,6S)-1-(2-cyanoethyl)-6-methylpiperidin-3-yl)amino)-1H-
pyrrolo[2,3-b]pyridine-5-carboxylate,

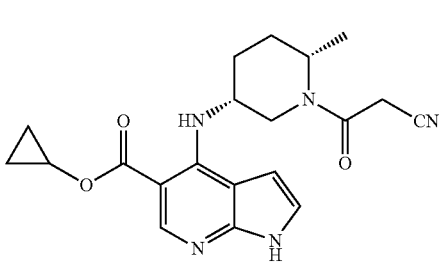

cyclopropyl 4-(((3R,6S)-1-(2-cyanoacetyl)-6-methylpiperidin-3-yl)amino)-
1H-pyrrolo[2,3-b]pyridine-5-carboxylate,

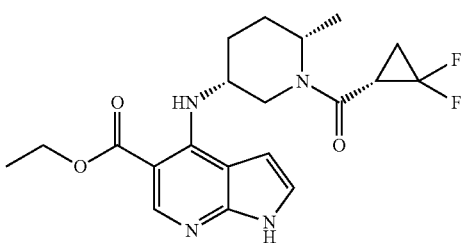

ethyl 4-(((3R,6S)-1-((S)-2,2-difluorocyclopropane-1-carbonyl)-6-
methylpiperidin-3-yl)amino)-1H-pyrrolo[2,3-b]pyridine-5-carboxylate,

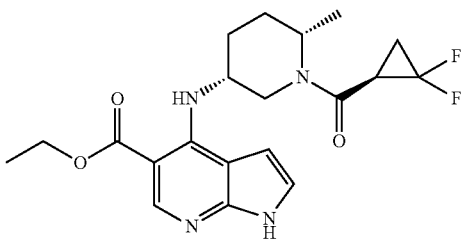

ethyl 4-(((3R,6S)-1-((R)-2,2-difluorocyclopropane-1-carbonyl)-6-
methylpiperidin-3-yl)amino)-1H-pyrrolo[2,3-b]pyridine-5-carboxylate,

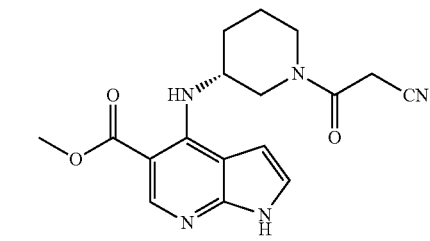

methyl (R)-4-((1-(2-cyanoacetyl)piperidin-3-yl)amino)-1H-pyrrolo[2,3-
b]pyridine-5-carboxylate,

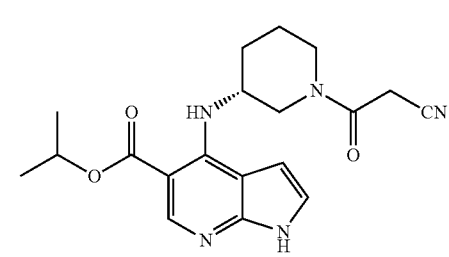

isopropyl (R)-4-((1-(2-cyanoacetyl)piperidin-3-yl)amino)-1H-pyrrolo[2,3-
b]pyridine-5-carboxylate,

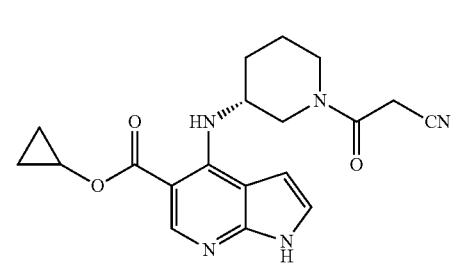

cyclopropyl (R)-4-((1-(2-cyanoacetyl)piperidin-3-yl)amino)-1H-pyrrolo[2,3-
b]pyridine-5-carboxylate, -continued

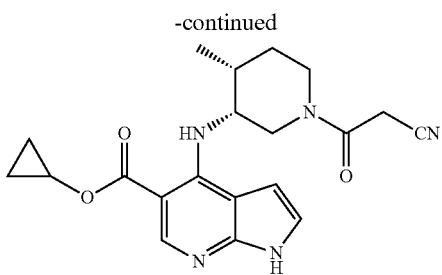

cyclopropyl 4-(((3R,4R)-1-(2-cyanoacetyl)-4-methylpiperidin-3-yl)amino)-
1H-pyrrolo[2,3-b]pyridine-5-carboxylate,

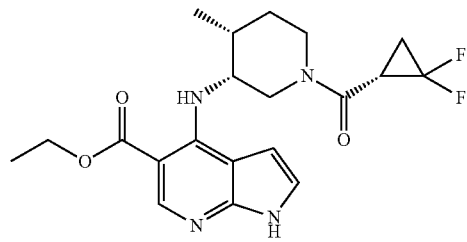

ethyl 4-(((3R,4R)-1-((S)-2,2-difluorocyclopropane-1-carbonyl)-4-
methylpiperidin-3-yl)amino)-1H-pyrrolo[2,3-b]pyridine-5-carboxylate,

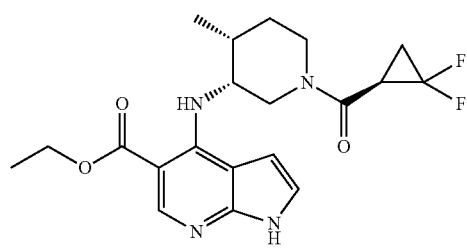

ethyl 4-(((3R,4R)-1-((R)-2,2-difluorocyclopropane-1-carbonyl)-4-
methylpiperidin-3-yl)amino)-1H-pyrrolo[2,3-b]pyridine-5-carboxylate,

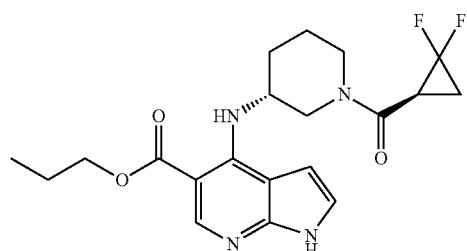

propyl 4-(((R)-1-((S)-2,2-difluorocyclopropane-1-carbonyl)piperidin-3-
yl)amino)-1H-pyrrolo[2,3-b]pyridine-5-carboxylate,

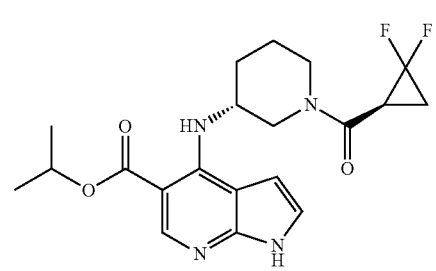

ispropyl 4-(((R)-1-((S)-2,2-difluorocyclopropane-1-carbonyl)piperidin-3-
yl)amino)-1H-pyrrolo[2,3-b]pyridine-5-carboxylate, or -continued

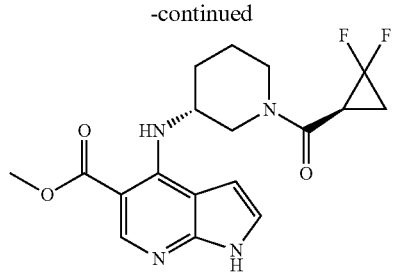

methyl 4-(((R)-1-((S)-2,2-difluorocyclopropane-1-carbonyl)piperidin-3-
yl)amino)-1H-pyrrolo[2,3-b]pyridine-5-carboxylate.

11. The compound of claim 9, wherein the compound is selected from the group consisting of:

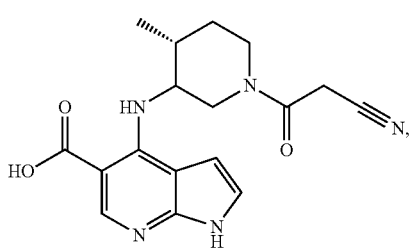

4-(((3R,4R)-1-(2-cyanoacetyl)-4-methylpiperidin-3-
yl)amino)-1H-pyrrolo[2,3-b]pyridine-5-
carboxylic acid,

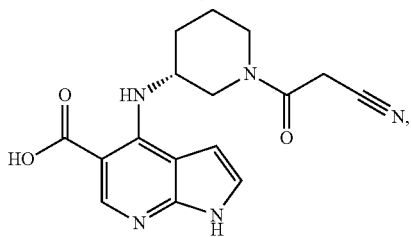

(R)-4-((1-(2-cyanoacetyl)piperidin-3-yl)amino)-
1H-pyrrolo[2,3-b]pyridine-5-carboxylic acid,

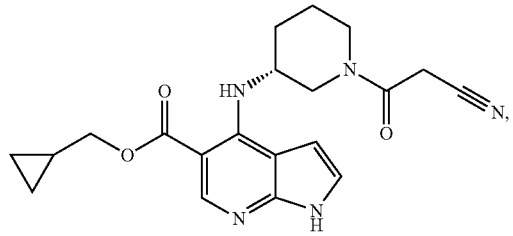

cyclopropylmethyl (R)-4-((1-(2-cyanoacetyl)piperidin-
3-yl)amino)-1H-pyrrolo[2,3-b]pyridine-5-carboxylate,

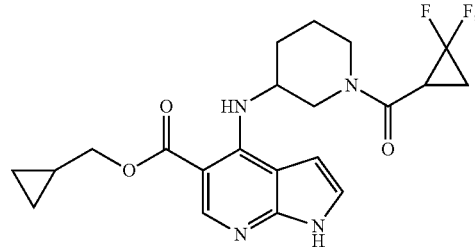

cyclopropylmethyl 4-((1-(2,2-difluorocyclopropane-1-
carbonyl)piperidin-3-yl)amino)-1H-pyrrolo[2,3-b]pyridine-5-
carboxylate,

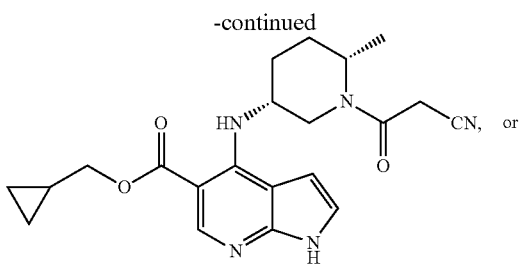

cyclopropylmenthyl 4-(((3R,6S)-1-(2-cyanoacetyl)-6-methylpiperidin-3-yl)amino-1H-pyrrolo[2,3-b]pyridine-5-carboxylate,

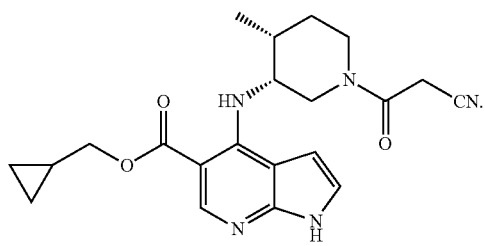

cyclopropylmentyl 4-(((3R,4R)-1-(2-cyanoacetyl)-4-methylpiperidin-3-yl)amino)-1H-pyrrolo[2,3-b]pyridine-5-carboxylate.

12. A pharmaceutical composition comprising a therapeutically effective amount of a compound of claim 1, a pharmaceutically acceptable salt thereof, a derivative thereof, or a combination thereof; and a pharmaceutically acceptable carrier.

13. A method of treating a JAK1- and/or JAK3-mediated disease in a subject in need thereof comprising administering to the subject a therapeutically effective amount of a compound of claim 1, a derivative thereof, or a combination thereof.

14. The method of claim 13, further comprising administering another therapeutic agent.

15. The method of claim 13, wherein said JAK1- and/or JAK3-mediated disease is selected from the group consisting of an autoimmune disorder, broad activation of the immune responses, bacterial infection, viral infection, inflammation, a chronic inflammatory disorder, an acute inflammatory disorder or condition, an auto-inflammatory disorder, a fibrotic disorders, a metabolic disorders, a neoplasm, a cardiovascular disorders, a cerebrovascular disorders, a skin disorder, pruritus, a hair loss disorder, a cancer, autoimmune connective tissue disease, an autoimmune condition, Still's disease, adult-onset Still's disease, Th17-associated inflammation, polychondritis, relapsing polychondritis, myositis, polymyositis, autoimmune myositis, dermatomyositis, juvenile dermatomyositis, myasthenia gravis, Arthritis, rheumatoid arthritis, juvenile rheumatoid arthritis, systemic-onset juvenile rheumatoid arthritis, osteoarthritis, infectious arthritis, inflammatory arthritis, inflammatory bowel disease-associated arthritis, idiopathic arthritis, juvenile idiopathic arthritis, systemic juvenile idiopathic arthritis, psoriatic arthritis, spondylitis/spondyloarthritis/spondyloarthropathy, ankylosing spondylitis, gout, scleroderma, systemic scleroderma, juvenile scleroderma, Reiter's syndrome/reactive arthritis, lyme disease, lupus/systemic lupus erythematosus (SLE), lupus erythematosus, pediatric systemic lupus erythematosus, cutaneous lupus, subacute cutaneous lupus, chronic cutaneous lupus/discoid lupus, chilblain lupus erythematosus, polymyalgia rheumatica, enthesitis, mixed connective tissue disease, enthesopathy, carditis, myocarditis, angiogenesis disorders, myelodysplastic syndrome, atherosclerosis, restenosis, restenosis of an atherosclerotic coronary artery, acute coronary syndrome, myocardial infarction, cardiac-allograft vasculopathy, transplant arteriopathy, vasculitis, large vessel vasculitis, small vessel vasculitis, giant-cell arteritis, polyarteritis nodosa, vasculitis syndromes, Takayasu's arteritis, Wegener's granulomatosis, Behcet's Disease, stimulator of interferon genes (STING) associated vasculopathy with onset in infancy (SAVI), a gastrointestinal disorder, enterocolitis, colitis, inflammatory bowel disease, ulcerative colitis, Crohn's disease, irritable bowel syndrome, enteritis syndrome/spastic colon, celiac disease, acute and chronic pancreatitis, primary biliary cirrhosis, primary sclerosing cholangitis, jaundice, cirrhosis, primary biliary cirrhosis, cirrhosis due to fatty liver disease, alcoholic and nonalcoholic steatosis, esophagitis, gastritis, gastric and duodenal ulcers, peritonitis, Nephropathy, immunologically mediated glomerulonephropathy, autoimmune nephropathy, membranous glomerulopathy, a chronic progressive nephropathy, diabetic kidney disease/diabetic nephropathy, renal fibrosis, renal ischemic/reperfusion injury, HIV associated nephropathy, ureteral obstructive nephropathy, glomerulosclerosis, proteinuria, nephrotic syndrome, polycystic kidney disease, autosomal dominant polycystic kidney disease, glomerulonephritis, chronic kidney disease, diabetic nephropathy, hypertension induced nephropathy, diabetic kidney disease, lupus nephritis, interstitial cystitis periodontitis, gingivitis pulmonary inflammation, sinusitis, pneumonia, bronchitis, asthma, bronchial asthma, Churg-Strauss syndrome, bronchiolitis, bronchiolitis obliterans, chronic obstructive pulmonary disease (COPD), interstitial lung disease, pulmonary fibrosis, idiopathic pulmonary fibrosis, acute lung injury, cystic fibrosis, chronic obstructive pulmonary disease, adult respiratory distress syndrome, acute lung injury, drug-induced lung injury, Meniere's disease, an ocular disorder, ocular inflammation, uveitis, dry eye/keratoconjunctivitis sicca, scleritis, episcleritis, keratitis/keratopathy, choroiditis, retinal vasculitis, optic neuritis, retinopathy, diabetic retinopathy, immune mediated retinopathy, macular degeneration, wet macular degeneration, age related macular degeneration, Mastocytosis, iron deficiency anemia, uremia, hypereosinophilic syndrome (HES), systemic mast cell disease (SMCD), myelodysplastic syndrome, idiopathic thrombocytic pupura, bone resorption diseases, a Neurodegenerative disorder, a neurological/neuromuscular disorders, multiple sclerosis, Parkinson's disease, Huntington's disease, amyotrophic lateral sclerosis (ALS), familial ALS, sporadic ALS, Alzheimer's disease, myasthenia gravis, Lambert-Eaton myasthenic syndrome (LEMS), Guillain-Barret syndrome, meningitis, encephalitis, traumatic brain injury, nervous system damage, delusional parasitosis, dysregulation of neuronal processes and sensory perception, stroke/neuronal ischemia, spinal cord injury, peripheral neuropathy, tactile hallucinations, spinal cord injury, psychiatric disease, pain, acute pain, chronic pain, neuropathic pain, fibromyalgia, paresthetica, nerve irritation, peripheral neuropathy, pruritus/itch atopic pruritus, xerotic pruritus, pruritus associated with psoriasis/psoriatic itch/psoriasis-associated itch, acute pruritus, chronic pruritus, idiopathic pruritus, chronic idiopathic itch, biliary itch, hepatobiliary-associated itch, renal associated itch/renal itch, uremic itch, cholestasis, intrahepatic cholestasis of pregnancy, lichen simplex chronicus associated pruritus, lymphoma-associated itch, leukemia-associated itch, prurigo nodularis, atopic dermatitis-associated itch, atopic itch/atopic puritis, bullous itch, brachioradial pruritus, neurogenic itch, neuropathic itch, notalgia paresthetica, pruritic popular eruption of HIV, psychogenic itch, swimmer's itch, pruritus or uremic itch, urticarial itch, a dermatologic disorders, dermatologic drug reactions/drug eruptions, xerosis/dry skin, skin rash, skin sensitization, skin irritation, sunburn, shaving, body louse, head lice/pediculosis, pubic lice, cutaneous larva migrans, scabies, parasitic infection, insect infestation, urticarial/hives, popular uritcaria, insect bites, insect stings, dandruff, fungal infection, herpes, varicella/chicken pox, eosinophilic folliculitis, dermatosis of pregnancy/pruritic urticarial papules and plaques of pregnancy (PUPP), inflammatory dermatoses, neutrophilic dermatoses, histiocytoid neutrophilic dermatosis, bowel-bypass syndrome dermatosis, psoriasis/psoriasis vulgaris, lichen planus, lichen sclerosus, acne, acne vulgaris, comedonal acne, inflammatory acne, nodulo-cystic acne, scarring acne, acne keloidalis nuchae, atopies, allergic contact sensitization, allergic dermatitis, dermatitis, atopic dermatitis/eczema, contact dermatitis, photodermatitis, seborrheic dermatitis, stasis dermatitis, acute febrile neutrophilic dermatosis (Sweet's syndrome), chronic atypical neutrophilic dermatosis with lipodystrophy and elevated temperature syndrome (CANDLE Syndrome), hidradenitis suppurativa, hives, pyoderma gangrenosum, alopecia, eyebrow alopecia, intranasal hair alopecia, scarring alopecia, central centrifugal cicatricial alopecia, nonscarring alopecia, alopecia areata (AA), patchy AA, alopecia totalis (AT), alopecia universalis (AU), ophiasis pattern alopecia areata, sisaihpo pattern alopecia areata, androgenetic/androgenic alopecia (AGA)/male and female pattern AGA, telogen effluvium, tinea capitis, hypotrichosis, hereditary hypotrichosis simplex, lichen planopilaris, frontal fibrosing alopecia, punctate palmoplantar keratoderma, erythema elevatinum diutinum (EED), neutrophilic eccrine hidradenitis, palisading neutrophilic granulomatous dermatitis, neutrophilic urticarial dermatosis, vitiligo, segmental vitiligo, unisegmental vitiligo, bisegmental vitiligo, multisegmental vitiligo, non-segmental vitiligo, acral, facial, acrofacial vitiligo, centrofacial vitiligo, mucosal vitiligo, confetti vitiligo, trichrome vitiligo, marginal inflammatory vitiligo, quadrichrome vitiligo, blue vitiligo, Koebner phenomenon, vulgaris vitiligo, generalized vitiligo, universal vitiligo, mixed vitiligo/nonsegmental associated with segmental vitiligo, focal vitiligo, solitary mucosal vitiligo, vitiligo with or without leukotricia, bullous diseases, immunobullous diseases, bullous pemphigoid, cicatricial pemphigoid, pemphigus vulgaris, linear IgA disease, gestational pemphigoid, xeroderma pigmentosum, disorders of fibrosis and scarring, fibroids, hepatic fibrosis, low grade scarring, scleroderma, increased fibrosis, keloids, post-surgical scars, wound healing, surgical scarring, radiation induced fibrosis, CNS scarring, alimentary track or gastrointestinal fibrosis, renal fibrosis, hepatic or biliary fibrosis, liver fibrosis, cardiac fibrosis, ophthalmic scarring, fibrosclerosis, scar growth, wound or scab healing, keloid, mediastinal fibrosis, myelofibrosis, retroperitoneal fibrosis/Ormond's disease, progressive massive fibrosis, nephrogenic systemic fibrosis, Sjorgren's syndrome, sarcoidosis, familial Mediterranean fever, Cryopyrin associated periodic syndrome, Muckle-Wells syndrome, familial cold auto-inflammatory syndrome/familial cold uticaria/TNF receptor associated periodic syndrome, neonatal-onset multisystem inflammatory disease, hyperoxia induced inflammation, reperfusion injury, post-surgical trauma, tissue injury, elevated temperature syndrome, diabetes, Type I diabetes, Type II diabetes, diabetes mellitus, Hashimoto's thyroiditis, Graves' disease, Addison's disease, Castleman's disease, hyperparathyroidism, menopause, obesity, steroid-resistance, glucose intolerance, metabolic syndrome, thyroid illness, hypophysitis, systemic immune senescence, autoimmune atrophic gastritis, autoimmune atrophic gastritis of pernicious anemia, autoimmune encephalomyelitis, autoimmune orchitis, Goodpasture's disease, Sjogren's syndrome, autoimmune thrombocytopenia, sympathetic ophthalmia, secondary hematologic manifestations of autoimmune diseases, autoimmune hemolytic syndromes, autoimmune hemolytic anemia, autoimmune and inflammatory hepatitis, autoimmune ovarian failure, autoimmune thrombocytopenia, silicone implant associated autoimmune disease, drug-induced autoimmunity, HIV-related autoimmune syndrome, metal-induced autoimmunity, autoimmune deafness, autoimmune thyroid disorders, allergy and allergic reactions, a Type I hypersensitivity reactions, a Type II hypersensitivity reactions, a Type III hypersensitivity reaction diseases, a Type IV hypersensitivity reaction, acute and chronic infection, sepsis syndrome, sepsis, septic shock, endotoxic shock, exotoxin-induced toxic shock, gram negative sepsis, gram positive sepsis, fungal sepsis, toxic shock syndrome, graft vs. host reaction/graft vs. host disease, allograft rejection, early transplantation rejection, lymphoma, leukemia, multiple myeloma, a solid tumor, teratoma, metastatic cancer, a bone disorders, internal cancer, bone cancer, mouth/pharynx cancer, esophagus cancer, larynx cancer, stomach cancer, intestinal cancer, colon cancer, rectum cancer, lung cancer, liver cancer, pancreas cancer, nerve cancer, brain cancer, head and neck cancer, throat cancer, ovary cancer, uterus cancer, prostate cancer, testis cancer, bladder cancer, kidney cancer, breast cancer, gall bladder cancer, cervix cancer, thyroid cancer, prostate cancer, eye cancer, skin cancer, a fibrotic cancer, fibroma, fibroadenomas, fibrosarcoma, a myeloproliferative disorder, neoplasm, hematopoietic neoplasm, a myeloid neoplasm, a lymphoid neoplasm, myelofibrosis, primary myelofibrosis, polycythemia vera, essential thrombocythemia, acute lymphocytic leukemia, acute and chronic myelogenous leukemia, chronic lymphocytic leukemia, acute lymphoblastic leukemia, chronic myelomonocytic leukemia (CMML), or promyelocytic leukemia, multiple myeloma, a myeloid malignancy myeloid metaplasia with myelofibrosis (MMM), primary myelofibrosis (PMF), idiopathic myelofibrosis (IMF), Hodgkin's disease, cutaneous lymphoma, cutaneous T-cell lymphoma, mycosis fungoides, B-cell lymphoma, T-cell lymphoma, mantle cell lymphoma, hairy cell lymphoma, Burkitt's lymphoma, mast cell tumors, Hodgkin's disease, non-Hodgkin's disease, Kaposi's sarcoma, rhabdomyosarcoma, seminoma, teratocarcinoma, osteosarcoma, thyroid follicular cancer, increased accumulation of exogenous opioids or synthetic opioids, notalgia paraesthetica, obsessive-compulsive disorders, nostalgia associated with obsessive-compulsive disorders, and a combination thereof.

16. The method of claim 14, wherein the other therapeutic agent is selected from a chemotherapeutic agent, an anti-proliferative agent, an anti-inflammatory agent, an immunomodulatory agent, immunosuppressive agent, a neurotrophic factor, an agent for treating cardiovascular disease, an agent for treating diabetes, an agent for treating immunodeficiency disorders, and a combination thereof.

17. A pharmaceutical composition comprising a therapeutically effective amount of a compound of claim 9, a pharmaceutically acceptable salt thereof, a derivative thereof, or a combination thereof and a pharmaceutically acceptable carrier.

18. A method of treating a JAK1- and/or JAK3-mediated disease in a subject in need thereof comprising administering to the subject a therapeutically effective amount of a compound of claim 9, a derivative thereof, or a combination thereof.

19. The method of claim 18, further comprising administering another therapeutic agent.

20. The method of claim 18, wherein said JAK1- and/or JAK3-mediated disease is selected from the group consisting of an autoimmune disorder, broad activation of the immune responses, bacterial infection, viral infection, inflammation, a chronic inflammatory disorder, an acute inflammatory disorder or condition, an auto-inflammatory disorder, a fibrotic disorder, a metabolic disorder, a neoplasm, a cardiovascular disorder, a cerebrovascular disorder, a skin disorder, pruritus, a hair loss disorder, a cancer, autoimmune connective tissue disease, an autoimmune condition, Still's disease, adult-onset Still's disease, Th17-associated inflammation, polychondritis, relapsing polychondritis, myositis, polymyositis, autoimmune myositis, dermatomyositis, juvenile dermatomyositis, myasthenia gravis, Arthritis, rheumatoid arthritis, juvenile rheumatoid arthritis, systemic-onset juvenile rheumatoid arthritis, osteoarthritis, infectious arthritis, inflammatory arthritis, inflammatory bowel disease-associated arthritis, idiopathic arthritis, juvenile idiopathic arthritis, systemic juvenile idiopathic arthritis, psoriatic arthritis, spondylitis/spondyloarthritis/spondyloarthropathy, ankylosing spondylitis, gout, scleroderma, systemic scleroderma, juvenile scleroderma, Reiter's syndrome/reactive arthritis, lyme disease, lupus/systemic lupus erythematosus (SLE), lupus erythematosus, pediatric systemic lupus erythematosus, cutaneous lupus, subacute cutaneous lupus, chronic cutaneous lupus/discoid lupus, chilblain lupus erythematosus, polymyalgia rheumatica, enthesitis, mixed connective tissue disease, enthesopathy, carditis, myocarditis, angiogenesis disorders, myelodysplastic syndrome, atherosclerosis, restenosis, restenosis of an atherosclerotic coronary artery, acute coronary syndrome, myocardial infarction, cardiac-allograft vasculopathy, transplant arteriopathy, vasculitis, large vessel vasculitis, small vessel vasculitis, giant-cell arteritis, polyarteritis nodosa, vasculitis syndromes, Takayasu's arteritis, Wegener's granulomatosis, Behcet's Disease, stimulator of interferon genes (STING) associated vasculopathy with onset in infancy (SAVI), a gastrointestinal disorder, enterocolitis, colitis, inflammatory bowel disease, ulcerative colitis, Crohn's disease, irritable bowel syndrome, enteritis syndrome/spastic colon, celiac disease, acute and chronic pancreatitis, primary biliary cirrhosis, primary sclerosing cholangitis, jaundice, cirrhosis, primary biliary cirrhosis, cirrhosis due to fatty liver disease, alcoholic and nonalcoholic steatosis, esophagitis, gastritis, gastric and duodenal ulcers, peritonitis, Nephropathy, immunologically mediated glomerulonephropathy, autoimmune nephropathy, membranous glomerulopathy, a chronic progressive nephropathy, diabetic kidney disease/diabetic nephropathy, renal fibrosis, renal ischemic/reperfusion injury, HIV associated nephropathy, ureteral obstructive nephropathy, glomerulosclerosis, proteinuria, nephrotic syndrome, polycystic kidney disease, autosomal dominant polycystic kidney disease, glomerulonephritis, chronic kidney disease, diabetic nephropathy, hypertension induced nephropathy, diabetic kidney disease, lupus nephritis, interstitial cystitis, periodontitis, gingivitis, pulmonary inflammation, sinusitis, pneumonia, bronchitis, asthma, bronchial asthma, Churg-Strauss syndrome, bronchiolitis, bronchiolitis obliterans, chronic obstructive pulmonary disease (COPD), interstitial lung disease, pulmonary fibrosis, idiopathic pulmonary fibrosis, acute lung injury, cystic fibrosis, chronic obstructive pulmonary disease, adult respiratory distress syndrome, acute lung injury, drug-induced lung injury, Meniere's disease, an ocular disorder, ocular inflammation, uveitis, dry eye/keratoconjunctivitis sicca, scleritis, episcleritis, keratitis/keratopathy, choroiditis, retinal vasculitis, optic neuritis, retinopathy, diabetic retinopathy, immune mediated retinopathy, macular degeneration, wet macular degeneration, dry age related macular degeneration, Mastocytosis, iron deficiency anemia, uremia, hypereosinophilic syndrome (HES), systemic mast cell disease (SMCD), myelodysplastic syndrome, idiopathic thrombocytic pupura, bone resorption diseases, a Neurodegenerative disorder, a neurological/neuromuscular disorder, multiple sclerosis, Parkinson's disease, Huntington's disease, amyotrophic lateral sclerosis (ALS), familial ALS, sporadic ALS, Alzheimer's disease, myasthenia gravis, Lambert-Eaton myasthenic syndrome (LEMS), Guillain-Barret syndrome, meningitis, encephalitis, traumatic brain injury, nervous system damage, delusional parasitosis, dysregulation of neuronal processes and sensory perception, stroke/neuronal ischemia, spinal cord injury, peripheral neuropathy, tactile hallucinations, spinal cord injury, psychiatric disease, pain, acute pain, chronic pain, neuropathic pain, fibromyalgia, paresthetica, nerve irritation, peripheral neuropathy, pruritus/itch atopic pruritus, xerotic pruritus, pruritus associated with psoriasis/psoriatic itch/psoriasis-associated itch, acute pruritus, chronic pruritus, idiopathic pruritus, chronic idiopathic itch, biliary itch, hepatobiliary-associated itch, renal associated itch/renal itch, uremic itch, cholestasis, intrahepatic cholestasis of pregnancy, lichen simplex chronicus associated pruritus, lymphoma-associated itch, leukemia-associated itch, prurigo nodularis, atopic dermatitis-associated itch, atopic itch/atopic puritis, bullous itch, brachioradial pruritus, neurogenic itch, neuropathic itch, notalgia paresthetica, pruritic popular eruption of HIV, psychogenic itch, swimmer's itch, pruritus or uremic itch, urticarial itch, a dermatologic disorder, dermatologic drug reactions/drug eruptions, xerosis/dry skin, skin rash, skin sensitization, skin irritation, sunburn, shaving, body louse, head lice/pediculosis, pubic lice, cutaneous larva migrans, scabies, parasitic infection, insect infestation, urticarial/hives, popular uritcaria, insect bites, insect stings, dandruff, fungal infection, herpes, varicella/chicken pox, eosinophilic folliculitis, dermatosis of pregnancy/pruritic urticarial papules and plaques of pregnancy (PUPP), inflammatory dermatoses, neutrophilic dermatoses, histiocytoid neutrophilic dermatosis, bowel-bypass syndrome dermatosis, psoriasis/psoriasis vulgaris, lichen planus, lichen sclerosus, acne, acne vulgaris, comedonal acne, inflammatory acne, nodulo-cystic acne, scarring acne, acne keloidalis nuchae, atopies, allergic contact sensitization, allergic dermatitis, dermatitis, atopic dermatitis/eczema, contact dermatitis, photodermatitis, seborrheic dermatitis, stasis dermatitis, acute febrile neutrophilic dermatosis (Sweet's syndrome), chronic atypical neutrophilic dermatosis with lipodystrophy and elevated temperature syndrome (CANDLE Syndrome), hidradenitis suppurativa, hives, pyoderma gangrenosum, alopecia, eyebrow alopecia, intranasal hair alopecia, scarring alopecia, central centrifugal cicatricial alopecia, nonscarring alopecia, alopecia areata (AA), patchy AA, alopecia totalis (AT), alopecia universalis (AU), ophiasis pattern alopecia areata, sisaihpo pattern alopecia areata, androgenetic/androgenic alopecia (AGA)/male and female pattern AGA, telogen effluvium, tinea capitis, hypotrichosis, hereditary hypotrichosis simplex, lichen planopilaris, frontal fibrosing alopecia, punctate palmoplantar keratoderma, erythema elevatinum diutinum (EED), neutrophilic eccrine hidradenitis, palisading neutrophilic granulomatous dermatitis, neutrophilic urticarial dermatosis, vitiligo, segmental vitiligo, unisegmental vitiligo, bisegmental vitiligo, multisegmental vitiligo, non-segmental vitiligo, acral, facial, acrofacial vitiligo, centrofacial vitiligo, mucosal vitiligo, confetti vitiligo, trichrome vitiligo, marginal inflammatory vitiligo, quadrichrome vitiligo, blue vitiligo, Koebner phenomenon, vulgaris vitiligo, generalized vitiligo, universal vitiligo, mixed vitiligo/nonsegmental associated with segmental vitiligo, focal vitiligo, solitary mucosal vitiligo, vitiligo with or without leukotricia, bullous diseases, immunobullous diseases, bullous pemphigoid, cicatricial pemphigoid, pemphigus vulgaris, linear IgA disease, gestational pemphigoid, xeroderma pigmentosum, disorders of fibrosis and scarring, fibroids, hepatic fibrosis, low grade scarring, scleroderma, increased fibrosis, keloids, post-surgical scars, wound healing, surgical scarring, radiation induced fibrosis, CNS scarring, alimentary track or gastrointestinal fibrosis, renal fibrosis, hepatic or biliary fibrosis, liver fibrosis, cardiac fibrosis, ophthalmic scarring, fibrosclerosis, scar growth, wound or scab healing, keloid, mediastinal fibrosis, myelofibrosis, retroperitoneal fibrosis/Ormond's disease, progressive massive fibrosis, nephrogenic systemic fibrosis, Sjorgren's syndrome, sarcoidosis, familial Mediterranean fever, Cryopyrin associated periodic syndrome, Muckle-Wells syndrome, familial cold auto-inflammatory syndrome/familial cold uticaria/TNF receptor associated periodic syndrome, neonatal-onset multisystem inflammatory disease, hyperoxia induced inflammation, reperfusion injury, post-surgical trauma, tissue injury, elevated temperature syndrome, diabetes, Type I diabetes, Type II diabetes, diabetes mellitus, Hashimoto's thyroiditis, Graves' disease, Addison's disease, Castleman's disease, hyperparathyroidism, menopause, obesity, steroid-resistance, glucose intolerance, metabolic syndrome, thyroid illness, hypophysitis, systemic immune senescence, autoimmune atrophic gastritis, autoimmune atrophic gastritis of pernicious anemia, autoimmune encephalomyelitis, autoimmune orchitis, Goodpasture's disease, Sjogren's syndrome, autoimmune thrombocytopenia, sympathetic ophthalmia, secondary hematologic manifestations of autoimmune diseases, autoimmune hemolytic syndromes, autoimmune hemolytic anemia, autoimmune and inflammatory hepatitis, autoimmune ovarian failure, autoimmune thrombocytopenia, silicone implant associated autoimmune disease, drug-induced autoimmunity, HIV-related autoimmune syndromes, metal-induced autoimmunity, autoimmune deafness, autoimmune thyroid disorders, allergy and allergic reactions, a Type I hypersensitivity reactions, a Type II hypersensitivity reactions, a Type III hypersensitivity reaction disease, and a Type IV hypersensitivity reaction, acute and chronic infection, sepsis syndrome, sepsis, septic shock, endotoxic shock, exotoxin-induced toxic shock, gram negative sepsis, gram positive sepsis, fungal sepsis, toxic shock syndrome, graft vs. host reaction/graft vs. host disease, allograft rejection, early transplantation rejection, lymphoma, leukemia, multiple myeloma, a solid tumor, teratoma, metastatic cancer, a bone disorders, internal cancer, bone cancer, mouth/pharynx cancer, esophagus cancer, larynx cancer, stomach cancer, intestinal cancer, colon cancer, rectum cancer, lung cancer, liver cancer, pancreas cancer, nerve cancer, brain cancer, head and neck cancer, throat cancer, ovary cancer, uterus cancer, prostate cancer, testis cancer, bladder cancer, kidney cancer, breast cancer, gall bladder cancer, cervix cancer, thyroid cancer, prostate cancer, eye cancer, skin cancer, a fibrotic cancer, fibroma, fibroadenomas, fibrosarcoma, a myeloproliferative disorder, neoplasm, hematopoietic neoplasm, a myeloid neoplasm, a lymphoid neoplasm, myelofibrosis, primary myelofibrosis, polycythemia vera, essential thrombocythemia, acute lymphocytic leukemia, acute and chronic myelogenous leukemia, chronic lymphocytic leukemia, acute lymphoblastic leukemia, chronic myelomonocytic leukemia (CMML), or promyelocytic leukemia, multiple myeloma, a myeloid malignancy myeloid metaplasia with myelofibrosis (MMM), primary myelofibrosis (PMF), idiopathic myelofibrosis (IMF), Hodgkin's disease, cutaneous lymphoma, cutaneous T-cell lymphoma, mycosis fungoides, B-cell lymphoma, T-cell lymphoma, mantle cell lymphoma, hairy cell lymphoma, Burkitt's lymphoma, mast cell tumors, Hodgkin's disease, non-Hodgkin's disease, Kaposi's sarcoma, rhabdomyosarcoma, seminoma, teratocarcinoma, osteosarcoma, thyroid follicular cancer, increased accumulation of exogenous opioids or synthetic opioids, notalgia paraesthetica, obsessive-compulsive disorders, nostalgia associated with obsessive-compulsive disorders, and a combination thereof.

21. The method of claim 19, wherein the other therapeutic agent is selected from a chemotherapeutic agent, an anti-proliferative agent, an anti-inflammatory agent, an immunomodulatory agent, immunosuppressive agent, a neurotrophic factor, an agent for treating cardiovascular disease, an agent for treating diabetes, an agent for treating immunodeficiency disorders, and a combination thereof.

* * * * *